(12) United States Patent
Masuyama et al.

(10) Patent No.: US 11,681,218 B2
(45) Date of Patent: Jun. 20, 2023

(54) COMPOUND, RESIST COMPOSITION AND METHOD FOR PRODUCING RESIST PATTERN

(71) Applicant: SUMITOMO CHEMICAL COMPANY, LIMITED, Tokyo (JP)

(72) Inventors: Tatsuro Masuyama, Osaka (JP); Yuichi Mukai, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 707 days.

(21) Appl. No.: 16/272,116

(22) Filed: Feb. 11, 2019

(65) Prior Publication Data
US 2019/0250508 A1 Aug. 15, 2019

(30) Foreign Application Priority Data
Feb. 14, 2018 (JP) .............................. JP2018-024466

(51) Int. Cl.
| | | |
|---|---|---|
| G03F 7/004 | (2006.01) | |
| G03F 7/039 | (2006.01) | |
| G03F 7/038 | (2006.01) | |
| C07D 407/12 | (2006.01) | |
| C07D 407/14 | (2006.01) | |
| C07D 407/08 | (2006.01) | |
| G03F 7/16 | (2006.01) | |
| C08G 61/02 | (2006.01) | |
| C07C 309/06 | (2006.01) | |
| C07D 305/06 | (2006.01) | |
| C08L 33/14 | (2006.01) | |

(52) U.S. Cl.
CPC ......... *G03F 7/0045* (2013.01); *C07D 407/12* (2013.01); *C07D 407/14* (2013.01); *G03F 7/0382* (2013.01); *G03F 7/0392* (2013.01); *G03F 7/0397* (2013.01); *G03F 7/168* (2013.01); *C07C 309/06* (2013.01); *C07D 305/06* (2013.01); *C07D 407/08* (2013.01); *C08G 61/025* (2013.01); *C08L 33/14* (2013.01)

(58) Field of Classification Search
CPC ... C07D 407/12; C07D 407/14; G03F 7/0392; G03F 7/0382
See application file for complete search history.

(56) References Cited

U.S. PATENT DOCUMENTS

| | | | | |
|---|---|---|---|---|
| 5,463,084 A * | 10/1995 | Crivello | ............... | C07D 305/06 522/168 |
| 5,981,616 A * | 11/1999 | Yamamura | ............ | G03F 7/0037 522/168 |
| 2006/0025542 A1* | 2/2006 | Musa | .................... | C07D 305/06 525/425 |
| 2011/0123936 A1* | 5/2011 | Hori | ...................... | G03F 7/0035 430/324 |
| 2012/0251945 A1 | 10/2012 | Ichikawa et al. | | |
| 2012/0282548 A1 | 11/2012 | Enomoto et al. | | |

(Continued)

FOREIGN PATENT DOCUMENTS

| | | |
|---|---|---|
| JP | 2011-141494 A | 7/2011 |
| JP | 2011-145424 A | 7/2011 |

(Continued)

OTHER PUBLICATIONS

Taiwanese Office Action and Search Report for Taiwanese Application No. 108104640, dated Apr. 26, 2022, with an English translation.

(Continued)

*Primary Examiner* — Duane Smith
*Assistant Examiner* — Nicholas E Brown
(74) *Attorney, Agent, or Firm* — Birch, Stewart, Kolasch & Birch, LLP

(57) ABSTRACT

The present invention can provide a salt capable of producing a resist pattern with satisfactory CD uniformity (CDU), and a resist composition.

A resist composition comprising a resin including a structural unit having an acid-labile group, an acid generator and a compound represented by formula (I):

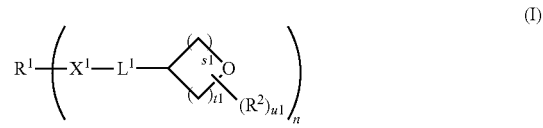

wherein, in formula (I),
$R^1$ represents a hydrocarbon group having 1 to 36 carbon atoms which may have a substituent,
$X^1$ represents *—CO—O—, *—O—CO—, *—O—CO—O— or *—O—, and * represents a bonding site to $R^1$,
$L^1$ represents a single bond or a hydrocarbon group having 1 to 36 carbon atoms which may have a substituent, and —$CH_2$— included in the hydrocarbon group may be replaced by —O—, —S—, —CO— or —$SO_2$—,
$R^2$ represents a saturated hydrocarbon group having 1 to 12 carbon atoms,
u1 represents an integer of 0 to 2,
s1 represents 1 or 2,
t1 represents 0 or 1, in which s1+t1 is 1 or 2,
n represents an integer of 2 or more, and
a plurality of $X^1$, $L^1$, s1, t1, $R^2$ and u1 each may be the same or different from each other.

13 Claims, No Drawings

(56) References Cited

U.S. PATENT DOCUMENTS

| | | | |
|---|---|---|---|
| 2012/0288691 A1 | 11/2012 | Iwato et al. | |
| 2013/0129988 A1 | 5/2013 | Yasuda et al. | |
| 2014/0209951 A1* | 7/2014 | Kong | C08G 65/18 |
| | | | 257/98 |
| 2014/0220497 A1 | 8/2014 | Hirano et al. | |
| 2014/0255833 A1 | 9/2014 | Yasuda et al. | |
| 2016/0147154 A1* | 5/2016 | Takizawa | G03F 7/038 |
| | | | 428/195.1 |

FOREIGN PATENT DOCUMENTS

| | | | |
|---|---|---|---|
| JP | 2012-242556 A | | 12/2012 |
| JP | 2012-252316 A | | 12/2012 |
| JP | 2012252080 A | * | 12/2012 |
| JP | 2013-109012 A | | 6/2013 |
| JP | 2014-34518 A | | 2/2014 |
| JP | 2014/153463 A | | 8/2014 |
| JP | 2014-157252 A | | 8/2014 |
| JP | 2014-532103 A | | 12/2014 |

OTHER PUBLICATIONS

Japanese Office Action dated Nov. 8, 2022 for Application No. 2019-023827 with an English translation.

\* cited by examiner

COMPOUND, RESIST COMPOSITION AND METHOD FOR PRODUCING RESIST PATTERN

TECHNICAL FIELD

The present invention relates to a compound, a resist composition, and a method for producing a resist pattern using the resist composition.

BACKGROUND ART

Patent Document 1 mentions a resist composition comprising a compound represented by the following formula, a resin including a structural unit having an acid-labile group and an acid generator.

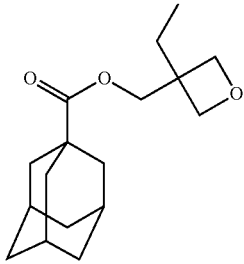

Patent Document 1 also mentions a resist composition comprising a compound of the following structural formula, a resin including a structural unit having an acid-labile group and an acid generator.

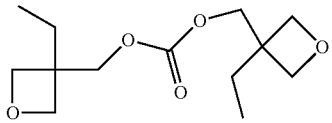

Patent Document 2 mentions a compound represented by the following formula.

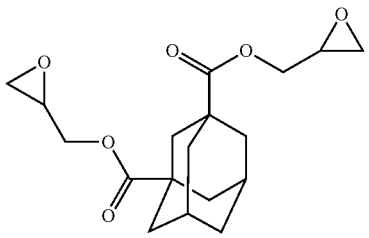 [SMILES: O=C(OCC1CO1)C12CC3CC(C1)CC(C(=O)OCC1CO1)(C3)C2]

PRIOR ART DOCUMENT

Patent Document

Patent Document 1: JP 2012-252316 A
Patent Document 2: JP 2014-034518 A

SUMMARY OF THE INVENTION

Problems to be Solved by the Invention

An object of the present invention is to provide a resist composition capable of producing a resist pattern with CD uniformity (CDU) which is better than that of a resist pattern formed from the above-mentioned resist composition.

Means for Solving the Problems

The present invention includes the following inventions.
[1] A resist composition comprising a resin including a structural unit having an acid-labile group, an acid generator and a compound represented by formula (I):

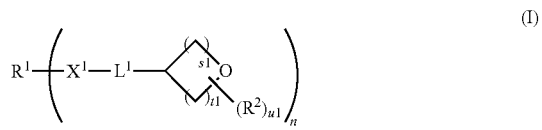

wherein, in formula (I),
$R^1$ represents a hydrocarbon group having 1 to 36 carbon atoms which may have a substituent,
$X^1$ represents *—CO—O—, *—O—CO—, *—O—CO—O— or *—O—, and * represents a bonding site to $R^1$,
$L^1$ represents a single bond or a hydrocarbon group having 1 to 36 carbon atoms which may have a substituent, and —$CH_2$— included in the hydrocarbon group may be replaced by —O—, —S—, —CO— or —$SO_2$—,
$R^2$ represents a saturated hydrocarbon group having 1 to 12 carbon atoms,
u1 represents an integer of 0 to 2,
s1 represents 1 or 2,
t1 represents 0 or 1, in which s1+t1 is 1 or 2,
n represents an integer of 2 or more, and
a plurality of $X^1$, $L^1$, s1, t1, $R^2$ and u1 each may be the same or different from each other.
[2] The resist composition according to [1], wherein $R^1$ is an alicyclic hydrocarbon group.
[3] The resist composition according to [1] or [2], wherein $X^1$ is *—CO—O— or *—O—CO—O— (* represents a bonding site to $R^1$).
[4] The resist composition according to any one of [1] to [3], wherein $L^1$ is a methylene group.
[5] The resist composition according to any one of [1] to [4], wherein the acid generator is a salt represented by formula (B1):

wherein, in formula (B1),
$Q^{b1}$ and $Q^{b2}$ each independently represent a fluorine atom or a perfluoroalkyl group having 1 to 6 carbon atoms,
$L^{b1}$ represents a divalent saturated hydrocarbon group having 1 to 24 carbon atoms, and —$CH_2$— included in the saturated hydrocarbon group may be replaced by —O— or —CO— and a hydrogen atom included in the saturated hydrocarbon group may be substituted with a fluorine atom or a hydroxy group,
Y represents a methyl group which may have a substituent or alicyclic hydrocarbon group having 3 to 18 carbon atoms which may have a substituent, and —$CH_2$— included in the alicyclic hydrocarbon group may be replaced by —O—, —$S(O)_2$— or —CO—, and $Z^+$ represents an organic cation.

[6] A method for producing a resist pattern, which comprises:
(1) a step of applying the resist composition according to any one of [1] to [5] on a substrate,
(2) a step of drying the applied composition to form a composition layer,
(3) a step of exposing the composition layer,
(4) a step of heating the exposed composition layer, and
(5) a step of developing the heated composition layer.
[7] A compound represented by formula (I1):

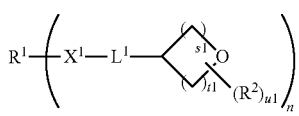

wherein, in formula (I1),
$R^1$ represents a hydrocarbon group having 1 to 36 carbon atoms which may have a substituent,
$X^1$ represents *—CO—O—, *—O—CO—, *—O—CO—O— or *—O—, and * represents a bonding site to $R^1$,
$L^1$ represents a single bond or a hydrocarbon group having 1 to 36 carbon atoms which may have a substituent, and —$CH_2$— included in the hydrocarbon group may be replaced by —O—, —S—, —CO— or —$SO_2$—,
$R^2$ represents a saturated hydrocarbon group having 1 to 12 carbon atoms,
u1 represents an integer of 0 to 2,
s1 represents 1 or 2,
t1 represents 0 or 1, in which s1+t1 is 2,
n represents an integer of 2 or more, and
a plurality of $X^1$, $L^1$, s1, t1, $R^2$ and u1 each may be the same or different.

Effects of the Invention

The present invention provides a resist composition capable of producing a resist pattern with satisfactory CD uniformity (CDU).

MODE FOR CARRYING OUT THE INVENTION

In the present specification, "(meth)acrylate" each mean "at least one of acrylate and methacrylate". Descriptions such as "(meth)acrylic acid" and "(meth)acryloyl" also have the same meanings.

Unless otherwise specified, like "aliphatic hydrocarbon group", groups capable of having a linear structure, a branched structure and/or a cyclic structure include all of these forms. "Aromatic hydrocarbon group" also includes a group in which a hydrocarbon group is bonded to an aromatic ring. When stereoisomers exist, all stereoisomers are included.

In the present specification, "solid component of the resist composition" means the total amount of components in which the below-mentioned solvent (E) is removed from the total amount of the resist composition.

[Resist Composition]

The resist composition of the present invention includes a resin including a structural unit having an acid-labile group (hereinafter sometimes referred to as "resin (A)"), an acid generator (hereinafter sometimes referred to as "acid generator (B)") and a compound represented by formula (I) (hereinafter sometimes referred to as "compound (I)"). The "acid-labile group" means a group having a leaving group which is eliminated by contact with an acid, thus forming a hydrophilic group (e.g., a hydroxy group or a carboxy group).

The resist composition of the present invention preferably includes a solvent (hereinafter sometimes referred to as "solvent (E)").

The resist composition of the present invention may further include a quencher (hereinafter sometimes referred to as "quencher (C)") and/or a resin including a structural unit containing a fluorine atom (hereinafter sometimes referred to as "resin (X)").

<Resin (A)>

The resin (A) includes a structural unit having an acid-labile group (hereinafter sometimes referred to as "structural unit (a1)"). It is preferred that the resin (A) further includes a structural unit other than the structural unit (a1). Examples of the structural unit other than the structural unit (a1) include a structural unit having no acid-labile group (hereinafter sometimes referred to as "structural unit (s)"), a structural unit other than the structural unit (a1) and the structural unit (s) (e.g., a structural unit having a halogen atom mentioned later (hereinafter sometimes referred to as "structural unit (a4)"), a structural unit having a non-leaving hydrocarbon group mentioned later (hereinafter sometimes referred to as "structural unit (a5)) and other structural units derived from monomers known in the art.

<Structural Unit (a1)>

The structural unit (a1) is derived from a monomer having an acid-labile group (hereinafter sometimes referred to as "monomer (a1)").

The acid-labile group contained in the resin (A) is preferably a group represented by formula (1) (hereinafter also referred to as group (1)) and/or a group represented by formula (2) (hereinafter also referred to as group (2)):

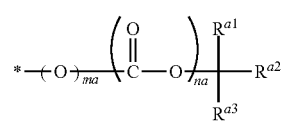

(1)

wherein, in formula (1), $R^{a1}$, $R^{a2}$ and $R^{a3}$ each independently represent an alkyl group having 1 to 8 carbon atoms, an alicyclic hydrocarbon group having 3 to 20 carbon atoms or groups obtained by combining these groups, or $R^{a1}$ and $R^{a2}$ are bonded each other to form a nonaromatic hydrocarbon ring having 3 to 20 carbon atoms together with carbon atoms to which $R^{a1}$ and $R^{a2}$ are bonded,
ma and na each independently represent 0 or 1, and at least one of ma and na represents 1, and
* represents a bonding site:

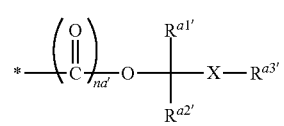

(2)

wherein, in formula (2), $R^{a1'}$ and $R^{a2'}$ each independently represent a hydrogen atom or a hydrocarbon group having 1 to 12 carbon atoms, $R^{a3'}$ represents a hydrocarbon group having 1 to 20 carbon atoms, or $R^{a2'}$ and $R^{a3'}$ are bonded each other to form a heterocyclic ring having 3 to 20 carbon atoms together with carbon atoms and X to which $R^{a2'}$ and $R^{a3'}$ are bonded, and —CH$_2$— included in the hydrocarbon group and the heterocyclic ring may be replaced by —O— or —S—, X represents an oxygen atom or a sulfur atom, na' represents 0 or 1, and

* represents a bonding site.

Examples of the alkyl group in $R^{a1}$, $R^{a2}$ and $R^{a3}$ include a methyl group, an ethyl group, a propyl group, a butyl group, a pentyl group, a hexyl group, a heptyl group, an octyl group and the like.

The alicyclic hydrocarbon group in $R^{a1}$, $R^{a2}$ and $R^{a3}$ may be either monocyclic and polycyclic. Examples of the monocyclic alicyclic hydrocarbon group include cycloalkyl groups such as a cyclopentyl group, a cyclohexyl group, a cycloheptyl group and a cyclooctyl group. Examples of the polycyclic alicyclic hydrocarbon group include a decahydronaphthyl group, an adamantyl group, a norbornyl group and the following groups (* represents a bonding site). The number of carbon atoms of the alicyclic hydrocarbon group for $R^{a1}$, $R^{a2}$ and $R^{a3}$ is preferably 3 to 16.

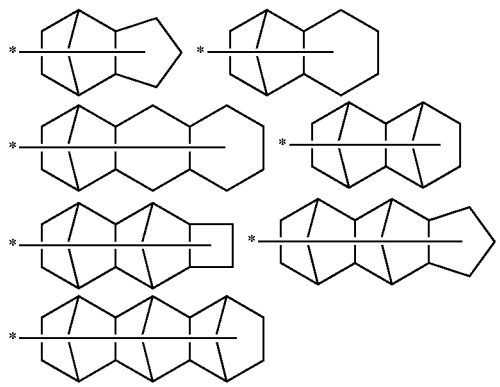

The group obtained by combining an alkyl group with an alicyclic hydrocarbon group includes, a for example, a methylcyclohexyl group, a dimethylcyclohexyl group, a methylnorbornyl group, a cyclohexylmethyl group, an adamantylmethyl group, an adamantyldimethyl group, a norbornylethyl group and the like.

Preferably, ma is 0 and na is 1.

When $R^{a1}$ and $R^{a2}$ are bonded each other to form a nonaromatic hydrocarbon ring, examples of —C($R^{a1}$)($R^{a2}$)($R^{a3}$) include the following rings. The nonaromatic hydrocarbon ring preferably has 3 to 12 carbon atoms. * represents a bonding site to —O—.

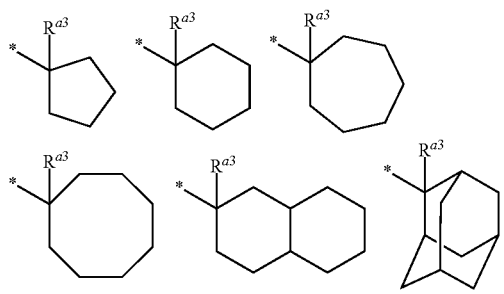

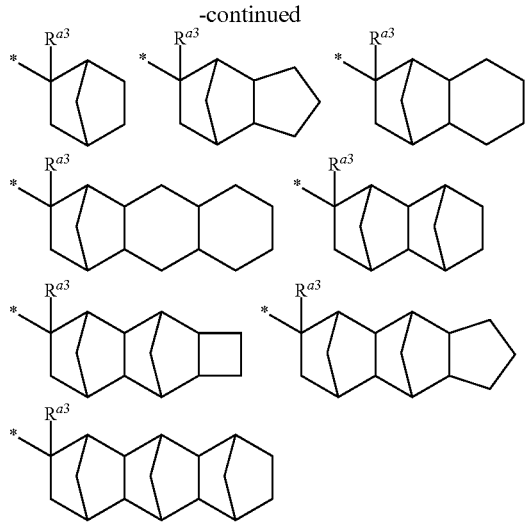

Examples of the hydrocarbon group in $R^{a1'}$, $R^{a2'}$ and $R^{a3'}$ include an alkyl group, an alicyclic hydrocarbon group, an aromatic hydrocarbon group and groups obtained by combining these groups.

Examples of the alkyl group and the alicyclic hydrocarbon group include those which are the same as mentioned in $R^{a1}$, $R^{a2}$ and $R^{a3}$.

Examples of the aromatic hydrocarbon group include aryl groups such as a phenyl group, a naphthyl group, an anthryl group, a biphenyl group and a phenanthryl group.

Examples of the group combined include a group obtained by combining the above-mentioned alkyl group and alicyclic hydrocarbon group (e.g., a cycloalkylalkyl group), an aralkyl group such as a benzyl group, an aromatic hydrocarbon group having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), an aromatic hydrocarbon group having an alicyclic hydrocarbon group (a p-cyclohexylphenyl group, a p-adamantylphenyl group, etc.), an aryl-cycloalkyl group such as a phenylcyclohexyl group, and the like.

When $R^{a2'}$ and $R^{a3'}$ are bonded each other to form a heterocyclic ring together with carbon atoms and X to which $R^{a2'}$ and $R^{a3'}$ are bonded, examples of —C($R^{a1'}$)($R^{a3'}$)—X—$R^{a2'}$ include the following rings. * represents a bonding site.

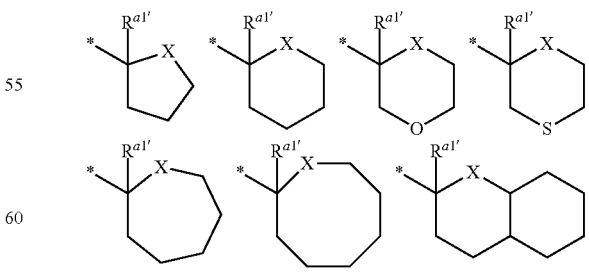

Among $R^{a1'}$ and $R^{a2'}$, at least one is preferably a hydrogen atom.

na' is preferably 0.

Examples of the group (1) include the following groups.

A group wherein, in formula (1), $R^{a1}$, $R^{a2}$ and $R^{a3}$ are alkyl groups, ma=0 and na=1. The group is preferably a tert-butoxycarbonyl group.

A group wherein, in formula (1), $R^{a1}$ and $R^{a2}$ are bonded each other to form an adamantyl group together with carbon atoms to which $R^{a1}$ and $R^{a2}$ are bonded, $R^{a3}$ is an alkyl group, ma=0 and na=1.

A group wherein, in formula (1), $R^{a1}$ and $R^{a2}$ are each independently an alkyl group, $R^{a3}$ is an adamantyl group, ma=0 and na=1.

Specific examples of the group (1) include the following groups. * represents a bonding site.

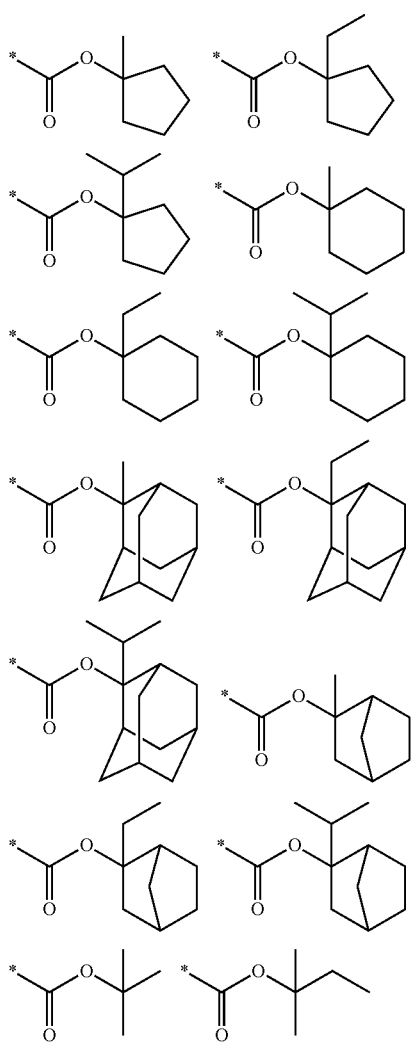

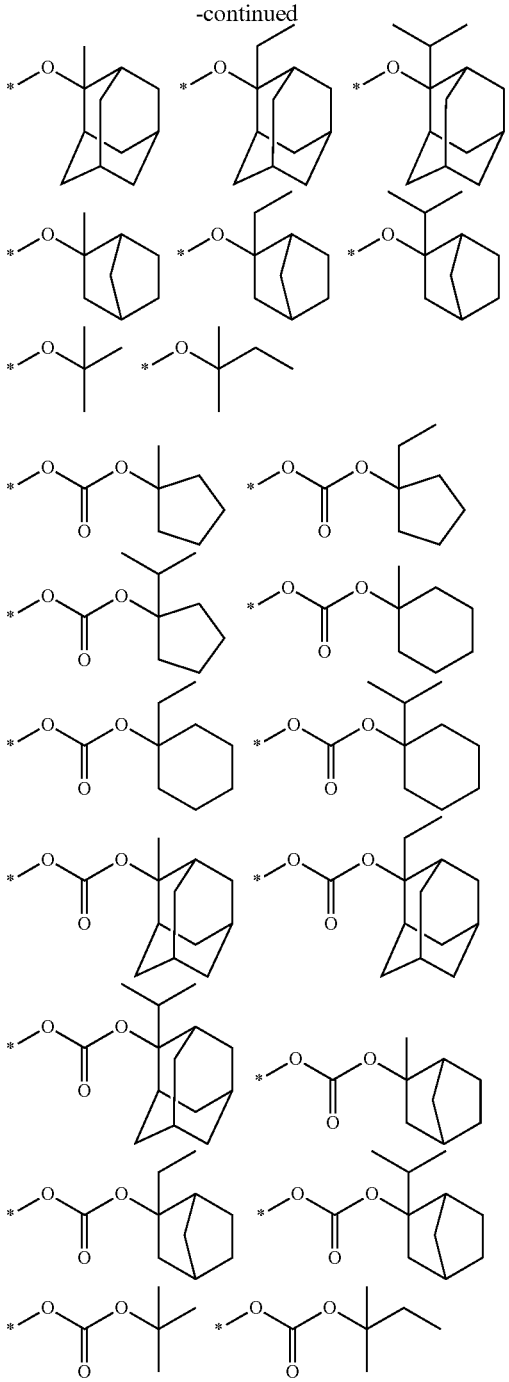

Specific examples of the group (2) include the following groups. * represents a bonding site.

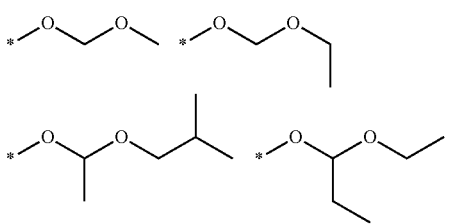

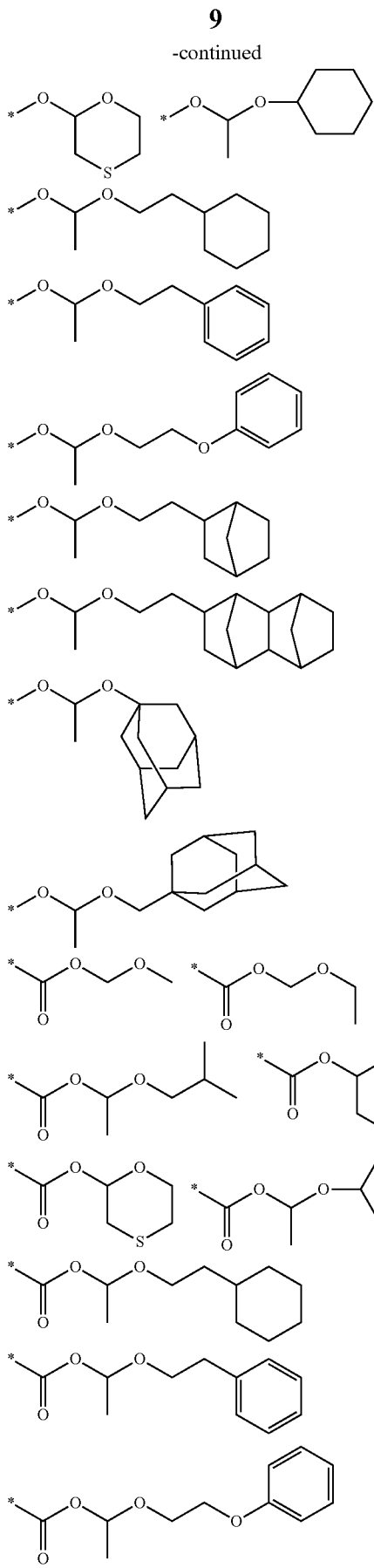

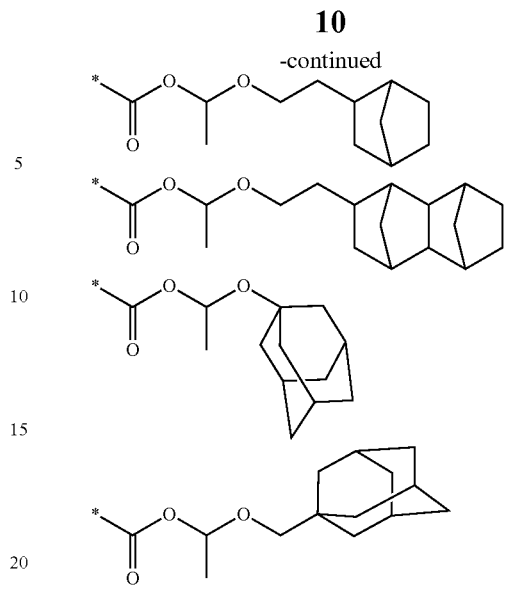

The monomer (a1) is preferably a monomer having an acid-labile group and an ethylenic unsaturated bond, and more preferably a (meth)acrylic monomer having an acid-labile group.

Among the (meth)acrylic monomers having an acid-labile group, those having an alicyclic hydrocarbon group having 5 to 20 carbon atoms are preferably exemplified. When a resin (A) including a structural unit derived from a monomer (a1) having a bulky structure such as an alicyclic hydrocarbon group is used in a resist composition, it is possible to improve the resolution of a resist pattern.

The structural unit derived from a (meth)acrylic monomer having a group (1) is preferably a structural unit represented by formula (a1-0) (hereinafter sometimes referred to as structural unit (a1-0)), a structural unit represented by formula (a1-1) (hereinafter sometimes referred to as structural unit (a1-1)) or a structural unit represented by formula (a1-2) (hereinafter sometimes referred to as structural unit (a1-2)). These structural units may be used alone, or two or more structural units may be used in combination.

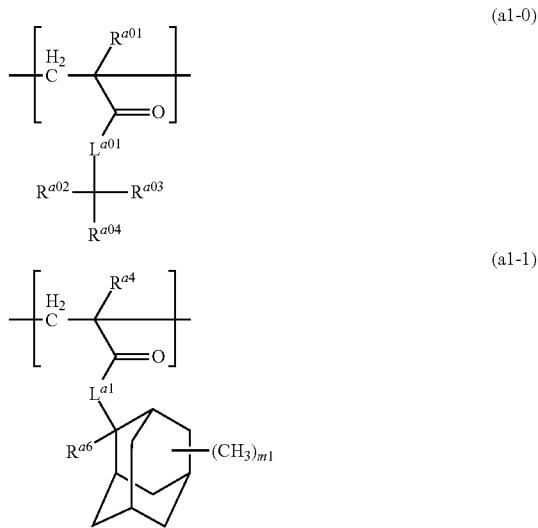

(a1-2)

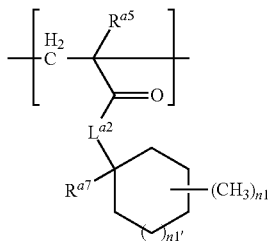

In formula (a1-0), formula (a1-1) and formula (a1-2), $L^{a01}$, $L^{a1}$ and $L^{a2}$ each independently represent —O— or *—O—$(CH_2)_{k1}$—CO—O—, k1 represents an integer of 1 to 7, and * represents a bonding site to —CO—, $R^{a01}$, $R^{a4}$ and $R^{a5}$ each independently represent a hydrogen atom or a methyl group, $R^{a02}$, $R^{a03}$ and $R^{a04}$ each independently represent an alkyl group having 1 to 8 carbon atoms, an alicyclic hydrocarbon group having 3 to 18 carbon atoms or groups obtained by combining these groups, $R^{a6}$ and $R^{a7}$ each independently represent an alkyl group having 1 to 8 carbon atoms, an alicyclic hydrocarbon group having 3 to 18 carbon atoms or groups obtained by combining these groups, m1 represents an integer of 0 to 14,
n1 represents an integer of 0 to 10, and
n1' represents an integer of 0 to 3.

$R^{a01}$, $R^{a4}$ and $R^{a5}$ are preferably a methyl group.

$L^{a01}$, $L^{a1}$ and $L^{a2}$ are preferably an oxygen atom or *—O—$(CH_2)_{k01}$—CO—O— (in which k01 is preferably an integer of 1 to 4, and more preferably 1), and more preferably an oxygen atom.

Examples of the alkyl group, the alicyclic hydrocarbon group and groups obtained by combining these groups in $R^{a02}$, $R^{a03}$, $R^{a04}$, $R^{a6}$ and $R^{a7}$ include the same groups as mentioned for $R^{a1}$, $R^{a2}$ and $R^{a3}$ of formula (1).

The number of the carbon atoms of the alkyl group in $R^{a02}$, $R^{a03}$ and $R^{a04}$ is preferably 1 to 6, more preferably a methyl group or an ethyl group, and still more preferably a methyl group.

The number of the carbon atoms of the alkyl group in $R^{a6}$ and $R^{a7}$ is preferably 1 to 6, more preferably a methyl group, an ethyl group or an isopropyl group, and still more preferably an ethyl group or an isopropyl group.

The number of carbon atoms of the alicyclic hydrocarbon group in $R^{a02}$, $R^{a03}$, $R^{a04}$, $R^{a6}$ and $R^{a7}$ is preferably 5 to 12, and more preferably 5 to 10.

The total number of carbon atoms of the group obtained by combining the alkyl group with the alicyclic hydrocarbon group is preferably 18 or less.

$R^{a02}$ and $R^{a03}$ are each independently preferably an alkyl group having 1 to 6 carbon atoms, and more preferably a methyl group or an ethyl group.

$R^{a04}$ is preferably an alkyl group having 1 to 6 carbon atoms or an alicyclic hydrocarbon group having 5 to 12 carbon atoms, and more preferably a methyl group, an ethyl group, a cyclohexyl group or an adamantyl group.

$R^{a6}$ and $R^{a7}$ are each independently preferably an alkyl group having 1 to 6 carbon atoms, more preferably a methyl group, an ethyl group or an isopropyl group, and still more preferably an ethyl group or an isopropyl group.

m1 is preferably an integer of 0 to 3, and more preferably 0 or 1.

n1 is preferably an integer of 0 to 3, and more preferably 0 or 1.

n1' is preferably 0 or 1.

The structural unit (a1-0) includes, for example, a structural unit represented by any one of formula (a1-0-1) to formula (a1-0-12) and a structural unit in which a methyl group corresponding to $R^{a01}$ in the structural unit (a1-0) is replaced by a hydrogen atom and is preferably a structural unit represented by any one of formula (a1-0-1) to formula (a1-0-10).

(a1-0-1)

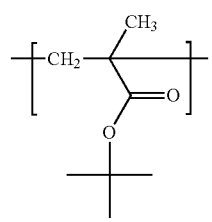

(a1-0-2)

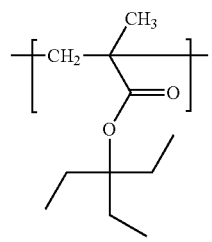

(a1-0-3)

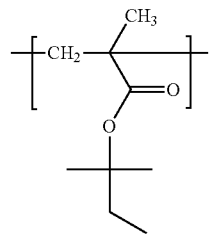

(a1-0-4)

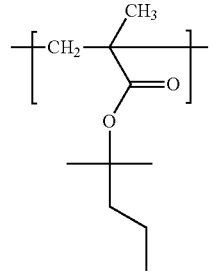

(a1-0-5)

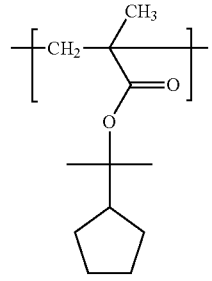

(a1-0-6) 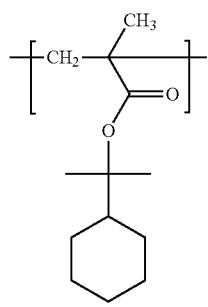

(a1-0-7) 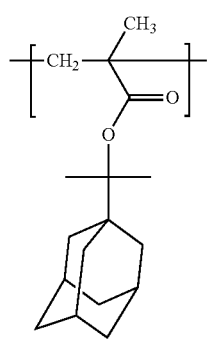

(a1-0-8) 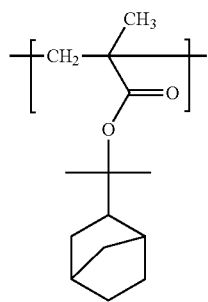

(a1-0-9) 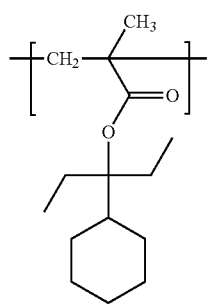

(a1-0-10) 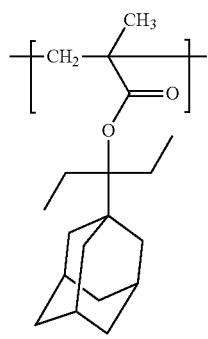

(a1-0-11) 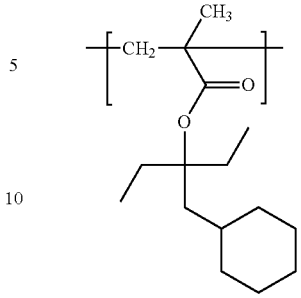

(a1-0-12) 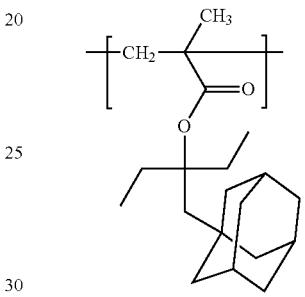

The structural unit (a1-1) includes, for example, structural units derived from the monomers mentioned in JP 2010-204646 A. Among these structural units, a structural unit represented by any one of formula (a1-1-1) to formula (a1-1-4) and a structural unit in which a methyl group corresponding to $R^{a4}$ in the structural unit (a1-1) is replaced by a hydrogen atom are preferred, and a structural unit represented by any one of formula (a1-1-1) to formula (a1-1-4) is more preferred.

(a1-1-1) 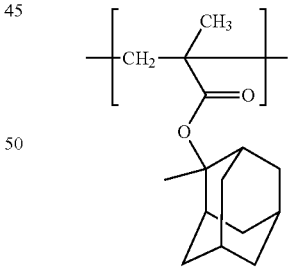

(a1-1-2) 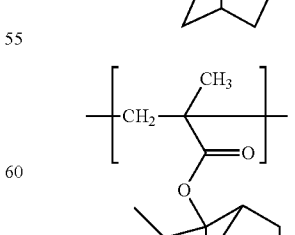

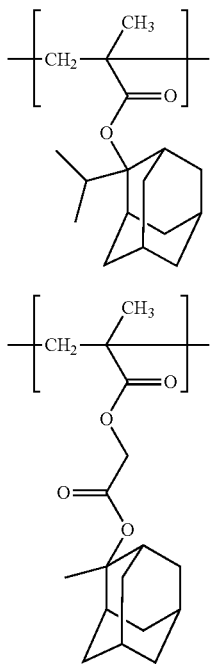

Examples of the structural unit (a1-2) include a structural unit represented by any one of formula (a1-2-1) to formula (a1-2-6) and a structural unit in which a methyl group corresponding to $R^{a5}$ in the structural unit (a1-2) is replaced by a hydrogen atom, and structural units represented by formula (a1-2-2), formula (a1-2-5) and formula (a1-2-6) are preferred.

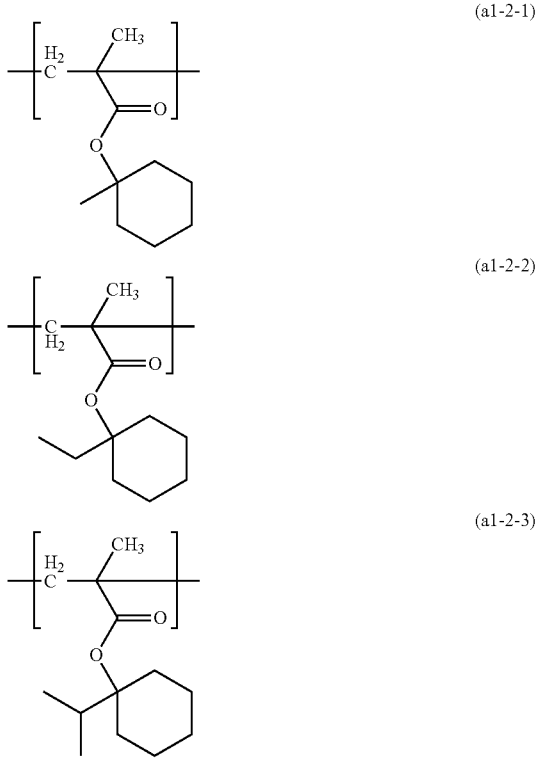

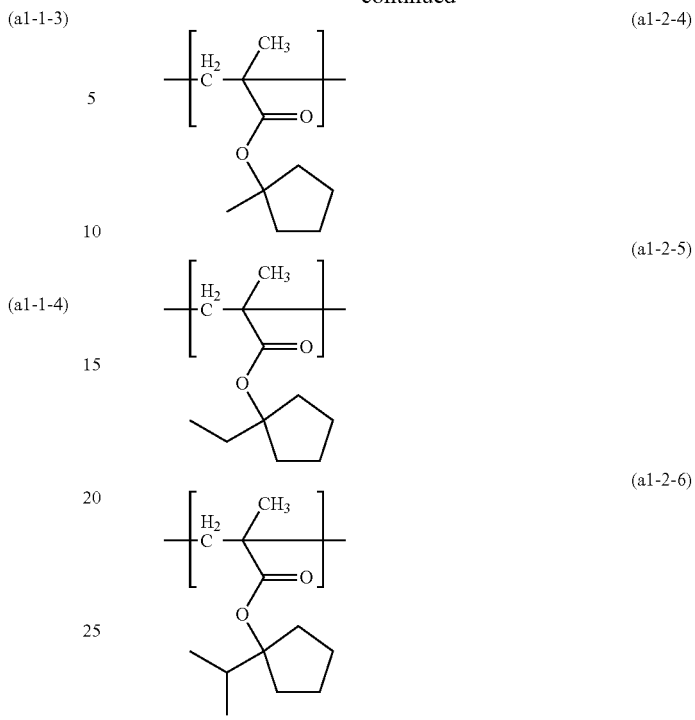

When the resin (A) includes a structural unit (a1-0) and/or a structural unit (a1-1) and/or a structural unit (a1-2), the total content thereof is usually 10 to 95 mol %, preferably 15 to 90 mol %, more preferably 15 to 85 mol %, still more preferably 15 to 70 mol %, yet more preferably 15 to 65 mol %, and particularly preferably 20 to 65 mol %, based on all structural units of the resin (A).

In the structural unit (a1), examples of the structural unit having a group (2) include a structural unit represented by formula (a1-4) (hereinafter sometimes referred to as "structural unit (a1-4)"):

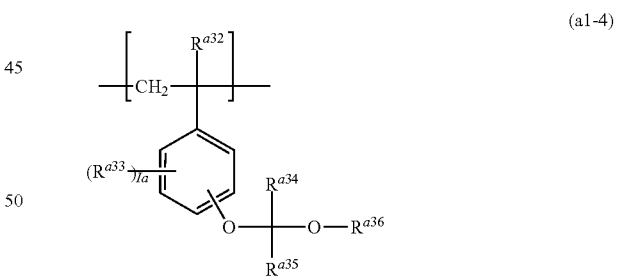

wherein, in formula (a1-4),
$R^{a32}$ represents a hydrogen atom, a halogen atom or an alkyl group having 1 to 6 carbon atoms which may have a halogen atom,
$R^{a33}$ represents a halogen atom, a hydroxy group, an alkyl group having 1 to 6 carbon atoms, an alkoxy group having 1 to 6 carbon atoms, an alkylcarbonyl group having 2 to 4 carbon atoms, an alkylcarbonyloxy group having 2 to 4 carbon atoms, an acryloyloxy group or a methacryloyloxy group.
la represents an integer of 0 to 4, and when la is 2 or more, a plurality of $R^{a33}$ may be the same or different from each other, and $R^{a34}$ and $R^{a35}$ each independently represent a hydrogen atom or a hydrocarbon group having 1 to 12 carbon atoms, $R^{a36}$ represents a hydrocarbon group having 1 to 20 carbon atoms, or $R^{a35}$ and $R^{a36}$ are bonded each other to form a divalent hydrocarbon group having 2 to 20 carbon atoms together with —C—O— to which $R^{a35}$ and $R^{a36}$ are bonded, and —CH$_2$— included in the hydrocarbon group and the divalent hydrocarbon group may be replaced by —O— or —S—.

Examples of the alkyl group in $R^{a32}$ and $R^{a33}$ include a methyl group, an ethyl group, a propyl group, an isopropyl group, a butyl group, a pentyl group and a hexyl group. The alkyl group is preferably an alkyl group having 1 to 4 carbon atoms, more preferably a methyl group or an ethyl group, and still more preferably a methyl group.

Examples of the halogen atom in $R^{a32}$ and $R^{a33}$ include a fluorine atom, a chlorine atom and a bromine atom.

Examples of the alkyl group having 1 to 6 carbon atoms which may have a halogen atom include a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group, a perfluorohexyl group and the like.

Examples of the alkoxy group include a methoxy group, an ethoxy group, a propoxy group, a butoxy group, a pentyloxy group and a hexyloxy group. Among these groups, an alkoxy group having 1 to 4 carbon atoms is preferred, a methoxy group or an ethoxy group are more preferred, and a methoxy group is still more preferred.

Examples of the alkylcarbonyl group include an acetyl group, a propionyl group and a butyryl group.

Examples of the alkylcarbonyloxy group include an acetyloxy group, a propionyloxy group, a butyryloxy group and the like.

Examples of the hydrocarbon group in $R^{a34}$, $R^{a35}$ and $R^{a36}$ include an alkyl group, an alicyclic hydrocarbon group, an aromatic hydrocarbon group and groups obtained by combining these groups, and examples of the alkyl group and the alicyclic hydrocarbon group include the same groups as the alkyl group and the alicyclic hydrocarbon group in $R^{a02}$, $R^{a03}$ and $R^{a04}$.

Examples of the aromatic hydrocarbon group include aryl groups such as a phenyl group, a naphthyl group, an anthryl group, a biphenyl group and a phenanthryl group.

Examples of the combined group include a group obtained by combining the above-mentioned alkyl group and alicyclic hydrocarbon group (e.g., a cycloalkylalkyl group), an aralkyl group such as a benzyl group, an aromatic hydrocarbon group having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), an aromatic hydrocarbon group having an alicyclic hydrocarbon group (a p-cyclohexylphenyl group, a p-adamantylphenyl group, etc.), an aryl-cyclohexyl group such as a phenylcyclohexyl group and the like. Particularly, examples of $R^{a36}$ include an alkyl group having 1 to 18 carbon atoms, an alicyclic hydrocarbon group having 3 to 18 carbon atoms, an aromatic hydrocarbon group having 6 to 18 carbon atoms or groups obtained by combining these groups.

In formula (a1-4), $R^{a32}$ is preferably a hydrogen atom, $R^{a33}$ is preferably an alkoxy group having 1 to 4 carbon atoms, more preferably a methoxy group and an ethoxy group, and still more preferably a methoxy group, la is preferably 0 or 1, and more preferably 0, $R^{a34}$ is preferably a hydrogen atom, and $R^{a35}$ is preferably an alkyl group having 1 to 12 carbon atoms or an alicyclic hydrocarbon group, and more preferably a methyl group or an ethyl group.

The hydrocarbon group for $R^{a36}$ is preferably an alkyl group having 1 to 18 carbon atoms, an alicyclic hydrocarbon group having 3 to 18 carbon atoms, an aromatic hydrocarbon group having 6 to 18 carbon atoms or groups formed by combining these groups, and more preferably an alkyl group having 1 to 18 carbon atoms, an alicyclic aliphatic hydrocarbon group having 3 to 18 carbon atoms or an aralkyl group having 7 to 18 carbon atoms. The alkyl group and the alicyclic hydrocarbon group in $R^{a36}$ are preferably unsubstituted. The aromatic hydrocarbon group in $R^{a36}$ is preferably an aromatic ring having an aryloxy group having 6 to 10 carbon atoms.

In the structural unit (a1-4), —O—C($R^{a34}$)($R^{a35}$)—O—$R^{a36}$ is eliminated by contact with an acid (e.g. p-toluenesulfonic acid) to form a hydroxy group.

The structural unit (a1-4) includes, for example, structural units derived from the monomers mentioned in JP 2010-204646 A. The structural unit preferably includes structural units represented by formula (a1-4-1) to formula (a1-4-12) and a structural unit in which a hydrogen atom corresponding to $R^{a32}$ in the constitutional unit (a1-4) is replaced by a methyl group, and more preferably structural units represented by formula (a1-4-1) to formula (a1-4-5) and formula (a1-4-10).

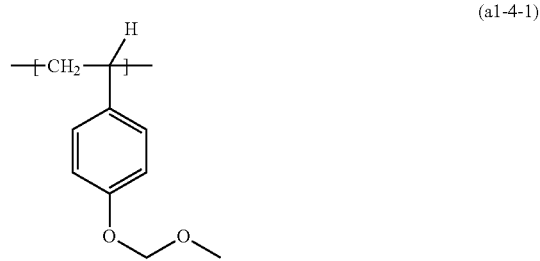

(a1-4-1)

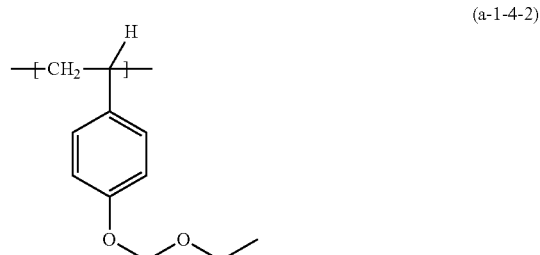

(a-1-4-2)

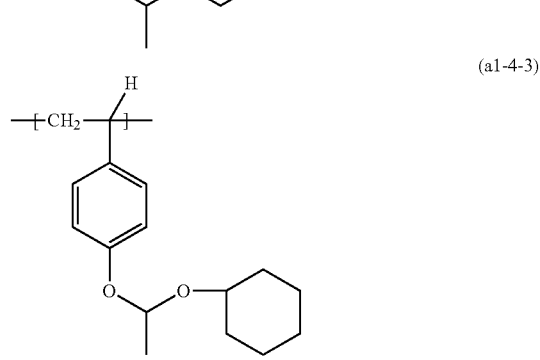

(a1-4-3)

(a-1-4-4)
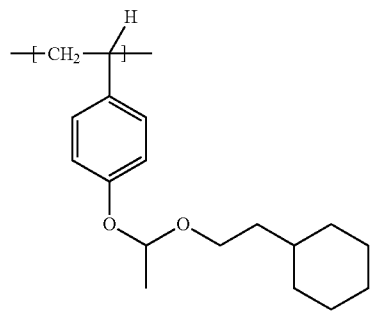
(a-1-4-5)
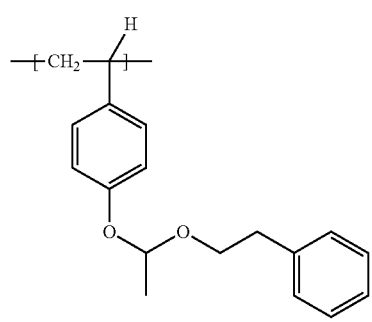
(a1-4-6)
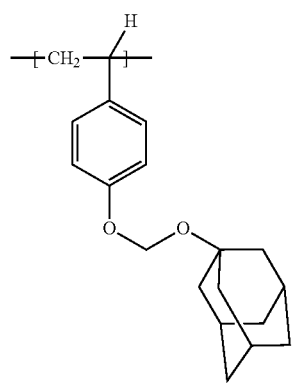
(a1-4-7)
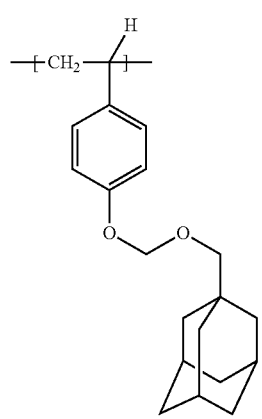
(a1-4-8)
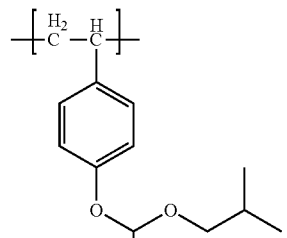
(a1-4-9)
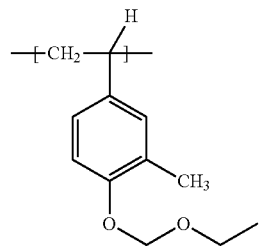
(a1-4-10)
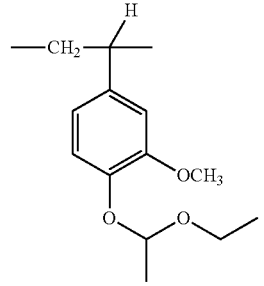
(a1-4-11)
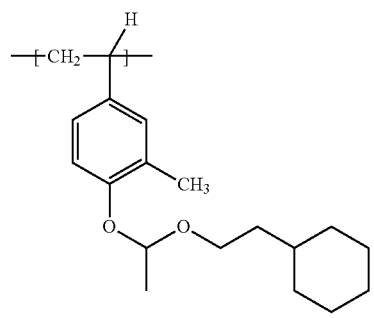
(a-1-4-12)
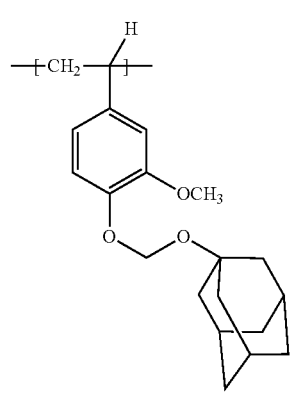
When the resin (A) includes the structural unit (a1-4), the content is preferably 10 to 95 mol %, more preferably 15 to 90 mol %, still more preferably 20 to 85 mol %, yet more preferably 20 to 70 mol %, and particularly preferably 20 to 60 mol %, based on the total of all structural units of the resin (A).

The structural unit derived from a (meth)acrylic monomer having a group (2) also includes a structural unit represented by formula (a1-5) (hereinafter sometimes referred to as "structural unit (a1-5)").

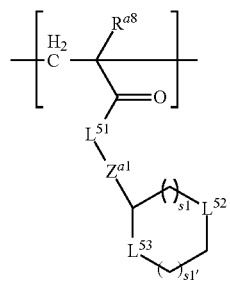

(a1-5)

In formula (a1-5), $R^{a8}$ represents an alkyl group having 1 to 6 carbon atoms which may have a halogen atom, a hydrogen atom or a halogen atom, $Z^{a1}$ represents a single bond or *—$(CH_2)_{h2}$—CO-$L^{54}$-, h3 represents an integer of 1 to 4, and * represents a bonding site to $L^{51}$, $L^{51}$, $L^{52}$, $L^{53}$ and $L^{54}$ each independently represent —O— or —S—, s1 represents an integer of 1 to 3, and s1' represents an integer of 0 to 3.

The halogen atom includes a fluorine atom and a chlorine atom and is preferably a fluorine atom. Examples of the alkyl group having 1 to 6 carbon atoms which may have a halogen atom include a methyl group, an ethyl group, a propyl group, a butyl group, a pentyl group, a hexyl group, a heptyl group, an octyl group, a fluoromethyl group and a trifluoromethyl group.

In formula (a1-5), $R^{a8}$ is preferably a hydrogen atom, a methyl group or a trifluoromethyl group, $L^{51}$ is preferably an oxygen atom, one of $L^{52}$ and $L^{53}$ is preferably —O— and the other one is preferably —S—, s1 is preferably 1, s1' is preferably an integer of 0 to 2, and $Z^{a1}$ is preferably a single bond or *—$CH_2$—CO—O—.

The structural unit (a1-5) includes, for example, structural units derived from the monomers mentioned in JP 2010-61117 A. Among these structural units, structural units represented by formula (a1-5-1) to formula (a1-5-4) are preferred, and structural units represented by formula (a1-5-1) or formula (a1-5-2) are more preferred.

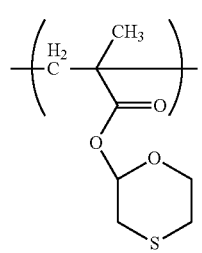

(a1-5-1)

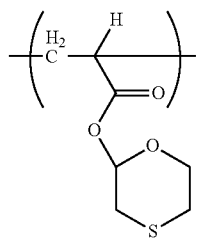

(a1-5-2)

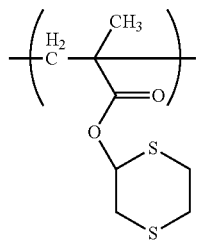

(a1-5-3)

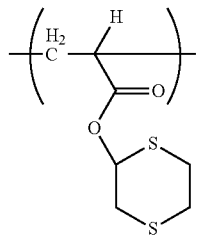

(a1-5-4)

When the resin (A) includes the structural unit (a1-5), the content is preferably 1 to 50 mol %, more preferably 3 to 45 mol %, still more preferably 5 to 40 mol %, and yet more preferably 5 to 30 mol %, based on all structural units of the resin (A).

The structural unit (a1) also includes the following structural units.

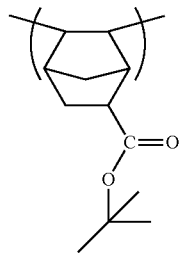

(a1-3-1)

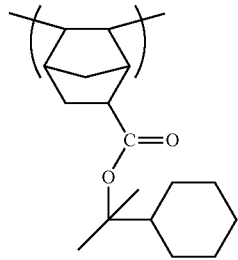

(a1-3-2)

-continued (a1-3-3)
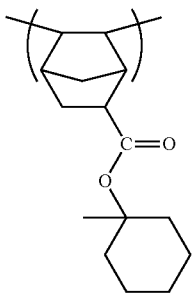

(a1-3-4)
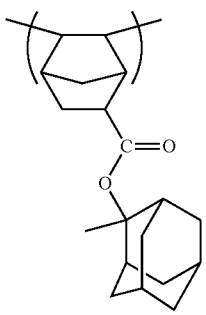

(a1-3-5)
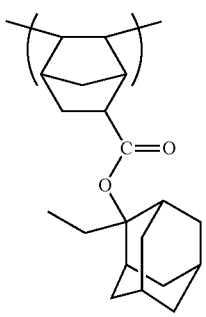

(a1-3-6)
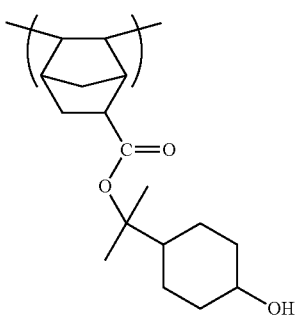

(a1-3-7)
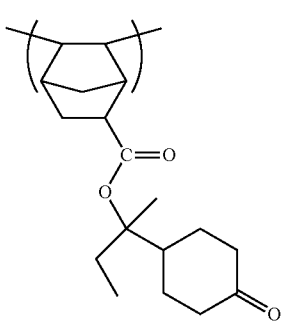

When the resin (A) includes the above-mentioned structural units such as (a1-3-1) to (a1-3-7), the content is preferably 10 to 95 mol %, more preferably 15 to 90 mol %, still more preferably 20 to 85 mol %, yet more preferably 20 to 70 mol %, and particularly preferably 20 to 60 mol %, based on all structural units of the resin (A).

<Structural Unit (s)>

The structural unit (s) is derived from a monomer having no acid-labile group (hereinafter sometimes referred to as "monomer (s)"). It is possible to use, as the monomer from which the structural unit (s) is derived, a monomer having no acid-labile group known in the resist field.

The structural unit (s) preferably has a hydroxy group or a lactone ring. When a resin including a structural unit having a hydroxy group and having no acid-labile group (hereinafter sometimes referred to as "structural unit (a2)") and/or a structural unit having a lactone ring and having no acid-labile group (hereinafter sometimes referred to as "structural unit (a3)") is used in the resist composition of the present invention, it is possible to improve the resolution of a resist pattern and the adhesion to a substrate.

<Structural Unit (a2)>

The hydroxy group possessed by the structural unit (a2) may be either an alcoholic hydroxy group or a phenolic hydroxy group.

When a resist pattern is produced from the resist composition of the present invention, in the case of using, as an exposure source, high energy rays such as KrF excimer laser (248 nm), electron beam or extreme ultraviolet light (EUV), it is preferred to use a structural unit (a2) having a phenolic hydroxy group as the structural unit (a2). When using ArF excimer laser (193 nm) or the like, a structural unit (a2) having an alcoholic hydroxy group is preferably used as the structural unit (a2), and it is more preferably to use a structural unit (a2-1) mentioned later. The structural unit (a2) may be included alone, or two or more structural units may be included.

In the structural unit (a2), examples of the structural unit having a phenolic hydroxy group include a structural unit represented by formula (a2-A) (hereinafter sometimes referred to as "structural unit (a2-A)"):

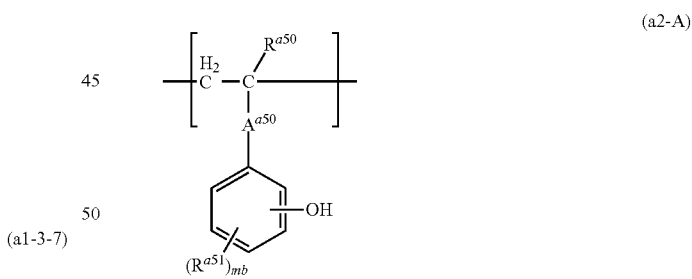

(a2-A)

wherein, in formula (a2-A), $R^{a50}$ represents a hydrogen atom, a halogen atom or an alkyl group having 1 to 6 carbon atoms which may have a halogen atom, $R^{a51}$ represents a halogen atom, a hydroxy group, an alkyl group having 1 to 6 carbon atoms, an alkoxy group having 1 to 6 carbon atoms, an alkylcarbonyl group having 2 to 4 carbon atoms, an alkylcarbonyloxy group having 2 to 4 carbon atoms, an acryloyloxy group or a methacryloyloxy group, $A^{a50}$ represents a single bond or *—$X^{a51}$-($A^{a52}$-$X^{a52}$)$_{nb}$—, and * represents a bonding site to carbon atoms to which —$R^{a50}$ is bonded, $A^{a52}$ represents an alkanediyl group having 1 to 6 carbon atoms, $X^{a51}$ and $X^{a52}$ each independently represent —O—, —CO—O— or —O—CO—, nb represents 0 or 1, and mb represents an integer of 0 to 4, and when mb is an integer of 2 or more, a plurality of $R^{a51}$ may be the same or different from each other.

Examples of the halogen atom in $R^{a50}$ include a fluorine atom, a chlorine atom and a bromine atom.

Examples of the alkyl group having 1 to 6 carbon atoms which may have a halogen atom in $R^{a50}$ include a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group and a perfluorohexyl group.

$R^{a50}$ is preferably a hydrogen atom or an alkyl group having 1 to 4 carbon atoms, more preferably a hydrogen atom, a methyl group or an ethyl group, and still more preferably a hydrogen atom or a methyl group.

Examples of the alkyl group in $R^{a51}$ include a methyl group, an ethyl group, a propyl group, an isopropyl group, a butyl group, a sec-butyl group, a tert-butyl group, a pentyl group and a hexyl group.

Examples of the alkoxy group in $R^{a51}$ include a methoxy group, an ethoxy group, a propoxy group, an isopropoxy group, a butoxy group, a sec-butoxy group and a tert-butoxy group. An alkoxy group having 1 to 4 carbon atoms is preferred, a methoxy group or an ethoxy group is more preferred, and a methoxy group is still more preferred.

Examples of the alkylcarbonyl group in $R^{a51}$ include an acetyl group, a propionyl group and a butyryl group.

Examples of the alkylcarbonyloxy group in $R^{a51}$ include an acetyloxy group, a propionyloxy group and a butyryloxy group.

$R^{a51}$ is preferably a methyl group.

Examples of *—$X^{51}$-($A^{a52}$-$X^{a52}$)$_{nb}$— include *—O—, *—CO—O—, *—O—CO—, *—CO—O-$A^{a52}$-CO—O—, *—O—CO-$A^{a52}$-O—, *—O-$A^{a52}$-CO—O—, *—CO—O-$A^{a52}$-O—CO— and *—O—CO-$A^{a52}$-O—CO—. Among these, *—CO—O—, *—CO—O-$A^{a52}$-CO—O— or *—O-$A^{a52}$-CO—O— is preferred.

Examples of the alkanediyl group include a methylene group, an ethylene group, a propane-1,3-diyl group, a propane-1,2-diyl group, a butane-1,4-diyl group, a pentane-1,5-diyl group, a hexane-1,6-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

$A^{a52}$ is preferably a methylene group or an ethylene group.

$A^{a50}$ is preferably a single bond, *—CO—O— or *—CO—O-$A^{a52}$-CO—O—, more preferably a single bond, *—CO—O— or *—CO—O—CH$_2$—CO—O—, and still more preferably a single bond or *—CO—O—.

mb is preferably 0, 1 or 2, more preferably 0 or 1, and particularly preferably 0.

The hydroxy group is preferably bonded to the o-position or the p-position of a benzene ring, and more preferably the p-position.

Examples of the structural unit (a2-A) include structural units derived from the monomers mentioned in JP 2010-204634 A and JP 2012-12577 A.

Examples of the structural unit (a2-A) include structural units represented by formula (a2-2-1) to formula (a2-2-6), and a structural unit in which a methyl group corresponding to $R^{a50}$ in the structural unit (a2-A) is replaced by a hydrogen atom in structural units represented by formula (a2-2-1) to formula (a2-2-6). The structural unit (a2-A) is preferably a structural unit represented by formula (a2-2-1), a structural unit represented by formula (a2-2-3), a structural unit represented by formula (a2-2-6), and a structural unit in which a methyl group corresponding to $R^{a50}$ in the structural unit (a2-A) is replaced by a hydrogen atom in the structural unit represented by formula (a2-2-1), a structural unit represented by formula (a2-2-3) or the structural unit represented formula (a2-2-6).

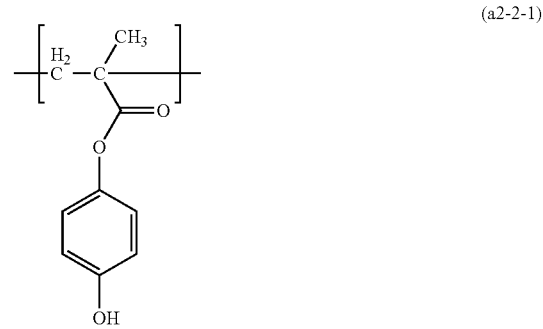

(a2-2-1)

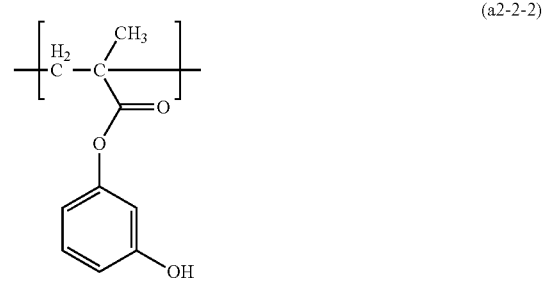

(a2-2-2)

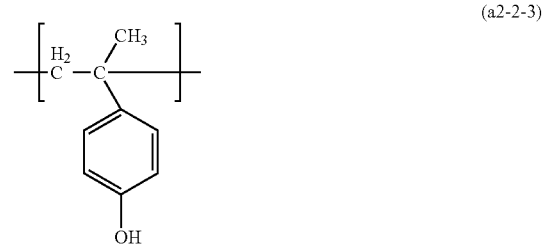

(a2-2-3)

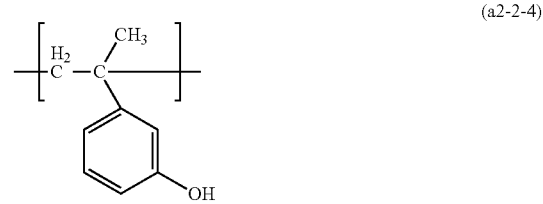

(a2-2-4)

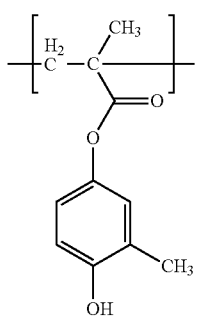
(a2-2-5)

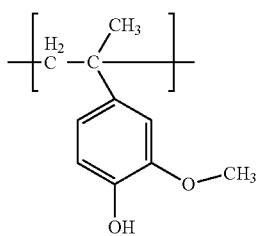
(a2-2-6)

When the structural unit (a2-A) is included in the resin (A), the content of the structural unit (a2-A) is preferably 5 to 80 mol %, more preferably 10 to 70 mol %, still more preferably 15 to 65 mol %, and yet more preferably 20 to 65 mol %, based on all structural units.

The structural unit (a2-A) can be included in the resin (A) by treating with an acid such as p-toluenesulfonic acid after polymerizing, for example, with a structural unit (a1-4). The structural unit (a2-A) can be included in the resin (A) by treating with an alkali such as tetramethylammonium hydroxide after polymerizing with acetoxystyrene.

Examples of the structural unit having an alcoholic hydroxy group in the structural unit (a2) include a structural unit represented by formula (a2-1) (hereinafter sometimes referred to as "structural unit (a2-1)").

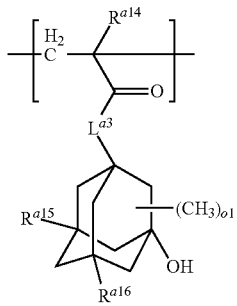
(a2-1)

In formula (a2-1), $L^{a3}$ represents —O— or *—O—$(CH_2)_{k2}$—CO—O—, k2 represents an integer of 1 to 7, and * represents a bonding site to —CO—, $R^{a14}$ represents a hydrogen atom or a methyl group, $R^{a15}$ and $R^{a16}$ each independently represent a hydrogen atom, a methyl group or a hydroxy group, and of represents an integer of 0 to 10.

In formula (a2-1), $L^{a3}$ is preferably —O— or —O—$(CH_2)_{f1}$—CO—O— (f1 represents an integer of 1 to 4), and more preferably —O—, $R^{a14}$ is preferably a methyl group, $R^{a15}$ is preferably a hydrogen atom, $R^{a16}$ is preferably a hydrogen atom or a hydroxy group, and o1 is preferably an integer of 0 to 3, and more preferably 0 or 1.

The structural unit (a2-1) includes, for example, structural units derived from the monomers mentioned in JP 2010-204646 A. A structural unit represented by any one of formula (a2-1-1) to formula (a2-1-6) is preferred, a structural unit represented by any one of formula (a2-1-1) to formula (a2-1-4) is more preferred, and a structural unit represented by formula (a2-1-1) or formula (a2-1-3) is still more preferred.

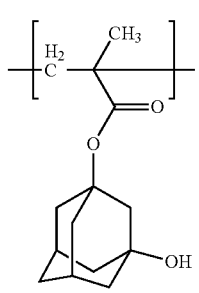
(a2-1-1)

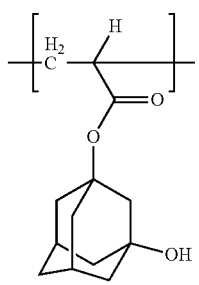
(a2-1-2)

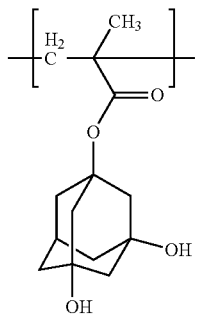
(a2-1-3)

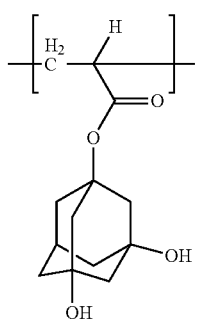
(a2-2-4)

-continued

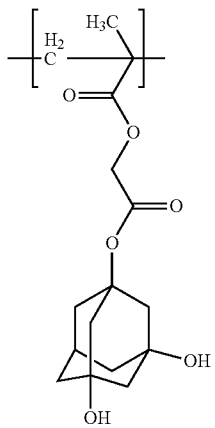
(a2-2-5)

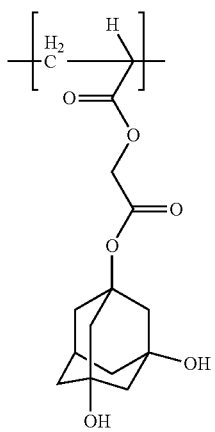
(a2-1-6)

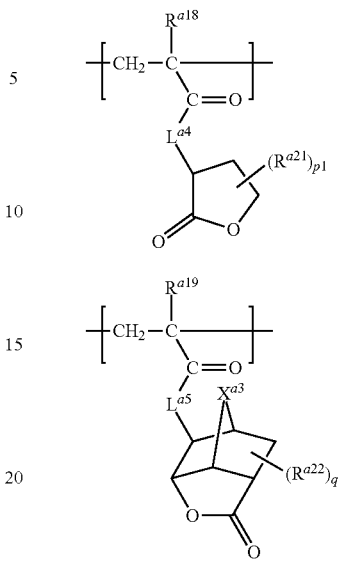
(a3-1)

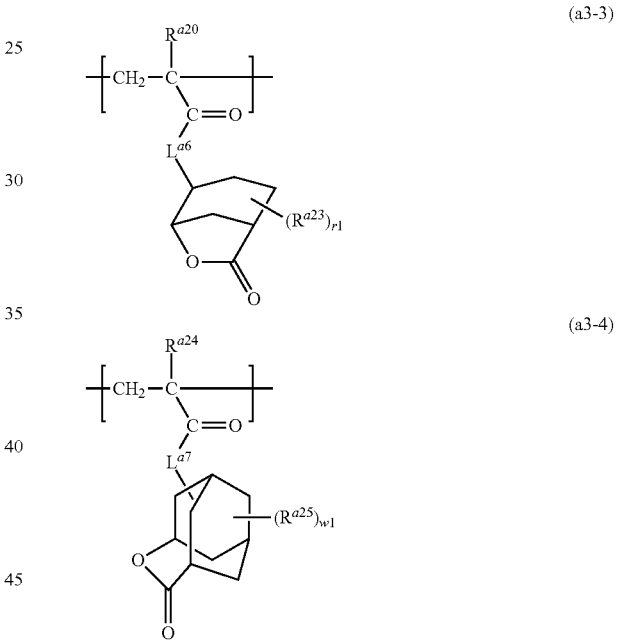
(a3-2)

(a3-3)

(a3-4)

When the resin (A) includes the structural unit (a2-1), the content is usually 1 to 45 mol %, preferably 1 to 40 mol %, more preferably 1 to 35 mol %, still more preferably 1 to 20 mol %, yet more preferably 1 to 10 mol %, and particularly preferably 1 to 5 mol %, based on all structural units of the resin (A).

<Structural Unit (a3)>

The lactone ring possessed by the structural unit (a3) may be a monocyclic ring such as a β-propiolactone ring, a γ-butyrolactone ring or a δ-valerolactone ring, or a condensed ring of a monocyclic lactone ring and the other ring. Preferably, a γ-butyrolactone ring, an adamantanelactone ring or a bridged ring including a γ-butyrolactone ring structure (e.g., a structural unit represented by the following formula (a3-2)) is exemplified.

The structural unit (a3) is preferably a structural unit represented by formula (a3-1), formula (a3-2), formula (a3-3) or formula (a3-4). These structural units may be included alone, or two or more structural units may be included:

wherein, in formula (a3-1), formula (a3-2), formula (a3-3) and formula (a3-4), $L^{a4}$, $L^{a5}$ and $L^{a6}$ each independently represent —O— or a group represented by *—O—$(CH_2)_{k3}$—CO—O— (k3 represents an integer of 1 to 7), $L^{a7}$ represents —O—, *—O-$L^{a8}$-O—, *—O-$L^{a8}$-CO—O—, *—O-$L^{a8}$-CO—O-$L^{a9}$-CO—O— or *—O-$L^{a8}$-O—CO-$L^9$-O—, $L^{a8}$ and $L^{a9}$ each independently represent an alkanediyl group having 1 to 6 carbon atoms,

* represents a bonding site to a carbonyl group, $R^{a18}$, $R^{a19}$ and $R^{a20}$ each independently represent a hydrogen atom or a methyl group, $R^{a24}$ represents an alkyl group having 1 to 6 carbon atoms which may have a halogen atom, a hydrogen atom or a halogen atom, $X^{a3}$ represents —$CH_2$— or an oxygen atom, $R^{a21}$ represents an aliphatic hydrocarbon group having 1 to 4 carbon atoms, $R^{a22}$, $R^{a23}$ and $R^{a25}$ each independently represent a carboxy group, a cyano group or an aliphatic hydrocarbon group having 1 to 4 carbon atoms, p1 represents an integer of 0 to 5, q1 represents an integer of 0 to 3, r1 represents an integer of 0 to 3, w1 represents an integer of 0 to 8, and when p1, q1, r1 and/or w1 is/are 2 or more, a plurality of $R^{a21}$, $R^{a22}$, $R^{a23}$ and/or $R^{a25}$ may be the same or different from each other.

Examples of the aliphatic hydrocarbon group in $R^{a21}$, $R^{a22}$, $R^{23}$ and $R^{a25}$ include alkyl groups such as a methyl group, an ethyl group, a propyl group, an isopropyl group, a butyl group, a sec-butyl group and a tert-butyl group.

Examples of the halogen atom in $R^{a24}$ include a fluorine atom, a chlorine atom, a bromine atom and an iodine atom.

Examples of the alkyl group in $R^{a24}$ include a methyl group, an ethyl group, a propyl group, an isopropyl group, a butyl group, a sec-butyl group, a tert-butyl group, a pentyl group and a hexyl group, and the alkyl group is preferably an alkyl group having 1 to 4 carbon atoms, and more preferably a methyl group or an ethyl group.

Examples of the alkyl group having a halogen atom in $R^{a24}$ include a trifluoromethyl group, a perfluoroethyl group, a perfluoropropyl group, a perfluoroisopropyl group, a perfluorobutyl group, a perfluorosec-butyl group, a perfluoro-tert-butyl group, a perfluoropentyl group, a perfluorohexyl group, a trichloromethyl group, a tribromomethyl group, a triiodomethyl group and the like.

Examples of the alkanediyl group in $L^{a8}$ and $L^{a9}$ include a methylene group, an ethylene group, a propane-1,3-diyl group, a propane-1,2-diyl group, a butane-1,4-diyl group, a pentane-1,5-diyl group, a hexane-1,6-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

In formula (a3-1) to formula (a3-3), preferably, $L^{a4}$ to $L^{a6}$ are each independently —O— or a group in which k3 is an integer of 1 to 4 in *—O—(CH$_2$)$_{k3}$—CO—O—, more preferably —O— and *—O—CH$_2$—CO—O—, and still more preferably an oxygen atom, $R^{a18}$ to $R^{a21}$ are preferably a methyl group, preferably, $R^{a22}$ and $R^{a23}$ are each independently a carboxy group, a cyano group or a methyl group, and preferably, p1, q1 and r1 are each independently an integer of 0 to 2, and more preferably 0 or 1.

In formula (a3-4), $R^{a24}$ is preferably a hydrogen atom or an alkyl group having 1 to 4 carbon atoms, more preferably a hydrogen atom, a methyl group or an ethyl group, and still more preferably a hydrogen atom or a methyl group, $R^{a25}$ is preferably a carboxy group, a cyano group or a methyl group, $L^{a7}$ is preferably —O— or *—O-$L^{a8}$-CO—O—, and more preferably —O—, —O—CH$_2$—CO—O— or —O—C$_2$H$_4$—CO—O—, and w1 is preferably an integer of 0 to 2, and more preferably 0 or 1.

Particularly, formula (a3-4) is preferably formula (a3-4)':

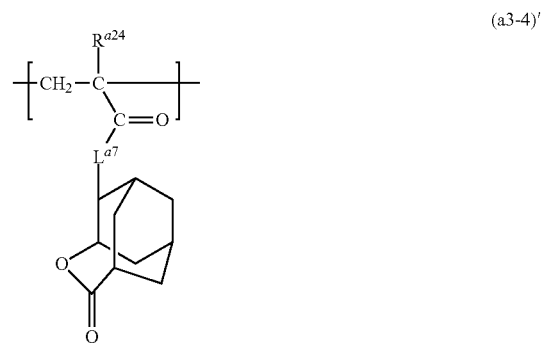

(a3-4)' wherein $R^{a24}$ and $L^{a7}$ are the same as defined above.

Examples of the structural unit (a3) include structural units derived from the monomers mentioned in JP 2010-204646 A, the monomers mentioned in JP 2000-122294 A and the monomers mentioned in JP 2012-41274 A. The structural unit (a3) is preferably a structural unit represented by any one of formula (a3-1-1), formula (a3-1-2), formula (a3-2-1), formula (a3-2-2), formula (a3-3-1), formula (a3-3-2) and formula (a3-4-1) to formula (a3-4-12), and structural units in which methyl groups corresponding to $R^{a18}$, $R^{a19}$, $R^{a20}$ and $R^{a24}$ in formula (a3-1) to formula (a3-4) are replaced by hydrogen atoms in the above structural units.

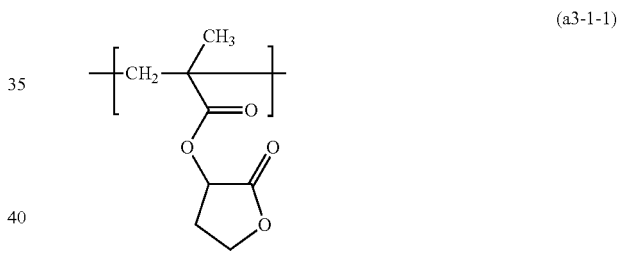

(a3-1-1)

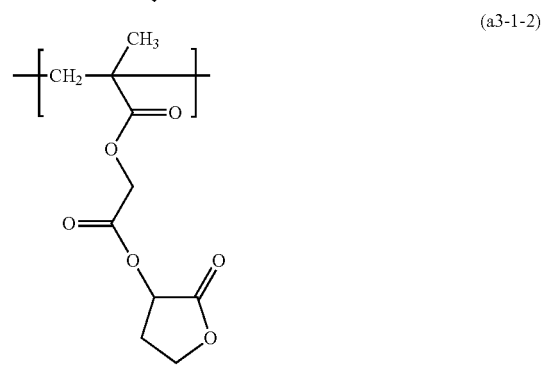

(a3-1-2)

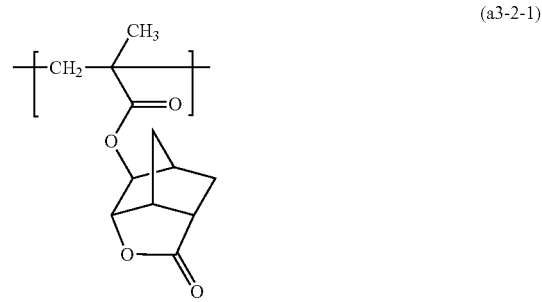

(a3-2-1)

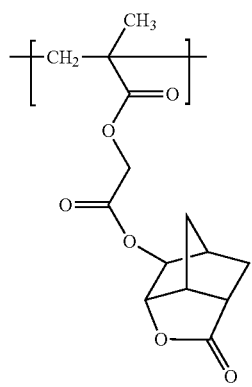
(a3-2-2)
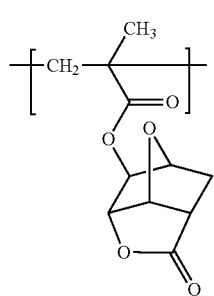
(a3x-2-1)
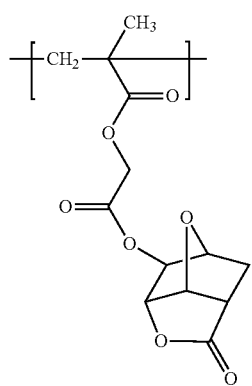
(a3-2x-2)
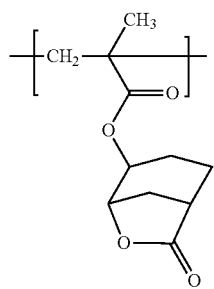
(a3-3-1)
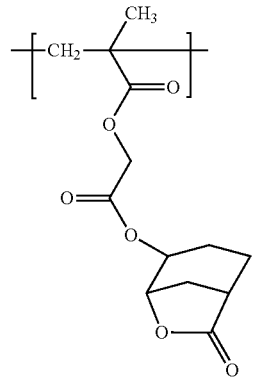
(a3-3-2)
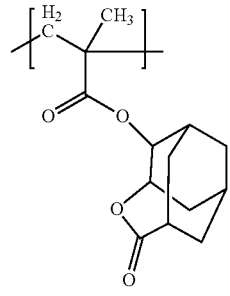
(a3-4-1)
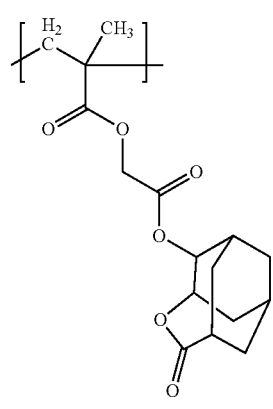
(a3-4-2)
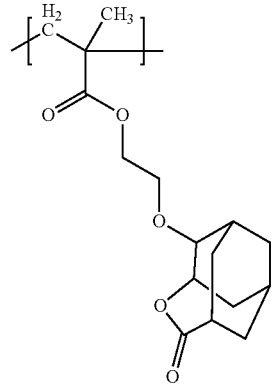
(a3-4-3)

(a3-4-4)
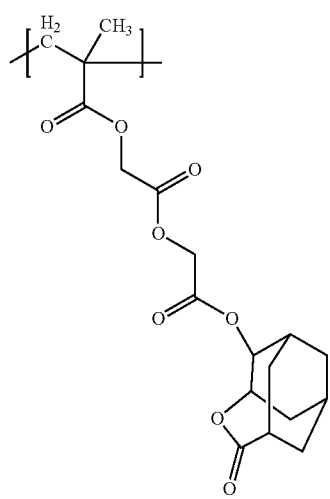
(a3-4-5)
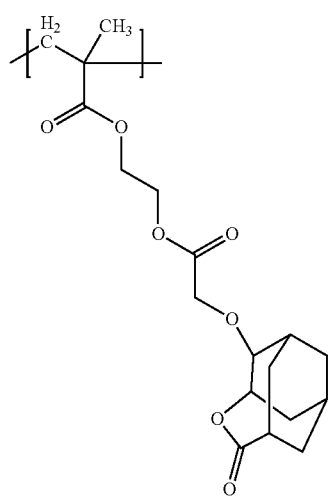
(a3-4-6)
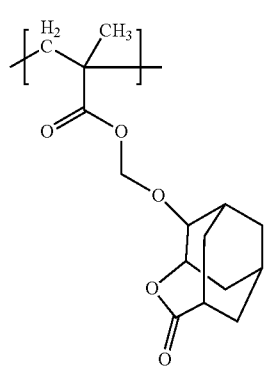
(a3-4-7)
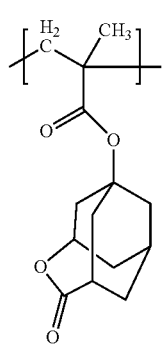
(a3-4-8)
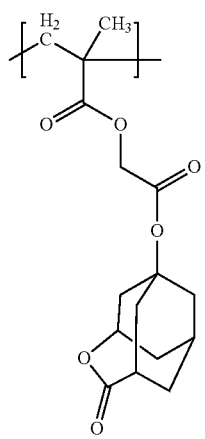
(a3-4-9)
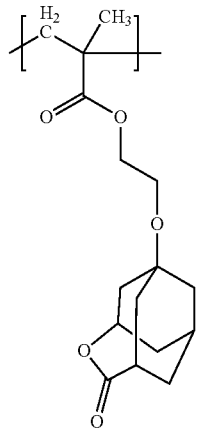

-continued

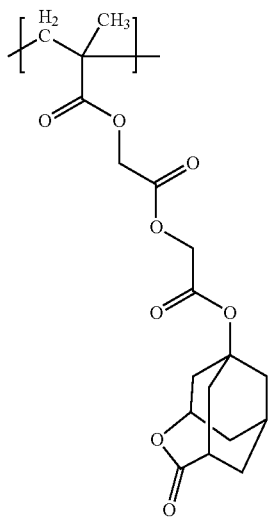
(a3-4-10)

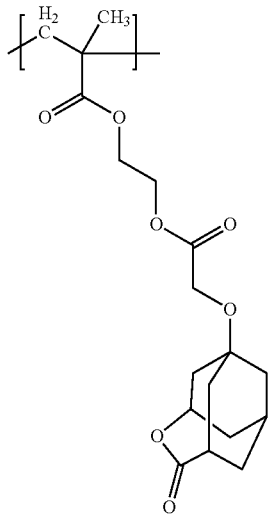
(a3-4-11)

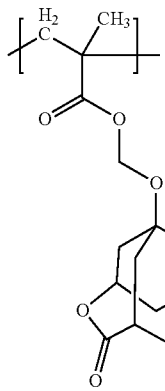
(a3-4-12)

When the resin (A) includes the structural unit (a3), the total content is usually 5 to 70 mol %, preferably 10 to 65 mol %, more preferably 10 to 60 mol %, still more preferably 20 to 55 mol %, and particularly preferably 30 to 50 mol %, based on all structural units of the resin (A).

Each content of the structural unit (a3-1), the structural unit (a3-2), the structural unit (a3-3) or the structural unit (a3-4) is preferably 5 to 60 mol %, more preferably 5 to 50 mol %, and still more preferably 10 to 50 mol %, based on all structural units of the resin (A).

<Structural Unit (a4)>

Examples of the structural unit (a4) include the following structural units:

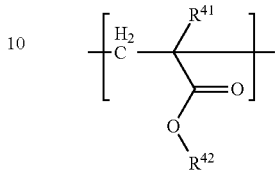
(a4)

wherein, in formula (a4), $R^{41}$ represents a hydrogen atom or a methyl group, and $R^{42}$ represents a saturated hydrocarbon group having 1 to 24 carbon atoms having a fluorine atom, and —$CH_2$— included in the saturated hydrocarbon group may be replaced by —O— or —CO.

Examples of the saturated hydrocarbon group represented by $R^{42}$ include a chain saturated hydrocarbon group and a monocyclic or polycyclic alicyclic saturated hydrocarbon group, and groups formed by combining these groups.

Examples of the chain saturated hydrocarbon group include a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group.

Examples of the monocyclic or polycyclic alicyclic saturated hydrocarbon group include cycloalkyl groups such as a cyclopentyl group, a cyclohexyl group, a cycloheptyl group and a cyclooctyl group; and polycyclic alicyclic saturated hydrocarbon groups such as a decahydronaphthyl group, an adamantyl group, a norbornyl group and the following groups (* represents a bonding site).

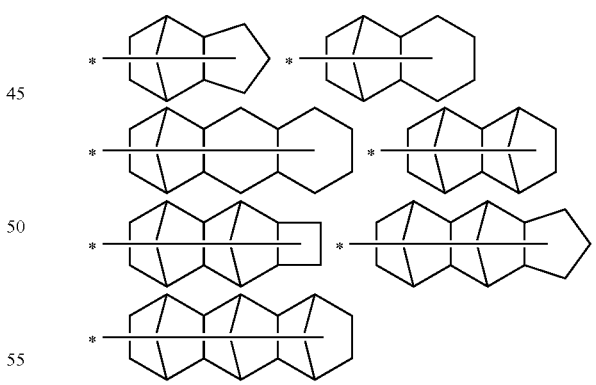

Examples of the group formed by combination include groups formed by combining one or more alkyl groups or one or more alkanediyl groups with one or more alicyclic saturated hydrocarbon groups, and include an alkanediyl group-alicyclic saturated hydrocarbon group, an alicyclic saturated hydrocarbon group-alkyl group, an alkanediyl group-alicyclic saturated hydrocarbon group-alkyl group and the like.

Examples of the structural unit (a4) include a structural unit represented by at least one selected from the group consisting of formula (a4-0), formula (a4-1), formula (a4-2), formula (a4-3) and formula (a4-4):

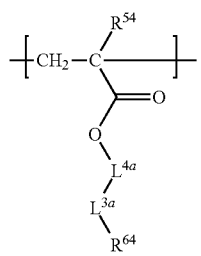
(a4-0)

wherein, in formula (a4-0), $R^{54}$ represents a hydrogen atom or a methyl group, $L^{4a}$ represents a single bond or an alkanediyl group having 1 to 4 carbon atoms, $L^{3a}$ represents a perfluoroalkanediyl group having 1 to 8 carbon atoms or a perfluorocycloalkanediyl group having 3 to 12 carbon atoms, and $R^{64}$ represents a hydrogen atom or a fluorine atom.

Examples of the alkanediyl group in $L^{4a}$ include linear alkanediyl groups such as a methylene group, an ethylene group, a propane-1,3-diyl group and a butane-1,4-diyl group; and branched alkanediyl groups such as an ethane-1,1-diyl group, a propane-1,2-diyl group, a butane-1,3-diyl group, a 2-methylpropane-1,3-diyl group and a 2-methylpropane-1,2-diyl group.

Examples of the perfluoroalkanediyl group in $L^{3a}$ include a difluoromethylene group, a perfluoroethylene group, a perfluoroethylfluoromethylene group, a perfluoropropane-1,3-diyl group, a perfluoropropane-1,2-diyl group, a perfluoropropane-2,2-diyl group, a perfluorobutane-1,4-diyl group, a perfluorobutane-2,2-diyl group, a perfluorobutane-1,2-diyl group, a perfluoropentane-1,5-diyl group, a perfluoropentane-2,2-diyl group, a perfluoropentane-3,3-diyl group, a perfluorohexane-1,6-diyl group, a perfluorohexane-2,2-diyl group, a perfluorohexane-3,3-diyl group, a perfluoroheptane-1,7-diyl group, a perfluoroheptane-2,2-diyl group, a perfluoroheptane-3,4-diyl group, a perfluoroheptane-4,4-diyl group, a perfluorooctane-1,8-diyl group, a perfluorooctane-2,2-diyl group, a perfluorooctane-3,3-diyl group, a perfluorooctane-4,4-diyl group and the like.

Examples of the perfluorocycloalkanediyl group in $L^{3a}$ include a perfluorocyclohexanediyl group, a perfluorocyclopentanediyl group, a perfluorocycloheptanediyl group, a perfluoroadamantanediyl group and the like.

$L^{4a}$ is preferably a single bond, a methylene group or an ethylene group, and more preferably a single bond or a methylene group.

$L^{3a}$ is preferably a perfluoroalkanediyl group having 1 to 6 carbon atoms, and more preferably a perfluoroalkanediyl group having 1 to 3 carbon atoms.

Examples of the structural unit (a4-0) include the following structural units, and structural units in which a methyl group corresponding to $R^{54}$ in the structural unit (a4-0) in the following structural units is replaced by a hydrogen atom:

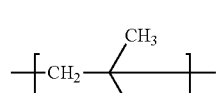
(a4-0-1)

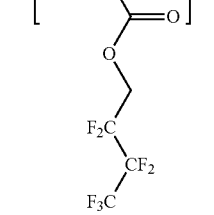
(a4-0-2)

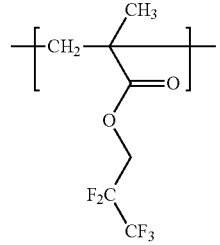
(a4-0-3)

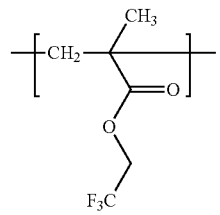
(a4-0-4)

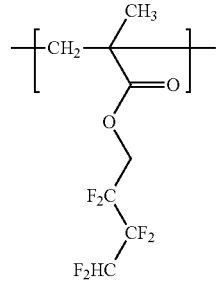
(a4-0-5)

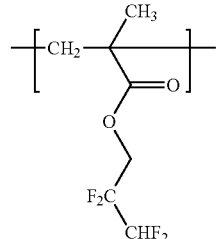
(a4-0-6)

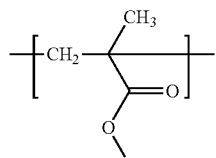
(a4-0-7)

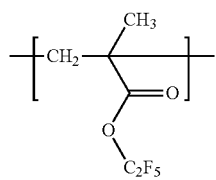
(a4-0-8)

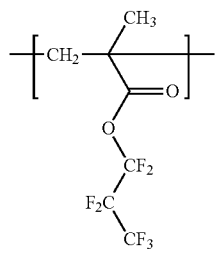
(a4-0-9)

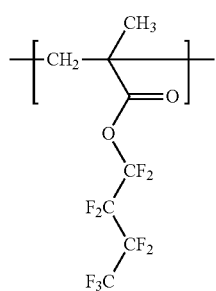
(a4-0-10)

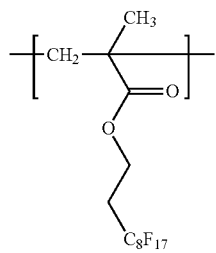
(a4-0-11)

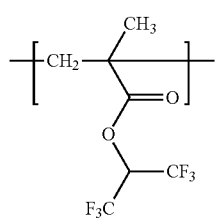
(a4-0-12)

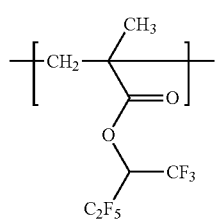
(a4-0-13)

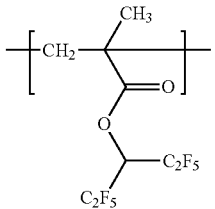
(a4-0-14)

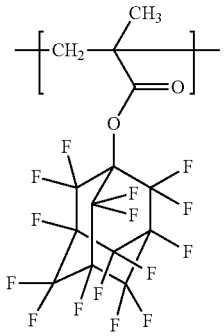
(a4-0-15)

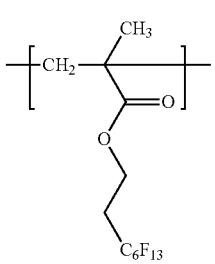
(a4-0-16)

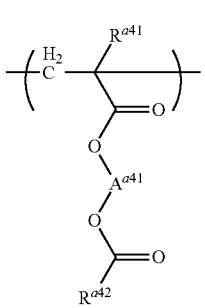
(a4-1)

wherein, in formula (a4-1), $R^{a41}$ represents a hydrogen atom or a methyl group, $R^{a42}$ represents a saturated hydrocarbon group having 1 to 20 carbon atoms which may have a substituent, and —CH$_2$— included in the saturated hydrocarbon group may be replaced by —O— or —CO—, $A^{a41}$ represents an alkanediyl group having 1 to 6 carbon atoms which may have a substituent or a group represented by formula (a-g1), in which at least one of $A^{a41}$ and $R^{a42}$ has, as a substituent, a fluorine atom:

$$*\text{-}A^{a42}\text{-}(X^{a41}\text{-}A^{a43}\text{-})_s X^{a42}\text{-}A^{a44}\text{-}* \quad \text{(a-g1)}$$

wherein, in formula (a-g1), s represents 0 or 1, $A^{a42}$ and $A^{a44}$ each independently represent a divalent saturated hydrocarbon group having 1 to 5 carbon atoms which may have a substituent, $A^{a43}$ represents a single bond or a divalent saturated hydrocarbon group having 1 to 5 carbon atoms which may have a substituent, $X^{a41}$ and $X^{a42}$ each independently represent —O—, —CO—, —CO—O— or —O—CO—, in which the total number of carbon atoms of $A^{a42}$, $A^{a43}$, $A^{a44}$, $X^{a41}$ and $X^{a42}$ is 7 or less], and

* is a bonding site and * at the right side is a bonding site to —O—CO—$R^{a42}$.

Examples of the saturated hydrocarbon group in $R^{a42}$ include a chain hydrocarbon group and a monocyclic or a polycyclic alicyclic hydrocarbon group, and groups formed by combining these groups.

Examples of the chain hydrocarbon group include a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group. Examples of the monocyclic or polycyclic alicyclic hydrocarbon group include cycloalkyl groups such as a cyclopentyl group, a cyclohexyl group, a cycloheptyl group and a cyclooctyl group; and polycyclic alicyclic hydrocarbon groups such as a decahydronaphthyl group, an adamantyl group, a norbornyl group and the following groups (* represents a bonding site).

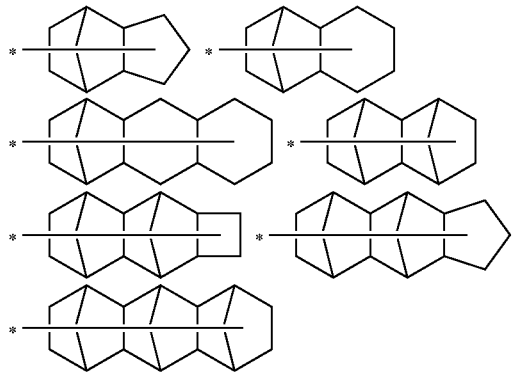

Examples of the group formed by combination include groups formed by combining one or more alkyl groups or one or more alkanediyl groups with one or more alicyclic hydrocarbon groups, and include an alkanediyl group-alicyclic hydrocarbon group, an alicyclic hydrocarbon group-alkyl group, an alkanediyl group-alicyclic hydrocarbon group-alkyl group and the like.

Examples of the substituent which may be possessed by $R^{a42}$ include at least one selected from the group consisting of a fluorine atom and a group represented by formula (a-g3).

$$*—X^{a43}-A^{a45} \quad (a\text{-}g3)$$

wherein, in formula (a-g3), $X^{a43}$ represents and oxygen atom, a carbonyl group, *—O—CO— or *—CO—O— (* represents a bonding site to $R^{a42}$)

$A^{a45}$ represents a saturated hydrocarbon group having 1 to 17 carbon atoms which may have a fluorine atom, and

* represents a bonding site.

In $R^{a42}$—$X^{a43}$-$A^{a45}$, when $R^{a42}$ has no fluorine atom, $A^{a45}$ represents a saturated hydrocarbon group having 1 to 17 carbon atoms which has at least one fluorine atom.

Examples of the saturated hydrocarbon group in $A^{a45}$ include alkyl groups such as a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group; monocyclic alicyclic hydrocarbon groups such as a cyclopentyl group, a cyclohexyl group, a cycloheptyl group and a cyclooctyl group; and polycyclic alicyclic hydrocarbon groups such as a decahydronaphthyl group, an adamantyl group, a norbornyl group and the following group (* represents a bonding site).

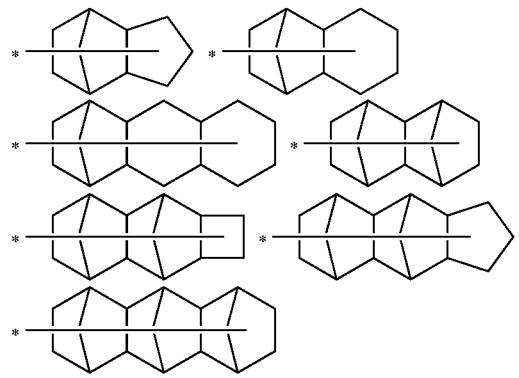

$R^{a42}$ is preferably a saturated hydrocarbon group which may have a fluorine atom, and more preferably an alkyl group having a fluorine atom and/or a saturated hydrocarbon group having a group represented by formula (a-g3).

When $R^{a42}$ is a saturated hydrocarbon group having a fluorine atom, a perfluoroalkyl group or a perfluorocycloalkyl group is preferred, a perfluoroalkyl group having 1 to 6 carbon atoms is more preferred, and a perfluoroalkyl group having 1 to 3 carbon atoms is still more preferred. Examples of the perfluoroalkyl group include a perfluoromethyl group, a perfluoroethyl group, a perfluoropropyl group, a perfluorobutyl group, a perfluoropentyl group, a perfluorohexyl group, a perfluoroheptyl group and a perfluorooctyl group. Examples of the perfluorocycloalkyl group include a perfluorocyclohexyl group and the like.

When $R^{a42}$ is a saturated hydrocarbon group having a group represented by formula (a-g3), the total number of carbon atoms of $R^{a42}$ is preferably 15 or less, and more preferably 12 or less, including the number of carbon atoms included in the group represented by formula (a-g3). When having the group represented by formula (a-g3) as the substituent, the number thereof is preferably 1.

When $R^{a42}$ is a saturated hydrocarbon group having the group represented by formula (a-g3), $R^{a42}$ is still more preferably a group represented by formula (a-g2):

$$*\text{-}A^{a46}\text{-}X^{a44}\text{-}A^{a47} \quad (a\text{-}g2)$$

wherein, in formula (a-g2), $A^{a46}$ represents a divalent saturated hydrocarbon group having 1 to 17 carbon atoms which may have a fluorine atom, $X^{a44}$ represents *—O—CO— or *—CO—O— (* represents a bonding site to $A^{a46}$)

$A^{a47}$ represents a saturated hydrocarbon group having 1 to 17 carbon atoms which may have a fluorine atom, the total number of carbon atoms of $A^{a46}$, $A^{a47}$ and $X^{a44}$ is 18 or less, and at least one of $A^{a46}$ and $A^{a47}$ has at least one fluorine atom, and

* represents a bonding site to a carbonyl group.

The number of carbon atoms of the saturated hydrocarbon group for $A^{a46}$ is preferably 1 to 6, and more preferably 1 to 3.

The number of carbon atoms of the saturated hydrocarbon group for $A^{a47}$ is preferably 4 to 15, and more preferably 5 to 12, and $A^{a47}$ is still more preferably a cyclohexyl group or an adamantyl group.

Preferred structure of the group represented by formula (a-g2) is the following structure (* is a bonding site to a carbonyl group).

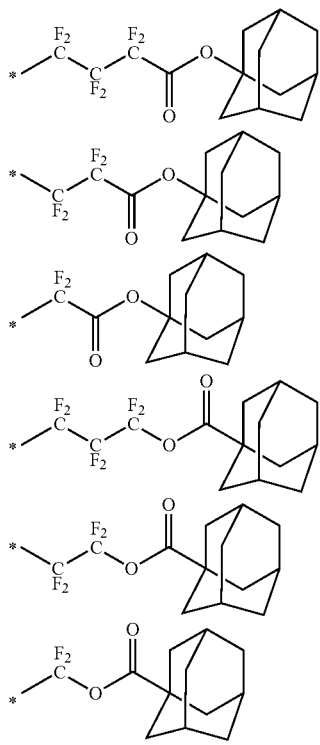

Examples of the alkanediyl group in $A^{a41}$ include linear alkanediyl groups such as a methylene group, an ethylene group, a propane-1,3-diyl group, a butane-1,4-diyl group, a pentane-1,5-diyl group and a hexane-1,6-diyl group; and branched alkanediyl groups such as a propane-1,2-diyl group, a butane-1,3-diyl group, a 2-methylpropane-1,2-diyl group, a 1-methylbutane-1,4-diyl group and a 2-methylbutane-1,4-diyl group.

Examples of the substituent in the alkanediyl group represented by $A^{a41}$ include a hydroxy group and an alkoxy group having 1 to 6 carbon atoms.

$A^{a41}$ is preferably an alkanediyl group having 1 to 4 carbon atoms, more preferably an alkanediyl group having 2 to 4 carbon atoms, and still more preferably an ethylene group.

Examples of the saturated hydrocarbon group represented by $A^{a42}$, $A^{a43}$ and $A^{a44}$ in the group represented by formula (a-g1) include a linear or branched alkanediyl group and a monocyclic divalent alicyclic saturated hydrocarbon group, and saturated hydrocarbon groups formed by combining an alkanediyl group and a divalent alicyclic saturated hydrocarbon group. Specific examples thereof include a methylene group, an ethylene group, a propane-1,3-diyl group, a propane-1,2-diyl group, a butane-1,4-diyl group, a 1-methylpropane-1,3-diyl group, a 2-methylpropane-1,3-diyl group, a 2-methylpropane-1,2-diyl group and the like.

Examples of the substituent of the saturated hydrocarbon group represented by $A^{a42}$, $A^{a43}$ and $A^{a44}$ include a hydroxy group and an alkoxy group having 1 to 6 carbon atoms.

s is preferably 0.

In a group represented by formula (a-g1), examples of the group in which $X^{a42}$ is —O—, —CO—, —CO—O— or —O—CO— include the following groups. In the following exemplification, * and  each represent a bonding site, and  is a bonding site to —O—CO—$R^{a42}$.

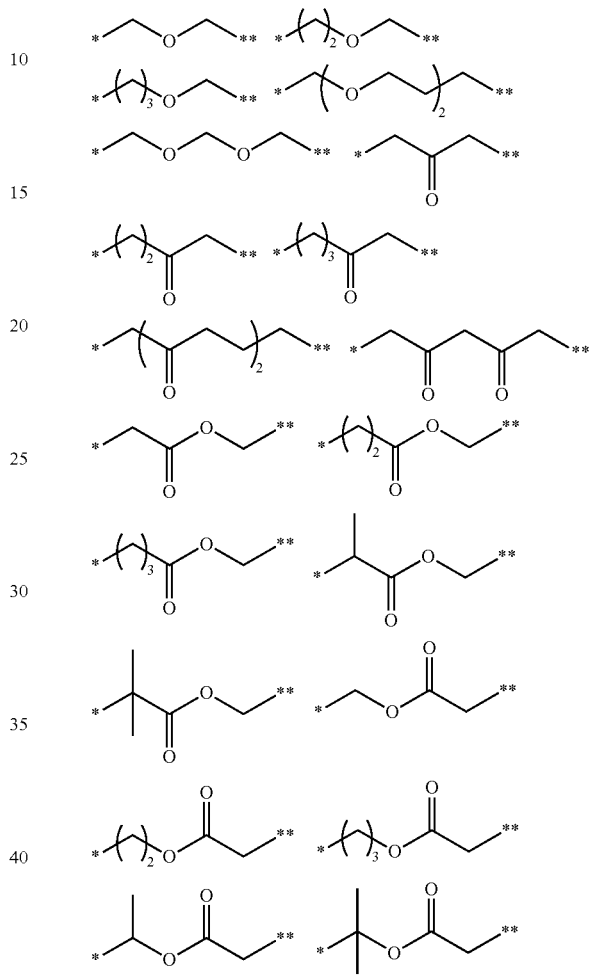

Examples of the structural unit represented by formula (a4-1) include the following structural units, and structural units in which a methyl group corresponding to $R^{a41}$ in the structural unit represented by formula (a4-1) in the following structural units is replaced by a hydrogen atom.

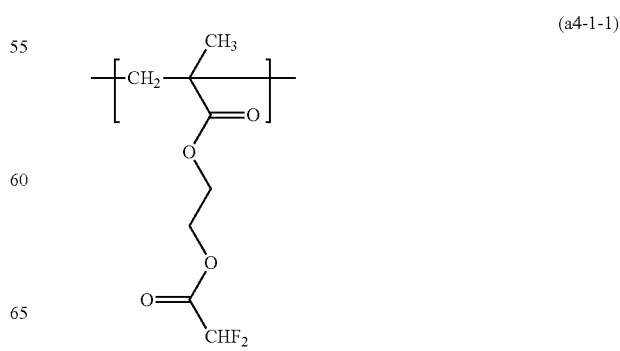

(a4-1-1)

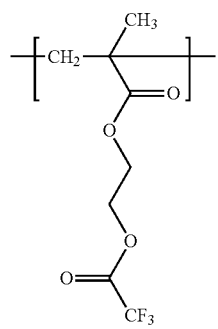
(a4-1-2)
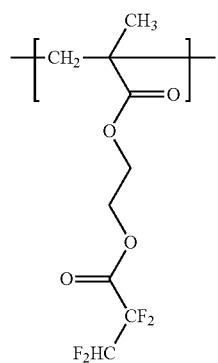
(a4-1-3)
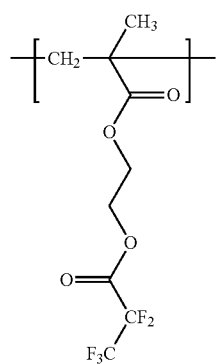
(a4-1-4)
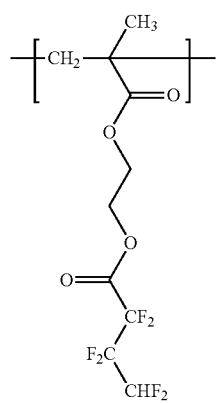
(a4-1-5)
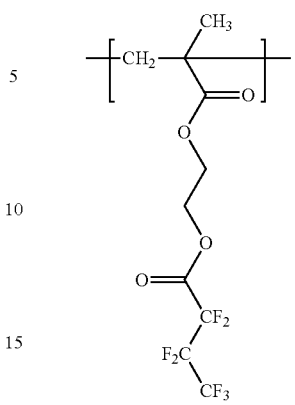
(a4-1-6)
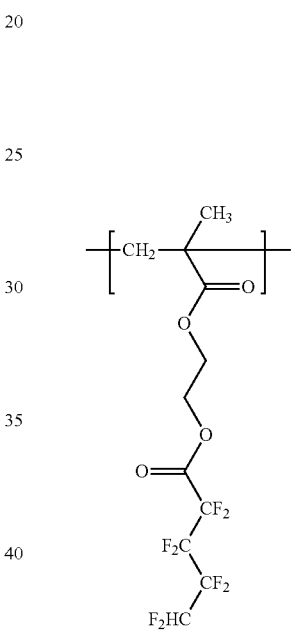
(a4-1-7)
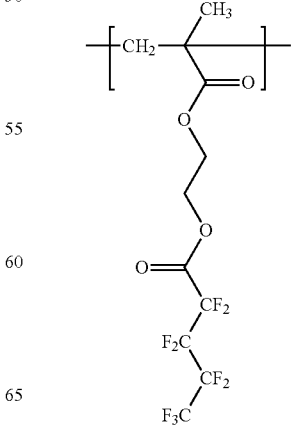
(a4-1-8)

(a4-1-9)
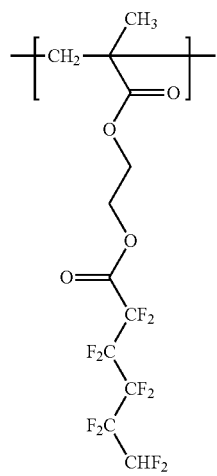
(a4-1-10)
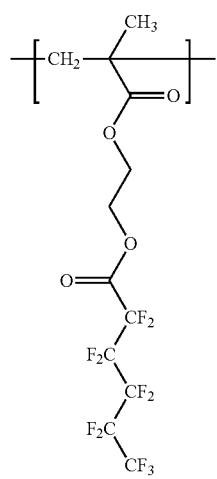
(a4-1-11)
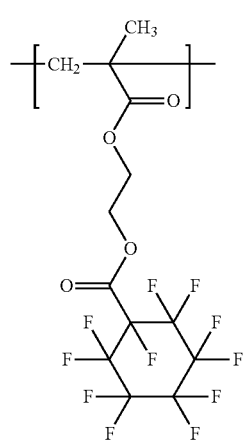
(a4-1'-1)
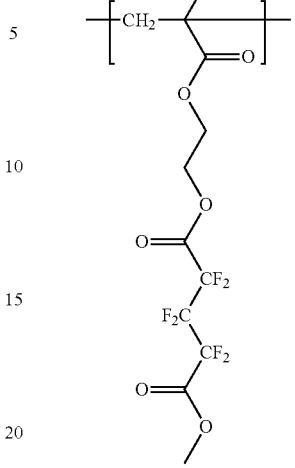
(a4-1'-2)
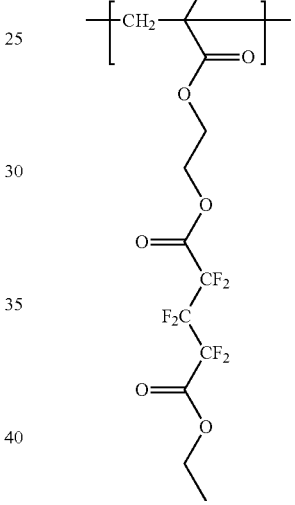
(a4-1'-3)
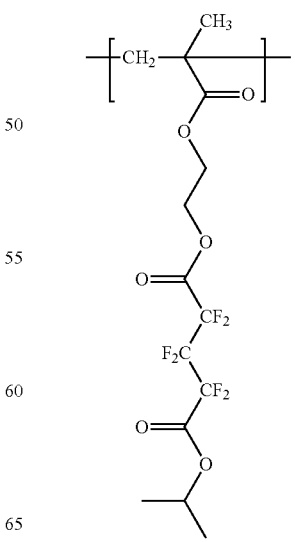

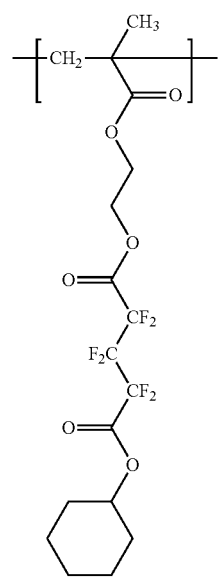 (a4-1'-4)
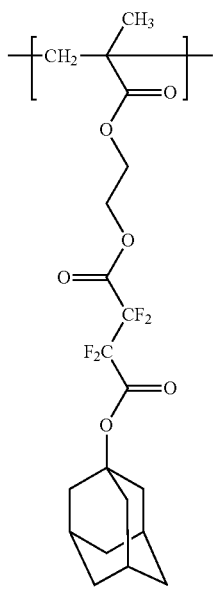 (a4-1'-6)
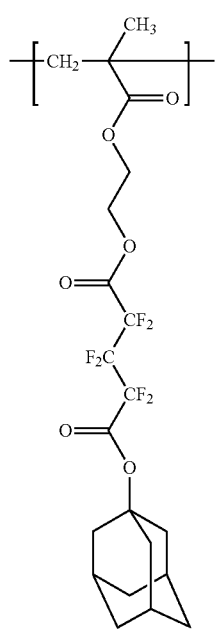 (a4-1'-5)
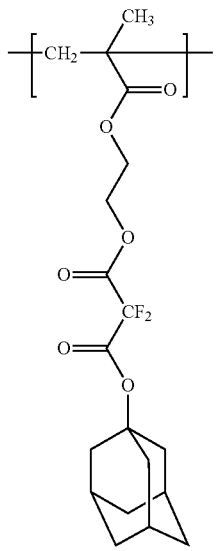 (a4-1'-7)

(a4-1'-8)
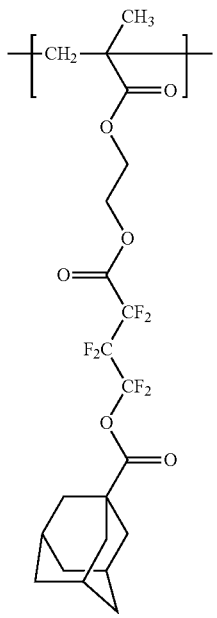

(a4-1'-9)
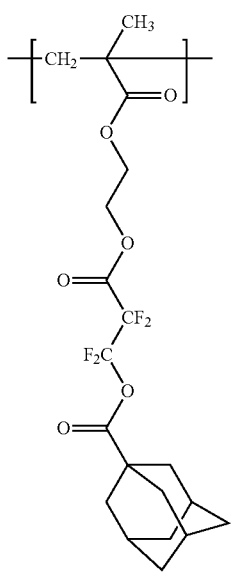

(a4-1'-10)
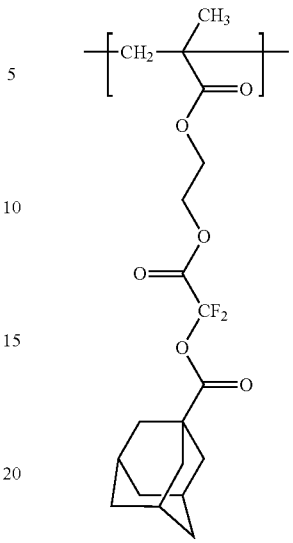

(a4-1'-11)
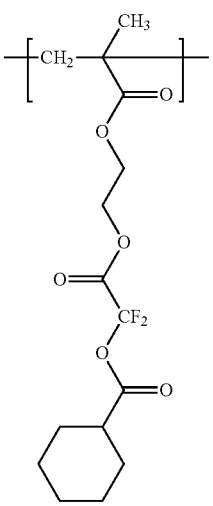

(a4-2)
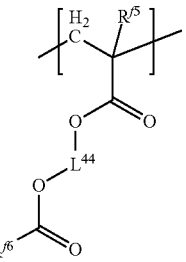

wherein, in formula (a4-2), $R^{f5}$ represents a hydrogen atom or a methyl group, $L^{44}$ represents an alkanediyl group having 1 to 6 carbon atoms, and —$CH_2$— included in the alkanediyl group may be replaced by —O— or —CO—, $R^{f6}$ represents a saturated hydrocarbon group having 1 to 20 carbon atoms having a fluorine atom, and the upper limit of the total number of carbon atoms of $L^{44}$ and $R^{f6}$ is 21.

Examples of the alkanediyl group having 1 to 6 carbon atoms for $L^{44}$ include the same groups as mentioned for $A^{a41}$.

Examples of the saturated hydrocarbon group for $R^{f6}$ include the same groups as mentioned for $R^{a42}$.

The alkanediyl group having 1 to 6 carbon atoms in $L^{44}$ is preferably an alkanediyl group having 2 to 4 carbon atoms, and more preferably an ethylene group.

The structural unit represented by formula (a4-2) includes, for example, structural units represented by formula (a4-1-1) to formula (a4-1-11). A structural unit in which a methyl group corresponding to $R^{f5}$ in the structural unit (a4-2) is replaced by a hydrogen atom is also exemplified as the structural unit represented by formula (a4-2):

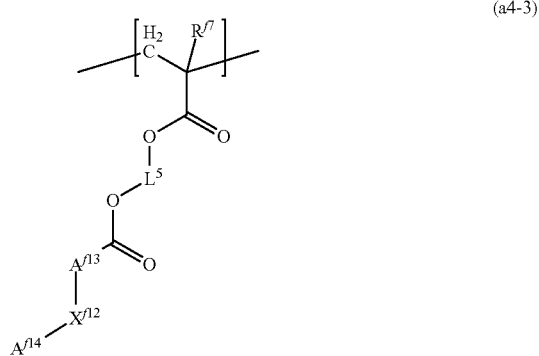

(a4-3)

wherein, in formula (a4-3), $R^{f7}$ represents a hydrogen atom or a methyl group, $L^5$ represents an alkanediyl group having 1 to 6 carbon atoms, $A^{f13}$ represents a divalent saturated hydrocarbon group having 1 to 18 carbon atoms which may have a fluorine atom, $X^{f12}$ represents *—O—CO— or *—CO—O— (* represents a bonding site to $A^{f13}$), $A^{f14}$ represents a saturated hydrocarbon group having 1 to 17 carbon atoms which may have a fluorine atom, and at least one of $A^{f13}$ and $A^{f14}$ has a fluorine atom, and the upper limit of the total number of carbon atoms of $L^5$, $A^{f13}$ and $A^{f14}$ is 20.

Examples of the alkanediyl group in $L^5$ include those which are the same as mentioned in the alkanediyl group for $A^{a41}$.

The saturated hydrocarbon group which may have a fluorine atom in $A^{f13}$ is preferably a chain saturated hydrocarbon group which may have a fluorine atom and an alicyclic saturated hydrocarbon group which may have a fluorine atom, and more preferably a perfluoroalkanediyl group.

Examples of the divalent chain saturated hydrocarbon group which may have a fluorine atom include alkanediyl groups such as a methylene group, an ethylene group, a propanediyl group, a butanediyl group and a pentanediyl group; and perfluoroalkanediyl groups such as a difluoromethylene group, a perfluoroethylene group, a perfluoropropanediyl group, a perfluorobutanediyl group and a perfluoropentanediyl group.

The alicyclic saturated hydrocarbon group which may have a fluorine atom may be either monocyclic or polycyclic. Examples of the monocyclic group include a cyclohexanediyl group and a perfluorocyclohexanediyl group. Examples of the polycyclic group include an adamantanediyl group, a norbornanediyl group, a perfluoroadamantanediyl group and the like.

Examples of the saturated hydrocarbon group and the saturated hydrocarbon group which may have a fluorine atom for $A^{f14}$ include the same groups as mentioned for $R^{a42}$. Among these groups, preferred are fluorinated alkyl groups such as a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group, a perfluorohexyl group, a heptyl group, a perfluoroheptyl group, an octyl group and a perfluorooctyl group; cyclopropylmethyl group, a cyclopropyl group, a cyclobutylmethyl group, a cyclopentyl group, a cyclohexyl group, a perfluorocyclohexyl group, an adamantyl group, an adamantylmethyl group, an adamantyldimethyl group, a norbornyl group, a norbornylmethyl group, a perfluoroadamantyl group, a perfluoroadamantylmethyl group and the like.

In formula (a4-3), $L^5$ is preferably an ethylene group.

The saturated hydrocarbon group for $A^{f13}$ is preferably a group including a chain saturated hydrocarbon group having 1 to 6 carbon atoms and an alicyclic saturated hydrocarbon group having 3 to 12 carbon atoms, and more preferably a chain saturated hydrocarbon group having 2 to 3 carbon atoms.

The saturated hydrocarbon group for $A^{f14}$ is preferably a group including a chain saturated hydrocarbon group having 3 to 12 carbon atoms and an alicyclic saturated hydrocarbon group having 3 to 12 carbon atoms, and more preferably a group including a chain saturated hydrocarbon group having 3 to 10 carbon atoms and an alicyclic saturated hydrocarbon group having 3 to 10 carbon atoms. Among these groups, $A^{f14}$ is preferably a group including an alicyclic saturated hydrocarbon group having 3 to 12 carbon atoms, and more preferably a cyclopropylmethyl group, a cyclopentyl group, a cyclohexyl group, a norbornyl group and an adamantyl group.

The structural unit represented by formula (a4-3) includes, for example, structural units represented by formula (a4-1'-1) to formula (a4-1'-11). A structural unit in which a methyl group corresponding to $R^{f7}$ in the structural unit (a4-3) is substitute with a hydrogen atom is also exemplified as the structural unit represented by formula (a4-3).

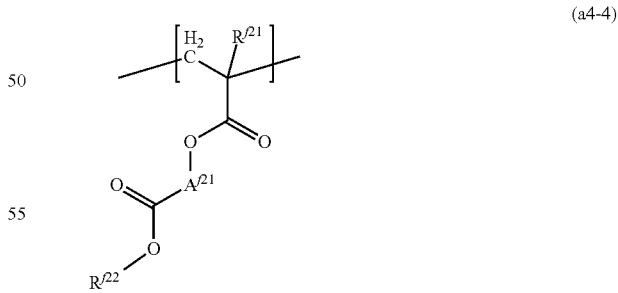

(a4-4)

In formula (a4-4), $R^{f21}$ represents a hydrogen atom or a methyl group, $A^{f21}$ represents —$(CH_2)_{j1}$—, —$(CH_2)_{j2}$—O—$(CH_2)_{j3}$— or —$(CH_2)_{j4}$—CO—O—$(CH_2)_{j5}$—, j1 to j5 each independently represent an integer of 1 to 6, and $R^{f22}$ represents a saturated hydrocarbon group having 1 to 10 carbon atoms having a fluorine atom.

Examples of the saturated hydrocarbon group for $R^{f22}$ include those which are the same as the saturated hydrocarbon group represented by $R^{a42}$. $R^{f22}$ is preferably an alkyl group having 1 to 10 carbon atoms having a fluorine atom or an alicyclic saturated hydrocarbon group having 1 to 10 carbon atoms having a fluorine atom, more preferably an alkyl group having 1 to 10 carbon atoms having a fluorine atom, and still more preferably, an alkyl group having 1 to 6 carbon atoms having a fluorine atom.

In formula (a4-4), $A^{f21}$ is preferably $-(CH_2)_{j1}-$, more preferably an ethylene group or a methylene group, and still more preferably a methylene group.

The structural unit represented by formula (a4-4) includes, for example, the following structural units and structural units in which a methyl group corresponding to $R^{f21}$ in the structural unit (a4-4) is replaced by a hydrogen atom in structural units represented by the following formulas.

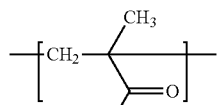

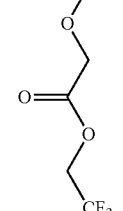

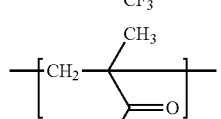

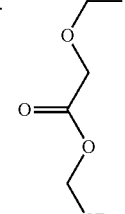

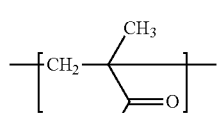

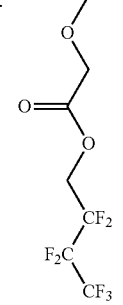

-continued

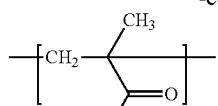

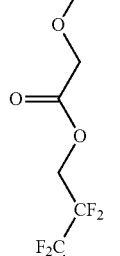

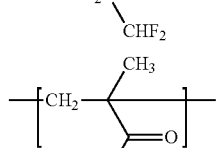

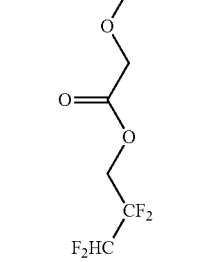

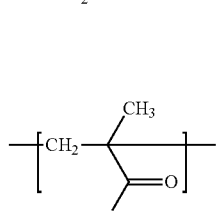

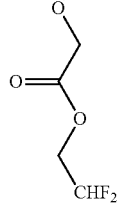

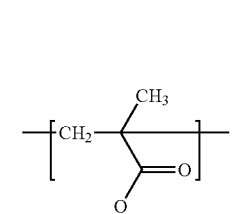

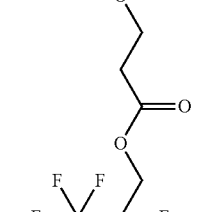

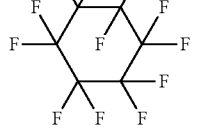

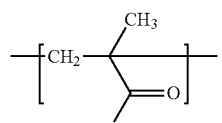
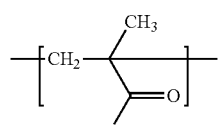
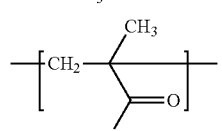
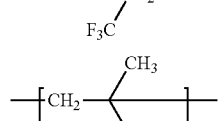
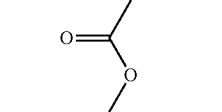
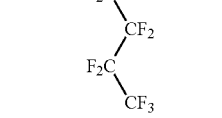
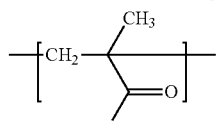
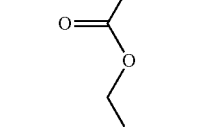
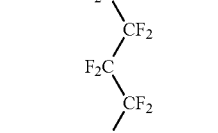
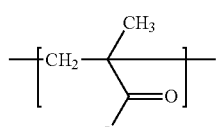
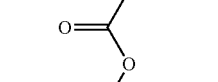
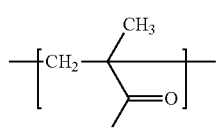
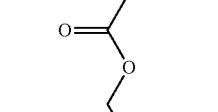
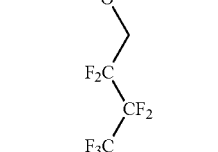

-continued

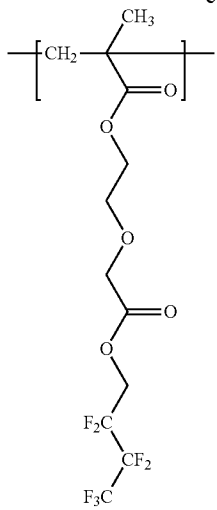

When the resin (A) includes the structural unit (a4), the content is preferably 1 to 20 mol %, more preferably 2 to 15 mol %, and still more preferably 3 to 10 mol %, based on all structural units of the resin (A).

<Structural Unit (a5)>

Examples of a non-leaving hydrocarbon group possessed by the structural unit (a5) include groups having a linear, branched or cyclic hydrocarbon group. Among these, the structural unit (a5) is preferably a group having an alicyclic hydrocarbon group.

The structural unit (a5) includes, for example, a structural unit represented by formula (a5-1):

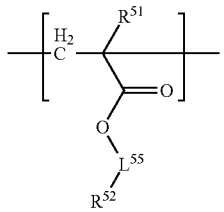

(a5-1)

wherein, in formula (a5-1), $R^{51}$ represents a hydrogen atom or a methyl group, $R^{52}$ represents an alicyclic hydrocarbon group having 3 to 18 carbon atoms, and a hydrogen atom included in the alicyclic hydrocarbon group may be replaced by an aliphatic hydrocarbon group having 1 to 8 carbon atoms, and $L^{55}$ represents a single bond or a saturated hydrocarbon group having 1 to 18 carbon atoms, and —$CH_2$— included in the saturated hydrocarbon group may be replaced by —O— or —CO—.

The alicyclic hydrocarbon group in $R^{52}$ may be either monocyclic or polycyclic. The monocyclic alicyclic hydrocarbon group includes, for example, a cyclopropyl group, a cyclobutyl group, a cyclopentyl group and a cyclohexyl group. The polycyclic alicyclic hydrocarbon group includes, for example, an adamantyl group and a norbornyl group.

The aliphatic hydrocarbon group having 1 to 8 carbon atoms includes, for example, alkyl groups such as a methyl group, an ethyl group, a propyl group, an isopropyl group, a butyl group, a sec-butyl group, a tert-butyl group, a pentyl group, a hexyl group, an octyl group and a 2-ethylhexyl group.

Examples of the alicyclic hydrocarbon group having a substituent includes a 3-hydroxyadamantyl group, a 3-methyladamantyl group and the like.

$R^{52}$ is preferably an unsubstituted alicyclic hydrocarbon group having 3 to 18 carbon atoms, and more preferably an adamantyl group, a norbornyl group or a cyclohexyl group.

Examples of the saturated hydrocarbon group in $L^{55}$ include a chain saturated hydrocarbon group and an alicyclic saturated hydrocarbon group, and a chain saturated hydrocarbon group is preferred.

The chain saturated hydrocarbon group includes, for example, alkanediyl groups such as a methylene group, an ethylene group, a propanediyl group, a butanediyl group and a pentanediyl group.

The alicyclic saturated hydrocarbon group may be either monocyclic or polycyclic. Examples of the monocyclic alicyclic saturated hydrocarbon group include cycloalkanediyl groups such as a cyclopentanediyl group and a cyclohexanediyl group. Examples of the polycyclic divalent alicyclic saturated hydrocarbon group include an adamantanediyl group and a norbornanediyl group.

The group in which —$CH_2$— included in the saturated hydrocarbon group represented by $L^{55}$ is replaced by —O— or —CO— includes, for example, groups represented by formula (L1-1) to formula (L1-4). In the following formulas, * and ** each represent a bonding site and * represents a bonding site to an oxygen atom.

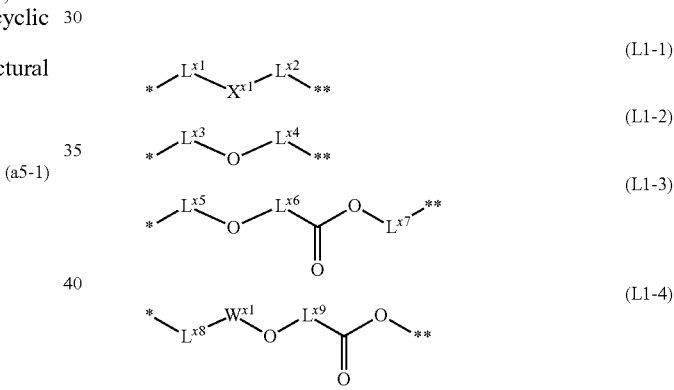

In formula (L1-1), $X^{x1}$ represents *—O—CO— or *—CO—O— (* represents a bonding site to $L^{x1}$), $L^{x1}$ represents an aliphatic saturated hydrocarbon group having 1 to 16 carbon atoms, $L^{x2}$ represents a single bond or an aliphatic saturated hydrocarbon group having 1 to 15 carbon atoms, and the total number of carbon atoms of $L^{x1}$ and $L^{x2}$ is 16 or less.

In formula (L1-2), $L^{x3}$ represents an aliphatic saturated hydrocarbon group having 1 to 17 carbon atoms, $L^{x4}$ represents a single bond or an aliphatic saturated hydrocarbon group having 1 to 16 carbon atoms, and the total number of carbon atoms of $L^{x3}$ and $L^{x4}$ is 17 or less.

In formula (L1-3), $L^{x5}$ represents an aliphatic saturated hydrocarbon group having 1 to 15 carbon atoms, $L^{x6}$ and $L^{x7}$ each independently represent a single bond or an aliphatic saturated hydrocarbon group having 1 to 14 carbon atoms, and the total number of carbon atoms of $L^{x5}$, $L^{x6}$ and $L^{x7}$ is 15 or less.

In formula (L1-4), $L^{x8}$ and $L^{x9}$ represents a single bond or an aliphatic saturated hydrocarbon group having 1 to 12 carbon atoms, $W^{x1}$ represents an alicyclic saturated hydrocarbon group having 3 to 15 carbon atoms, and the total number of carbon atoms of $L^{x8}$, $L^{x9}$ and $W^{x1}$ is 15 or less.

$L^{x1}$ is preferably an aliphatic saturated hydrocarbon group having 1 to 8 carbon atoms, and more preferably a methylene group or an ethylene group.

$L^{x2}$ is preferably a single bond or an aliphatic saturated hydrocarbon group having 1 to 8 carbon atoms, and more preferably a single bond.

$L^{x3}$ is preferably an aliphatic saturated hydrocarbon group having 1 to 8 carbon atoms.

$L^{x4}$ is preferably a single bond or an aliphatic saturated hydrocarbon group having 1 to 8 carbon atoms.

$L^{x5}$ is preferably an aliphatic saturated hydrocarbon group having 1 to 8 carbon atoms, and more preferably a methylene group or an ethylene group.

$L^{x6}$ is preferably a single bond or an aliphatic saturated hydrocarbon group having 1 to 8 carbon atoms, and more preferably a methylene group or an ethylene group.

$L^{x7}$ is preferably a single bond or an aliphatic saturated hydrocarbon group having 1 to 8 carbon atoms.

$L^{x8}$ is preferably a single bond or an aliphatic saturated hydrocarbon group having 1 to 8 carbon atoms, and more preferably a single bond or a methylene group.

$L^{x9}$ is preferably a single bond or an aliphatic saturated hydrocarbon group having 1 to 8 carbon atoms, and more preferably a single bond or a methylene group.

$W^{x1}$ is preferably an alicyclic saturated hydrocarbon group having 3 to 10 carbon atoms, and more preferably a cyclohexanediyl group or an adamantanediyl group.

The group represented by formula (L1-1) includes, for example, the following groups.

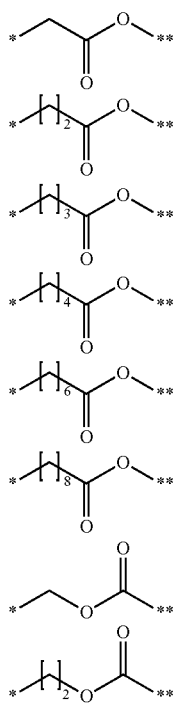

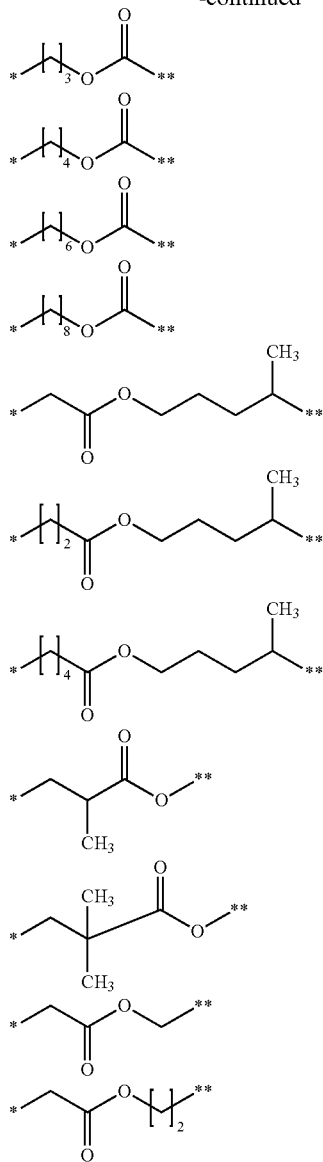

The group represented by formula (L1-2) includes, for example, the following groups.

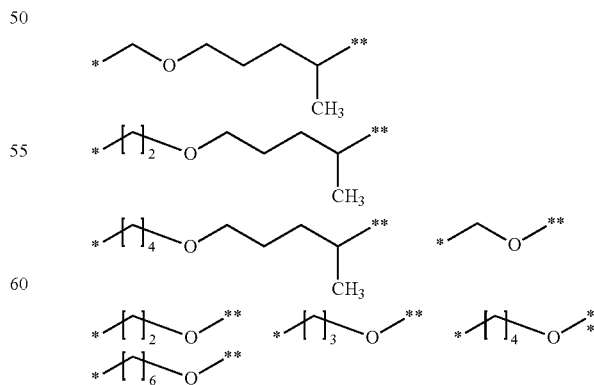

The group represented by formula (L1-3) includes, for example, the following groups.

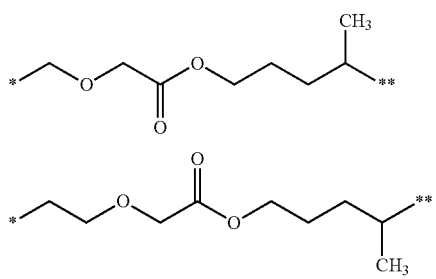
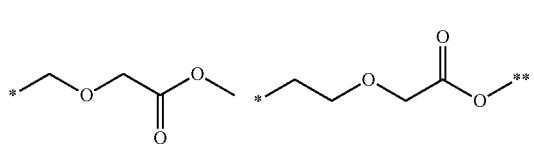

The group represented by formula (L1-4) includes, for example, the following groups.

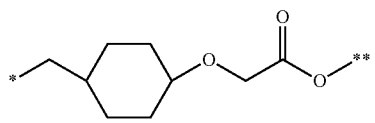
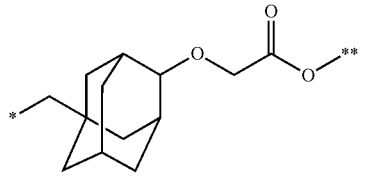
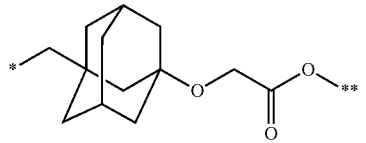
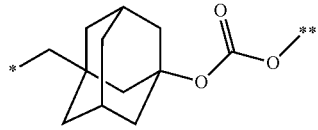
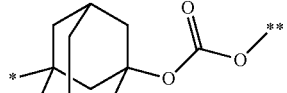
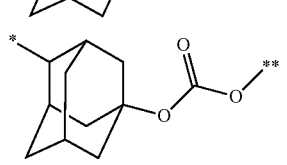

$L^{55}$ is preferably a single bond or a group represented by formula (L1-1).

Examples of the structural unit (a5-1) include the following structural units and structural units in which a methyl group corresponding to $R^{51}$ in the structural unit (a5-1) in the following structural units is replaced by a hydrogen atom.

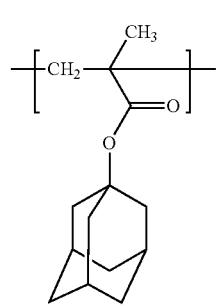

(a5-1-1)

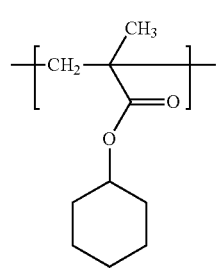

(a5-1-2)

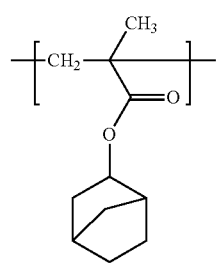

(a5-1-3)

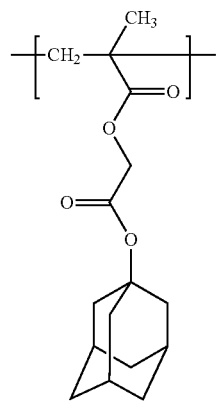

(a5-1-4)

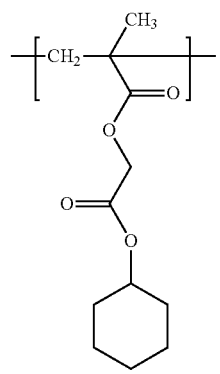

(a5-1-5)

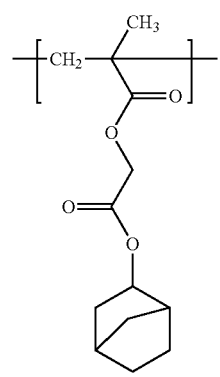 (a5-1-6)
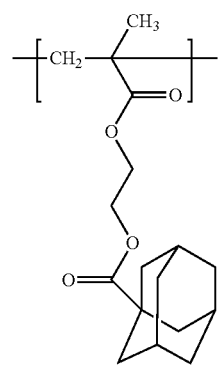 (a5-1-7)
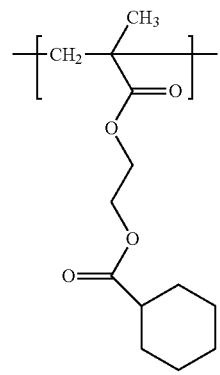 (a5-1-8)
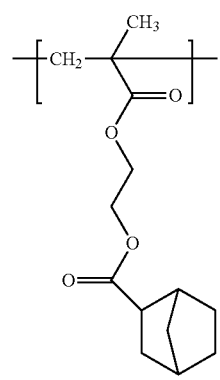 (a5-1-9)
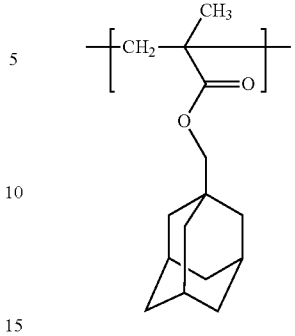 (a5-1-10)
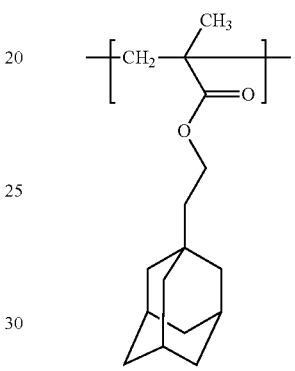 (a5-1-11)
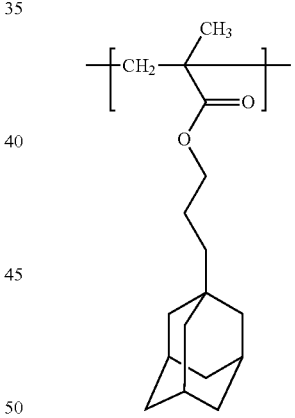 (a5-1-12)
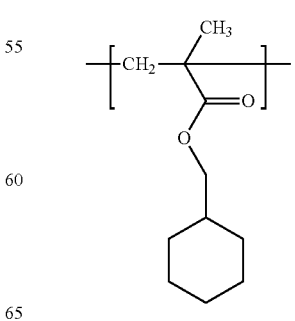 (a5-1-13)

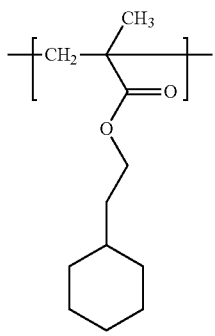
(a5-1-14)

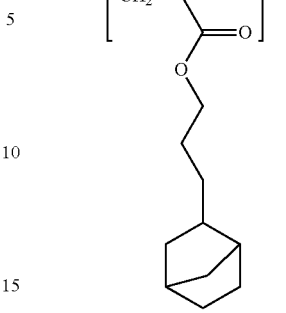
(a5-1-18)

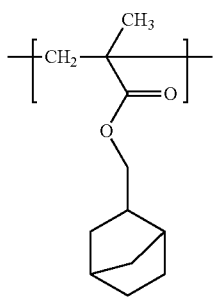
(a5-1-15)

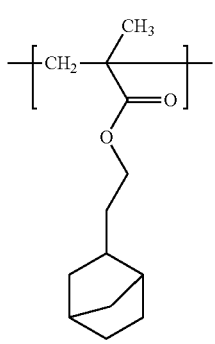
(a5-1-17)

(a5-1-16)

When the resin (A) includes the structural unit (a5), the content is preferably 1 to 30 mol %, more preferably 2 to 20 mol %, and still more preferably 3 to 15 mol %, based on all structural units of the resin (A).

<Structural Unit (II)>

The resin (A) may further include a structural unit which is decomposed upon exposure to radiation to generate an acid (hereinafter sometimes referred to as "structural unit (II)"). Specific examples of the structural unit (II) include the structural units mentioned in JP 2016-79235 A, and a structural unit having a sulfonate group or a carboxylate group and an organic cation in a side chain or a structural unit having a sulfonio group and an organic anion in a side chain are preferred.

The structural unit having a sulfonate group or a carboxylate group and an organic cation in a side chain is preferably a structural unit represented by formula (II-2-A'):

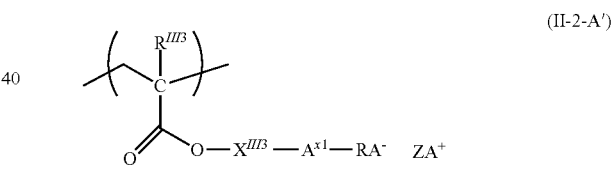
(II-2-A')

wherein, in formula (II-2-A'), $X^{III3}$ represents a divalent saturated hydrocarbon group having 1 to 18 carbon atoms, —CH$_2$— included in the saturated hydrocarbon group may be replaced by —O—, —S— or —CO—, and a hydrogen atom included in the saturated hydrocarbon group may be replaced by a halogen atom, an alkyl group having 1 to 6 carbon atoms which may have a halogen atom, or a hydroxy group, $A^{x1}$ represents an alkanediyl group having 1 to 8 carbon atoms, and a hydrogen atom included in the alkanediyl group may be substituted with a fluorine atom or a perfluoroalkyl group having 1 to 6 carbon atoms, $RA^-$ represents a sulfonate group or a carboxylate group, $R^{III3}$ represents a hydrogen atom, a halogen atom or an alkyl group having 1 to 6 carbon atoms which may have a halogen atom, and $ZA^+$ represents an organic cation.

Examples of the halogen atom represented by $R^{III3}$ include a fluorine atom, a chlorine atom, a bromine atom and an iodine atom.

Examples of the alkyl group having 1 to 6 carbon atoms which may have a halogen atom represented by $R^{III3}$ include those which are the same as the alkyl group having 1 to 6 carbon atoms which may have a halogen atom represented by $R^{a8}$.

Examples of the alkanediyl group having 1 to 8 carbon atoms represented by $A^{x1}$ include a methylene group, an ethylene group, a propane-1,3-diyl group, a butane-1,4-diyl group, a pentane-1,5-diyl group, a hexane-1,6-diyl group, a ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group, a 2-methylbutane-1,4-diyl group and the like.

Examples of the perfluoroalkyl group having 1 to 6 carbon atoms in which a hydrogen atom may be substituted in $A^{x1}$ include a trifluoromethyl group, a perfluoroethyl group, a perfluoropropyl group, a perfluoroisopropyl group, a perfluorobutyl group, a perfluorosec-butyl group, a perfluorotert-butyl group, a perfluoropentyl group, a perfluorohexyl group and the like.

Examples of the divalent saturated hydrocarbon group having 1 to 18 carbon atoms represented by $X^{III3}$ include a linear or branched alkanediyl group, a monocyclic or a polycyclic alicyclic saturated hydrocarbon group, or a combination thereof.

Specific examples thereof include linear alkanediyl groups such as a methylene group, an ethylene group, a propane-1,3-diyl group, a propane-1,2-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group and a dodecane-1,12-diyl group; branched alkanediyl groups such as a butane-1,3-diyl group, a 2-methylpropane-1,3-diyl group, a 2-methylpropane-1,2-diyl group, a pentane-1,4-diyl group and a 2-methylbutane-1,4-diyl group; cycloalkanediyl groups such as a cyclobutane-1,3-diyl group, a cyclopentane-1,3-diyl group, a cyclohexane-1,4-diyl group and a cyclooctane-1,5-diyl group; and polycyclic alicyclic saturated hydrocarbon groups such as a norbornane-1,4-diyl group, a norbornane-2,5-diyl group, an adamantane-1,5-diyl group and an adamantane-2,6-diyl group.

Those in which —$CH_2$— included in the saturated hydrocarbon group are replaced by —O—, —S— or —CO— include, for example, divalent groups represented by formula (X1) to formula (X53). Before replacing —$CH_2$— included in the saturated hydrocarbon group by —O—, —S— or —CO—, the number of carbon atoms is 17 or less. In the following formulas, * and ** represent a bonding site and * represents a bonding site to $A^{x1}$.

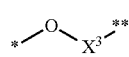

(X1)

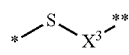

(X2)

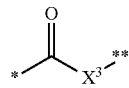

(X3)

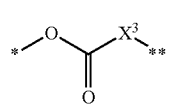

(X4)

-continued

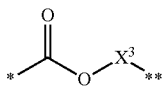

(X5)

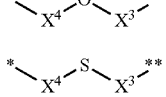

(X6)

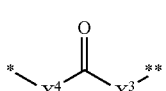

(X7)

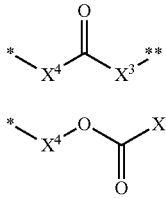

(X8)

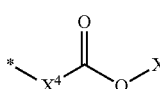

(X9)

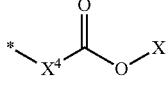

(X10)

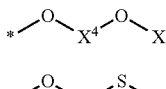

(X11)

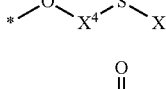

(X12)

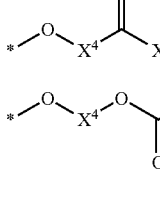

(X13)

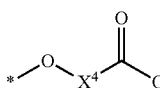

(X14)

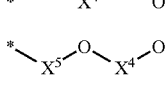

(X15)

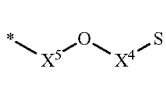

(X16)

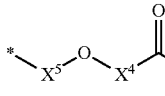

(X17)

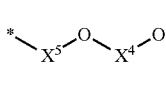

(X18)

(X19)

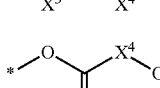

(X20)

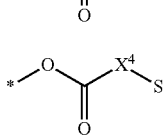

(X21)

(X22)

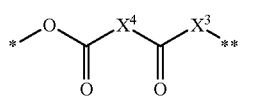 (X23)
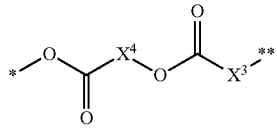 (X24)
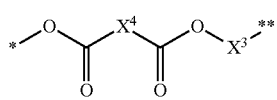 (X25)
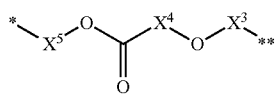 (X26)
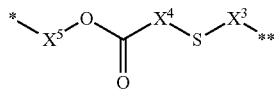 (X27)
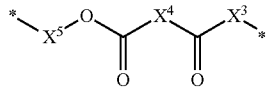 (X28)
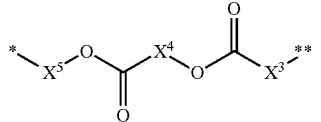 (X29)
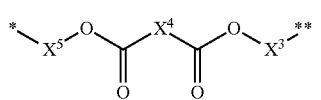 (X30)
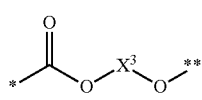 (X31)
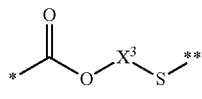 (X32)
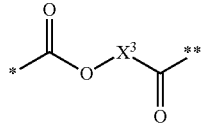 (X33)
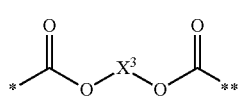 (X34)
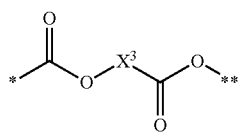 (X35)
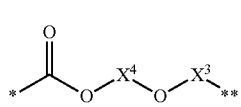 (X36)
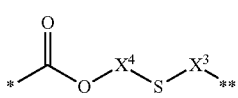 (X37)
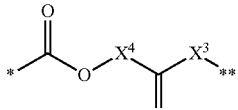 (X38)
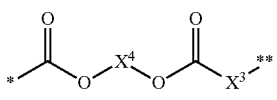 (X39)
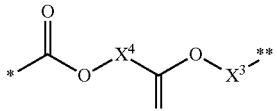 (X40)
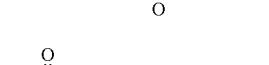 (X41)
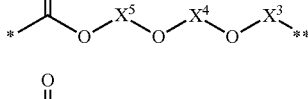 (X42)
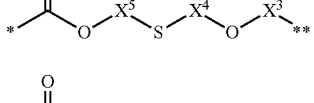 (X43)
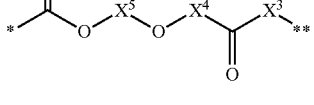 (X44)
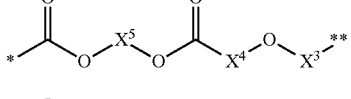 (X45)
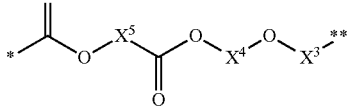 (X46)
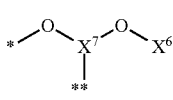 (X47)
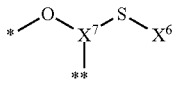 (X48)
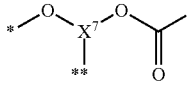 (X49)
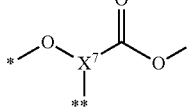 (X50)

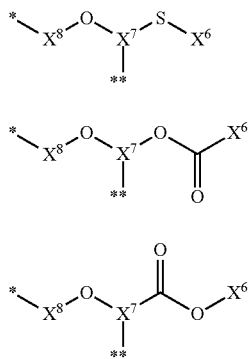

(X51)

(X52)

(X53)

X³ represents a saturated hydrocarbon group having 1 to 16 carbon atoms.

X⁴ represents a saturated hydrocarbon group having 1 to 15 carbon atoms.

X⁵ represents a saturated hydrocarbon group having 1 to 13 carbon atoms.

X⁶ represents a saturated hydrocarbon group having 1 to 14 carbon atoms.

X⁷ represents a saturated hydrocarbon group having 1 to 14 carbon atoms.

X⁸ represents a saturated hydrocarbon group having 1 to 13 carbon atoms.

Examples of the organic cation represented by $ZA^+$ include an organic onium cation, an organic sulfonium cation, an organic iodonium cation, an organic ammonium cation, a benzothiazolium cation and an organic phosphonium cation. Among these organic cations, an organic sulfonium cation and an organic iodonium cation are preferred, and an arylsulfonium cation is more preferred. Specific examples thereof include a cation represented by any one of formula (b2-1) to formula (b2-4) (hereinafter sometimes referred to as "cation (b2-1)" according to the number of formula).

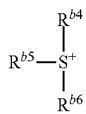

(b2-1)

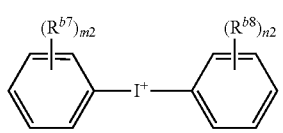

(b2-2)

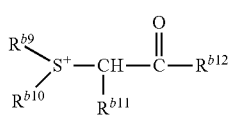

(b2-3)

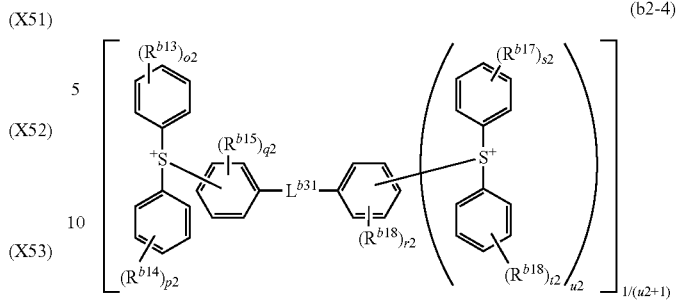

(b2-4)

In formula (b2-1) to formula (b2-4), $R^{b4}$ to $R^{b6}$ each independently represent a chain hydrocarbon group having 1 to 30 carbon atoms, an alicyclic hydrocarbon group having 3 to 36 carbon atoms or an aromatic hydrocarbon group having 6 to 36 carbon atoms, a hydrogen atom included in the chain hydrocarbon group may be substituted with a hydroxy group, an alkoxy group having 1 to 12 carbon atoms, an alicyclic hydrocarbon group having 3 to 12 carbon atoms or an aromatic hydrocarbon group having 6 to 18 carbon atoms, a hydrogen atom included in the alicyclic hydrocarbon group may be substituted with a halogen atom, an aliphatic hydrocarbon group having 1 to 18 carbon atoms, an alkylcarbonyl group having 2 to 4 carbon atoms or a glycidyloxy group, and a hydrogen atom included in the aromatic hydrocarbon group may be substituted with a halogen atom or an alkoxy group having 1 to 12 carbon atoms, $R^{b4}$ and $R^{b5}$ may be bonded each other to form a ring together with sulfur atoms to which $R^{b4}$ and $R^{b5}$ are bonded, and —CH₂— included in the ring may be replaced by —O—, —S— or —CO—, $R^{b7}$ and $R^{b8}$ each independently represent a hydroxy group, an aliphatic hydrocarbon group having 1 to 12 carbon atoms or an alkoxy group having 1 to 12 carbon atoms, m2 and n2 each independently represent an integer of 0 to 5, when m2 is 2 or more, a plurality of $R^{b7}$ may be the same or different, and when n2 is 2 or more, a plurality of $R^{b8}$ may be the same or different, $R^{b9}$ and $R^{b10}$ each independently represent a chain hydrocarbon group having 1 to 36 carbon atoms or an alicyclic hydrocarbon group having 3 to 36 carbon atoms, $R^{b9}$ and $R^{b10}$ may be bonded each other to form a ring together with sulfur atoms to which $R^{b9}$ and $R^{b10}$ are bonded, and —CH₂— included in the ring may be replaced by —O—, —S— or —CO—, $R^{b11}$ represents a hydrogen atom, a chain hydrocarbon group having 1 to 36 carbon atoms, an alicyclic hydrocarbon group having 3 to 36 carbon atoms or an aromatic hydrocarbon group having 6 to 18 carbon atoms, $R^{b12}$ represents a chain hydrocarbon group having 1 to 12 carbon atoms, an alicyclic hydrocarbon group having 3 to 18 carbon atoms or an aromatic hydrocarbon group having 6 to 18 carbon atoms, a hydrogen atom included in the chain hydrocarbon may be substituted with an aromatic hydrocarbon group having 6 to 18 carbon atoms, and a hydrogen atom included in the aromatic hydrocarbon group may be substituted with an alkoxy group having 1 to 12 carbon atoms or an alkylcarbonyloxy group having 1 to 12 carbon atoms, $R^{b11}$ and $R^{b12}$ may be bonded each other to form a ring, including —CH—CO— to which $R^{b11}$ and $R^{b12}$ are bonded, and —CH₂— included in the ring may be replaced by —O—, —S— or —CO—, $R^{b13}$ to $R^{b18}$ each independently represent a hydroxy group, an aliphatic hydrocarbon group having 1 to 12 carbon atoms or an alkoxy group having 1 to 12 carbon atoms, $L^{b31}$ represents a sulfur atom or an oxygen atom, o2, p2, s2 and t2 each independently represent an integer of 0 to 5, q2 and r2 each independently represent an integer of 0 to 4, u2 represents 0 or 1, and when o2 is 2 or more, a plurality of $R^{b13}$ are the same or different, when p2 is 2 or more, a plurality of $R^{b14}$ are the same or different, when q2 is 2 or more, a plurality of $R^{b15}$ are the same or different, when r2 is 2 or more, a plurality of $R^{b16}$ are the same or different, when s2 is 2 or more, a plurality of $R^{b17}$ are the same or different, and when t2 is 2 or more, a plurality of $R^{b18}$ are the same or different.

The aliphatic hydrocarbon group represents a chain hydrocarbon group and an alicyclic hydrocarbon group.

Examples of the chain hydrocarbon group include alkyl groups such as a methyl group, an ethyl group, a propyl group, an isopropyl group, a butyl group, a sec-butyl group, a tert-butyl group, a pentyl group, a hexyl group, an octyl group and a 2-ethylhexyl group. Particularly, the chain hydrocarbon group for $R^{b9}$ to $R^{b12}$ preferably has 1 to 12 carbon atoms.

The alicyclic hydrocarbon group may be either monocyclic or polycyclic, and examples of the monocyclic alicyclic hydrocarbon group include cycloalkyl groups such as a cyclopropyl group, a cyclobutyl group, a cyclopentyl group, a cyclohexyl group, a cycloheptyl group, a cyclooctyl group and a cyclodecyl group. Examples of the polycyclic alicyclic hydrocarbon group include a decahydronaphthyl group, an adamantyl group, a norbornyl group and the following groups.

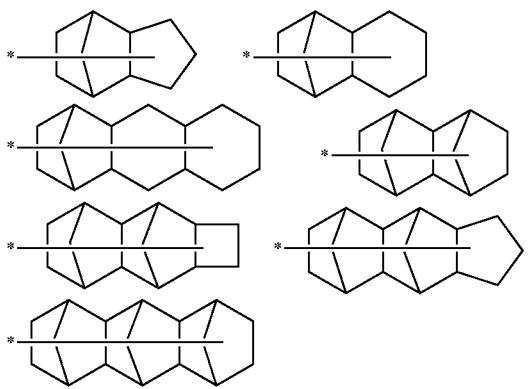

Particularly, the alicyclic hydrocarbon group for $R^{b9}$ to $R^{b12}$ preferably has 3 to 18 carbon atoms, and more preferably 4 to 12 carbon atoms.

Examples of the alicyclic hydrocarbon group in which a hydrogen atom is substituted with an aliphatic hydrocarbon group include a methylcyclohexyl group, a dimethylcyclohexyl group, a 2-methyladamantan-2-yl group, a 2-ethyladamantan-2-yl group, a 2-isopropyladamantan-2-yl group, a methylnorbornyl group, an isobornyl group and the like. In the alicyclic hydrocarbon group in which a hydrogen atom is substituted with an aliphatic hydrocarbon group, the total number of carbon atoms of the alicyclic hydrocarbon group and the aliphatic hydrocarbon group is preferably 20 or less.

Examples of the aromatic hydrocarbon group include aryl groups such as a phenyl group, a biphenyl group, a naphthyl group and a phenanthryl group.

The aromatic hydrocarbon group may have a chain hydrocarbon group or an alicyclic hydrocarbon group, and examples thereof include an aromatic hydrocarbon group having a chain hydrocarbon group having 1 to 18 carbon atoms (a tolyl group, a xylyl group, a cumenyl group, a mesityl group, a p-ethylphenyl group, a p-tert-butylphenyl group, a 2,6-diethylphenyl group, a 2-methyl-6-ethylphenyl group, etc.) and an aromatic hydrocarbon group having an alicyclic hydrocarbon group having 3 to 18 carbon atoms (a p-cyclohexylphenyl group, a p-adamantylphenyl group, etc.).

Examples of the aromatic hydrocarbon group in which a hydrogen atom is substituted with an alkoxy group include a p-methoxyphenyl group and the like.

Examples of the chain hydrocarbon group in which a hydrogen atom is substituted with an aromatic hydrocarbon group include aralkyl groups such as a benzyl group, a phenethyl group, a phenylpropyl group, a trityl group, a naphthylmethyl group, a naphthylethyl group and the like.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the alkylcarbonyl group include an acetyl group, a propionyl group and a butyryl group.

Examples of the halogen atom include a fluorine atom, a chlorine atom, a bromine atom and an iodine atom.

Examples of the alkylcarbonyloxy group include a methylcarbonyloxy group, an ethylcarbonyloxy group, a propylcarbonyloxy group, an isopropylcarbonyloxy group, a butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethylhexylcarbonyloxy group.

The ring formed by bonding $R^{b4}$ and $R^{b5}$ each other, together with sulfur atoms to which $R^{b4}$ and $R^{b5}$ are bonded, may be a monocyclic, polycyclic, aromatic, nonaromatic, saturated or unsaturated ring. This ring includes a ring having 3 to 18 carbon atoms and is preferably a ring having 4 to 18 carbon atoms. The ring containing a sulfur atom includes a 3-membered to 12-membered ring and is preferably a 3-membered to 7-membered ring and includes, for example, the following rings.

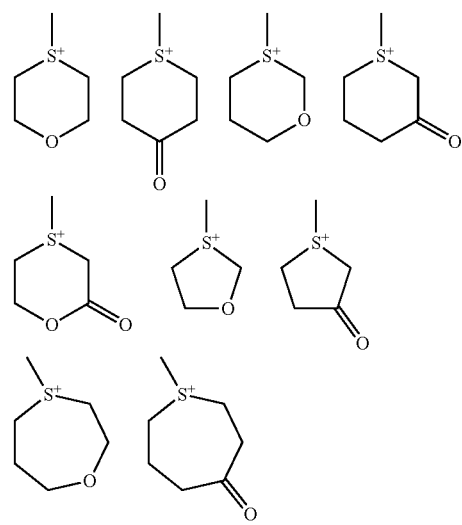

The ring formed by bonding $R^{b9}$ and $R^{b10}$ each other may be a monocyclic, polycyclic, aromatic, nonaromatic, saturated or unsaturated ring. This ring includes a 3-membered to 12-membered ring and is preferably a 3-membered to 7-membered ring. The ring includes, for example, a thiolan-1-ium ring (tetrahydrothiophenium ring), a thian-1-ium ring, a 1,4-oxathian-4-ium ring and the like.

The ring formed by bonding $R^{b11}$ and $R^{b12}$ each other may be a monocyclic, polycyclic, aromatic, nonaromatic, saturated or unsaturated ring. This ring includes a 3-membered to 12-membered ring and is preferably a 3-membered to 7-membered ring. Examples thereof include an oxocycloheptane ring, an oxocyclohexane ring, an oxonorbornane ring, an oxoadamantane ring and the like.

Among cation (b2-1) to cation (b2-4), a cation (b2-1) is preferred.

Examples of the cation (b2-1) include the following cations.

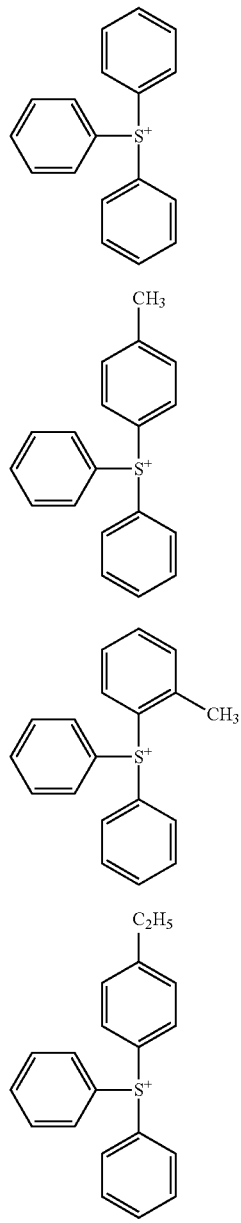

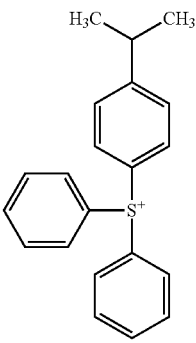

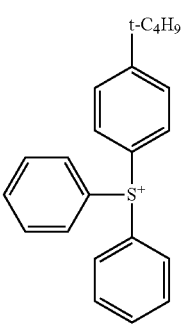

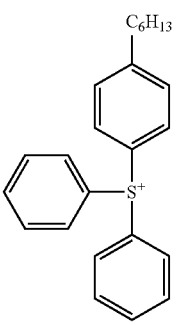

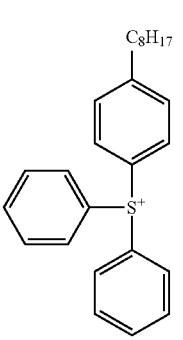

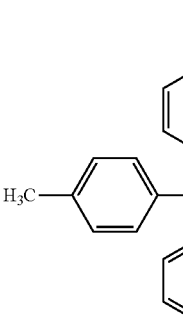

(b2-c-10)
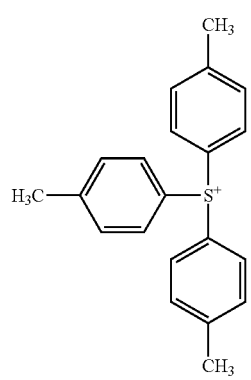
(b2-c-11)
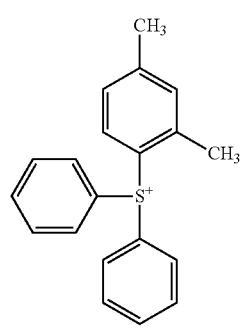
(b2-c-12)
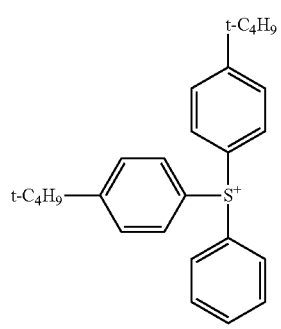
(b2-c-13)
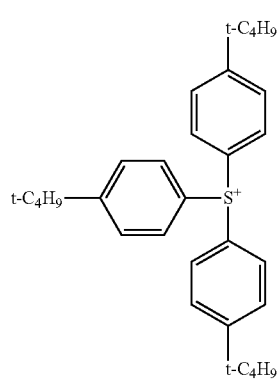
(b2-c-14)
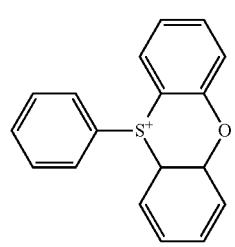
(b2-c-15)
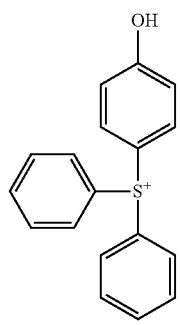
(b2-c-16)
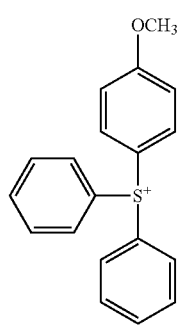
(b2-c-17)
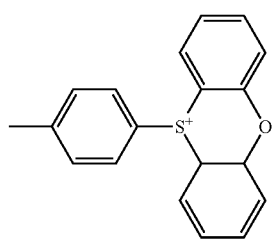
(b2-c-18)
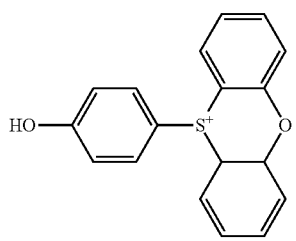
(b2-c-19)
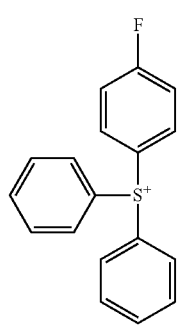

(b2-c-20)
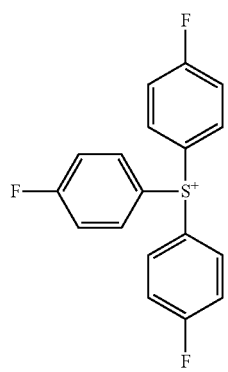
(b2-c-21)
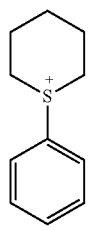
(b2-c-22)
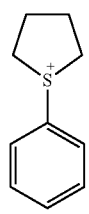
(b2-c-23)
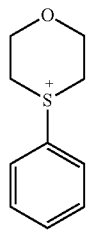
(b2-c-24)
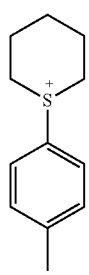
(b2-c-25)
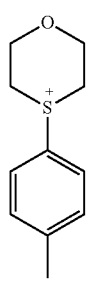
(b2-c-26)
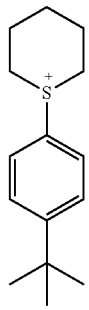
(b2-c-27)
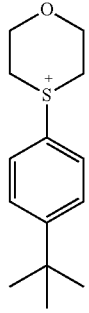
Examples of the cation (b2-2) include the following cations.
(b2-c-28)
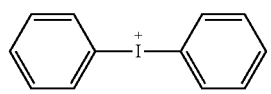
(b2-c-29)
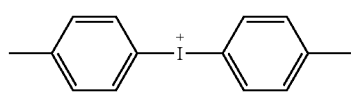
(b2-c-30)
Examples of the cation (b2-3) include the following cations.
(b2-c-31)
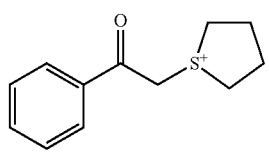
(b2-c-32)
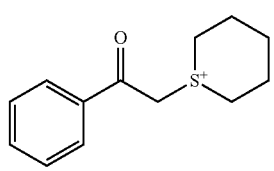

(b2-c-33)
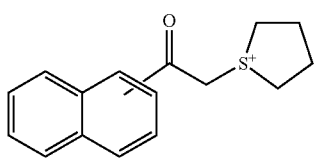
(b2-c-34)
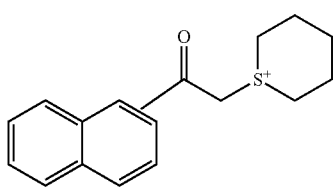
Examples of the cation (b2-4) include the following cations.
(b2-c-35)
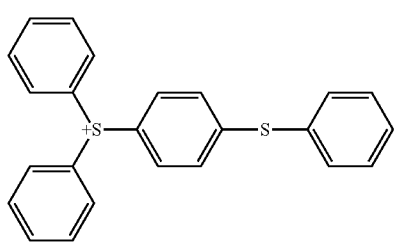
(b2-c-36)
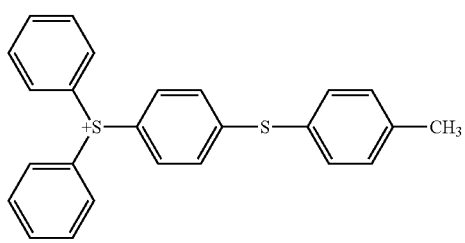
(b2-c-37)
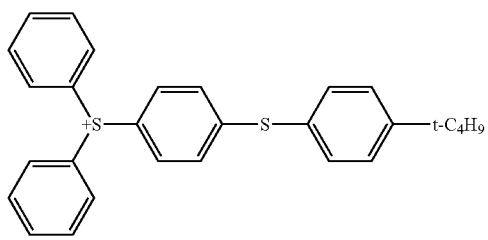
(b2-c-38)
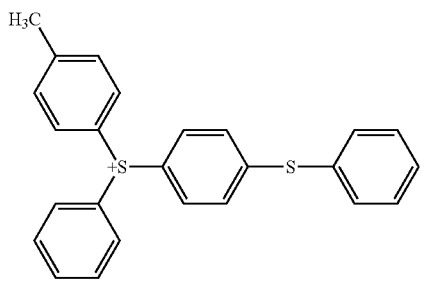
(b2-c-39)
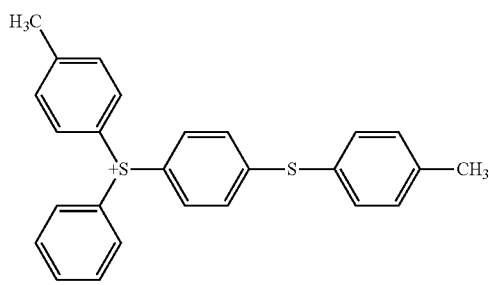
(b2-c-40)
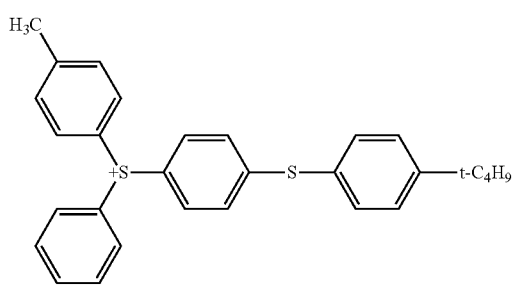
(b2-c-41)
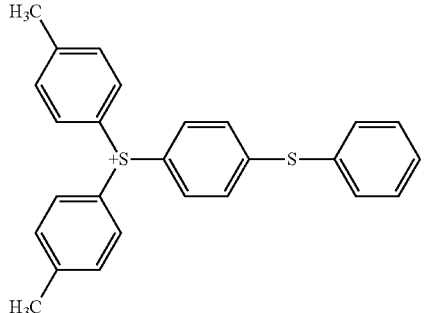
(b2-c-42)
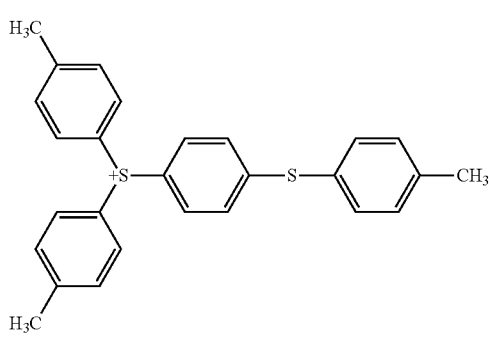
(b2-c-43)
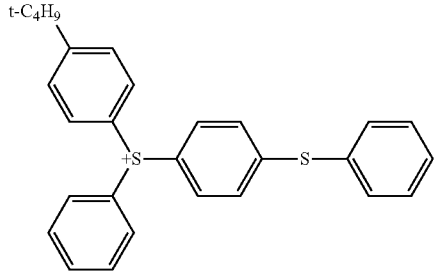

-continued (b2-c-44)
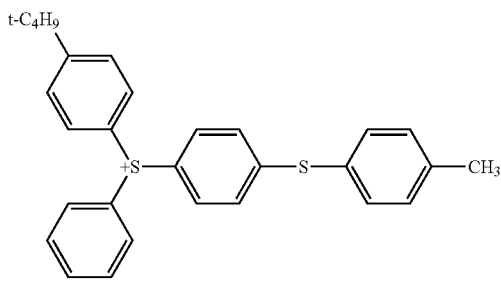

(b2-c-45)
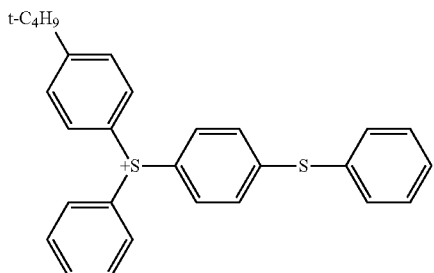

(b2-c-46)
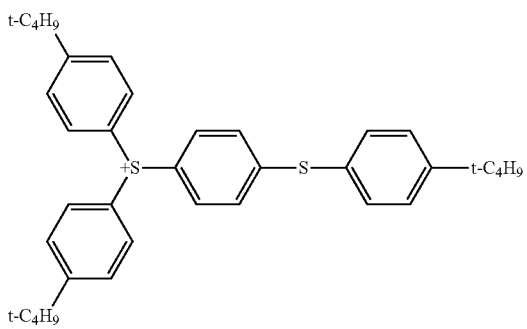

The structural unit represented by formula (II-2-A') is preferably a structural unit represented by formula (II-2-A):

(II-2-A)
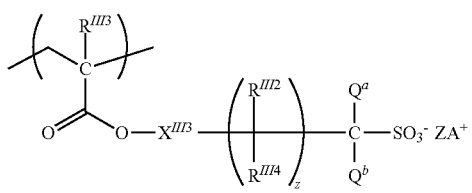

wherein, in formula (II-2-A), $R^{III3}$, $X^{III3}$ and $ZA^+$ are the same as defined above, z represents an integer of 0 to 6, $R^{III2}$ and $R^{III4}$ each independently represent a hydrogen atom, a fluorine atom or a perfluoroalkyl group having 1 to 6 carbon atoms, and when z is 2 or more, a plurality of $R^{III2}$ and $R^{III4}$ may be the same or different from each other, and $Q^a$ and $Q^b$ each independently represent a fluorine atom or a perfluoroalkyl group having 1 to 6 carbon atoms.

Examples of the perfluoroalkyl group having 1 to 6 carbon atoms represented by $R^{III2}$, $R^{III4}$, $Q^a$ and $Q^b$ include those which are the same as the perfluoroalkyl group having 1 to 6 carbon atoms that is a substituent of the above-mentioned $A^{x1}$.

The structural unit represented by formula (II-2-A) is preferably a structural unit represented by formula (II-2-A-1):

(II-2-A-1)
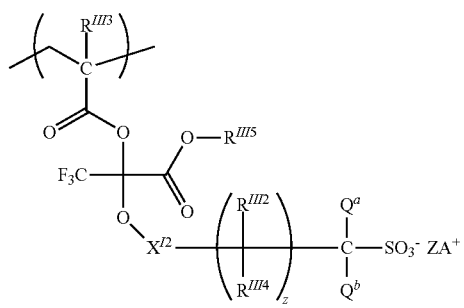

wherein, in formula (II-2-A-1), $R^{III2}$, $R^{III3}$, $R^{III4}$, $Q^a$, $Q^b$, z and $ZA^+$ are the same as defined above, $R^{III5}$ represents a saturated hydrocarbon group having 1 to 12 carbon atoms, and $X^{12}$ represents a saturated hydrocarbon group having 1 to 11 carbon atoms, —$CH_2$— included in the saturated hydrocarbon group may be replaced by —O—, —S— or —CO—, and a hydrogen atom included in the saturated hydrocarbon group may be substituted with a halogen atom or a hydroxy group.

Examples of the saturated hydrocarbon group having 1 to 12 carbon atoms represented by $R^{III5}$ include linear or branched alkyl groups such as a methyl group, an ethyl group, a propyl group, an isopropyl group, a butyl group, a sec-butyl group, a tert-butyl group, a pentyl group, a hexyl group, a heptyl group, an octyl group, a nonyl group, a decyl group, an undecyl group and a dodecyl group.

Examples of the divalent saturated hydrocarbon group represented by $X^{12}$ include those which are the same as the divalent saturated hydrocarbon group represented by $X^{III3}$.

The structural unit represented by formula (II-2-A-1) is more preferably a structural unit represented by formula (II-2-A-2):

(II-2-A-2)
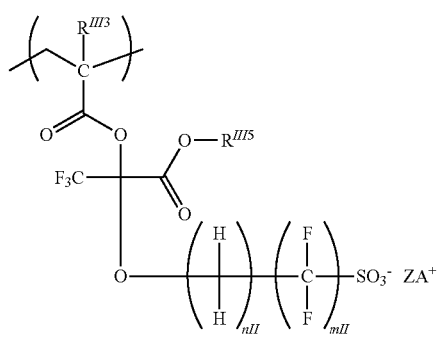

wherein, in formula (II-2-A-2), $R^{III3}$, $R^{III5}$ and $ZA^+$ are the same as defined above, and mII and nII each independently represent 1 or 2.

The structural unit represented by formula (II-2-A') includes, for example, the following structural units and the structural units mentioned in WO 2012/050015 A. ZA$^+$ represents an organic cation.
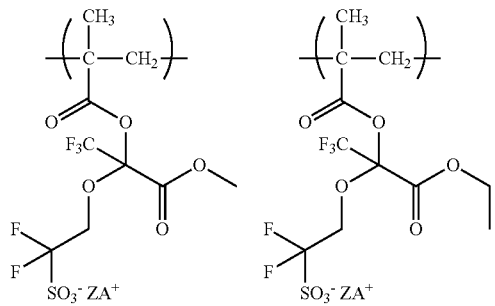
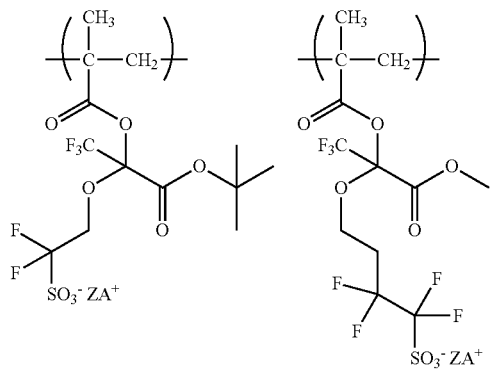
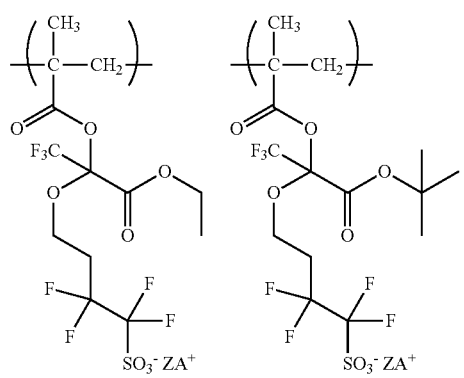
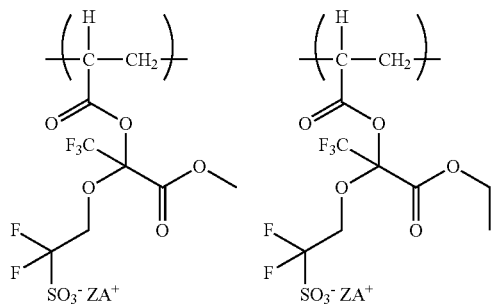
-continued
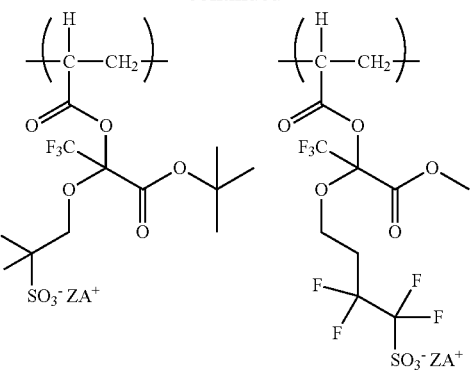
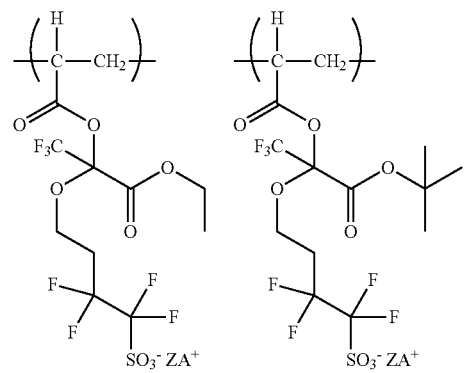
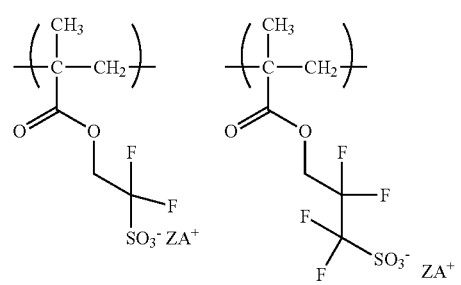
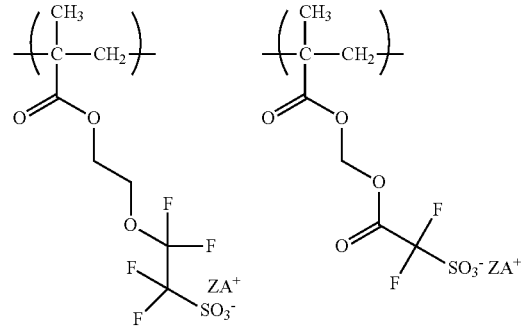

-continued

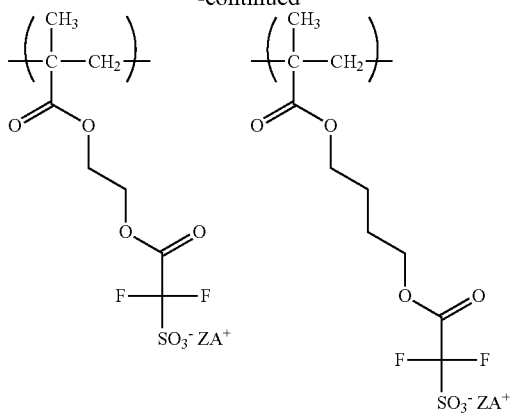

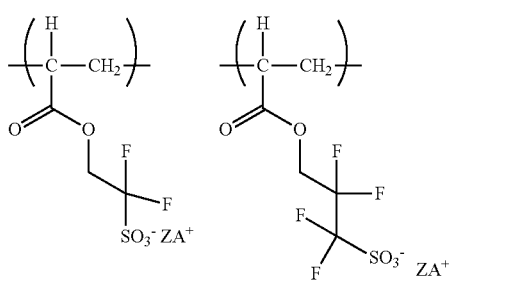

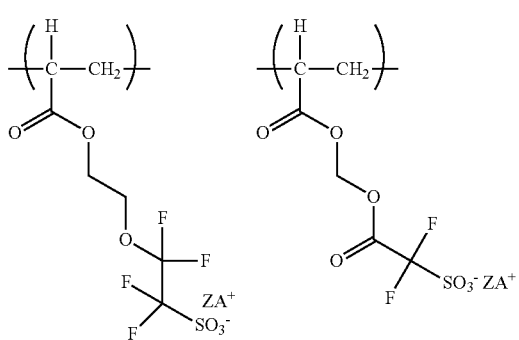

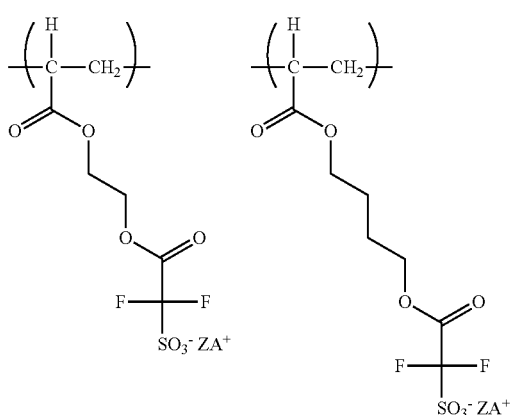

The structural unit having a sulfonio group and an organic anion in a side chain is preferably a structural unit represented by formula (II-1-1):

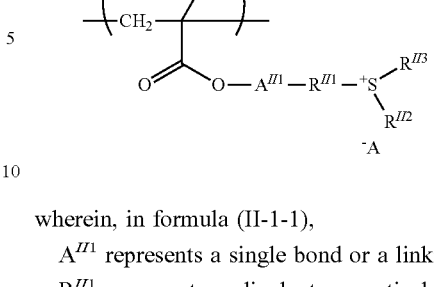

wherein, in formula (II-1-1), $A^{II1}$ represents a single bond or a linking group, $R^{II1}$ represents a divalent aromatic hydrocarbon group having 6 to 18 carbon atoms, $R^{II2}$ and $R^{II3}$ each independently represent a hydrocarbon group having 1 to 18 carbon atoms, and $R^{II2}$ and $R^{II3}$ may be bonded each other to form a ring together with sulfur atoms to which $R^{II2}$ and $R^{II3}$ are bonded, $R^{II4}$ represents a hydrogen atom, a halogen atom or an alkyl group having 1 to 6 carbon atoms which may have a halogen atom, and $A^-$ represents an organic anion.

The divalent linking group represented by $A^{II1}$ includes, for example, a saturated hydrocarbon group having 1 to 18 carbon atoms, and —$CH_2$— included in the saturated hydrocarbon group may be replaced by —O—, —S— or —CO—. Specific examples thereof include those which are the same as the divalent saturated hydrocarbon group having 1 to 18 carbon atoms represented by $X^{III3}$.

Examples of the divalent aromatic hydrocarbon group having 6 to 18 carbon atoms represented by $R^{II1}$ include a phenylene group and a naphthylene group.

Examples of the hydrocarbon group represented by $R^{II2}$ and $R^{II3}$ include those which are the same as the hydrocarbon group represented by $R^{a3'}$.

Examples of the halogen atom represented by $R^{II4}$ include a fluorine atom, a chlorine atom, a bromine atom and an iodine atom.

Examples of the alkyl group having 1 to 6 carbon atoms which may have a halogen atom represented by $R^{II4}$ include those which are the same as the alkyl group having 1 to 6 carbon atoms which may have a halogen atom represented by $R^{a8}$.

Examples of the structural unit including a cation in formula (II-1-1) include the following structural units.

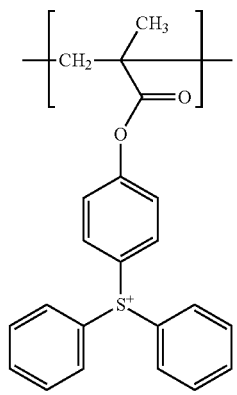

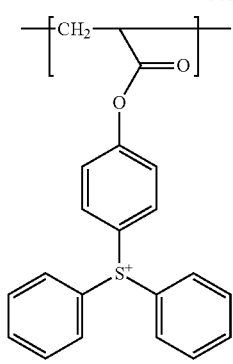
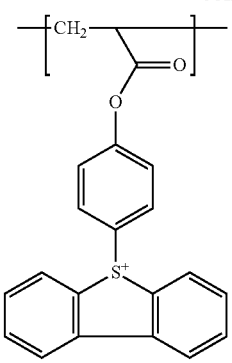
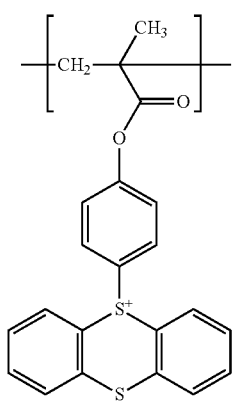
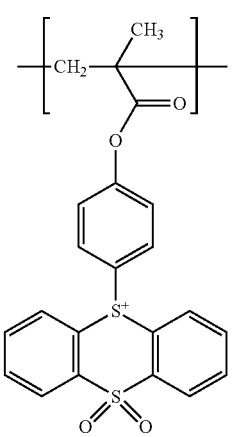
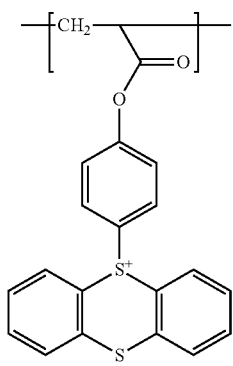
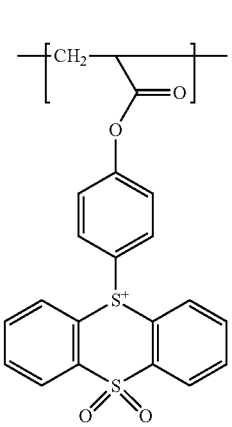
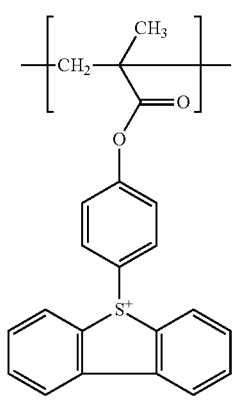
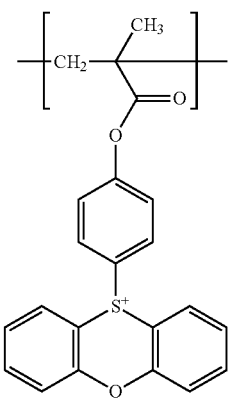

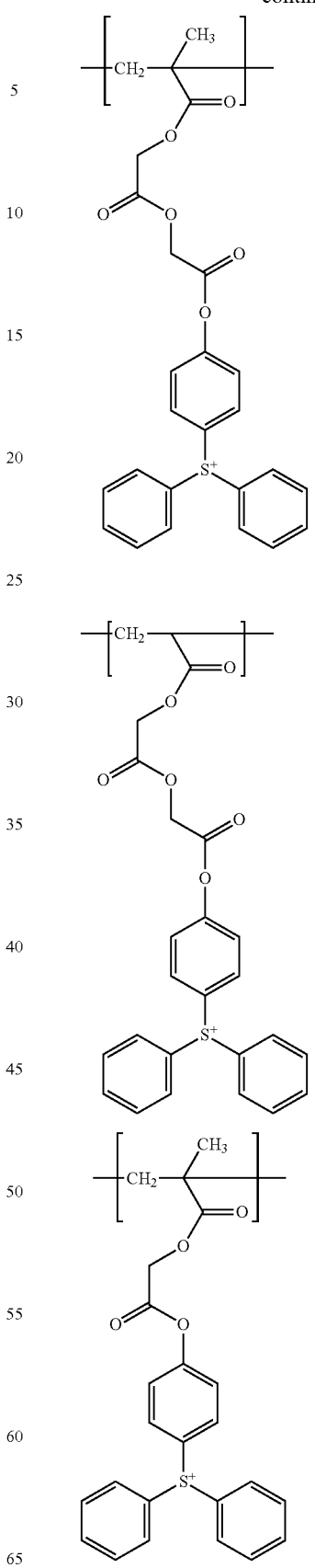

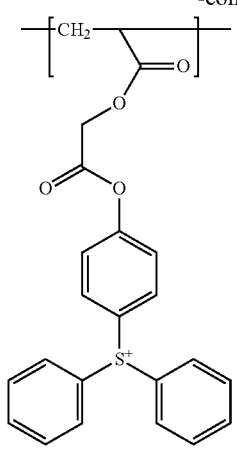
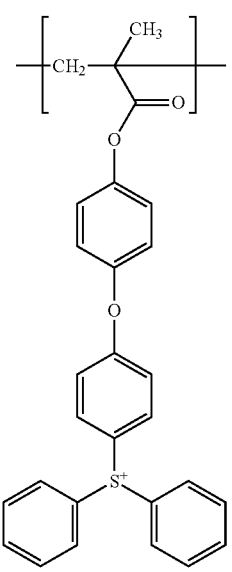
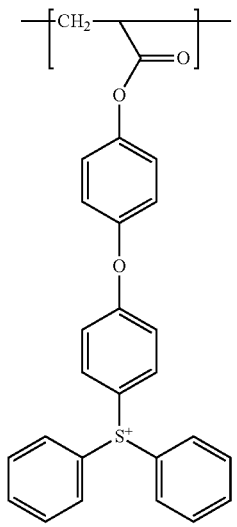
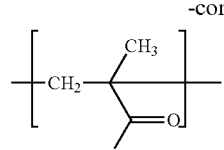
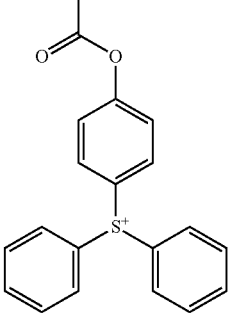
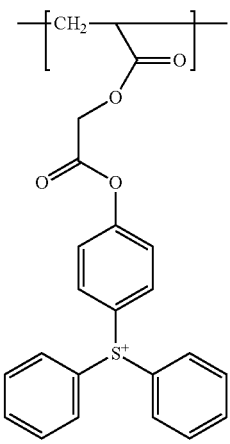
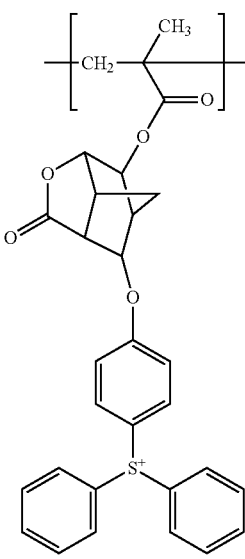

-continued

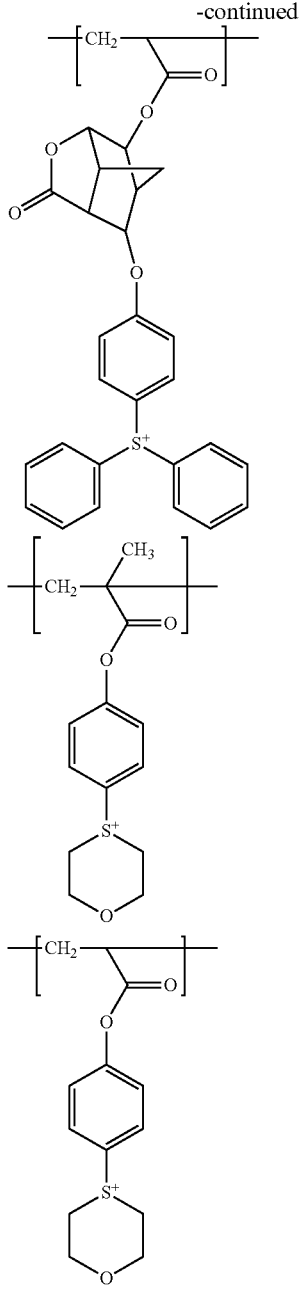

Examples of the organic anion represented by A⁻ include a sulfonic acid anion, a sulfonylimide anion, a sulfonylmethide anion and a carboxylic acid anion. The organic anion represented by A⁻ is preferably a sulfonic acid anion, and the sulfonic acid anion is more preferably an anion included in the below-mentioned salt represented by formula (B1).

Examples of the sulfonylimide anion represented by A⁻ include the followings.

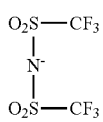
(I-b-1)

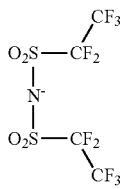
(I-b-2)

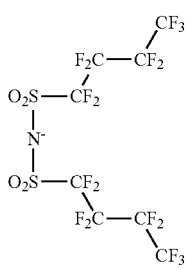
(I-b-3)

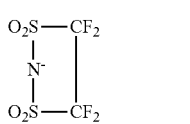
(I-b-4)

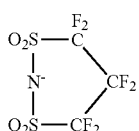
(I-b-5)

Examples of the sulfonylmethide anion include the followings.

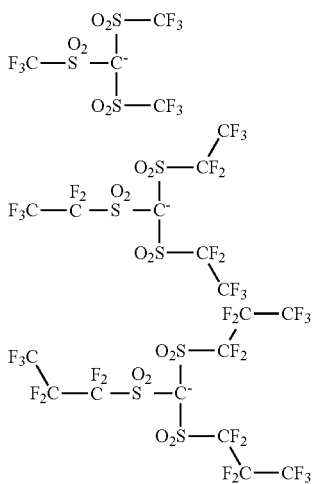

Examples of the carboxylic acid anion include the followings.

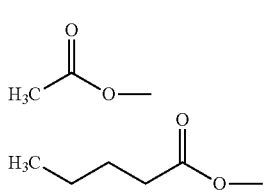

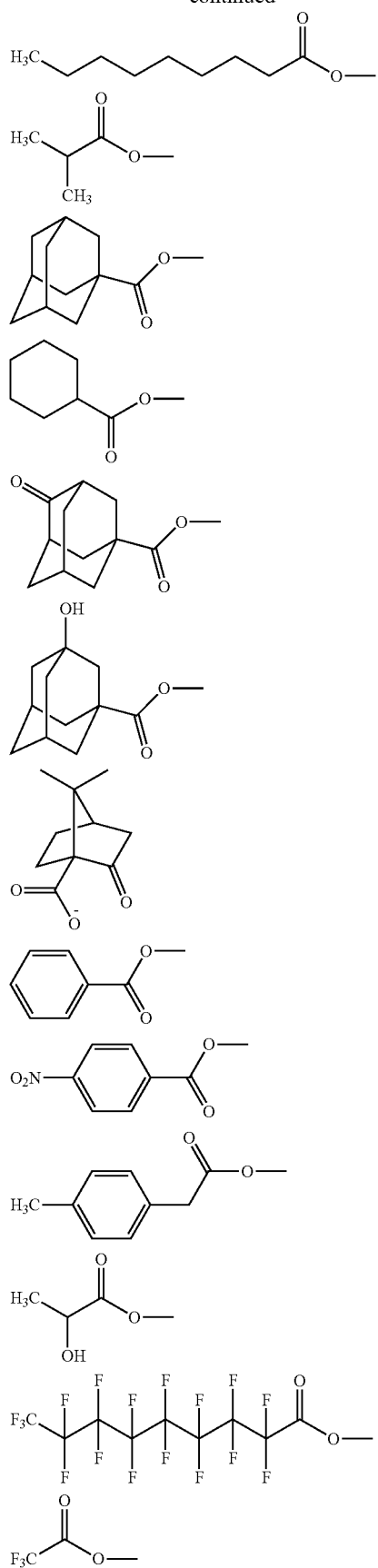
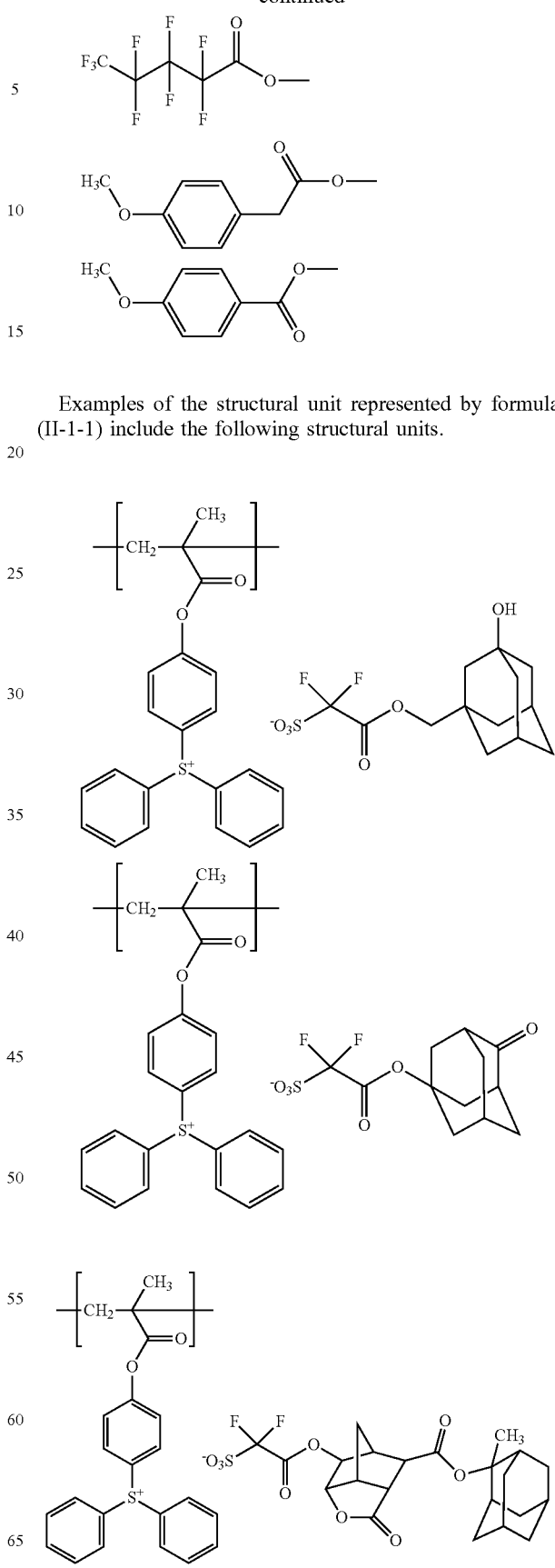
Examples of the structural unit represented by formula (II-1-1) include the following structural units.

-continued

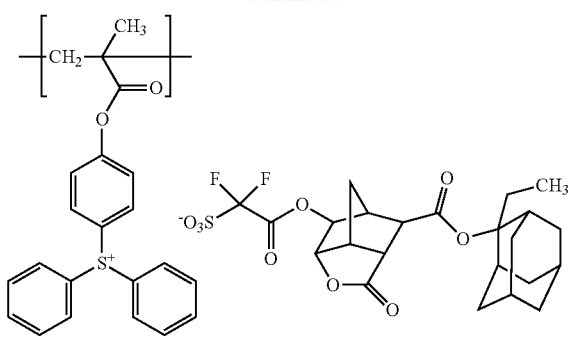

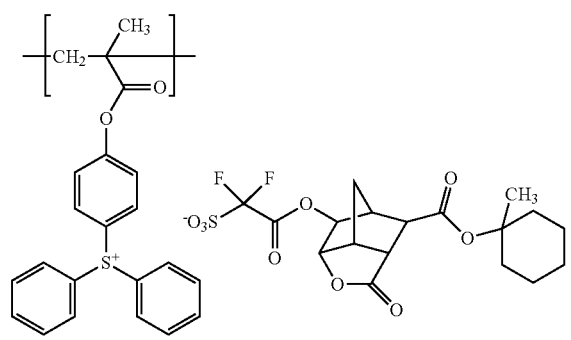

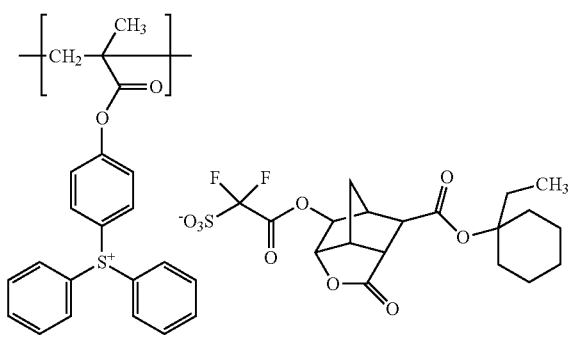

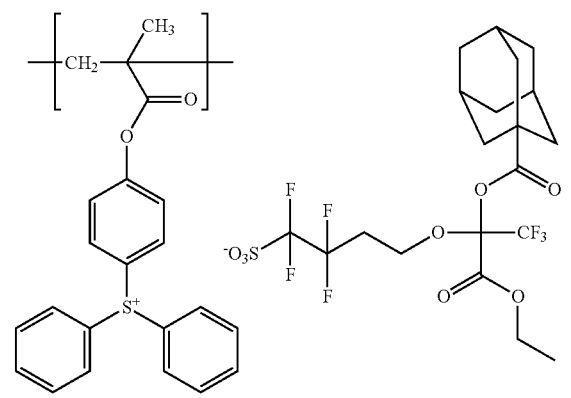

-continued

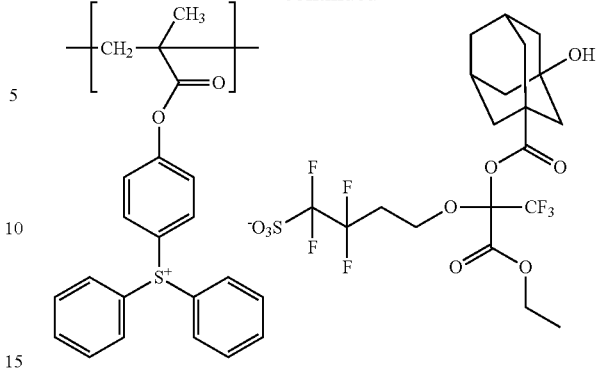

When the structural unit (II) is included in the resin (A), the content of the structural unit (II) is preferably 1 to 20 mol %, more preferably 2 to 15 mol %, and still more preferably 3 to 10 mol %, based on all structural units of the resin (A).

The resin (A) may include structural units other than the structural units mentioned above, and examples of such structural unit include structural units well-known in the art.

The resin (A) is preferably a resin composed of a structural unit (a1) and a structural unit (s), i.e. a copolymer of a monomer (a1) and a monomer (s).

The structural unit (a1) is preferably at least one selected from the group consisting of a structural unit (a1-0), structural unit (a1-0X), a structural unit (a1-1) and a structural unit (a1-2) (preferably the structural unit having a cyclohexyl group, and a cyclopentyl group), and more preferably at least two selected from the group consisting of a structural unit (a1-0), a structural unit (a1-0X), a structural unit (a1-1) and a structural unit (a1-2) (preferably the structural unit having a cyclohexyl group or a cyclopentyl group).

The structural unit (s) is preferably at least one selected from the group consisting of a structural unit (a2) and a structural unit (a3). The structural unit (a2) is preferably a structural unit represented by formula (a2-1). The structural unit (a3) is preferably at least one selected from the group consisting of a structural unit represented by formula (a3-1), a structural unit represented by formula (a3-2) and a structural unit represented by formula (a3-4).

The respective structural units constituting the resin (A) may be used alone, or two or more structural units may be used in combination. Using a monomer from which these structural units are derived, it is possible to produce by a known polymerization method (e.g., radical polymerization method). The content of the respective structural units included in the resin (A) can be adjusted according to the amount of the monomer used in the polymerization.

The weight-average molecular weight of the resin (A) is preferably 2,000 or more (more preferably 2,500 or more, and still more preferably 3,000 or more), and 50,000 or less (more preferably 30,000 or less, and still more preferably 15,000 or less). In the present specification, the weight-average molecular weight is a value determined by gel permeation chromatography under the conditions mentioned in Examples.

<Resin (X)>

The resin (X) is a resin including a structural unit having a fluorine atom. Examples of the resin (X) include a resin composed only of a structural unit (a4) and a resin composed of a structural unit (a4) and a structural unit (a5).

In the resin (X), the content of the structural unit (a4) is preferably 30 mol % or more, more preferably 40 mol % or more, and still more preferably 45 mol % or more, based on the total of all structural units of the resin (X).

Examples of the structural unit, which may be further included in the resin (X), include a structural unit (a1), a structural unit (a2), a structural unit (a3) and structural units derived from other known monomers. Particularly, the resin (X) is preferably a resin composed only of a structural unit (a4) and/or a structural unit (a5), and more preferably a resin composed only of a structural unit (a4).

The respective structural unit constituting the resin (X) may be used alone, or two or more structural units may be used in combination. Using a monomer from which these structural units are derived, it is possible to produce by a known polymerization method (e.g., radical polymerization method). The content of the respective structural units included in the resin (X) can be adjusted according to the amount of the monomer used in the polymerization.

The weight-average molecular weight of the resin (X) is preferably 6,000 or more (more preferably 7,000 or more), and 80,000 or less (more preferably 60,000 or less). The measurement means of the weight-average molecular weight of the resin (X) is the same as in the case of the resin (A).

When the resist composition includes the resin (X), the content is preferably 1 to 60 parts by mass, more preferably 1 to 50 parts by mass, still more preferably 1 to 40 parts by mass, particularly preferably 1 to 30 parts by mass, and particularly preferably 1 to 8 parts by mass, based on 100 parts by mass of the resin (A).

The total content of the resin (A) and the resin (X) in the resist composition is preferably 80% by mass or more and 99% by mass or less, and more preferably 90% by mass or more and 99% by mass or less, based on the solid component of the resist composition. The solid component of the resist composition and the content of the resin thereto can be measured by a known analysis means such as liquid chromatography or gas chromatography.

In the resist composition of the present invention, by using the resin (A) and the resin (X) in combination, defects of the resulting resist pattern can be reduced.

<Acid Generator (B)>

Either nonionic or ionic acid generator may be used as the acid generator (B). Examples of the nonionic acid generator include sulfonate esters (e.g., 2-nitrobenzyl ester, aromatic sulfonate, oxime sulfonate, N-sulfonyloxyimide, sulfonyloxyketone, diazonaphthoquinone 4-sulfonate), sulfones (e.g., disulfone, ketosulfone, sulfonyldiazomethane) and the like. Typical examples of the ionic acid generator include onium salts containing an onium cation (e.g., diazonium salt, phosphonium salt, sulfonium salt, iodonium salt). Examples of the anion of the onium salt include sulfonic acid anion, sulfonylimide anion, sulfonylmethide anion and the like.

Specific examples of the acid generator (B) include compounds generating an acid upon exposure to radiation mentioned in JP 63-26653 A, JP 55-164824 A, JP 62-69263 A, JP 63-146038 A, JP 63-163452 A, JP 62-153853 A, JP 63-146029 A, U.S. Pat. Nos. 3,779,778, 3,849,137, DE Patent No. 3914407 and EP Patent No. 126,712. Compounds produced by a known method may also be used. Two or more acid generators (B) may also be used in combination.

The acid generator (B) is preferably a fluorine-containing acid generator, and more preferably a salt represented by formula (B1) (hereinafter sometimes referred to as "acid generator (B1)"):

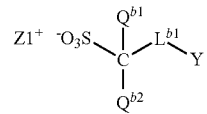

(B1)

wherein, in formula (B1), $Q^{b1}$ and $Q^{b2}$ each independently represent a fluorine atom or a perfluoroalkyl group having 1 to 6 carbon atoms, $L^{b1}$ represents a divalent saturated hydrocarbon group having 1 to 24 carbon atoms, —CH$_2$— included in the divalent saturated hydrocarbon group may be replaced by —O— or —CO—, and a hydrogen atom included in the divalent saturated hydrocarbon group may be substituted with a fluorine atom or a hydroxy group, Y represents a methyl group which may have a substituent or an alicyclic hydrocarbon group having 3 to 18 carbon atoms which may have a substituent, and —CH$_2$— included in the alicyclic hydrocarbon group may be replaced by —O—, —S(O)$_2$— or —CO—, and $Z1^+$ represents an organic cation.

Examples of the perfluoroalkyl group represented by $Q^{b1}$ and $Q^{b2}$ include a trifluoromethyl group, a perfluoroethyl group, a perfluoropropyl group, a perfluoroisopropyl group, a perfluorobutyl group, a perfluorosec-butyl group, a perfluorotert-butyl group, a perfluoropentyl group and a perfluorohexyl group.

Preferably, $Q^{b1}$ and $Q^{b2}$ are each independently a fluorine atom or trifluoromethyl group, and more preferably, both are fluorine atoms.

Examples of the divalent saturated hydrocarbon group in $L^{b1}$ include a linear alkanediyl group, a branched alkanediyl group, and a monocyclic or polycyclic divalent alicyclic saturated hydrocarbon group, or the divalent saturated hydrocarbon group may be a group formed by using two or more of these groups in combination.

Specific examples thereof include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group;

branched alkanediyl groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group and a 2-methylbutane-1,4-diyl group;

monocyclic divalent alicyclic saturated hydrocarbon groups which are cycloalkanediyl groups such as a cyclobutane-1,3-diyl group, a cyclopentane-1,3-diyl group, a cyclohexane-1,4-diyl group and a cyclooctane-1,5-diyl group; and polycyclic divalent alicyclic saturated hydrocarbon groups such as a norbornane-1,4-diyl group, a norbornane-2,5-diyl group, an adamantane-1,5-diyl group and an adamantane-2,6-diyl group.

The group in which —CH$_2$— included in the divalent saturated hydrocarbon group represented by $L^{b1}$ is replaced by —O— or —CO— includes, for example, a group represented by any one of formula (b1-1) to formula (b1-3). In groups represented by formula (b1-1) to formula (b1-3) and groups represented by formula (b1-4) to formula (b1-11) which are specific examples thereof, * and ** represent a bonding site and * represents a bonding site to —Y.

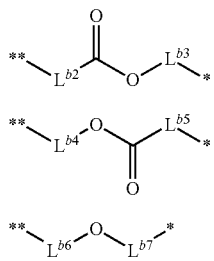

In formula (b1-1), $L^{b2}$ represents a single bond or a divalent saturated hydrocarbon group having 1 to 22 carbon atoms, and a hydrogen atom included in the saturated hydrocarbon group may be substituted with a fluorine atom, $L^{b3}$ represents a single bond or a divalent saturated hydrocarbon group having 1 to 22 carbon atoms, a hydrogen atom included in the saturated hydrocarbon group may be substituted with a fluorine atom or a hydroxy group, and —CH$_2$— included in the saturated hydrocarbon group may be replaced by —O— or —CO—, and the total number of carbon atoms of $L^{b2}$ and $L^{b3}$ is 22 or less.

In formula (b1-2), $L^{b4}$ represents a single bond or a divalent saturated hydrocarbon group having 1 to 22 carbon atoms, and a hydrogen atom included in the saturated hydrocarbon group may be substituted with a fluorine atom, $L^{b5}$ represents a single bond or a divalent saturated hydrocarbon group having 1 to 22 carbon atoms, a hydrogen atom included in the saturated hydrocarbon group may be substituted with a fluorine atom or a hydroxy group, and —CH$_2$— included in the saturated hydrocarbon group may be replaced by —O— or —CO—, and the total number of carbon atoms of $L^{b4}$ and $L^{b5}$ is 22 or less.

In formula (b1-3), $L^{b6}$ represents a single bond or a divalent saturated hydrocarbon group having 1 to 23 carbon atoms, and a hydrogen atom included in the saturated hydrocarbon group may be substituted with a fluorine atom or a hydroxy group, $L^{b7}$ represents a single bond or a divalent saturated hydrocarbon group having 1 to 23 carbon atoms, a hydrogen atom included in the saturated hydrocarbon group may be substituted with a fluorine atom or a hydroxy group, and —CH$_2$— included in the saturated hydrocarbon group may be replaced by —O— or —CO—, and the total number of carbon atoms of $L^{b6}$ and $L^{b7}$ is 23 or less.

In groups represented by formula (b1-1) to formula (b1-3), when —CH$_2$— included in the saturated hydrocarbon group is replaced by —O— or —CO—, the number of carbon atoms before replacement is taken as the number of carbon atoms of the saturated hydrocarbon group.

Examples of the divalent saturated hydrocarbon group include those which are the same as the divalent saturated hydrocarbon group of $L^{b1}$.

$L^{b2}$ is preferably a single bond.

$L^{b3}$ is preferably a divalent saturated hydrocarbon group having 1 to 4 carbon atoms.

$L^{b4}$ is preferably a divalent saturated hydrocarbon group having 1 to 8 carbon atoms, and a hydrogen atom included in the divalent saturated hydrocarbon group may be substituted with a fluorine atom.

$L^{b5}$ is preferably a single bond or a divalent saturated hydrocarbon group having 1 to 8 carbon atoms.

$L^{b6}$ is preferably a single bond or a divalent saturated hydrocarbon group having 1 to 4 carbon atoms, and a hydrogen atom included in the saturated hydrocarbon group may be substituted with a fluorine atom.

$L^{b7}$ is preferably a single bond or a divalent saturated hydrocarbon group having 1 to 18 carbon atoms, a hydrogen atom included in the saturated hydrocarbon group may be substituted with a fluorine atom or a hydroxy group, and —CH$_2$— included in the divalent saturated hydrocarbon group may be replaced by —O— or —CO—.

The group in which —CH$_2$— included in the divalent saturated hydrocarbon group represented by $L^{b1}$ is replaced by —O— or —CO— is preferably a group represented by formula (b1-1) or formula (b1-3).

Examples of the group represented by formula (b1-1) include groups represented by formula (b1-4) to formula (b1-8).

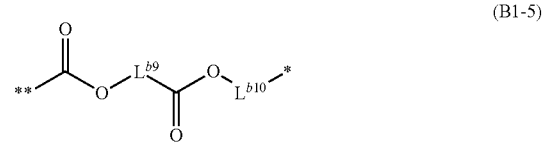

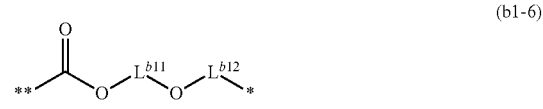

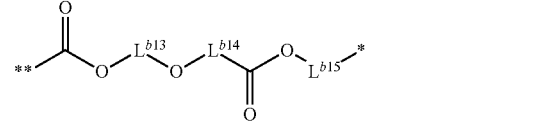

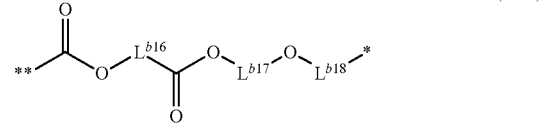

In formula (b1-4), $L^{b8}$ represents a single bond or a divalent saturated hydrocarbon group having 1 to 22 carbon atoms, and a hydrogen atom included in the saturated hydrocarbon group may be substituted with a fluorine atom or a hydroxy group.

In formula (b1-5), $L^{b9}$ represents a divalent saturated hydrocarbon group having 1 to 20 carbon atoms, and —CH$_2$— included in the divalent saturated hydrocarbon group may be replaced by —O— or —CO—, $L^{b10}$ represents a single bond or a divalent saturated hydrocarbon group having 1 to 19 carbon atoms, and a hydrogen atom included in the divalent saturated hydrocarbon group may be substituted with a fluorine atom or a hydroxy group, and the total number of carbon atoms of $L^{b9}$ and $L^{b10}$ is 20 or less.

In formula (b1-6), $L^{b11}$ represents a divalent saturated hydrocarbon group having 1 to 21 carbon atoms, $L^{b12}$ represents a single bond or a divalent saturated hydrocarbon group having 1 to 20 carbon atoms, and a hydrogen atom included in the divalent saturated hydrocarbon group may be substituted with a fluorine atom or a hydroxy group, and the total number of carbon atoms of $L^{b11}$ and $L^{b12}$ is 21 or less.

In formula (b1-7), $L^{b13}$ represents a divalent saturated hydrocarbon group having 1 to 19 carbon atoms, $L^{b14}$ represents a single bond or a divalent saturated hydrocarbon group having 1 to 18 carbon atoms, and —CH$_2$— included in the divalent saturated hydrocarbon group may be replaced by —O— or —CO—, $L^{b15}$ represents a single bond or a divalent saturated hydrocarbon group having 1 to 18 carbon atoms, and a hydrogen atom included in the divalent saturated hydrocarbon group may be substituted with a fluorine atom or a hydroxy group, and the total number of carbon atoms of $L^{b13}$ to $L^{b15}$ is 19 or less.

In formula (b1-8), $L^{b16}$ represents a divalent saturated hydrocarbon group having 1 to 18 carbon atoms, and —CH$_2$— included in the divalent saturated hydrocarbon group may be replaced by —O— or —CO—, $L^{b17}$ represents a divalent saturated hydrocarbon group having 1 to 18 carbon atoms, $L^{b18}$ represents a single bond or a divalent saturated hydrocarbon group having 1 to 17 carbon atoms, and a hydrogen atom included in the divalent saturated hydrocarbon group may be substituted with a fluorine atom or a hydroxy group, and the total number of carbon atoms of $L^{b16}$ to $L^{b18}$ is 19 or less.

$L^{b8}$ is preferably a divalent saturated hydrocarbon group having 1 to 4 carbon atoms.

$L^{b9}$ is preferably a divalent saturated hydrocarbon group having 1 to 8 carbon atoms.

$L^{b10}$ is preferably a single bond or a divalent saturated hydrocarbon group having 1 to 19 carbon atoms, and more preferably a single bond or a divalent saturated hydrocarbon group having 1 to 8 carbon atoms.

$L^{b11}$ is preferably a divalent saturated hydrocarbon group having 1 to 8 carbon atoms.

$L^{b12}$ is preferably a single bond or a divalent saturated hydrocarbon group having 1 to 8 carbon atoms.

$L^{b13}$ is preferably a divalent saturated hydrocarbon group having 1 to 12 carbon atoms.

$L^{b14}$ is preferably a single bond or a divalent saturated hydrocarbon group having 1 to 6 carbon atoms.

$L^{b15}$ is preferably a single bond or a divalent saturated hydrocarbon group having 1 to 18 carbon atoms, and more preferably a single bond or a divalent saturated hydrocarbon group having 1 to 8 carbon atoms.

$L^{b16}$ is preferably a divalent saturated hydrocarbon group having 1 to 12 carbon atoms.

$L^{b17}$ is preferably a divalent saturated hydrocarbon group having 1 to 6 carbon atoms.

$L^{b18}$ is preferably a single bond or a divalent saturated hydrocarbon group having 1 to 17 carbon atoms, and more preferably a single bond or a divalent saturated hydrocarbon group having 1 to 4 carbon atoms.

Examples of the group represented by formula (b1-3) include groups represented by formula (b1-9) to formula (b1-11).

(b1-9)

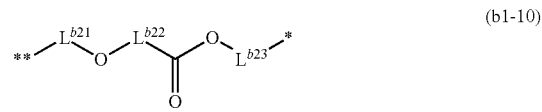

(b1-10)

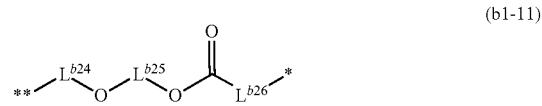

(b1-11)

In formula (b1-9), $L^{b19}$ represents a single bond or a divalent saturated hydrocarbon group having 1 to 23 carbon atoms, and a hydrogen atom included in the saturated hydrocarbon group may be substituted with a fluorine atom, $L^{b20}$ represents a single bond or a divalent saturated hydrocarbon group having 1 to 23 carbon atoms, and a hydrogen atom included in the saturated hydrocarbon group may be substituted with a fluorine atom, a hydroxy group or an alkylcarbonyloxy group, —CH$_2$— included in the alkylcarbonyloxy group may be replaced by —O— or —CO—, and a hydrogen atom included in the alkylcarbonyloxy group may be substituted with a hydroxy group, and the total number of carbon atoms of $L^{b19}$ and $L^{b20}$ is 23 or less.

In formula (b1-10), $L^{b21}$ represents a single bond or a divalent saturated hydrocarbon group having 1 to 21 carbon atoms, and a hydrogen atom included in the saturated hydrocarbon group may be substituted with a fluorine atom, $L^{b22}$ represents a single bond or a divalent saturated hydrocarbon group having 1 to 21 carbon atoms, $L^{b23}$ represents a single bond or a divalent saturated hydrocarbon group having 1 to 21 carbon atoms, and a hydrogen atom included in the saturated hydrocarbon group may be substituted with a fluorine atom, a hydroxy group or an alkylcarbonyloxy group, —CH$_2$— included in the alkylcarbonyloxy group may be replaced by —O— or —CO—, and a hydrogen atom included in the alkylcarbonyloxy group may be substituted with a hydroxy group, and the total number of carbon atoms of $L^{b21}$, $L^{b22}$ and $L^{b23}$ is 21 or less.

In formula (b1-11), $L^{b24}$ represents a single bond or a divalent saturated hydrocarbon group having 1 to 20 carbon atoms, and a hydrogen atom included in the saturated hydrocarbon group may be substituted with a fluorine atom, $L^{b25}$ represents a divalent saturated hydrocarbon group having 1 to 21 carbon atoms, $L^{b26}$ represents a single bond or a divalent saturated hydrocarbon group having 1 to 20 carbon atoms, a hydrogen atom included in the saturated hydrocarbon group may be substituted with a fluorine atom, a hydroxy group or an alkylcarbonyloxy group, —CH$_2$— included in the alkylcarbonyloxy group may be replaced by —O— or —CO—, and a hydrogen atom included in the alkylcarbonyloxy group may be substituted with a hydroxy group, and the total number of carbon atoms of $L^{b24}$, $L^{b25}$ and $L^{b26}$ is 21 or less.

In groups represented by formula (b1-9) to formula (b1-11), when a hydrogen atom included in the saturated hydrocarbon group is substituted with an alkylcarbonyloxy group, the number of carbon atoms before substitution is taken as the number of carbon atoms of the saturated hydrocarbon group.

Examples of the alkylcarbonyloxy group include an acetyloxy group, a propionyloxy group, a butyryloxy group, a cyclohexylcarbonyloxy group, an adamantylcarbonyloxy group and the like.

Examples of the group represented by formula (b1-4) include the followings:

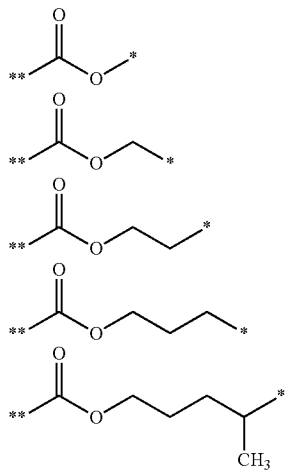

wherein * and ** represent a bonding site, and * represents a bonding site to Y.

Examples of the group represented by formula (b1-5) include the followings:

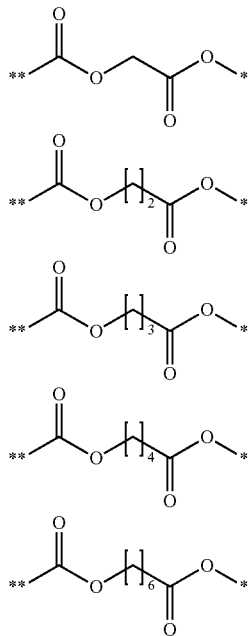

-continued

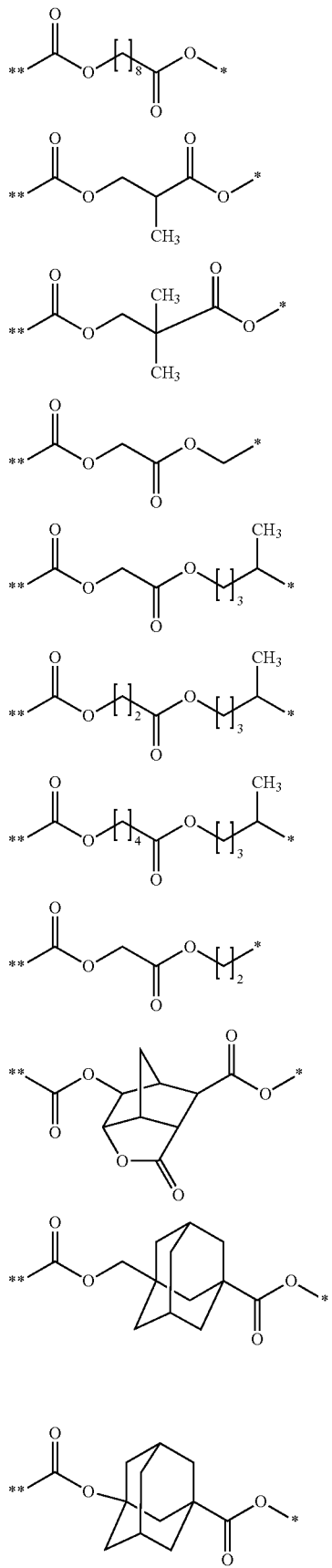

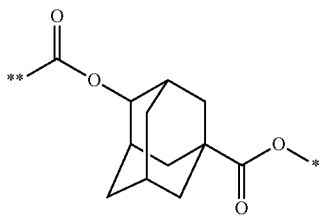
wherein * and ** represent a bonding site, and * represents a bonding site to Y.
Examples of the group represented by formula (b1-6) include the followings:
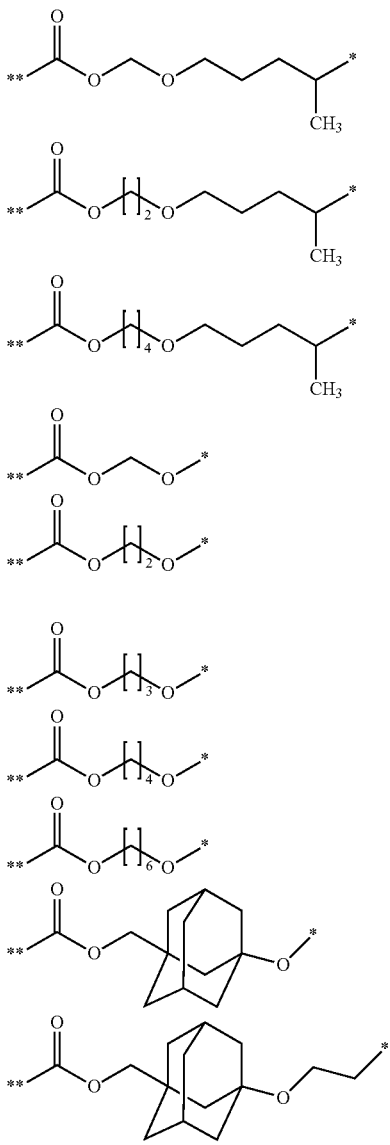
wherein * and ** represent a bonding site, and * represents a bonding site to Y.
Examples of the group represented by formula (b1-7) include the followings:
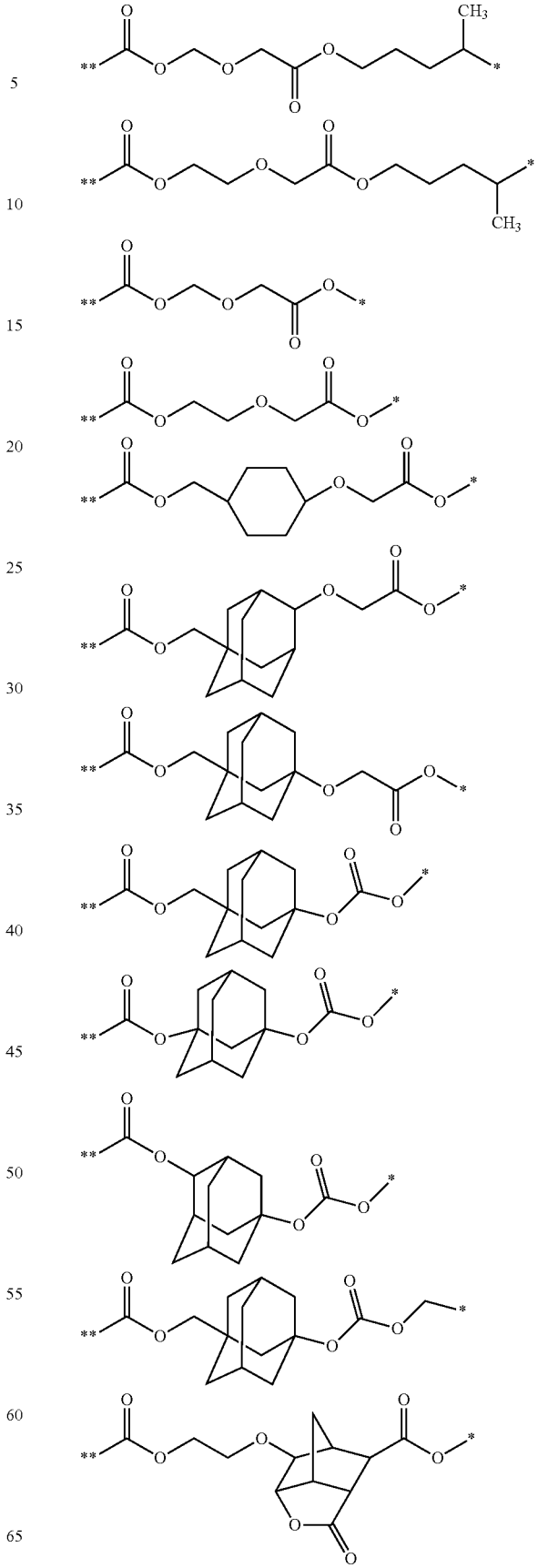

-continued

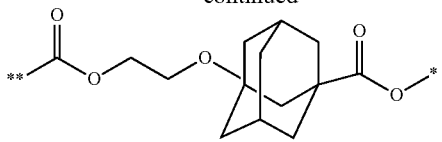

wherein * and ** represent a bonding site, and * represents a bonding site to Y.

Examples of the group represented by formula (b1-8) include the followings:

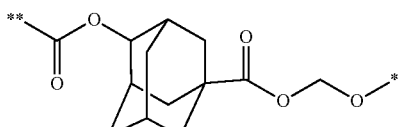

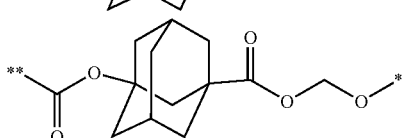

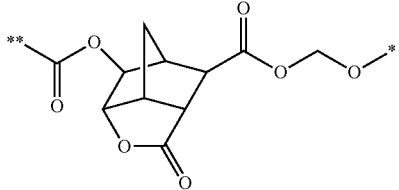

wherein * and ** represent a bonding site, and * represents a bonding site to Y.

Examples of the group represented by formula (b1-2) include the followings:

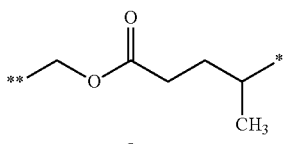

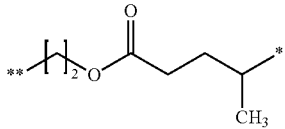

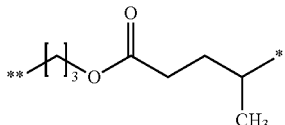

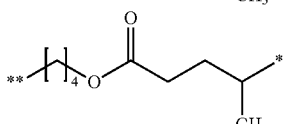

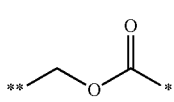

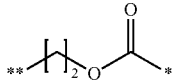

-continued

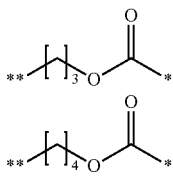

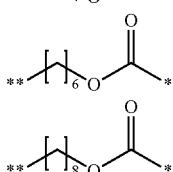

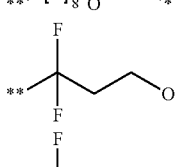

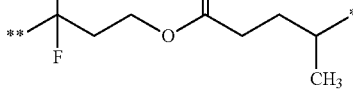

wherein * and ** represent a bonding site, and * represents a bonding site to Y.

Examples of the group represented by formula (b1-9) include the followings:

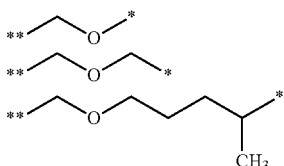

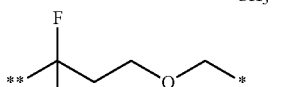

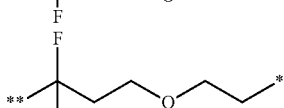

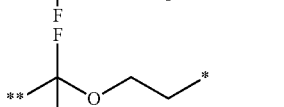

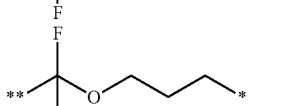

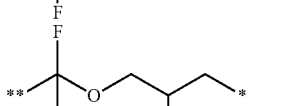

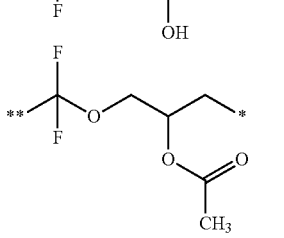

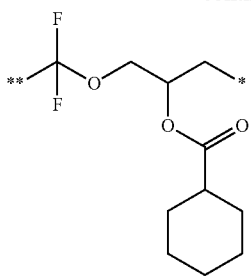
wherein * and ** represent a bonding site, and * represents a bonding site to Y.
Examples of the group represented by formula (b1-10) include the followings:
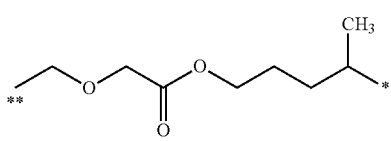
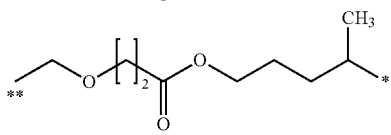
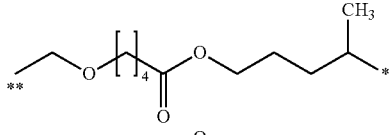
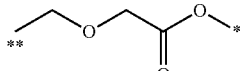
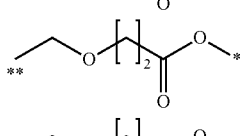
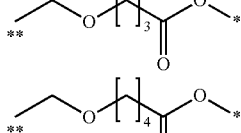
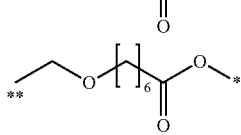
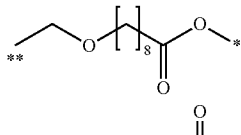
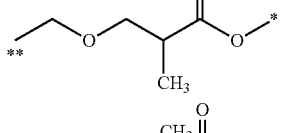
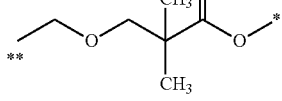
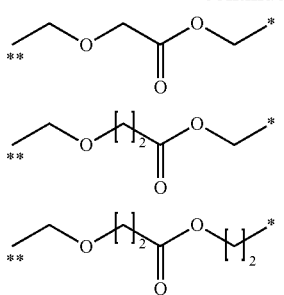
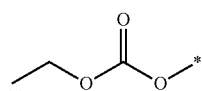
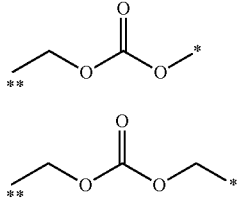
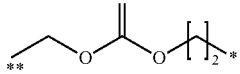
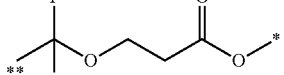
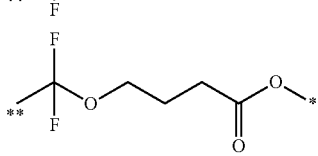
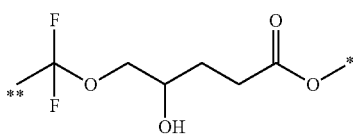
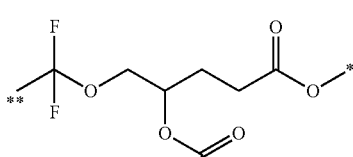
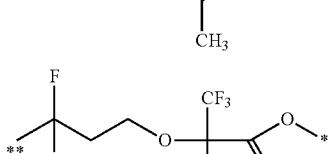
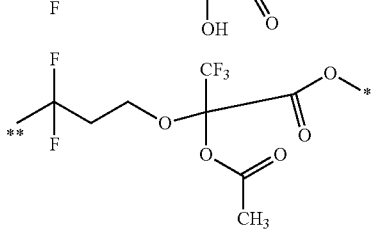

-continued
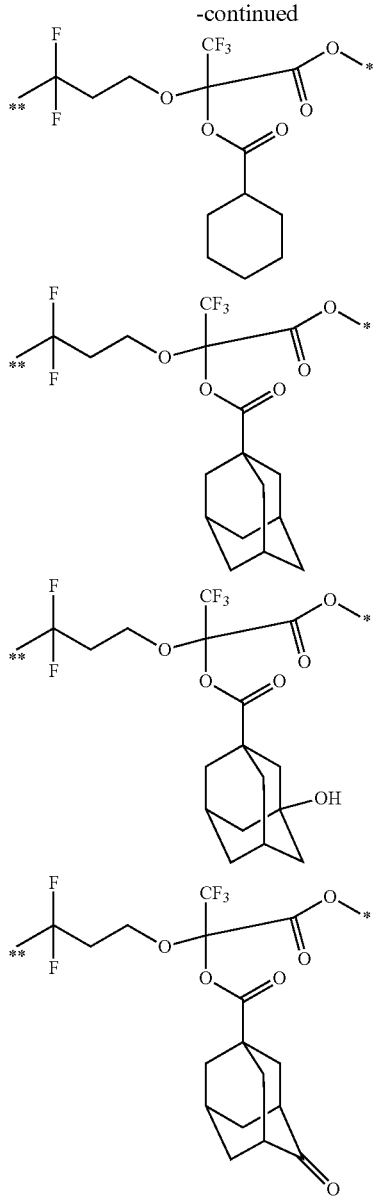
wherein * and ** represent a bonding site, and * represents a bonding site to Y.
Examples of the group represented by formula (b1-11) include the followings:
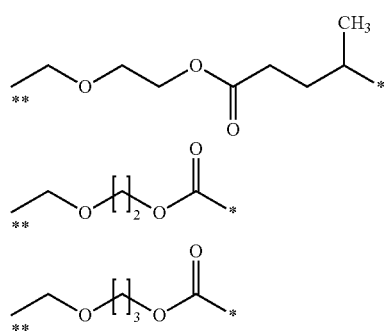
-continued
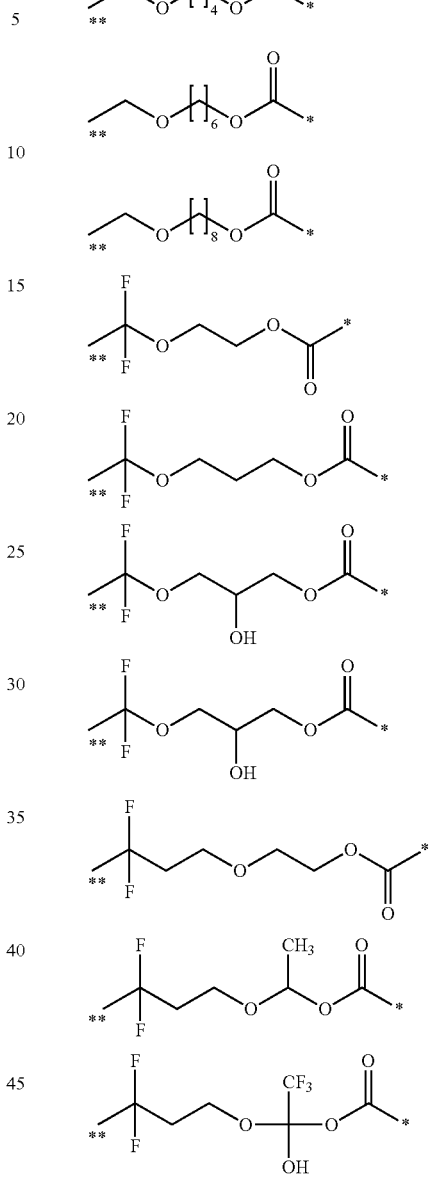
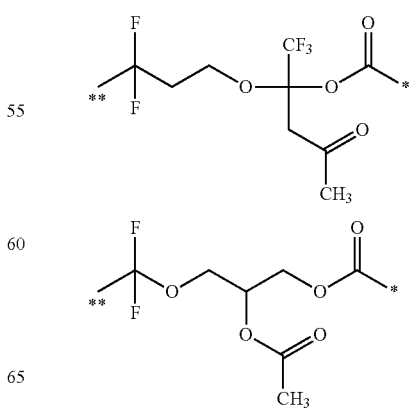

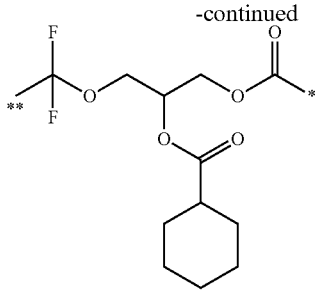

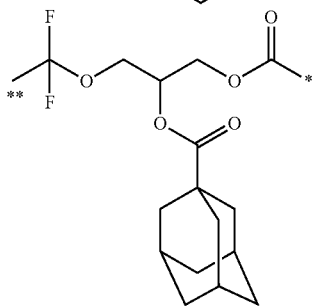

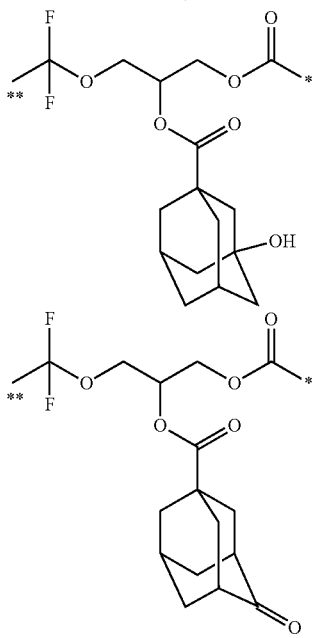

wherein * and ** represent a bonding site, and * represents a bonding site to Y.

Examples of the alicyclic hydrocarbon group represented by Y include groups represented by formula (Y1) to formula (Y11) and formula (Y36) to formula (Y38).

When —CH$_2$— included in the alicyclic hydrocarbon group represented by Y is replaced by —O—, —S(O)$_2$— or —CO—, the number may be 1, or 2 or more. Examples of such group include groups represented by formula (Y12) to formula (Y35) and formula (Y39) to formula (Y41).

 (Y1)

 (Y2)

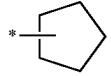 (Y3)

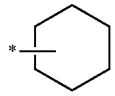 (Y4)

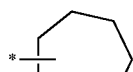 (Y5)

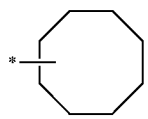 (Y6)

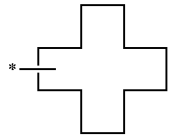 (Y7)

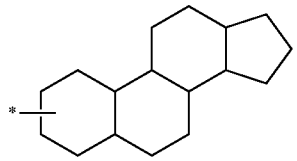 (Y8)

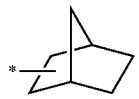 (Y9)

 (Y10)

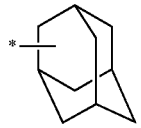 (Y11)

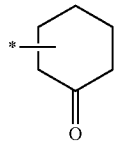 (Y12)

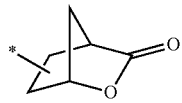 (Y13)

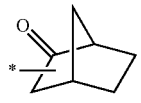 (Y14)

-continued
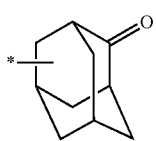 (Y15)
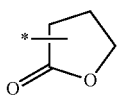 (Y16)
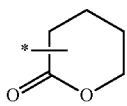 (Y17)
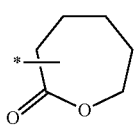 (Y18)
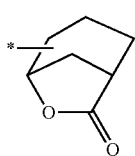 (Y19)
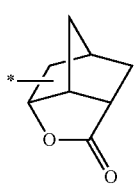 (Y20)
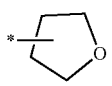 (Y21)
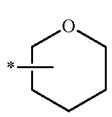 (Y22)
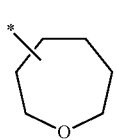 (Y23)
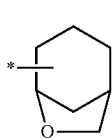 (Y24)
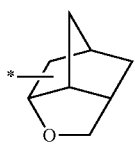 (Y25)
-continued
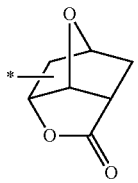 (Y26)
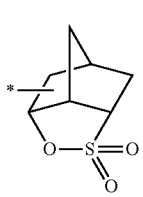 (Y27)
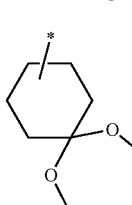 (Y28)
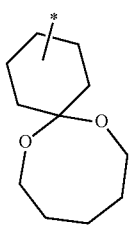 (Y29)
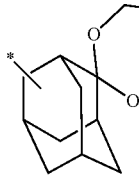 (Y30)
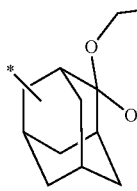 (Y31)
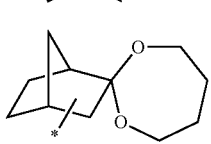 (Y32)
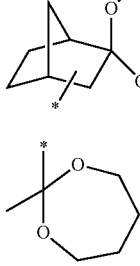 (Y33)
(Y34)

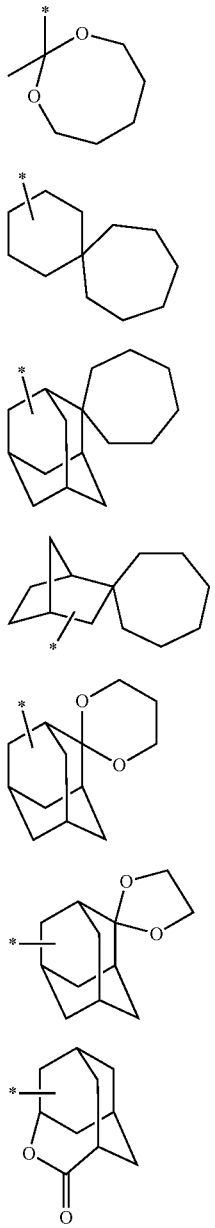

(Y35)
(Y36)
(Y37)
(Y38)
(Y39)
(Y40)
(Y41)

The alicyclic hydrocarbon group represented by Y is preferably a group represented by any one of formula (Y1) to formula (Y20), formula (Y26), formula (Y27), formula (Y30), formula (Y31) and formula (Y39) to formula (Y41), more preferably a group represented by formula (Y11), formula (Y15), formula (Y16), formula (Y20), formula (Y26), formula (Y27), formula (Y30) to formula (Y31), or formula (Y39) or formula (Y40), and still more preferably a group represented by formula (Y11), formula (Y15), formula (Y20), formula (Y30), formula (Y39) or formula (Y40).

When the alicyclic hydrocarbon group represented by Y is a spiro ring including an oxygen atom, such as formula (Y28) to formula (Y35) and formula (Y39) or formula (Y40), the alkanediyl group between two oxygen atoms preferably includes one or more fluorine atoms. Among alkanediyl groups included in a ketal structure, it is preferred that a methylene group adjacent to the oxygen atom is not substituted with a fluorine atom.

Examples of the substituent of the methyl group represented by Y include a halogen atom, a hydroxy group, an alicyclic hydrocarbon group having 3 to 16 carbon atoms, an aromatic hydrocarbon group having 6 to 18 carbon atoms, a glycidyloxy group, a —$(CH_2)_{ja}$—CO—O—$R^{b1}$ group or a —$(CH_2)_{ja}$—O—CO—$R^{b1}$ group (wherein $R^{b1}$ represents an alkyl group having 1 to 16 carbon atoms, an alicyclic hydrocarbon group having 3 to 16 carbon atoms, an aromatic hydrocarbon group having 6 to 18 carbon atoms or groups obtained by combining these groups, ja represents an integer of 0 to 4, and —$CH_2$— included in the alkyl group having 1 to 16 carbon atoms and the alicyclic hydrocarbon group having 3 to 16 carbon atoms may be replaced by —O—, —$SO_2$— or —CO—) and the like.

Examples of the substituent of the alicyclic hydrocarbon group represented by Y include a halogen atom, a hydroxy group, an alkyl group having 1 to 12 carbon atoms which may be replaced by a hydroxy group, an alicyclic hydrocarbon group having 3 to 16 carbon atoms, an alkoxy group having 1 to 12 carbon atoms, an aromatic hydrocarbon group having 6 to 18 carbon atoms, an aralkyl group having 7 to 21 carbon atoms, an alkylcarbonyl group having 2 to 4 carbon atoms, a glycidyloxy group, a —$(CH_2)_{ja}$—CO—O—$R^{b1}$ group or —$(CH_2)_{ja}$—O—CO—$R^{b1}$ group (wherein $R^{b1}$ represents an alkyl group having 1 to 16 carbon atoms, an alicyclic hydrocarbon group having 3 to 16 carbon atoms, an aromatic hydrocarbon group having 6 to 18 carbon atoms or groups obtained by combining these groups, ja represents an integer of 0 to 4, and —$CH_2$— included in the alkyl group having 1 to 16 carbon atoms and the alicyclic hydrocarbon group having 3 to 16 carbon atoms may be replaced by —O—, —$S(O)_2$— or —CO—) and the like.

Examples of the halogen atom include a fluorine atom, a chlorine atom, a bromine atom and an iodine atom.

The alicyclic hydrocarbon group includes, for example, a cyclopentyl group, a cyclohexyl group, a cycloheptyl group, a cyclooctyl group, a norbornyl group, an adamantyl group and the like.

The alicyclic hydrocarbon group may have a chain hydrocarbon group, and examples thereof include a methylcyclohexyl group, a dimethylcyclohexyl group and the like.

The aromatic hydrocarbon group includes, for example, aryl groups such as a phenyl group, a biphenylyl group, a naphthyl group, an anthryl group, and a phenanthryl group.

The aromatic hydrocarbon group may have a chain hydrocarbon group or an alicyclic hydrocarbon group and examples thereof include an aromatic hydrocarbon group having a chain hydrocarbon group having 1 to 18 carbon atoms (a tolyl group, a xylyl group, a cumenyl group, a mesityl group, a p-ethylphenyl group, a p-tert-butylphenyl group, a 2,6-diethylphenyl group, a 2-methyl-6-ethylphenyl group, etc.) and an aromatic hydrocarbon group having alicyclic hydrocarbon group having 3 to 18 carbon atoms (a p-cyclohexylphenyl group, a p-adamantylphenyl group, etc.).

The alkyl group includes, for example, a methyl group, an ethyl group, a propyl group, an isopropyl group, a butyl group, a sec-butyl group, a tert-butyl group, a pentyl group, a hexyl group, a heptyl group, a 2-ethylhexyl group, an octyl group, a nonyl group, a decyl group, an undecyl group, a dodecyl group and the like.

Examples of the alkyl group substituted with a hydroxy group include hydroxyalkyl groups such as a hydroxymethyl group and a hydroxyethyl group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the aralkyl group include a benzyl group, a phenethyl group, a phenylpropyl group, a naphthylmethyl group and a naphthylethyl group.

The alkylcarbonyl group includes, for example, an acetyl group, a propionyl group and a butyryl group.

Examples of Y include the followings.

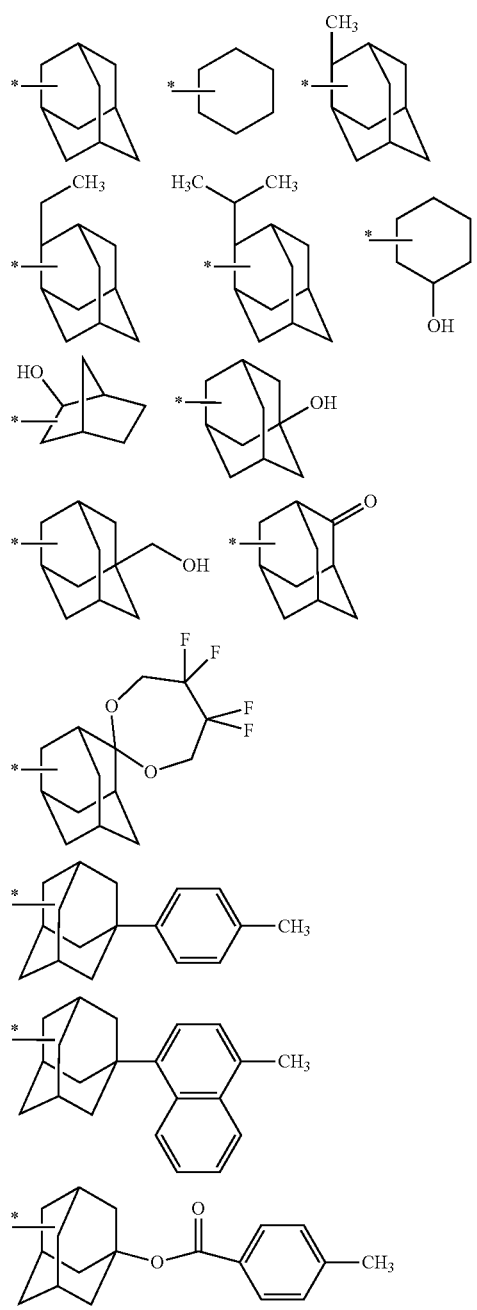

-continued

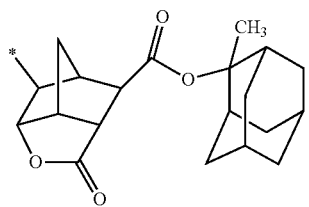

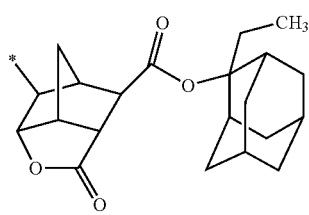

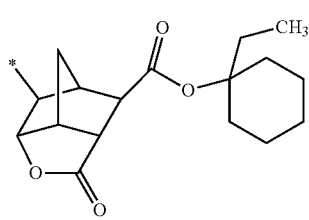

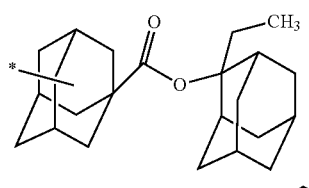

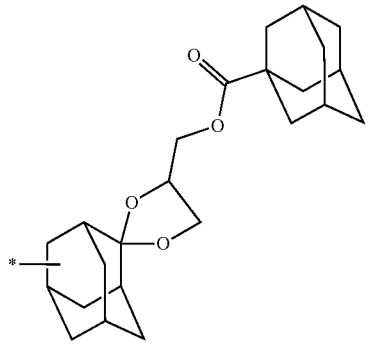

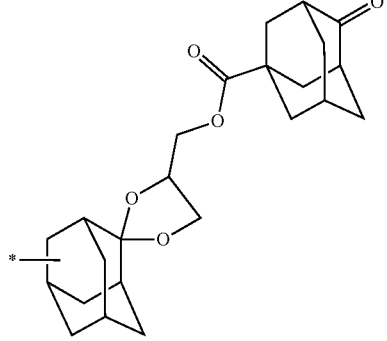

129
-continued
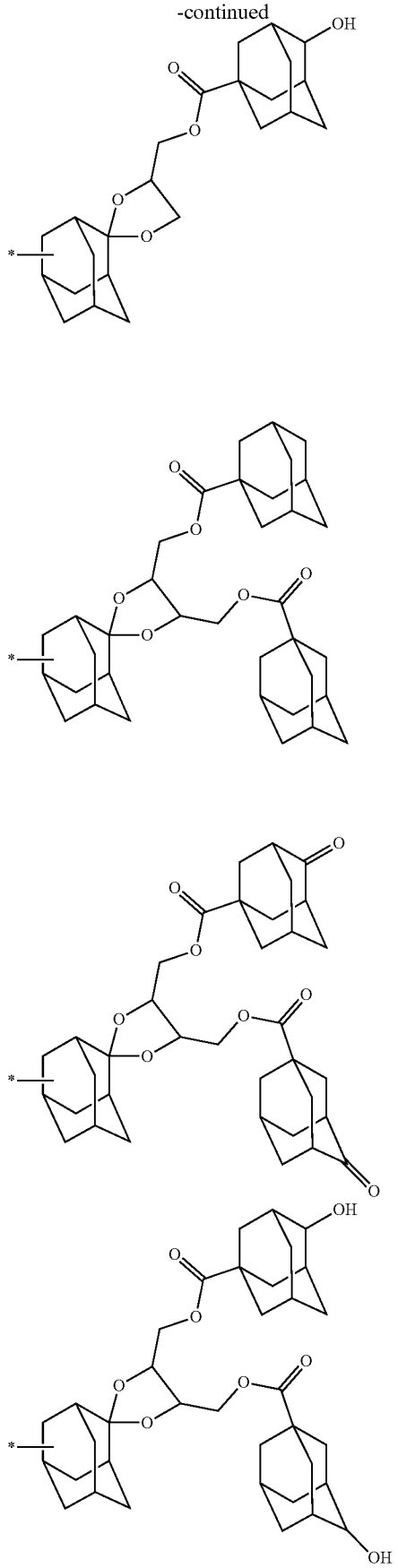
130
-continued
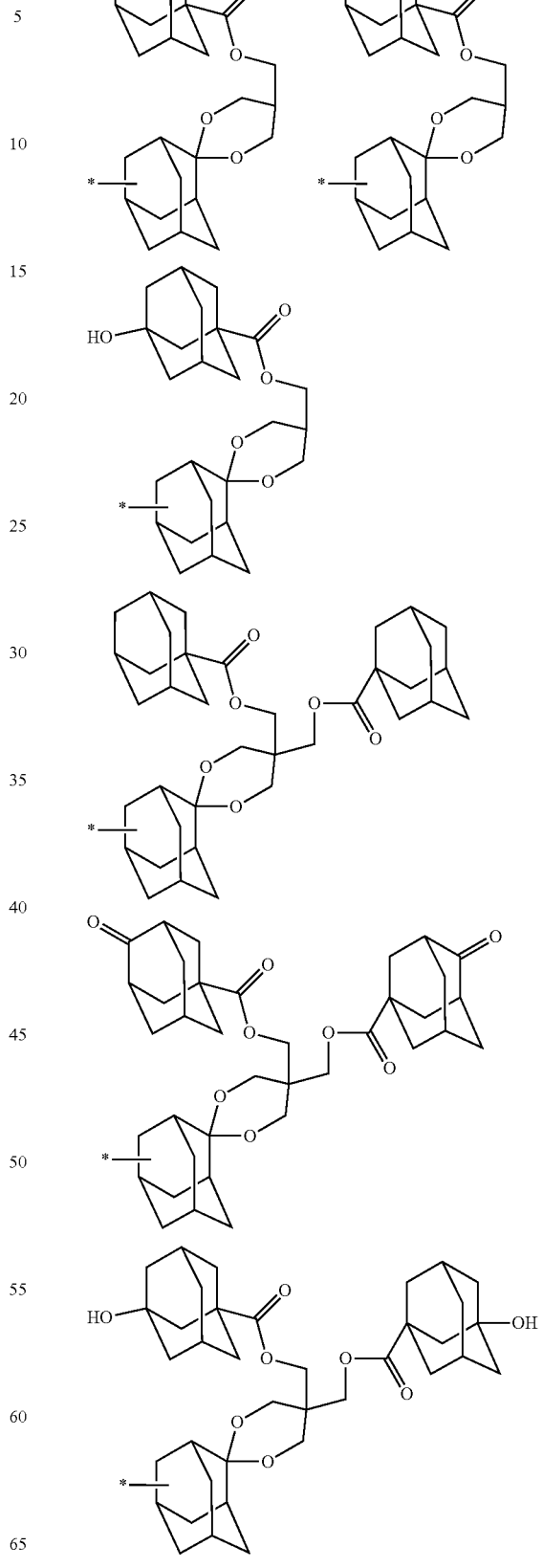

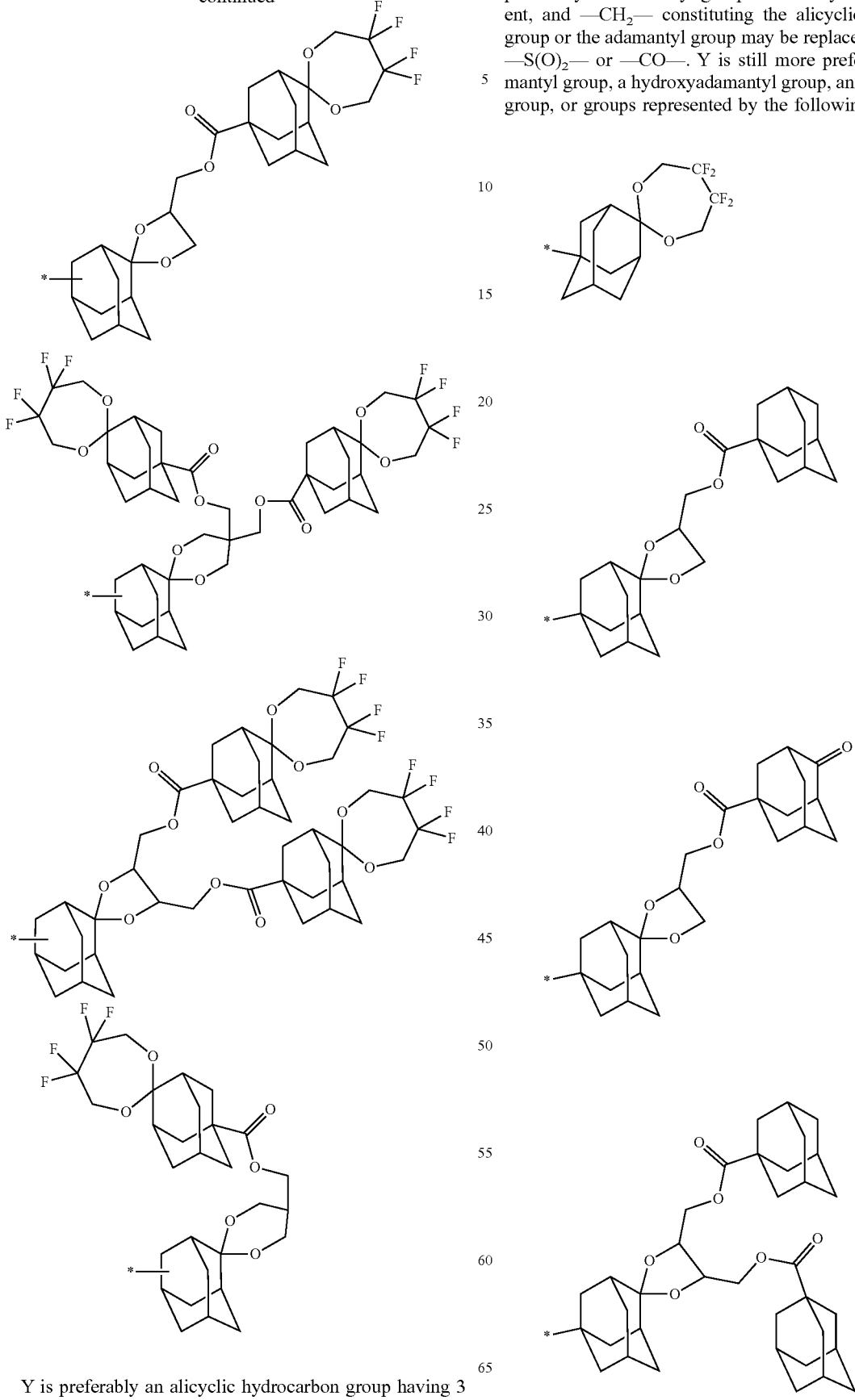

preferably an adamantyl group which may have a substituent, and —CH$_2$— constituting the alicyclic hydrocarbon group or the adamantyl group may be replaced by —CO—, —S(O)$_2$— or —CO—. Y is still more preferably an adamantyl group, a hydroxyadamantyl group, an oxoadamantyl group, or groups represented by the followings.

Y is preferably an alicyclic hydrocarbon group having 3 to 18 carbon atoms which may have a substituent, more

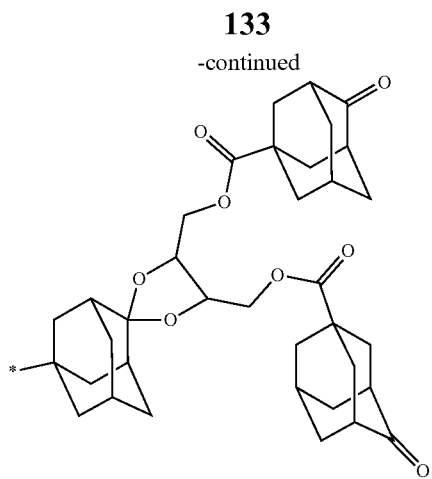
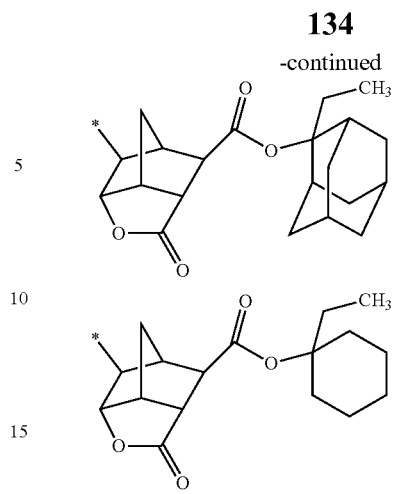
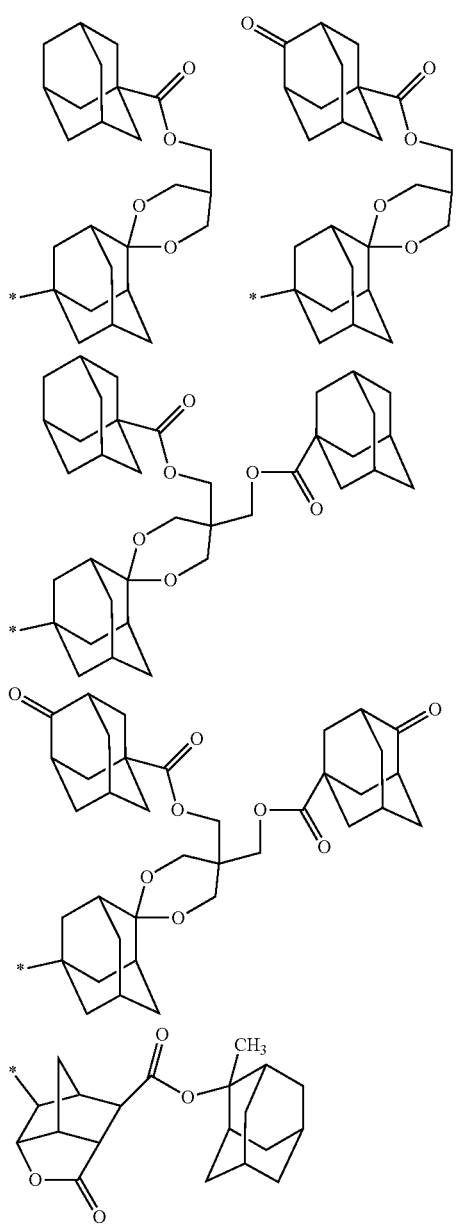

The sulfonic acid anion in the salt represented by formula (B1) is preferably anions represented by formula (B1-A-1) to formula (B1-A-55) [hereinafter sometimes referred to as "anion (B1-A-1)" according to the number of formula], and more preferably an anion represented by any one of formula (B1-A-1) to formula (B1-A-4), formula (B1-A-9), formula (B1-A-10), formula (B1-A-24) to formula (B1-A-33), formula (B1-A-36) to formula (B1-A-40) and formula (B1-A-47) to formula (B1-A-55).

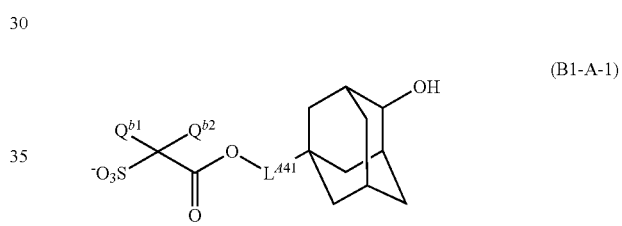

(B1-A-1)

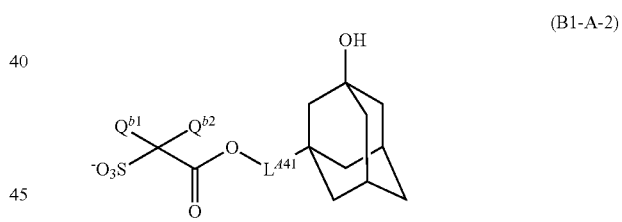

(B1-A-2)

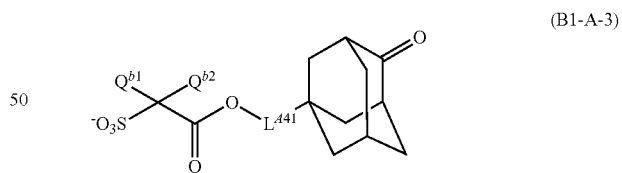

(B1-A-3)

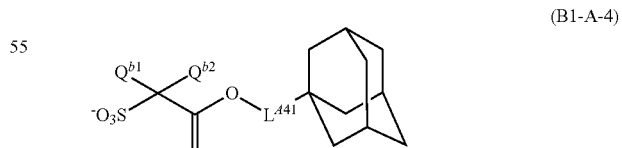

(B1-A-4)

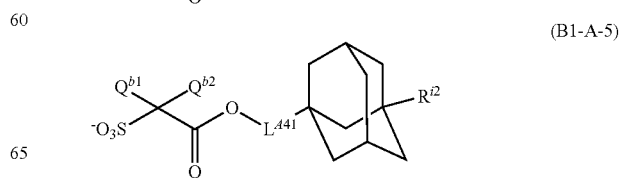

(B1-A-5)

(B1-A-6)
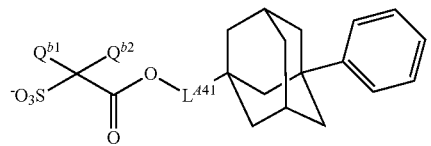
(B1-A-7)
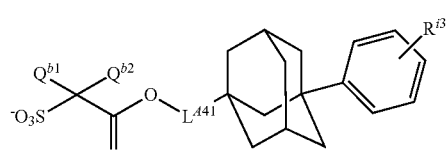
(B1-A-8)
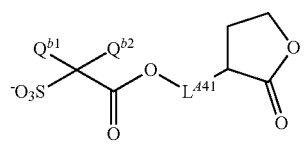
(B1-A-9)
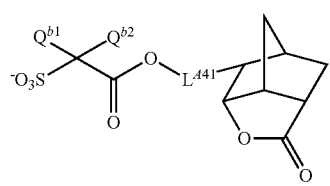
(B1-A-10)
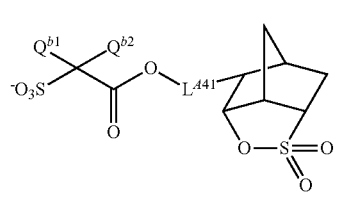
(B1-A-11)
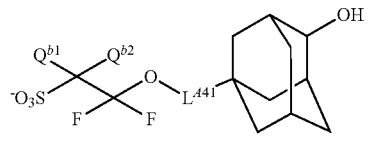
(B1-A-12)
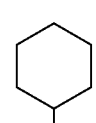
(B1-A-13)
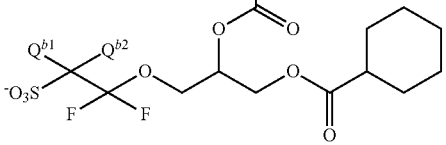
(B1-A-14)
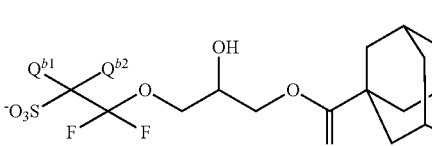
(B1-A-15)
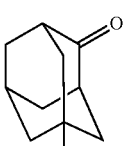
(B1-A-16)
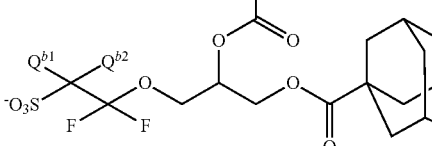
(B1-A-17)
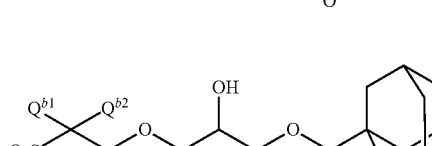
(B1-A-18)
(B1-A-19)
(B1-A-20)
(B1-A-21)

(B1-A-22) 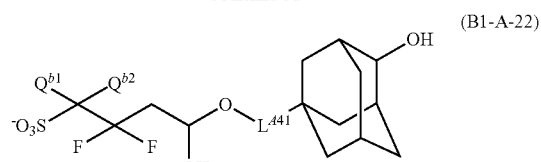
(B1-A-23) 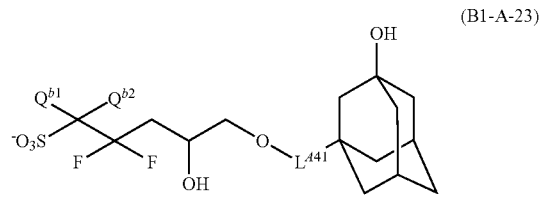
(B1-A-24) 
(B1-A-25) 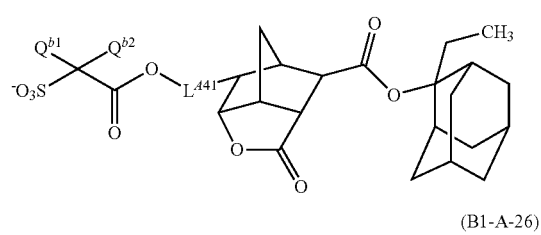
(B1-A-26) 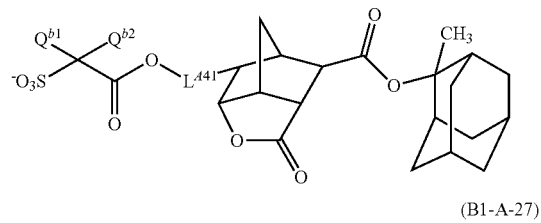
(B1-A-27) 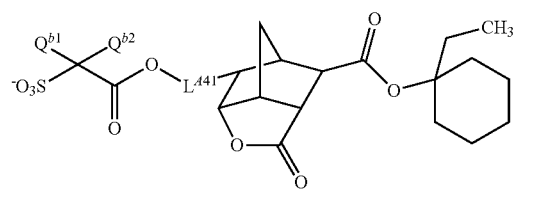
(B1-A-28) 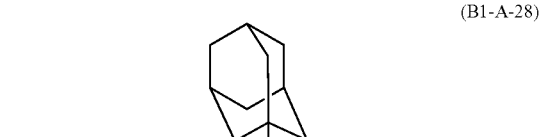
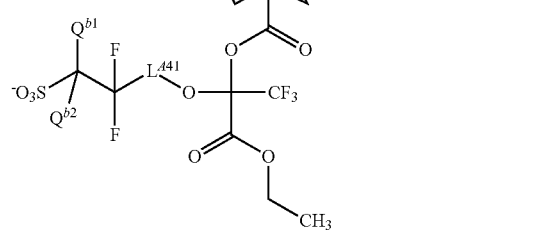
(B1-A-29) 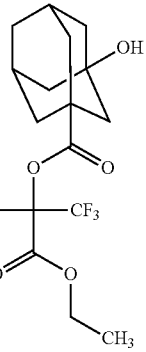
(B1-A-30) 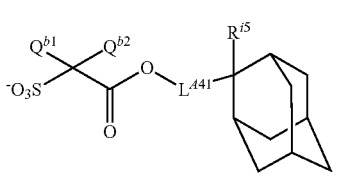
(B1-A-31) 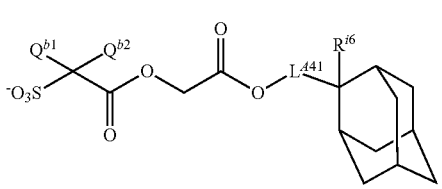
(B1-A-32) 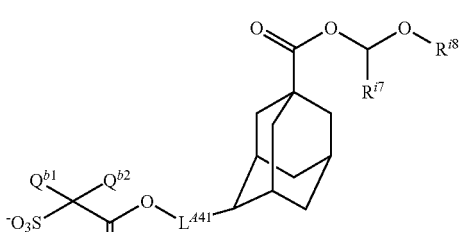
(B1-A-33) 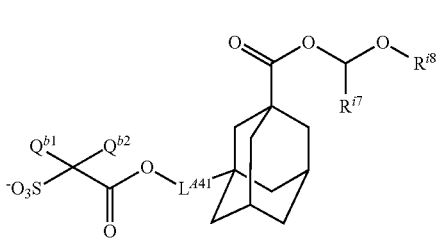
(B1-A-34) 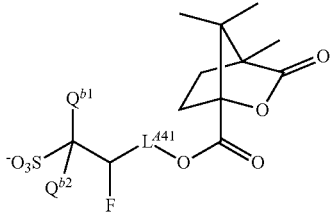

(B1-A-35) (B1-A-36) (B1-A-37) (B1-A-38) (B1-A-39) (B1-A-40) (B1-A-41) (B1-A-42) (B1-A-43) (B1-A-44) (B1-A-45) (B1-A-46) (B1-A-47) (B1-A-48)

-continued (B1-A-49)
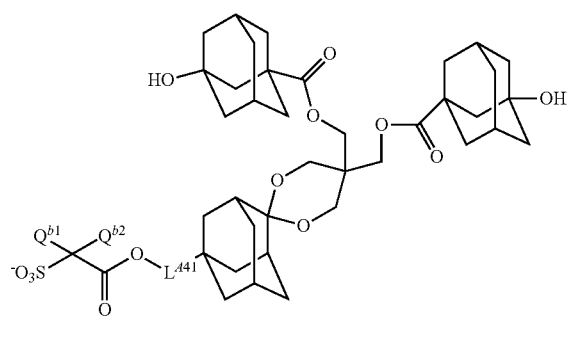

(B1-A-50)
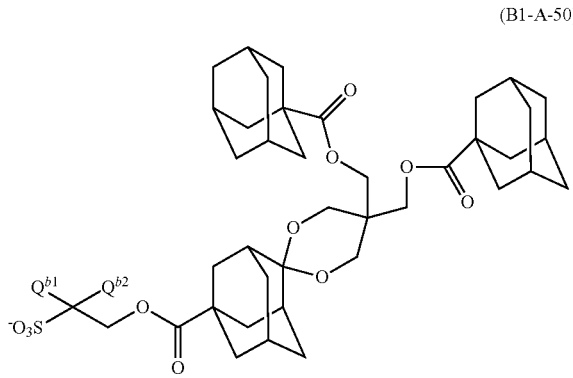

(B1-A-51)
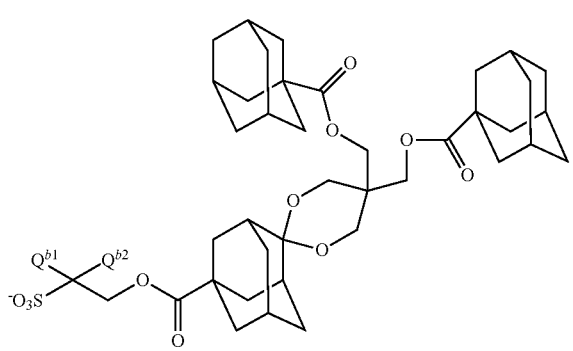

(B1-A-52)
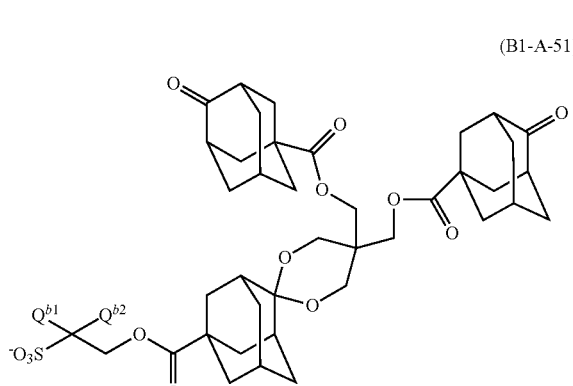

-continued (B1-A-53)
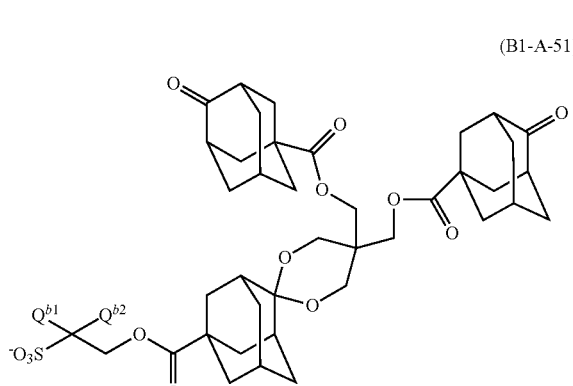

(B1-A-54)
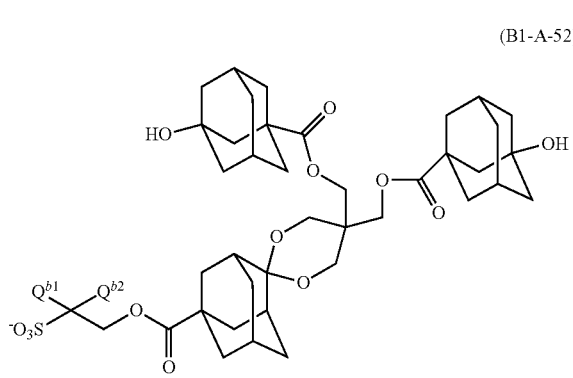

(B1-A-55)
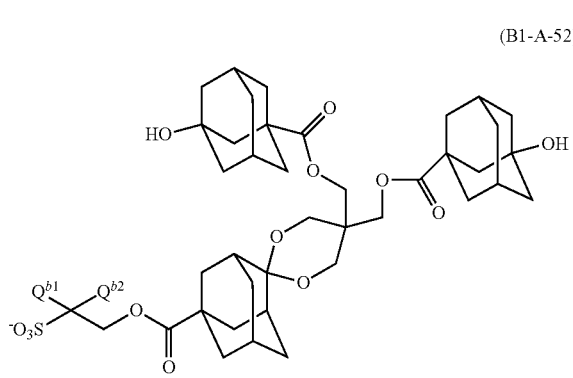

$R^{12}$ to $R^{17}$ each independently represent, for example, an alkyl group having 1 to 4 carbon atoms, and preferably a methyl group or an ethyl group. $R^{18}$ is, for example, an aliphatic hydrocarbon group having 1 to 12 carbon atoms, preferably an alkyl group having 1 to 4 carbon atoms, an alicyclic hydrocarbon group having 5 to 12 carbon atoms or groups formed by combining these groups, and more preferably a methyl group, an ethyl group, a cyclohexyl group or an adamantyl group. $LA^{41}$ is a single bond or an alkanediyl group having 1 to 4 carbon atoms.

$Q^{b1}$ and $Q^{b2}$ are the same as defined above.

Specific examples of the sulfonic acid anion in the salt represented by formula (B1) include anions mentioned in JP 2010-204646 A.

Examples of the sulfonic acid anion in the salt represented by formula (B1) are preferably anions represented by formula (B1a-1) to formula (B1a-34).

(B1a-1)
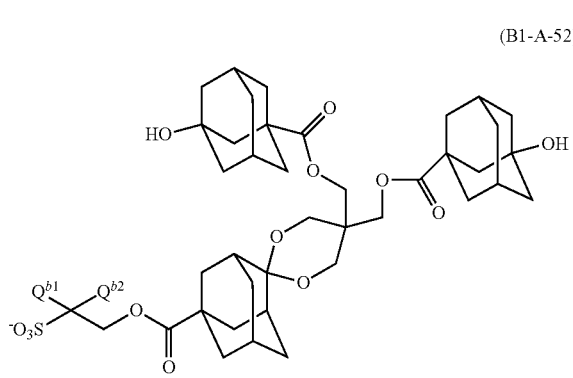

(B1a-2)
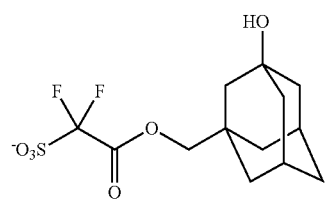
(B1a-3)
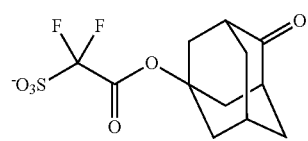
(B1a-4)
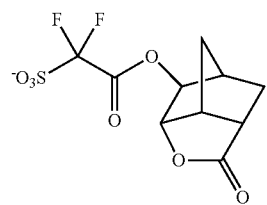
(B1a-5)
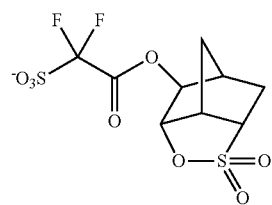
(B1a-6)
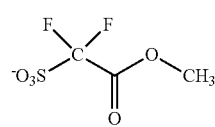
(B1a-7)
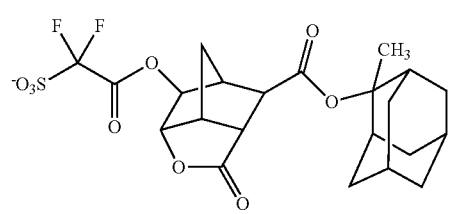
(B1a-8)
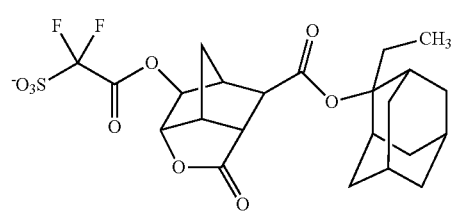
(B1a-9)
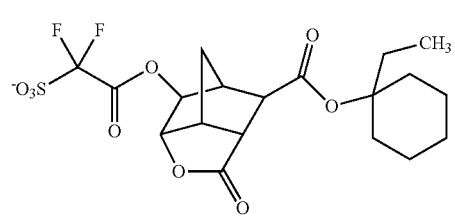
(B1a-10)
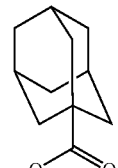
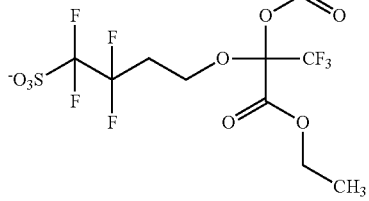
(B1a-11)
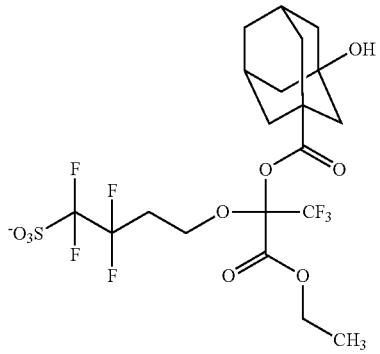
(B1a-12)
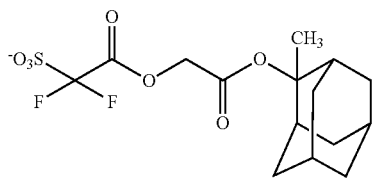
(B1a-13)
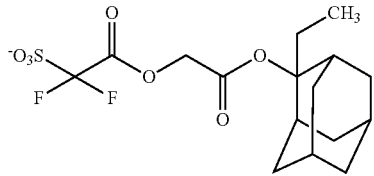
(B1a-14)
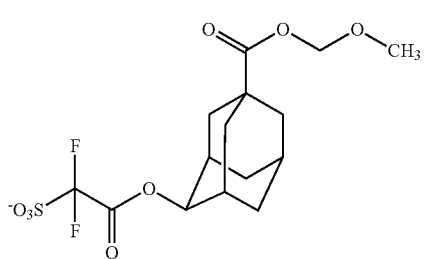

(B1a-15) 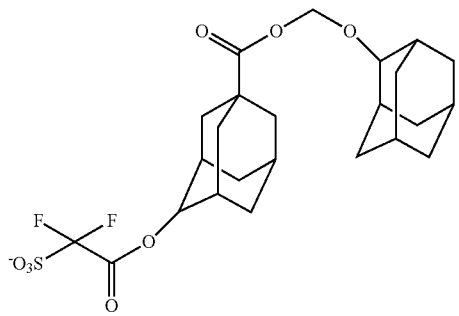
(B1a-16) 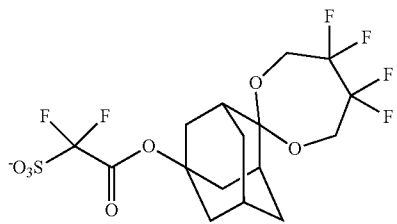
(B1a-17) 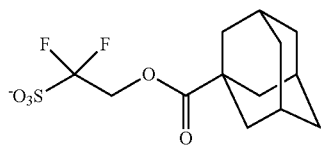
(B1a-18) 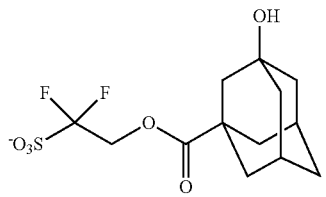
(B1a-19) 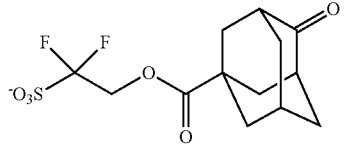
(B1a-20) 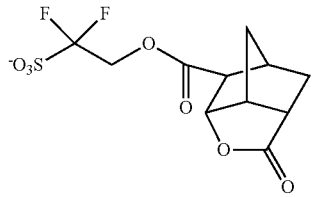
(B1a-21) 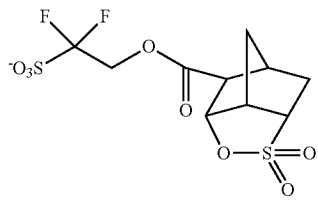
(B1a-22) 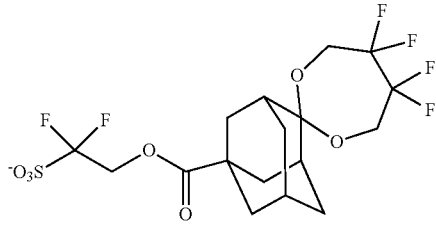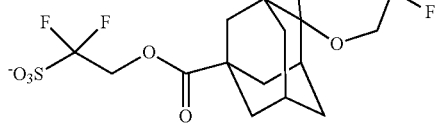
(B1a-23) 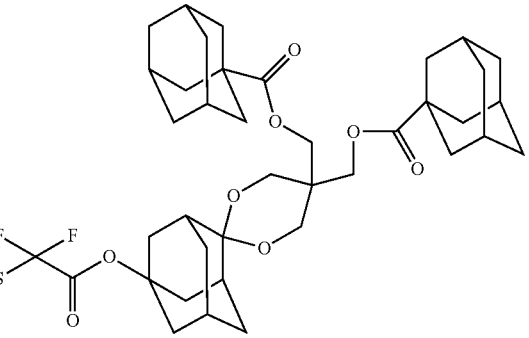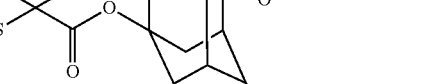
(B1a-24) 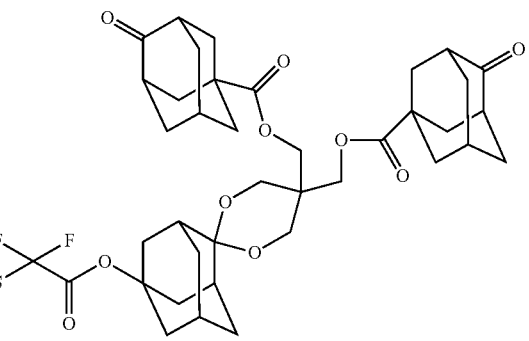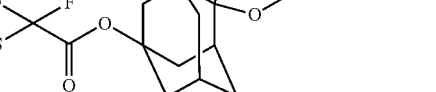
(B1a-25) 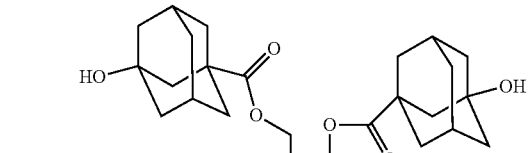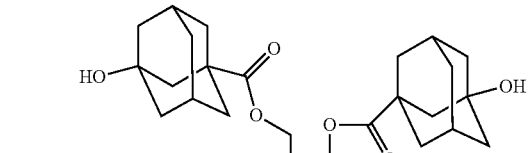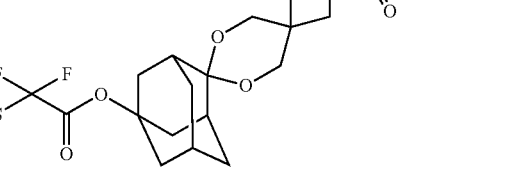

-continued (B1a-26)
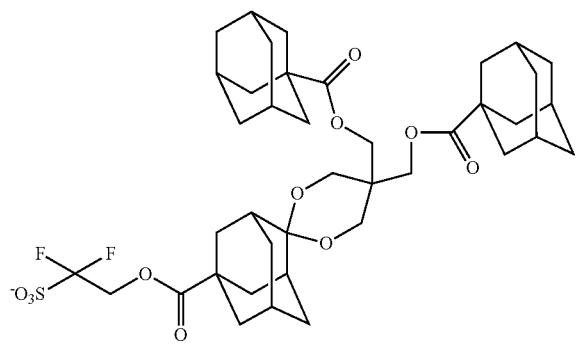

(B1a-27)
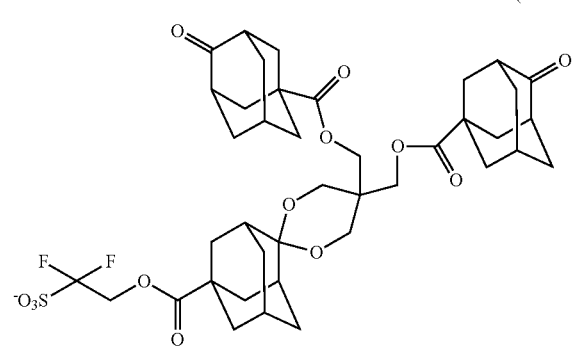

(B1a-28)
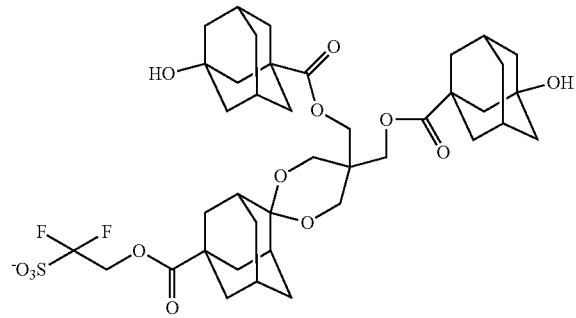

(B1a-29)
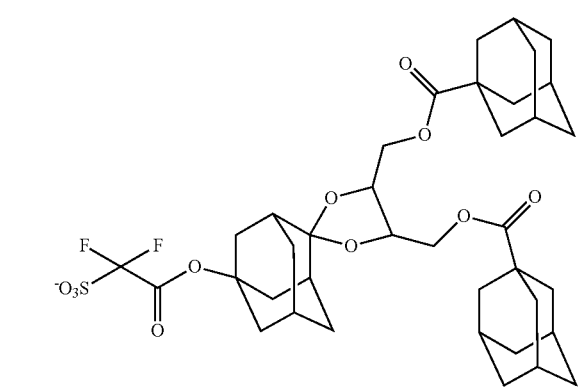

-continued (B1a-30)
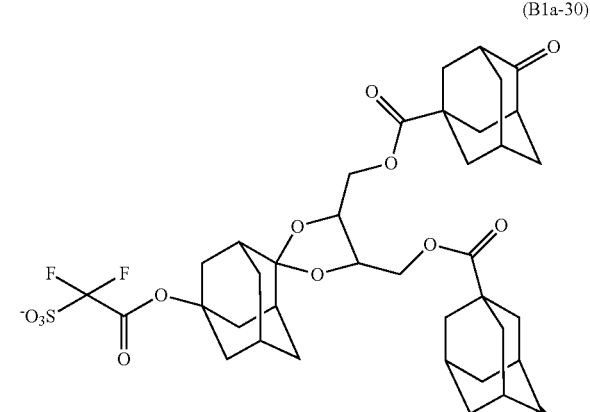

(B1a-31)
(B1a-32)
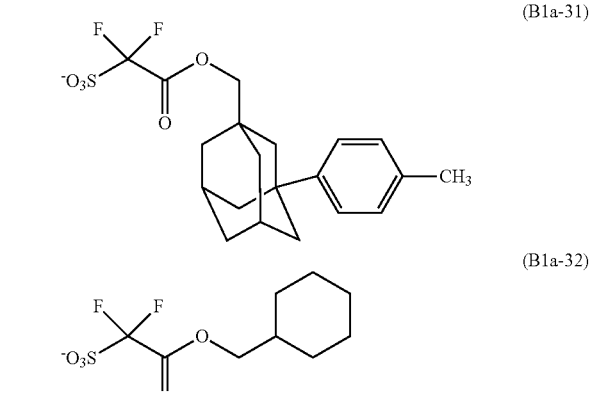

(B1a-33)
(B1a-34)
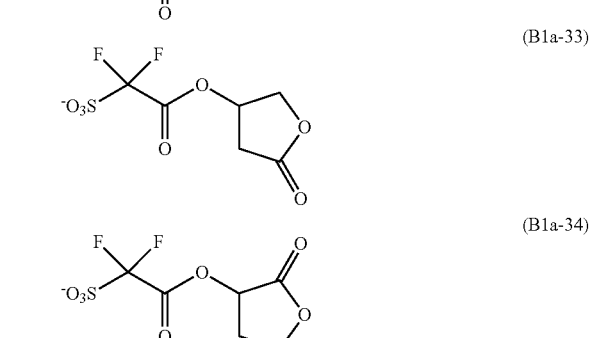

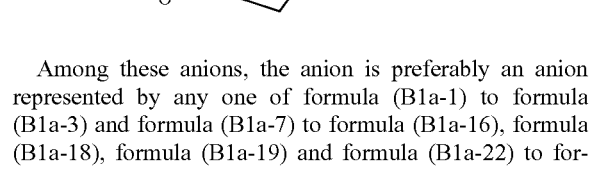

Among these anions, the anion is preferably an anion represented by any one of formula (B1a-1) to formula (B1a-3) and formula (B1a-7) to formula (B1a-16), formula (B1a-18), formula (B1a-19) and formula (B1a-22) to formula (B1a-30).

Examples of the organic cation of $Z^+$ include those which are the same as $ZA^+$ in the structural unit represented by formula (II-2-A').

The acid generator (B) is a combination of the above-mentioned sulfonic acid anions and the above-mentioned organic cations, and these can be optionally combined. Examples of the acid generator (B) are preferably combinations of anions represented by any one of formula (B1a-1) to formula (B1a-3) and formula (B1a-7) to formula (B1a-16), formula (B1a-18), formula (B1a-19) and formula (B1a-22) to formula (B1a-34) with a cation (b2-1) or a cation (b2-3).

Examples of the acid generator (B) are preferably those represented by formula (B1-1) to formula (B1-48). Among these, those containing an arylsulfonium cation are preferred, and those represented by formula (B1-1) to formula (B1-3), formula (B1-5) to formula (B1-7), formula (B1-11) to formula (B1-14), formula (B1-20) to formula (B1-26), formula (B1-29) and formula (B1-31) to formula (B1-48) are particularly preferred.
(B1-1)
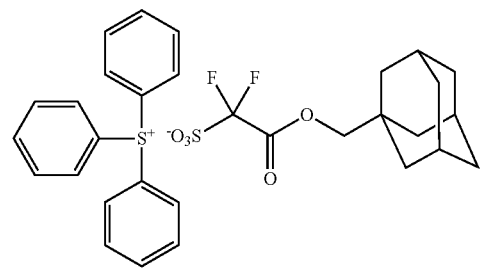
(B1-2)
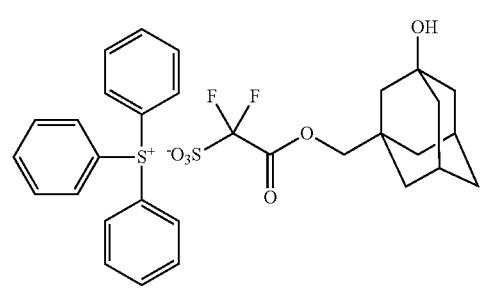
(B1-3)
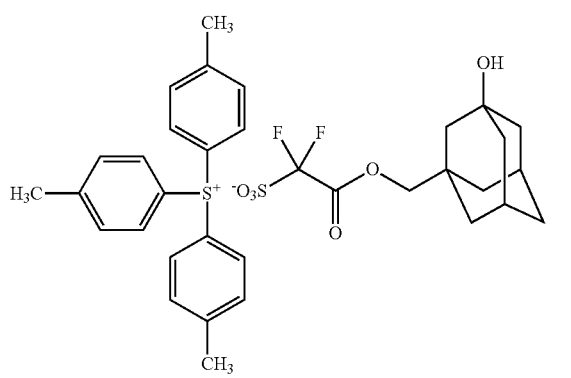
(B1-4)
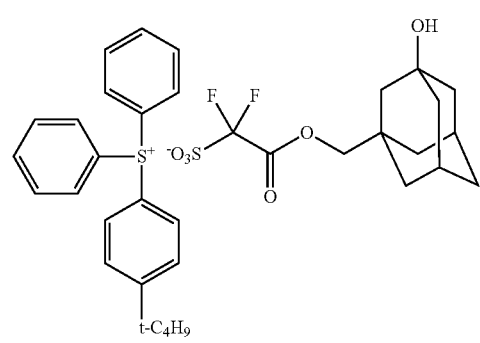
-continued
(B1-5)
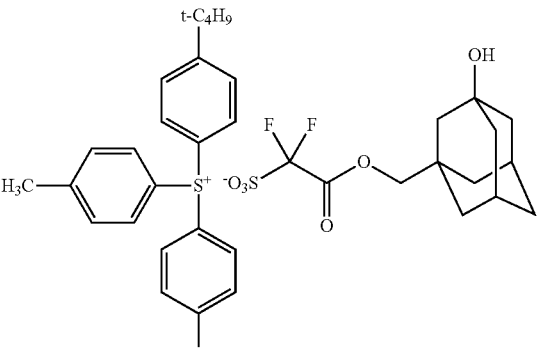
(B1-6)
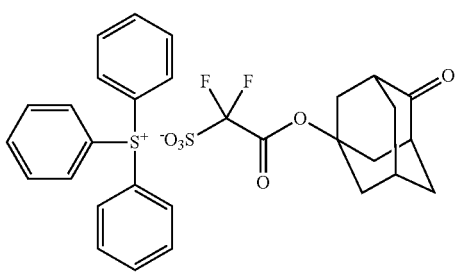
(B1-7)
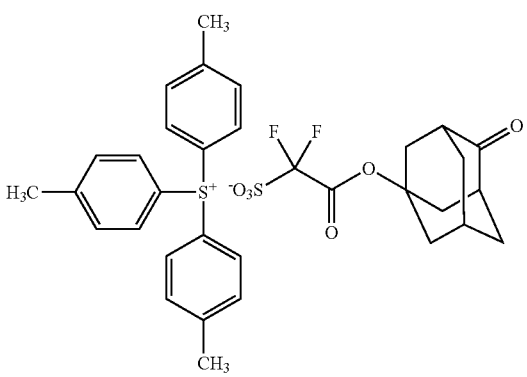
(B1-8)
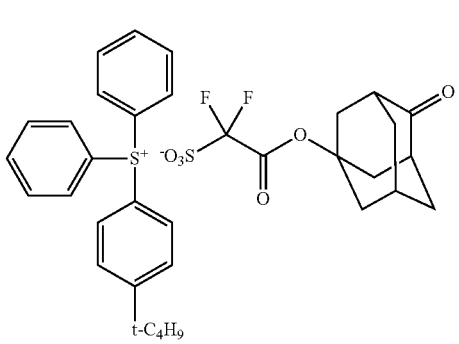

(B1-9)
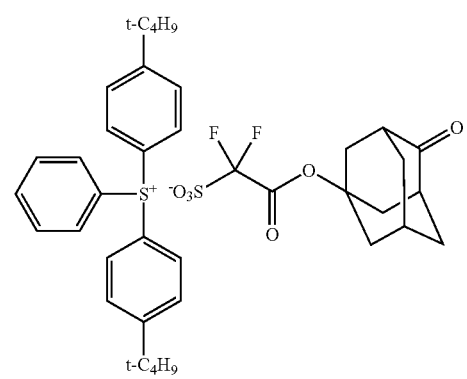
(B1-10)
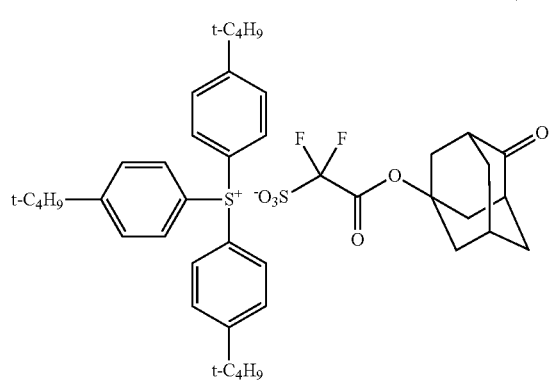
(B1-11)
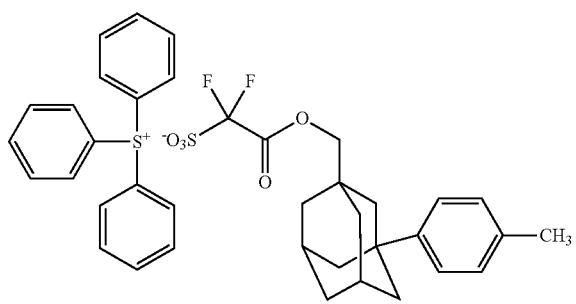
(B1-12)
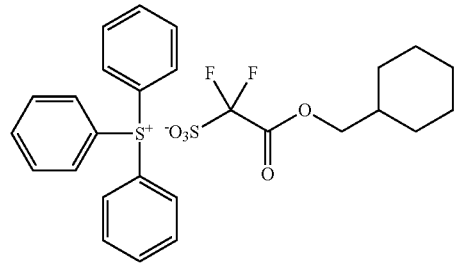
(B1-13)
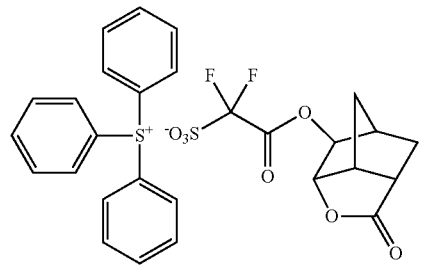
(B1-14)
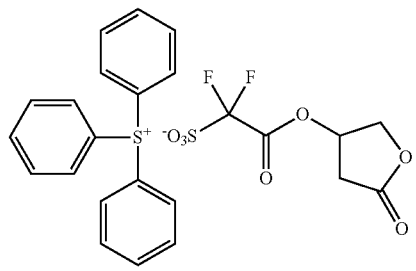
(B1-15)
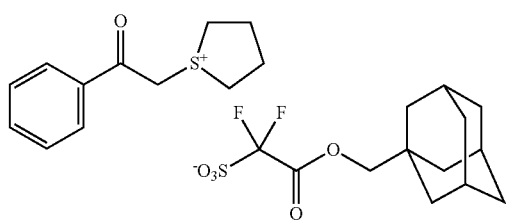
(B1-16)
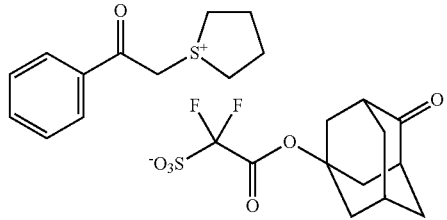
(B1-17)
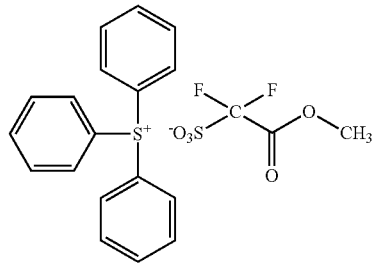
(B1-18)
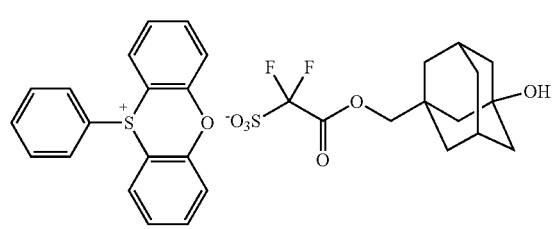
(B1-19)
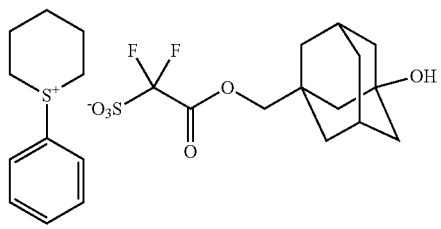

-continued
(B1-20)
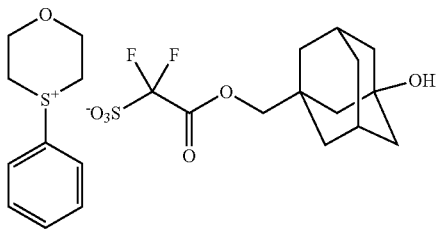
(B1-21)
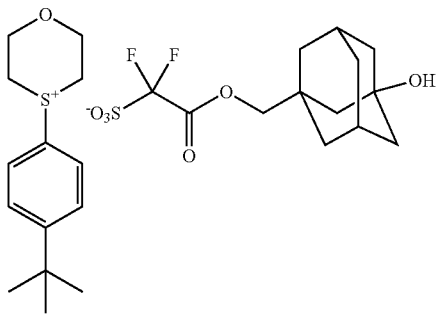
(B1-22)
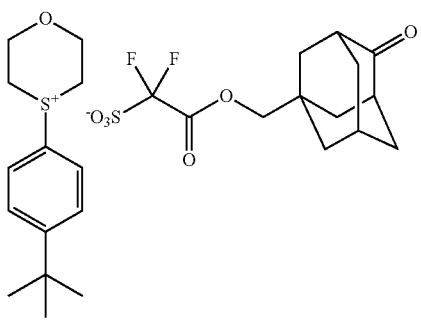
(B1-23)
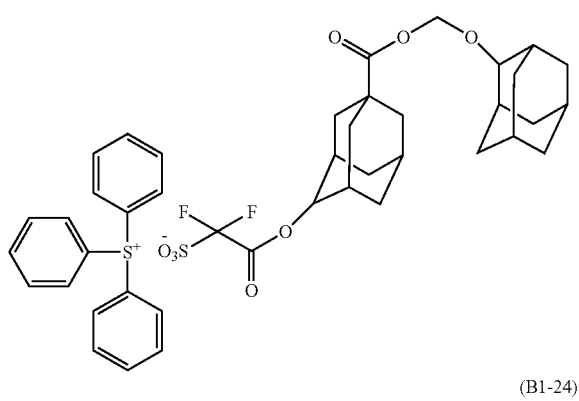
(B1-24)
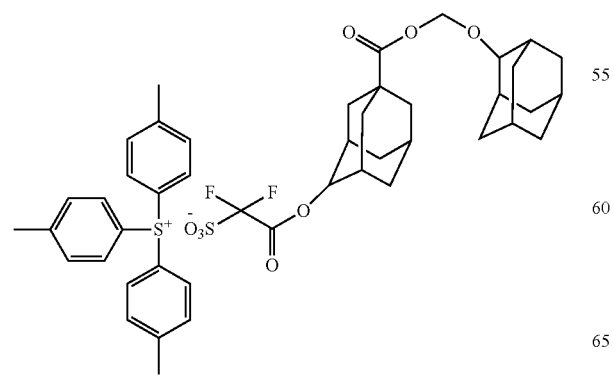
-continued
(B1-25)
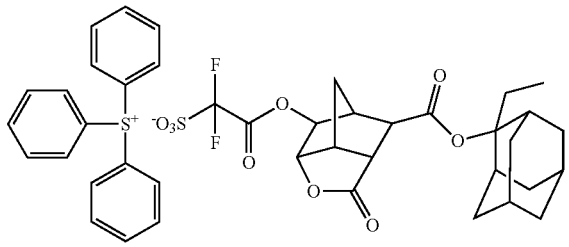
(B1-26)
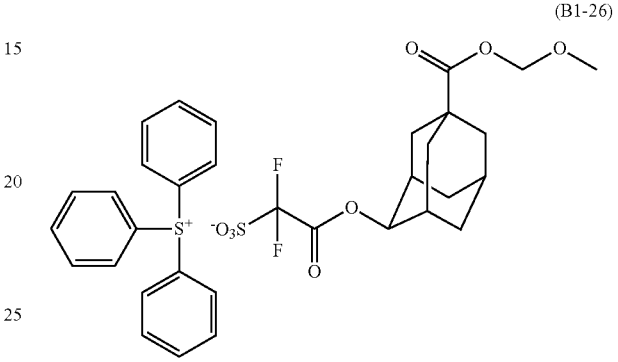
(B1-27)
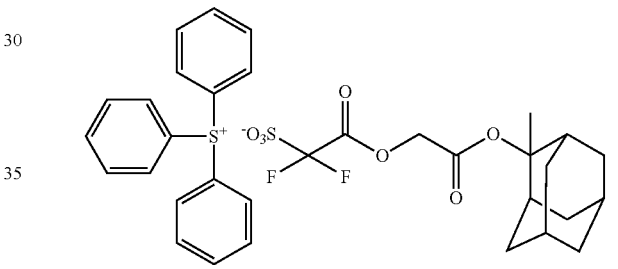
(B1-28)
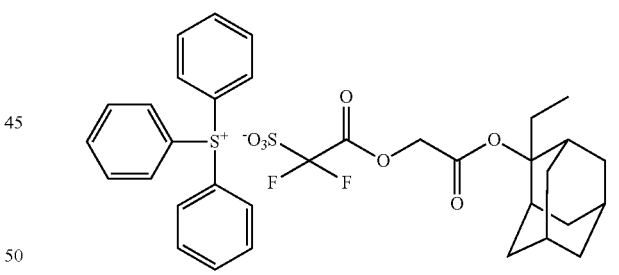
(B1-29)
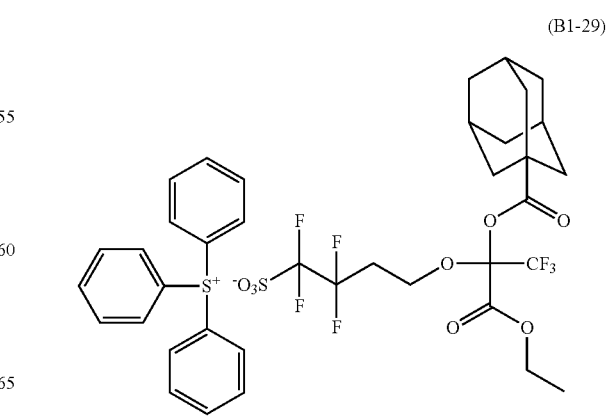

-continued
(B1-30)
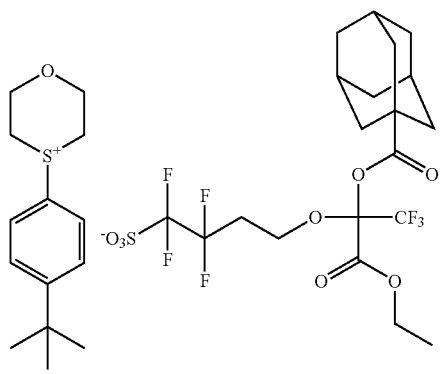
(B1-31)
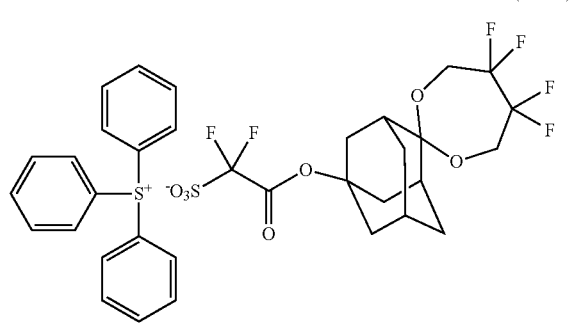
(B1-32)
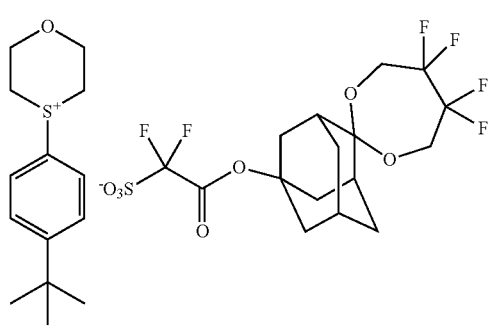
(B1-33)
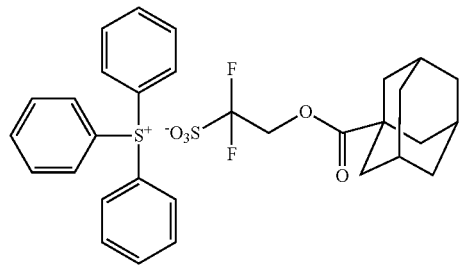
(B1-34)
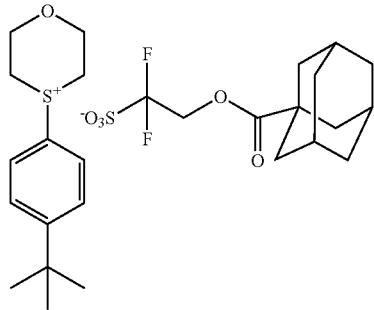
(B1-35)
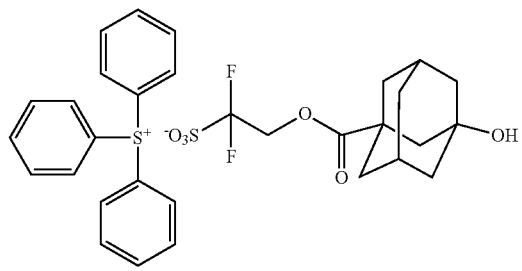
(B1-36)
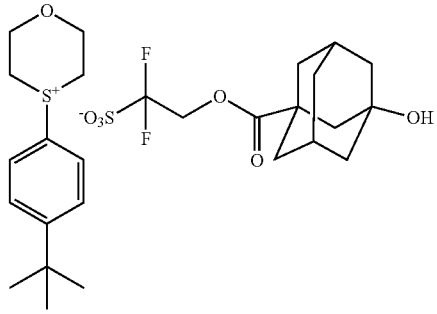
(B1-37)
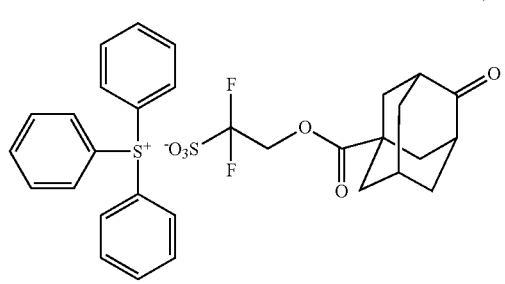
(B1-38)
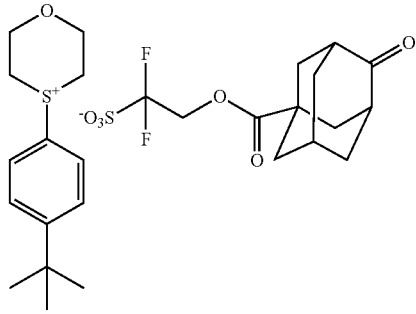
(B1-39)
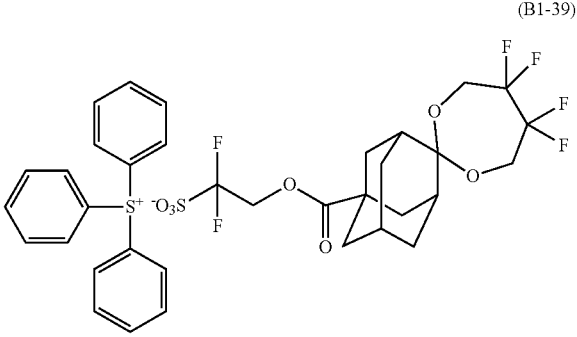

-continued
(B1-40)
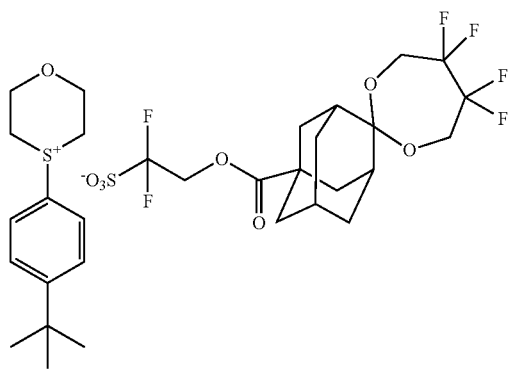
(B1-41)
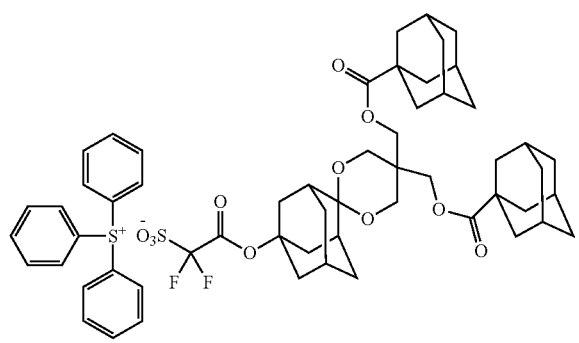
(B1-42)
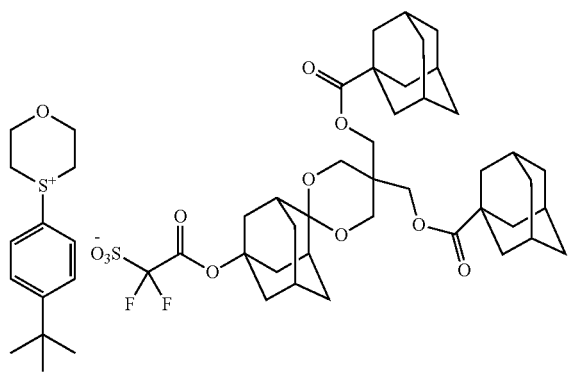
(B1-43)
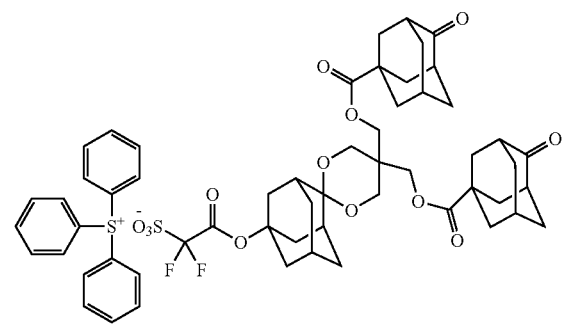
-continued
(B1-44)
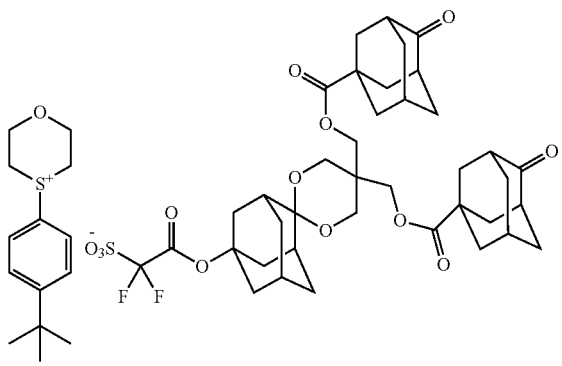
(B1-45)
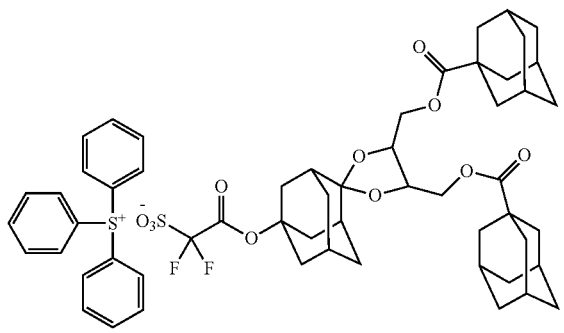
(B1-46)
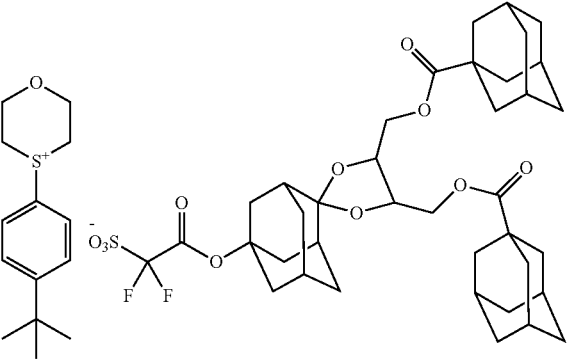
(B1-47)
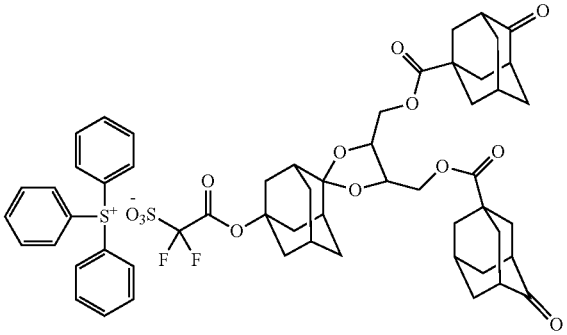

-continued (B1-48)

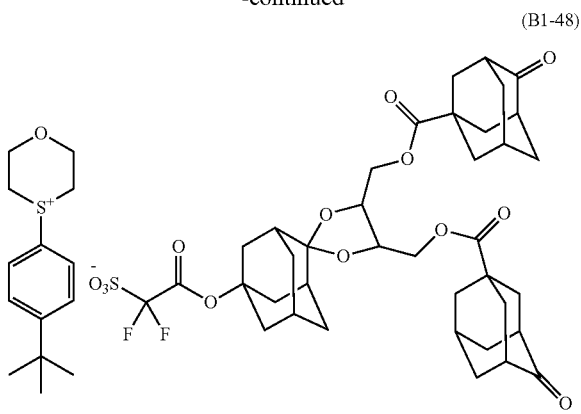

In the resist composition of the present invention, the content of the acid generator is preferably 1 part by mass or more and 40 parts by mass or less, and more preferably 3 parts by mass or more and 35 parts by mass or less, based on 100 parts by mass of the resin (A). The resist composition of the present invention may contain either the acid generator (B) alone or a plurality of the acid generators.

[Compound (I)]

When n is 2, the hydrocarbon group having 1 to 36 carbon atoms for $R^1$ includes a divalent aliphatic hydrocarbon group (an alkanediyl group, an alkenediyl group, an alkynediyl and a monocyclic or polycyclic divalent alicyclic hydrocarbon group), a divalent aromatic hydrocarbon group and the like, and may be a hydrocarbon group obtained by combining two or more of these groups.

When n is 3, $R^1$ represents a group in which one hydrogen atom is removed from the divalent hydrocarbon group mentioned when n is 2.

When n is 4, $R^1$ represents a group in which two hydrogen atoms are removed from the divalent hydrocarbon group mentioned when n is 2.

When n is 5 or more, similarly, $R^1$ represents a group in which (n-2) hydrogen atoms are removed from the divalent hydrocarbon group mentioned when n is 2.

N is preferably 2 or more, and more preferably 3 or more.

Examples of the alkanediyl group include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group and a dodecane-1,12-diyl group; and branched alkanediyl groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group and a 2-methylbutane-1,4-diyl group.

Examples of the alkenediyl group include an ethenediyl group, a propanediyl group, an isopropanediyl group, a butenediyl group, an isobutenediyl group, a tert-butenediyl group, a pentenediyl group, a hexenediyl group, a heptenediyl group, an octynediyl group, an isooctynediyl group and a nonenediyl group.

Examples of the alkynediyl group include an ethynediyl group, a propynediyl group, an isopropynediyl group, a butynediyl group, an isobutynediyl group, a tert-butynediyl group, a pentynediyl group, a hexynediyl group, an octynediyl group, a nonynediyl group and the like.

Examples of the monocyclic alicyclic hydrocarbon group include monocyclic cycloalkanediyl groups such as a cyclobutane-1,3-diyl group, a cyclopentane-1,3-diyl group, a cyclohexane-1,4-diyl group, a cyclohexene-3,6-diyl group and a cyclooctane-1,5-diyl group.

Examples of the polycyclic alicyclic hydrocarbon group include polycyclic cycloalkanediyl groups such as a norbornane-1,4-diyl group, a norbornane-2,5-diyl group, a 5-norbornene-2,3-diyl group, an adamantane-1,5-diyl group, an adamantane-2,6-diyl group and the like.

Examples of the divalent aromatic hydrocarbon group include a phenylene group, a naphthylene group, an anthrylene group, a biphenylene group, a phenanthrene group and the like.

The hydrocarbon group obtained by combining two or more groups includes a group obtained by combining an alkanediyl group with an alicyclic hydrocarbon group and/or an aromatic hydrocarbon group, and examples thereof include -alicyclic hydrocarbon group-alkanediyl group-, -alkanediyl group-alicyclic hydrocarbon group-, -alkanediyl group-alicyclic hydrocarbon group-alkanediyl group-, -cycloalkanediyl group-alkanediyl group-, -alkanediyl group-cycloalkanediyl group-, -alkanediyl group-cycloalkanediyl group-alkanediyl group-, -alkanediyl group-aromatic hydrocarbon group-, -aromatic hydrocarbon group-alkanediyl group- and the like.

The divalent hydrocarbon group having 1 to 36 carbon atoms represented by $R^1$ may have one substituent or a plurality of substituents.

Examples of the substituent which may be possessed by the hydrocarbon group for $R^1$ include a halogen atom, a cyano group, a hydroxy group, a carboxy group, an alkoxy group having 1 to 12 carbon atoms, an alkoxycarbonyl group having 2 to 13 carbon atoms, an alkylcarbonyl group having 2 to 13 carbon atoms, an alkylcarbonyloxy group having 2 to 13 carbon atoms and the like.

Examples of the halogen atom include a fluorine atom, a chlorine atom, a bromine atom and an iodine atom.

Examples of the alkoxy group having 1 to 12 carbon atoms include a methoxy group, an ethoxy group, a propoxy group, a butoxy group, a pentyloxy group, a hexyloxy group, an octyloxy group, a 2-ethylhexyloxy group, a nonyloxy group, a decyloxy group, an undecyloxy group, a dodecyloxy group and the like.

The alkoxycarbonyl group having 2 to 13 carbon atoms, the alkylcarbonyl group having 2 to 13 carbon atoms and the alkylcarbonyloxy group having 2 to 13 carbon atoms represent groups in which a carbonyl group or a carbonyloxy group is bonded to the above-mentioned alkyl group or alkoxy group.

Examples of the alkoxycarbonyl group having 2 to 13 carbon atoms include a methoxycarbonyl group, an ethoxycarbonyl group, a butoxycarbonyl group and the like, examples of the alkylcarbonyl group having 2 to 13 carbon atoms include an acetyl group, a propionyl group and a butyryl group, and examples of the alkylcarbonyloxy group having 2 to 13 carbon atoms include an acetyloxy group, a propionyloxy group, a butyryloxy group and the like.

$R^1$ is preferably an alicyclic hydrocarbon group having 3 to 18 carbon atoms, more preferably a polycyclic alicyclic hydrocarbon group having 3 to 18 carbon atoms, and still more preferably an adamantanediyl group or an adamantanetriyl group.

$X^1$ is preferably *—CO—O— or *—O—CO—O— (* represents a bonding site to $R^1$).

The hydrocarbon group having 1 to 36 carbon atoms for $L^1$ includes an aliphatic hydrocarbon group (an alkanediyl group, an alkenediyl group, an alkynediyl and a monocyclic or polycyclic alicyclic hydrocarbon group), an aromatic hydrocarbon group and the like, and may be a divalent hydrocarbon group obtained by combining two or more of these groups.

Examples of the alkanediyl group include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group and a dodecane-1,12-diyl group; and branched alkanediyl groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group and a 2-methylbutane-1,4-diyl group.

Examples of the alkenediyl group include an ethenediyl group, a propanediyl group, an isopropanediyl group, a butenediyl group, an isobutenediyl group, a tert-butenediyl group, a pentenediyl group, a hexenediyl group, a heptenediyl group, an octynediyl group, an isooctynediyl group and a nonenediyl group.

Examples of the alkynediyl group include an ethynediyl group, a propynediyl group, an isopropynediyl group, a butynediyl group, an isobutynediyl group, a tert-butynediyl group, a pentynediyl group, a hexynediyl group, an octynediyl group, a nonynediyl group and the like.

Examples of the monocyclic alicyclic hydrocarbon group include monocyclic cycloalkanediyl groups such as a cyclobutane-1,3-diyl group, a cyclopentane-1,3-diyl group, a cyclohexane-1,4-diyl group, a cyclohexene-3,6-diyl group and a cyclooctane-1,5-diyl group.

Examples of the polycyclic alicyclic hydrocarbon group include polycyclic cycloalkanediyl groups such as a norbornane-1,4-diyl group, a norbornane-2,5-diyl group, a 5-norbornene-2,3-diyl group, an adamantane-1,5-diyl group, an adamantane-2,6-diyl group and the like.

Examples of the divalent aromatic hydrocarbon group include a phenylene group, a naphthylene group, an anthrylene group, a biphenylene group, a phenanthrene group and the like.

The hydrocarbon group obtained by combining two or more groups includes a group obtained by combining an alkanediyl group with an alicyclic hydrocarbon group and/or an aromatic hydrocarbon group, and examples thereof include -alicyclic hydrocarbon group-alkanediyl group-, -alkanediyl group-alicyclic hydrocarbon group-, -alkanediyl group-alicyclic hydrocarbon group-alkanediyl group-, -cycloalkanediyl group-alkanediyl group-, -alkanediyl group-cycloalkanediyl group-, -alkanediyl group-cycloalkanediyl group-alkanediyl group-, -alkanediyl group-aromatic hydrocarbon group-, -aromatic hydrocarbon group-alkanediyl group- and the like.

The divalent hydrocarbon group having 1 to 36 carbon atoms represented by $L^1$ may have one substituent or a plurality of substituents.

Examples of the substituent which may be possessed by the hydrocarbon group for $L^1$ include a halogen atom, a cyano group and the like.

A hydroxy group (a group in which —$CH_2$— included in a methyl group is replaced by —O—), a carboxy group (a group in which —$CH_2$—$CH_2$— included in an ethyl group is replaced by —O—CO—), an alkoxy group having 1 to 12 carbon atoms (a group in which —$CH_2$— included in an alkyl group having 2 to 13 carbon atoms is replaced by —O—), an alkoxycarbonyl group having 2 to 13 carbon atoms (a group in which —$CH_2$—$CH_2$— included in an alkyl group having 4 to 15 carbon atoms is replaced by —O—CO—), an alkylcarbonyl group having 2 to 13 carbon atoms (a group in which —$CH_2$— included in an alkyl group having 3 to 14 carbon atoms is replaced by —CO—) and an alkylcarbonyloxy group having 2 to 13 carbon atoms (a group in which —$CH_2$—$CH_2$— included in an alkyl group having 4 to 15 carbon atoms is replaced by —CO—O—) are taken as groups in which —$CH_2$— included in a hydrocarbon group is replaced by —O— or —CO—.

Examples of the halogen atom include a fluorine atom, a chlorine atom, a bromine atom and an iodine atom.

Examples of the alkoxy group having 1 to 12 carbon atoms include a methoxy group, an ethoxy group, a propoxy group, a butoxy group, a pentyloxy group, a hexyloxy group, an octyloxy group, a 2-ethylhexyloxy group, a nonyloxy group, a decyloxy group, an undecyloxy group, a dodecyloxy group and the like.

The alkoxycarbonyl group having 2 to 13 carbon atoms, the alkylcarbonyl group having 2 to 13 carbon atoms and the alkylcarbonyloxy group having 2 to 13 carbon atoms represent groups in which a carbonyl group or a carbonyloxy group is bonded to the above-mentioned alkyl group or alkoxy group.

Examples of the alkoxycarbonyl group having 2 to 13 carbon atoms include a methoxycarbonyl group, an ethoxycarbonyl group, a butoxycarbonyl group and the like, examples of the alkylcarbonyl group having 2 to 13 carbon atoms include an acetyl group, a propionyl group and a butyryl group, and examples of the alkylcarbonyloxy group having 2 to 13 carbon atoms include an acetyloxy group, a propionyloxy group, a butyryloxy group and the like.

—$CH_2$— included in the hydrocarbon group having 1 to 36 carbon atoms for $L^1$ may be replaced by —O—, —S—, —CO— or —$SO_2$—.

When the hydrocarbon group having 1 to 36 carbon atoms for $L^1$ has a substituent or —$CH_2$— included in the hydrocarbon group is replaced by —O—, —S—, —CO— or —$SO_2$—, the number of carbon atoms before replacement is taken as the number of carbon atoms of the saturated hydrocarbon group.

$L^1$ is preferably an alkanediyl group having 1 to 6 carbon atoms (—$CH_2$— included in the alkanediyl group may be replaced by —O— or —CO—) or a group obtained by combining an alkanediyl group having 1 to 6 carbon atoms (—$CH_2$— included in the alkanediyl group may be replaced by —O— or —CO—) with an alicyclic hydrocarbon group having 3 to 18 carbon atoms (—$CH_2$— included in the alicyclic hydrocarbon group may be replaced by —O—, —S—, —CO— or —$SO_2$—), more preferably a methylene group or *-$L^A$-CO—O—$CH_2$— ($L^A$ represents an alicyclic hydrocarbon group, and * represents a bonding site to $X^1$), still more preferably a methylene group or *-$L^{A1}$-CO—O—$CH_2$— ($L^{A1}$ represents a polycyclichydrocarbon group, and * represents a bonding site to $X^1$), yet more preferably a methylene group or *-Ad-CO—O—$CH_2$— (Ad represents an adamantanediyl group, and * represents a bonding site to $X^1$), and particularly preferably a methylene group.

The compound (I) is preferably represented by the following formulas.

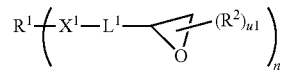

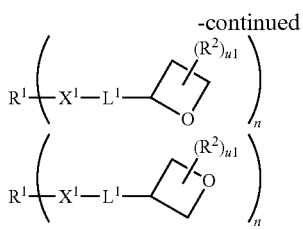

s1 is preferably 1, t1 is preferably 0 or 1, and s1+t1 is preferably 1 or 2, t1 is more preferably 1, and s1+t1 is more preferably 2.

The group in which u1 is 1 and $R^2$ is bonded to the carbon atom adjacent to $L^1$ in formula (I) is represented by the following formulas.

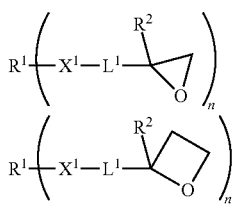

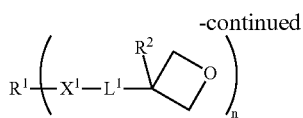

Examples of the saturated hydrocarbon group for $R^2$ include an alkyl group, an alicyclic hydrocarbon group and a combination thereof.

Examples of the alkyl group for $R^2$ include alkyl groups such as a methyl group, an ethyl group, a propyl group, an isopropyl group, a butyl group, an isobutyl group, a tert-butyl group, a pentyl group, a hexyl group, an octyl group and a nonyl group. The number of carbon atoms of the alkyl group is preferably 1 to 9, and more preferably 1 to 4.

The alicyclic hydrocarbon group may be monocyclic, polycyclic or spiro ring. Examples of the alicyclic hydrocarbon group include monocyclic cycloalkyl groups such as a cyclopropyl group, a cyclobutyl group, a cyclopentyl group, a cyclohexyl group, a cyclooctyl group, a cyclononyl group, a cyclodecyl group and a cyclododecyl group, and polycyclic cycloalkyl groups such as a norbornyl group and an adamantyl group.

n is preferably an integer of 4 or less, and more preferably 2 or 3.

The compound (I) includes, for example, compounds represented by the following formulas.

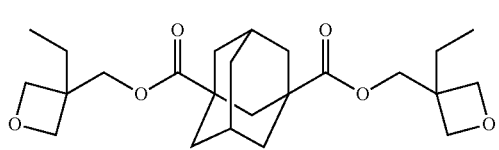
(I-1)

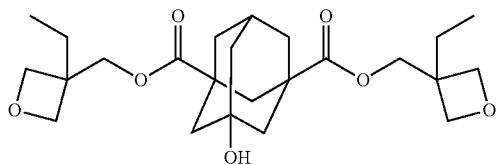
(I-2)

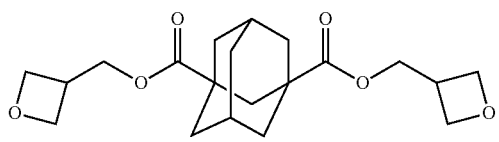
(I-3)

(I-4)

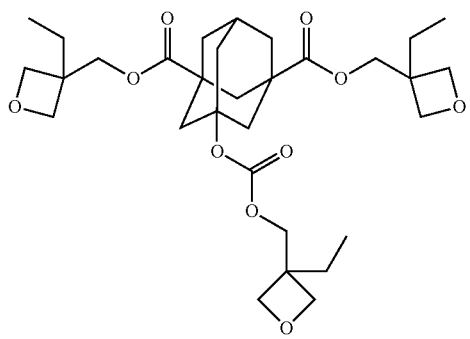
(I-5)

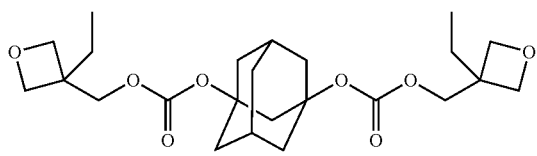
(I-6)

-continued
(I-7)
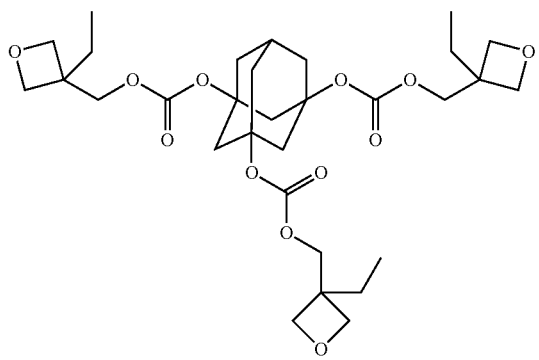
(I-8)
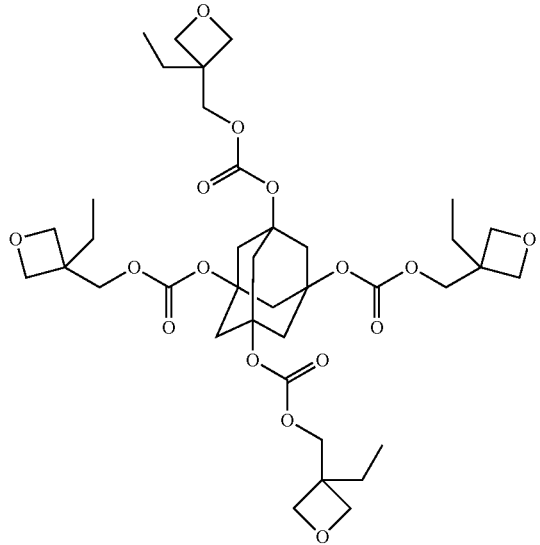
(I-9)
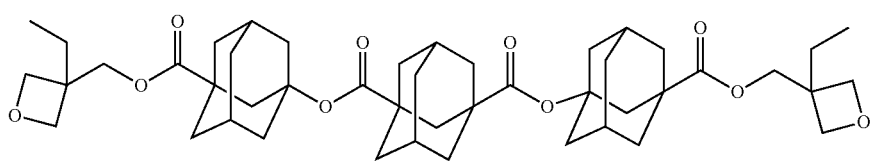
(I-10)
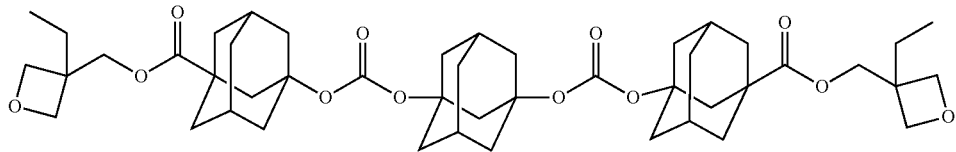
(I-11)
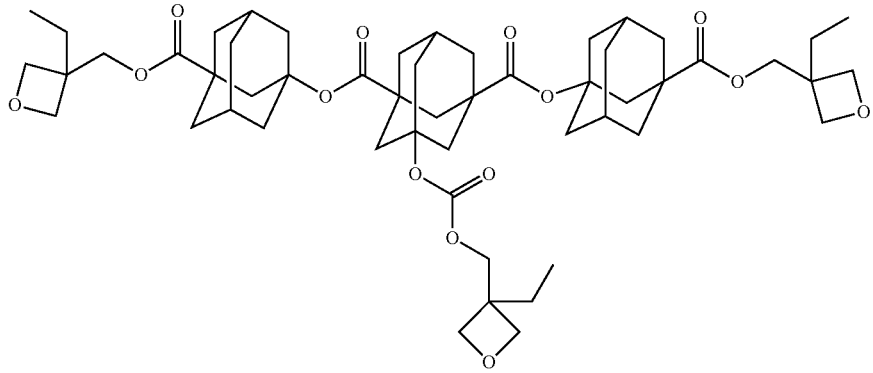
(I-12)
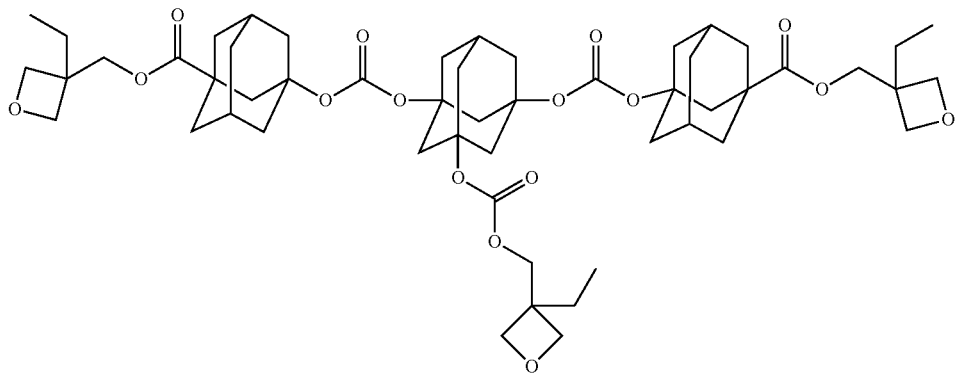

-continued
(I-13) 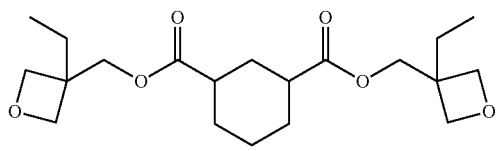
(I-14) 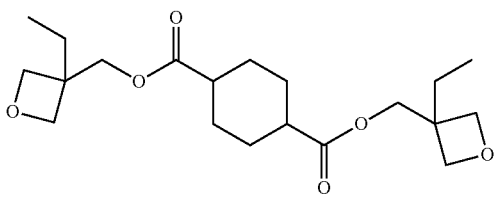
(I-15) 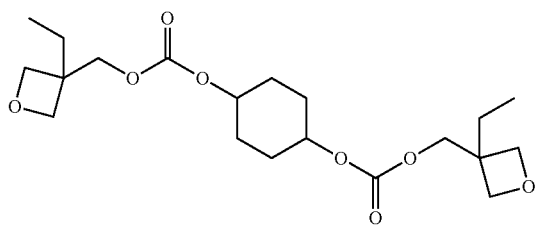
(I-16) 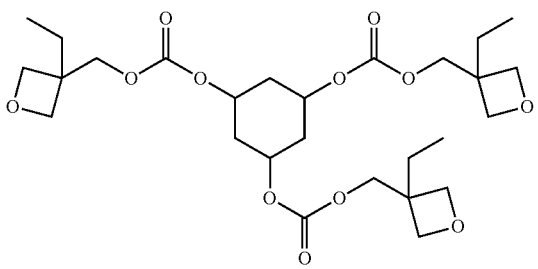
(I-17) 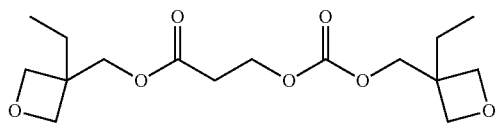
(I-18) 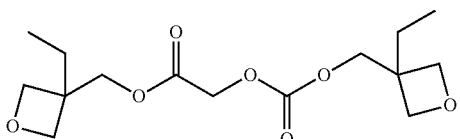
(I-19) 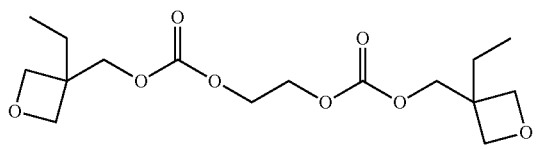
(I-20) 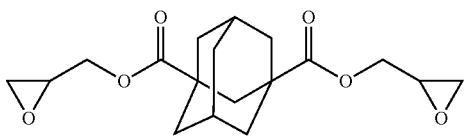
(I-21) 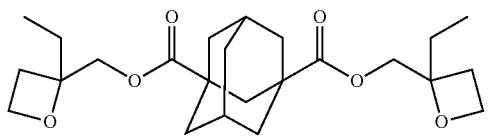
(I-22) 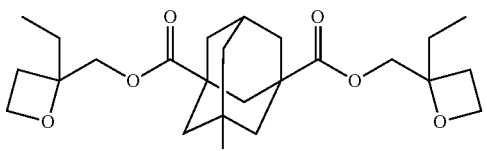
(I-23) 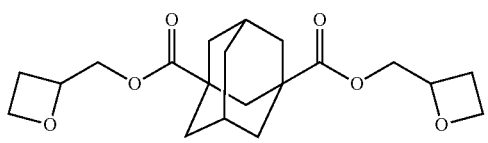
(I-24) 
(I-25) 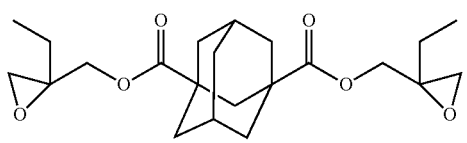
(I-26) 
(I-27) 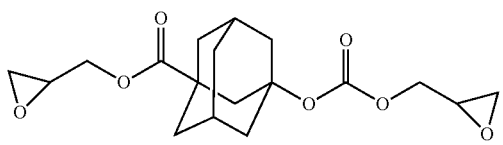
(I-28) 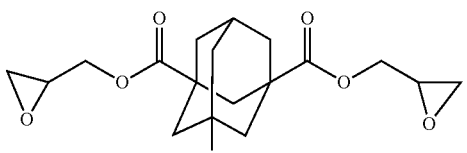

-continued
(I-29)
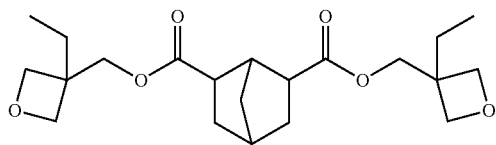
(I-30)
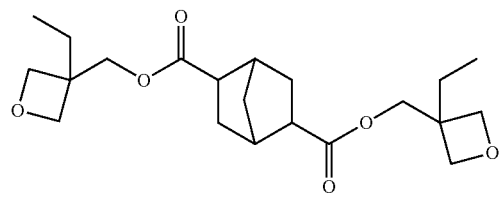
(I-31)
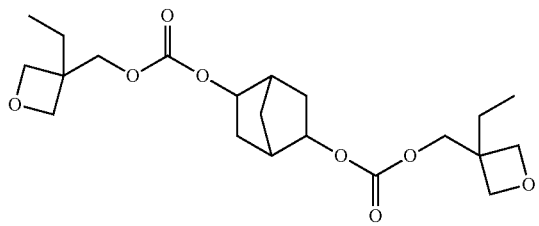
(I-32)
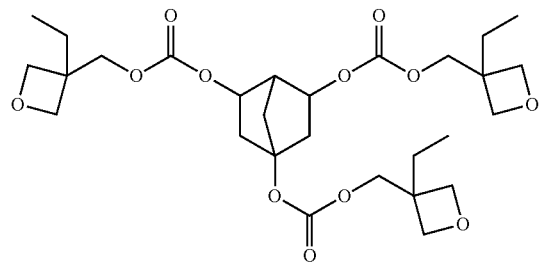
(I-33)
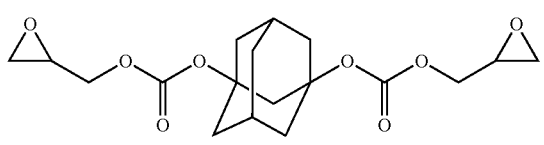
(I-34)
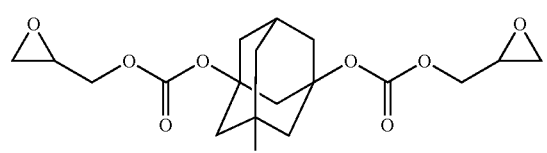
(I-35)
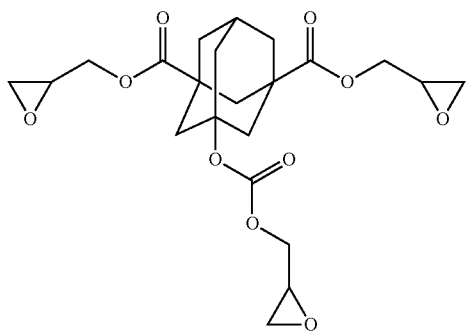
(I-36)
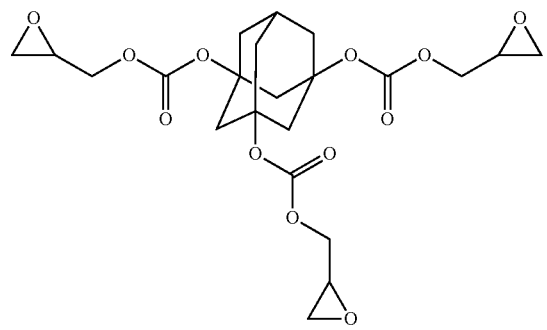
(I-37)
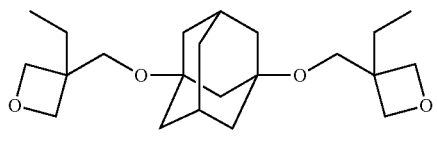
(I-38)
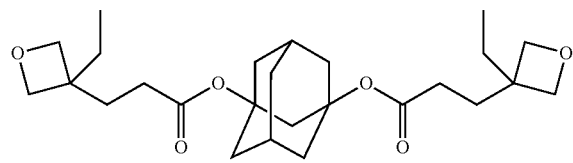
(I-39)
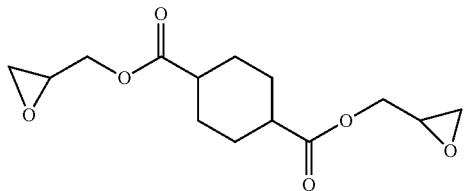
(I-40)
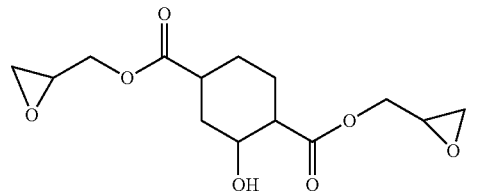

<Method for Producing Compound (I)>

The compound (compound represented by formula (I1I) in which $X^1$ is *—CO—O— (* represents a bonding site to $R^1$) in the compound (I) can be produced, for example, by reacting a compound represented by formula (I1-a) with carbonyldiimidazole in a solvent, followed by further reacting with a compound represented by formula (I1-b):

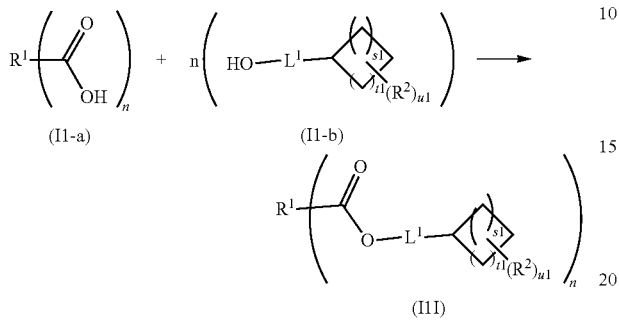

wherein all symbols are the same as defined above.

Examples of the solvent in this reaction include chloroform, acetonitrile and the like.

The reaction temperature is usually 5° C. to 80° C., and the reaction time is usually 0.5 hour to 24 hours.

The compound represented by formula (I1-a) includes compounds represented by the following formulas and is easily available on the market.

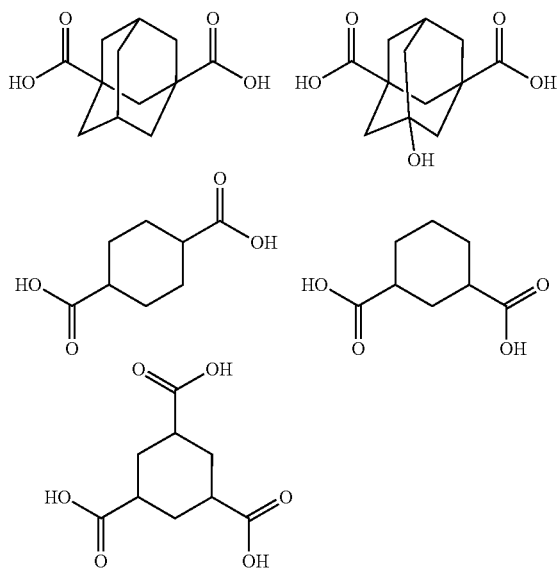

The compound represented by formula (I1-b) includes compounds represented by the following formulas and is easily available on the market.

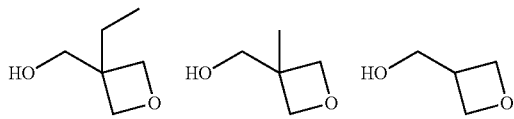

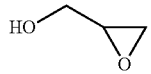

A compound (compound represented by formula (I2I)) in which $X^1$ is *—O—CO— (* represents a bonding site to $R^1$) in the compound (I) can be produced, for example, by reacting a compound represented by formula (I2-b) with carbonyldiimidazole in a solvent, followed by further reaction with a compound represented by formula (I2-a):

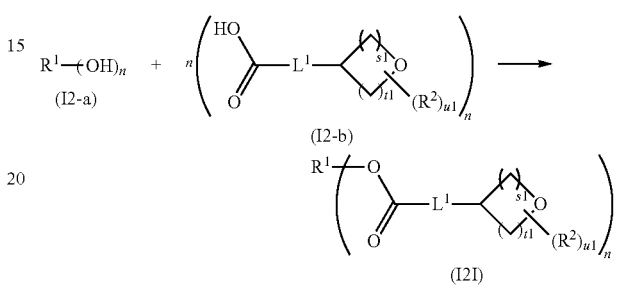

wherein all symbols are the same as defined above.

Examples of the solvent in this reaction include chloroform, acetonitrile and the like.

The reaction temperature is usually 5° C. to 80° C., and the reaction time is usually 0.5 hour to 24 hours.

The compound represented by formula (I2-a) includes compounds represented by the following formulas and is easily available on the market.

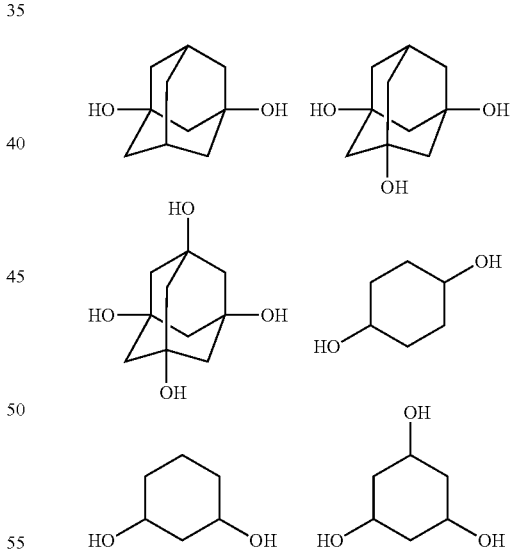

The compound represented by formula (I2-b) includes compounds represented by the following formulas and is easily available on the market.

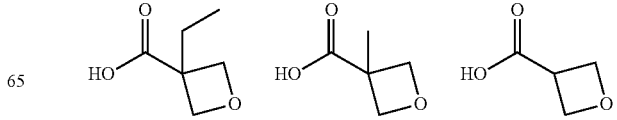

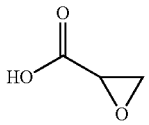

The compound (compound represented by formula (I3I)) in which $X^1$ is *—O—CO—O— (* represents a bonding site to $R^1$) in the compound (I) can be produced, for example, by reacting a compound represented by formula (I2-a) with carbonyldiimidazole in a solvent, followed by further reaction with a compound represented by formula (I1-b):

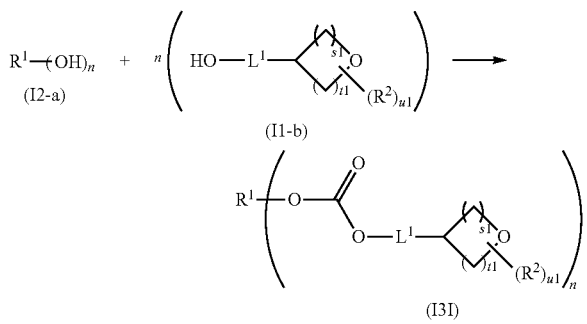

wherein all symbols are the same as defined above.

Examples of the solvent in this reaction include chloroform, acetonitrile and the like.

The reaction temperature is usually 5° C. to 80° C., and the reaction time is usually 0.5 hour to 24 hours.

The compound (compound represented by formula (I4I)) in which $X^1$ is, *—O— (* represents a bonding site to $R^1$) in the compound (I) can be produced, for example, by reacting a compound represented by formula (I2-a) with a compound represented by formula (I1-b) in the presence of a base catalyst in a solvent:

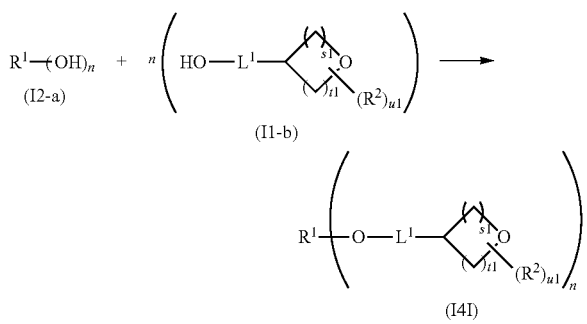

wherein all symbols are the same as defined above.

Examples of the base in this reaction include potassium hydroxide and the like.

Examples of the solvent in this reaction include chloroform, acetonitrile, tetrahydrofuran, dimethylformamide and the like.

The reaction temperature is usually 5° C. to 80° C., and the reaction time is usually 0.5 hour to 24 hours.

The content of the compound (I) is usually 0.001 to 20% by mass, preferably 0.005 to 15% by mass, and more preferably 0.01 to 10% by mass, based on the solid component of the resist composition.

The compound (I) functions as a quencher in the resist composition. The resist composition of the present invention may include one compound (I) or may use two or more compounds (I) in combination.

<Solvent (E)>

The content of the solvent (E) in the resist composition is usually 90% by mass or more and 99.9% by mass or less, preferably 92% by mass or more and 99% by mass or less, and more preferably 94% by mass or more and 99% by mass or less. The content of the solvent (E) can be measured, for example, by a known analysis means such as liquid chromatography or gas chromatography.

Examples of the solvent (E) include glycol ether esters such as ethylcellosolve acetate, methylcellosolve acetate and propylene glycol monomethyl ether acetate; glycol ethers such as propylene glycol monomethyl ether; esters such as ethyl lactate, butyl acetate, amyl acetate and ethyl pyruvate; ketones such as acetone, methyl isobutyl ketone, 2-heptanone and cyclohexanone; and cyclic esters such as γ-butyrolactone. The solvent (E) may be used alone, or two or more solvents may be used.

<Quencher (C)>

Examples of the quencher (C) include a basic nitrogen-containing organic compound, and a salt generating an acid having an acidity lower than that of an acid generated from an acid generator (B). The content of the quencher (C) is preferably about 0.01 to 5% by mass based on the amount of the solid component of the resist composition.

Examples of the basic nitrogen-containing organic compound include amine and an ammonium salt. Examples of the amine include an aliphatic amine and an aromatic amine. Examples of the aliphatic amine include a primary amine, a secondary amine and a tertiary amine.

Examples of the amine include 1-naphthylamine, 2-naphthylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl)propane, 1,2-di(4-pyridyloxy)ethane, di(2-pyridyl)ketone, 4,4'-dipyridyl sulfide, 4,4'-dipyridyl disulfide, 2,2'-dipyridylamine, 2,2'-dipicolylamine, bipyridine and the like, preferably diisopropylaniline, and more preferably 2,6-diisopropylaniline.

Examples of the ammonium salt include tetramethylammonium hydroxide, tetraisopropylammonium hydroxide, tetrabutylammonium hydroxide, tetrahexylammonium hydroxide, tetraoctylammonium hydroxide, phenyltrimethylammonium hydroxide, 3-(trifluoromethyl)phenyltrimethylammonium hydroxide, tetra-n-butylammonium salicylate and choline.

The acidity in a salt generating an acid having an acidity lower than that of an acid generated from the acid generator (B) is indicated by the acid dissociation constant (pKa). Regarding the salt generating an acid having an acidity lower than that of an acid generated from the acid generator (B), the acid dissociation constant of an acid generated from the salt usually meets the following inequality: $-3<pKa$, preferably $-1<pKa<7$, and more preferably $0<pKa<5$.

Examples of the salt generating an acid having an acidity lower than that of an acid generated from the acid generator (B) include salts represented by the following formulas, a salt represented by formula (D) mentioned in JP 2015-147926 A (hereinafter sometimes referred to as "weak acid inner salt (D)", and salts mentioned in JP 2012-229206 A, JP 2012-6908 A, JP 2012-72109 A, JP 2011-39502 A and JP 2011-191745 A. The salt generating an acid having an acidity lower than that of an acid generated from the acid generator (B) is preferably a weak acid inner salt (D).

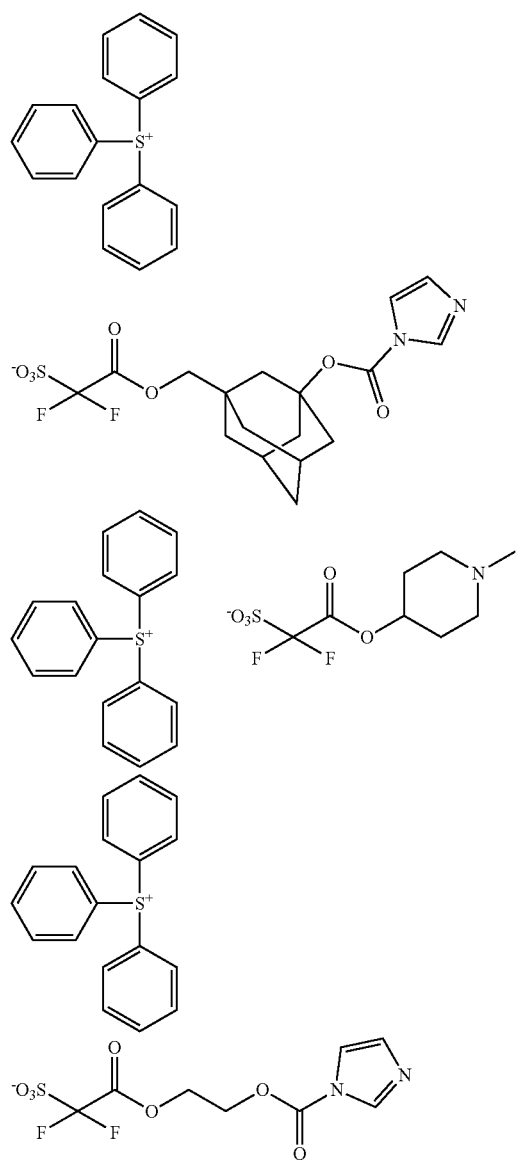

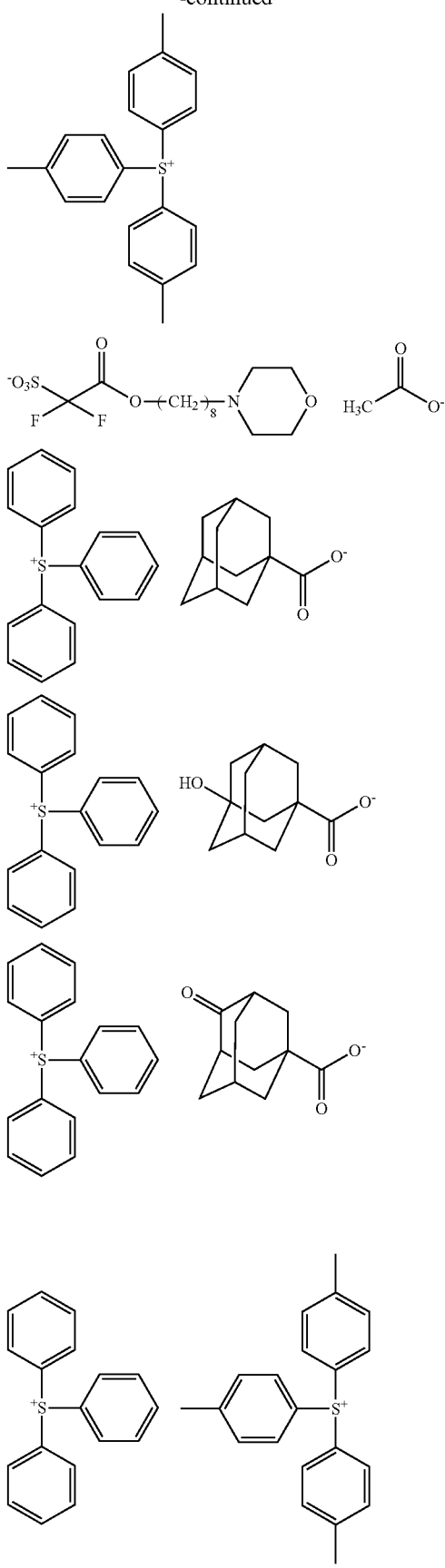

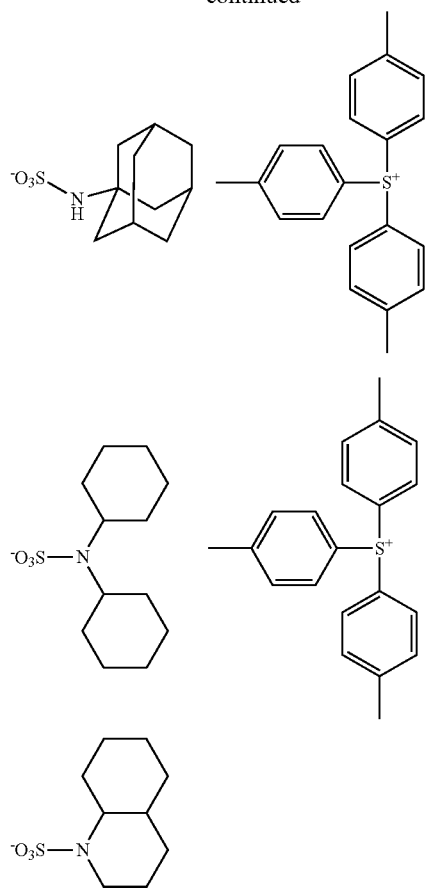
Examples of the weak acid inner salt (D) include the following salts.
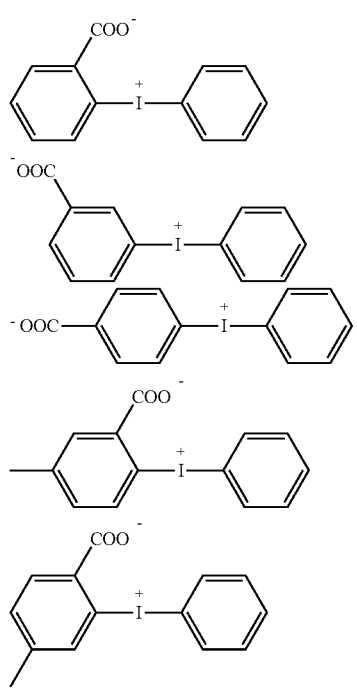
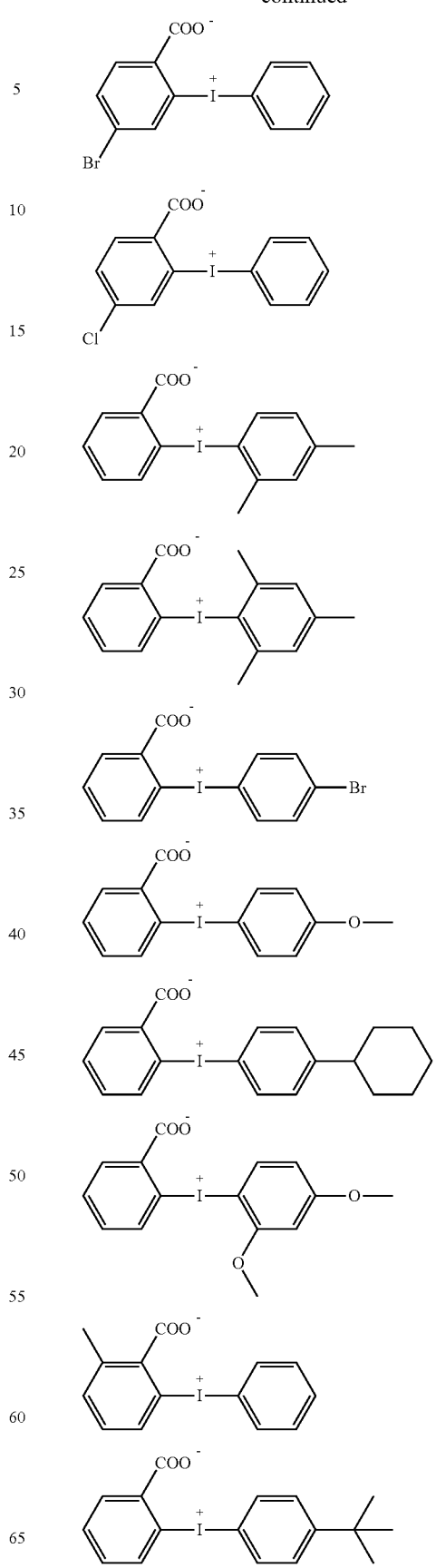

-continued

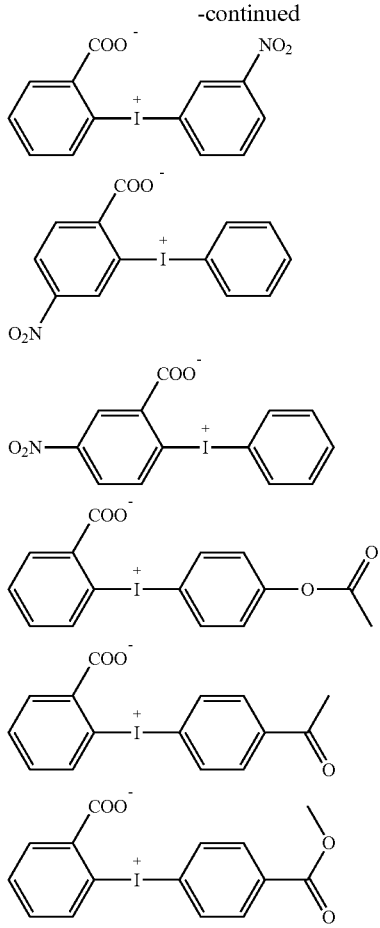

When the resist composition includes the quencher (C), the content of the quencher (C) in the solid component of the resist composition is usually 0.01 to 5% by mass, and preferably 0.01 to 3% by mass.

<Other Components>

The resist composition of the present invention may also include components other than the components mentioned above (hereinafter sometimes referred to as "other components (F)"). The other components (F) are not particularly limited and it is possible to use various additives known in the resist field, for example, sensitizers, dissolution inhibitors, surfactants, stabilizers and dyes.

<Preparation of Resist Composition>

The resist composition of the present invention can be prepared by mixing a compound (I), a resin (A) and an acid generator (B), as well as a resin (X), a solvent (E), quencher (C) and other components (F) which are optionally used. The order of mixing these components is any order and is not particularly limited. It is possible to select, as the temperature during mixing, appropriate temperature from 10 to 40° C., according to the type of the resin, the solubility in the solvent (E) of the resin and the like. It is possible to select, as the mixing time, appropriate time from 0.5 to 24 hours according to the mixing temperature. The mixing means is not particularly limited and it is possible to use mixing with stirring.

After mixing the respective components, the mixture is preferably filtered through a filter having a pore diameter of about 0.003 to 0.2 μm.

<Method for Producing Resist Pattern>

The method for producing a resist pattern of the present invention comprises:

(1) a step of applying the resist composition of the present invention on a substrate,
(2) a step of drying the applied composition to form a composition layer,
(3) a step of exposing the composition layer,
(4) a step of heating the exposed composition layer, and
(5) a step of developing the heated composition layer.

The resist composition can be usually applied on a substrate using a conventionally used apparatus, such as a spin coater. Examples of the substrate include inorganic substrates such as a silicon wafer. Before applying the resist composition, the substrate may be washed, and an organic antireflection film may be formed on the substrate.

The solvent is removed by drying the applied composition to form a composition layer. Drying is performed by evaporating the solvent using a heating device such as a hot plate (so-called "prebake"), or a decompression device. The heating temperature is preferably 50 to 200° C. and the heating time is preferably 10 to 180 seconds. The pressure during drying under reduced pressure is preferably about 1 to $1.0 \times 10^5$ Pa.

The composition layer thus obtained is usually exposed using an aligner or a liquid immersion aligner. It is possible to use, as an exposure source, various exposure sources, for example, exposure sources capable of emitting laser beam in an ultraviolet region such as KrF excimer laser (wavelength of 248 nm), ArF excimer laser (wavelength of 193 nm) and $F_2$ excimer laser (wavelength of 157 nm), an exposure source capable of emitting harmonic laser beam in a far-ultraviolet or vacuum ultra violet region by wavelength-converting laser beam from a solid-state laser source (YAG or semiconductor laser), an exposure source capable of emitting electron beam or EUV and the like. In the present specification, such exposure to radiation is sometimes collectively referred to as exposure. The exposure is usually performed through a mask corresponding to a pattern to be required. When electron beam is used as the exposure source, exposure may be performed by direct writing without using the mask.

The exposed composition layer is subjected to a heat treatment (so-called "post-exposure bake") to promote the deprotection reaction in an acid-labile group. The heating temperature is usually about 50 to 200° C., and preferably about 70 to 150° C.

The heated composition layer is usually developed with a developing solution using a development apparatus. Examples of the developing method include a dipping method, a paddle method, a spraying method, a dynamic dispensing method and the like. The developing temperature is preferably, for example, 5 to 60° C. and the developing time is preferably, for example, 5 to 300 seconds. It is possible to produce a positive resist pattern or negative resist pattern by selecting the type of the developing solution as follows.

When the positive resist pattern is produced from the resist composition of the present invention, an alkaline developing solution is used as the developing solution. The alkaline developing solution may be various aqueous alkaline solutions used in this field. Examples thereof include aqueous solutions of tetramethylammonium hydroxide and (2-hydroxyethyl)trimethylammonium hydroxide (commonly known as choline). The surfactant may be contained in the alkaline developing solution.

It is preferred that the developed resist pattern is washed with ultrapure water and then water remaining on the substrate and the pattern is removed.

When the negative resist pattern is produced from the resist composition of the present invention, a developing solution containing an organic solvent (hereinafter sometimes referred to as "organic developing solution") is used as the developing solution.

Examples of the organic solvent contained in the organic developing solution include ketone solvents such as 2-hexanone and 2-heptanone; glycol ether ester solvents such as propylene glycol monomethyl ether acetate; ester solvents such as butyl acetate; glycol ether solvents such as propylene glycol monomethyl ether; amide solvents such as N,N-dimethylacetamide; and aromatic hydrocarbon solvents such as anisole.

The content of the organic solvent in the organic developing solution is preferably 90% by mass or more and 100% by mass or less, more preferably 95% by mass or more and 100% by mass or less, and still more preferably the organic developing solution is substantially composed of the organic solvent.

Particularly, the organic developing solution is preferably a developing solution containing butyl acetate and/or 2-heptanone. The total content of butyl acetate and 2-heptanone in the organic developing solution is preferably 50% by mass or more and 100% by mass or less, more preferably 90% by mass or more and 100% by mass or less, and still more preferably the organic developing solution is substantially composed of butyl acetate and/or 2-heptanone.

The surfactant may be contained in the organic developing solution. A trace amount of water may be contained in the organic developing solution.

During development, the development may be stopped by replacing by a solvent with the type different from that of the organic developing solution.

The developed resist pattern is preferably washed with a rinsing solution. The rinsing solution is not particularly limited as long as it does not dissolve the resist pattern, and it is possible to use a solution containing an ordinary organic solvent which is preferably an alcohol solvent or an ester solvent.

After washing, the rinsing solution remaining on the substrate and the pattern is preferably removed.

<Applications>

The resist composition of the present invention is suitable as a resist composition for exposure of KrF excimer laser, a resist composition for exposure of ArF excimer laser, a resist composition for exposure of electron beam (EB) or a resist composition for exposure of EUV, particularly a resist composition for a thick film (having a thickness of 150 nm to 1,000 nm) for exposure of ArF excimer laser, and the resist composition is useful for fine processing of semiconductors.

EXAMPLES

The present invention will be described more specifically by way of Examples. Percentages and parts expressing the contents or amounts used in the Examples are by mass unless otherwise specified.

The weight-average molecular weight is a value determined by gel permeation chromatography under the following conditions.

Equipment: HLC-8120 GPC type (manufactured by TOSOH CORPORATION)

Column: TSKgel Multipore $H_{XL}$-M×3+guardcolumn (manufactured by TOSOH CORPORATION)

Eluent: tetrahydrofuran

Flow rate: 1.0 mL/min

Detector: RI detector

Column temperature: 40° C.

Injection amount: 100 μl

Molecular weight standards: polystyrene standard (manufactured by TOSOH CORPORATION)

Structures of compounds were confirmed by measuring a molecular ion peak using mass spectrometry (Liquid Chromatography: Model 1100, manufactured by Agilent Technologies, Inc., Mass Spectrometry: Model LC/MSD, manufactured by Agilent Technologies, Inc.). The value of this molecular ion peak in the following Examples is indicated by "MASS".

Example 1

Synthesis of Compound Represented by Formula (I-1)

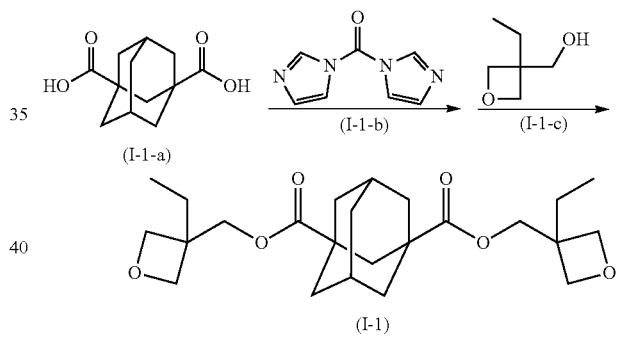

2.24 Parts of a compound represented by formula (I-1-a) and 30 parts of acetonitrile were mixed, followed by stirring at 23° C. for 30 minutes, mixing of 3.56 parts of a compound represented by formula (I-1-b) and further stirring at 50° C. for 2 hours. To the reaction product thus obtained, 2.32 parts of a compound represented by formula (I-1-c) was added, followed by stirring at 50° C. for 4 hours and further cooling to 23° C. To the reaction mixture thus obtained, 50 parts of chloroform and 20 parts of an aqueous 5% oxalic acid solution were added and, after stirring at 23° C. for 30 minutes, an organic layer was isolated through separation. To the organic layer thus obtained, 20 parts of ion-exchanged water was added and, after stirring at 23° C. for 30 minutes, an organic layer was isolated through separation. This water washing operation was repeated five times. The organic layer thus obtained was concentrated and the concentrated mass was isolated from a column (silica gel 60 N (spherical, neutral) 100-210 μm; manufactured by Kanto Chemical Co., Inc., developing solvent:ethyl acetate) to obtain 2.62 parts of a compound represented by formula (I-1).

MASS (ESI (+) Spectrum): 421.3 $[M+H]^+$

Example 2

Synthesis of Compound Represented by Formula (I-2)

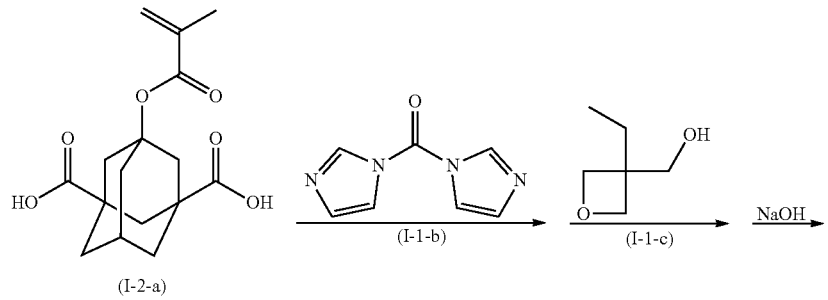

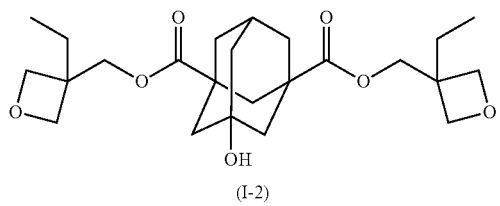

3.08 Parts of a compound represented by formula (I-2-a) and 30 parts of acetonitrile were mixed, followed by stirring at 23° C. for 30 minutes, mixing of 3.56 parts of a compound represented by formula (I-1-b) and further stirring at 50° C. for 2 hours. To the reaction product thus obtained, 2.32 parts of a compound represented by formula (I-1-c) was added, followed by stirring at 50° C. for 4 hours and further cooling to 23° C. To the reaction mixture thus obtained, 50 parts of chloroform and 20 parts of an aqueous 5% oxalic acid solution were added and, after stirring at 23° C. for 30 minutes, an organic layer was isolated through separation. To the organic layer thus obtained, 20 parts of ion-exchanged water was added and, after stirring at 23° C. for 30 minutes, an organic layer was isolated through separation. This water washing operation was repeated five times. The organic layer thus obtained was concentrated, and the concentrated residue thus obtained were mixed with 50 parts of methanol and 5 parts of an aqueous 10% sodium hydroxide solution, followed by stirring at 23° C. for 18 hours. To the mixture thus obtained, 100 parts of chloroform and 30 parts of ion-exchanged water were added and, after stirring at 23° C. for 30 minute, an organic layer was isolated through separation. To the organic layer thus obtained, 50 parts of ion-exchanged water was added and, after stirring at 23° C. for 30 minutes, an organic layer was isolated through separation. This water washing operation was repeated five times. The organic layer thus obtained was concentrated, and the concentrated mass was isolated from a column (silica gel 60 N (spherical, neutral) 100-210 μm; manufactured by Kanto Chemical Co., Inc., developing solvent:ethyl acetate) to obtain 3.44 parts of a compound represented by formula (I-2).

MASS (ESI (+) Spectrum): 437.3 [M+H]$^+$

Example 3

Synthesis of Compound Represented by Formula (I-5)

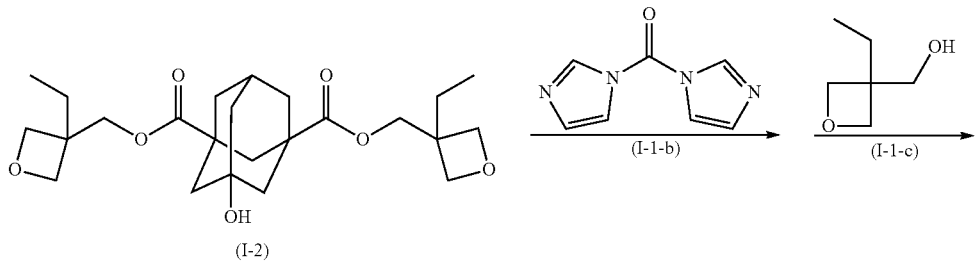

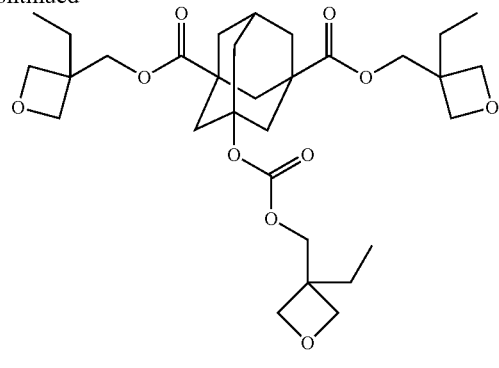

(I-5)

2.18 Parts a compound represented by formula (I-2) and 30 parts of acetonitrile were mixed, followed by stirring at 23° C. for 30 minutes, mixing of 0.85 part of a compound represented by formula (I-1-b) and further stirring at 50° C. for 2 hours. To the reaction product thus obtained, 0.58 part of a compound represented by formula (I-1-c) was added, followed by stirring at 50° C. for 4 hours and further cooling to 23° C. To the reaction mixture thus obtained, 50 parts of chloroform and 20 parts of an aqueous 5% oxalic acid solution were added and, after stirring at 23° C. for 30 minutes, an organic layer was isolated through separation. To the organic layer thus obtained, 20 parts of ion-exchanged water was added and, after stirring at 23° C. for 30 minutes, an organic layer was isolated through separation. This water washing operation was repeated five times. The organic layer thus obtained was concentrated, and the concentrated mass was isolated from a column (silica gel 60 N (spherical, neutral) 100-210 μm; manufactured by Kanto Chemical Co., Inc., developing solvent:ethyl acetate) to obtain 1.69 parts of a compound represented by formula (I-5).

MASS (ESI (+) Spectrum): 579.3 [M+H]⁺

Example 4

Synthesis of Compound Represented by Formula (I-6)

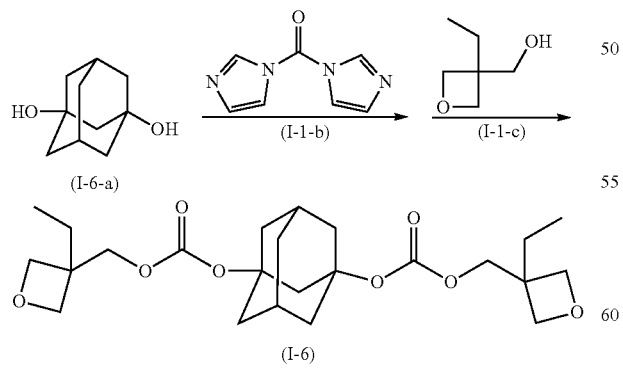

1.68 Parts of a compound represented by formula (I-6-a) and 30 parts of acetonitrile were mixed, followed by stirring at 23° C. for 30 minutes, mixing of 3.56 parts of a compound represented by formula (I-1-b) and further stirring at 50° C. for 2 hours. To the reaction product thus obtained, 2.32 parts of a compound represented by formula (I-1-c) was added, followed by stirring at 50° C. for 4 hours and further cooling to 23° C. To the reaction mixture thus obtained, 50 parts of chloroform and 20 parts of an aqueous 5% oxalic acid solution were added and, after stirring at 23° C. for 30 minute, an organic layer was isolated through separation. To the organic layer thus obtained, 20 parts of ion-exchanged water was added and, after stirring at 23° C. for 30 minute, an organic layer was isolated through separation. This water washing operation was repeated five times. The organic layer thus obtained was concentrated, and the concentrated mass was isolated from a column (silica gel 60 N (spherical, neutral) 100-210 μm; manufactured by Kanto Chemical Co., Inc., developing solvent:ethyl acetate) to obtain 2.04 parts of a compound represented by formula (I-6).

MASS (ESI (+) Spectrum): 453.2 [M+H]⁺

Example 5

Synthesis of Compound Represented by Formula (I-7)

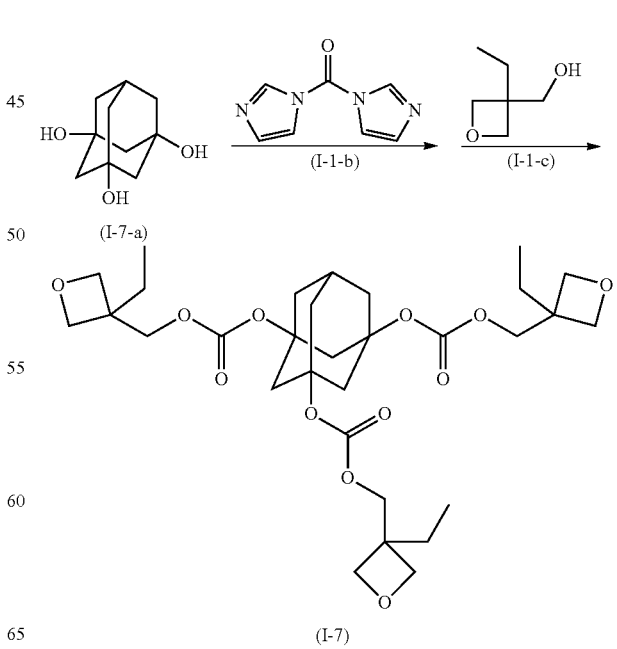

1.84 Parts of a compound represented by formula (I-7-a) and 30 parts of acetonitrile were mixed, followed by stirring at 23° C. for 30 minutes, mixing of 5.35 parts of a compound represented by formula (I-1-b) and further stirring at 50° C. for 2 hours. To the reaction product thus obtained, 3.48 parts of a compound represented by formula (I-1-c) was added, followed by stirring at 50° C. for 4 hours and further cooling to 23° C. To the reaction mixture thus obtained, 50 parts of chloroform and 20 parts of an aqueous 5% oxalic acid solution were added and, after stirring at 23° C. for 30 minutes, an organic layer was isolated through separation. To the organic layer thus obtained, 20 parts of ion-exchanged water was added and, after stirring at 23° C. for 30 minutes, an organic layer was isolated through separation. This water washing operation was repeated five times. The organic layer thus obtained was concentrated, and the concentrated mass was isolated from a column (silica gel 60 N (spherical, neutral) 100-210 μm; manufactured by Kanto Chemical Co., Inc., developing solvent:ethyl acetate) to obtain 1.58 parts of a compound represented by formula (I-7).

MASS (ESI (+) Spectrum): 611.3 [M+H]⁺

Example 6

Synthesis of Compound Represented by Formula (I-20)

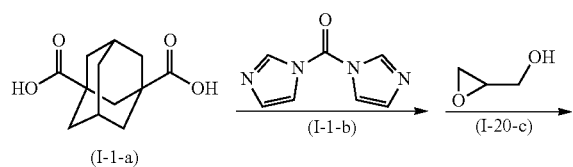

-continued

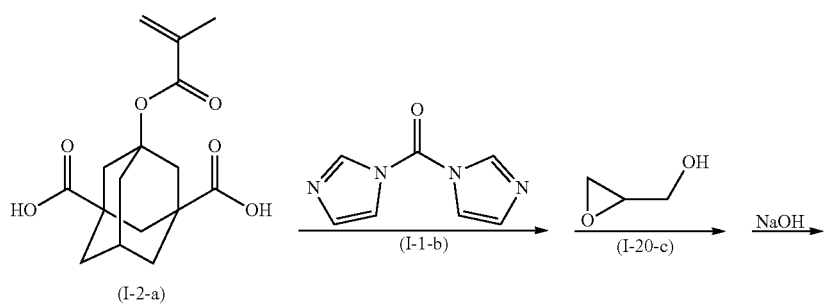

(I-20)

2.24 Parts of a compound represented by formula (I-1-a) and 30 parts of acetonitrile were mixed, followed by stirring at 23° C. for 30 minutes, mixing of 3.56 parts of a compound represented by formula (I-1-b) and further stirring at 50° C. for 2 hours. To the reaction product thus obtained, 1.48 parts of a compound represented by formula (I-20-c) was added, followed by stirring at 50° C. for 4 hours and further cooling to 23° C. To the reaction mixture thus obtained, 50 parts of chloroform and 20 parts of an aqueous 5% oxalic acid solution were added and, after stirring at 23° C. for 30 minutes, an organic layer was isolated through separation. To the organic layer thus obtained, 20 parts of ion-exchanged water was added and, after stirring at 23° C. for 30 minutes, an organic layer was isolated through separation. This water washing operation was repeated five times. The organic layer thus obtained was concentrated, and the concentrated mass was isolated from a column (silica gel 60 N (spherical, neutral) 100-210 μm; manufactured by Kanto Chemical Co., Inc., developing solvent:ethyl acetate) to obtain 2.01 parts of a compound represented by formula (I-20).

MASS (ESI (+) Spectrum): 337.2 [M+H]⁺

Example 7

Synthesis of Compound Represented by Formula (I-28)

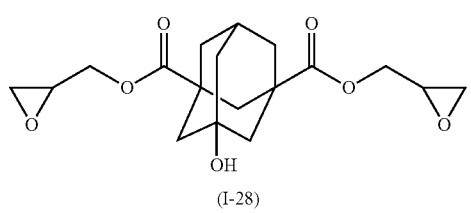

3.08 Parts of a compound represented by formula (I-2-a) and 30 parts of acetonitrile were mixed, followed by stirring at 23° C. for 30 minutes, mixing of 3.56 parts of a compound represented by formula (I-1-b) and further stirring at 50° C. for 2 hours. To the reaction product thus obtained, 1.48 parts of a compound represented by formula (I-20-c) was added, followed by stirring at 50° C. for 4 hours and further cooling to 23° C. To the reaction mixture thus obtained, 50 parts of chloroform and 20 parts of an aqueous 5% oxalic acid solution were added and, after stirring at 23° C. for 30 minutes, an organic layer was isolated through separation. To the organic layer thus obtained, 20 parts of ion-exchanged water was added and, after stirring at 23° C. for 30 minutes, an organic layer was isolated through separation. This water washing operation was repeated five times. The organic layer thus obtained was concentrated, and the concentrated residue thus obtained was mixed with 50 parts of methanol and 5 parts of an aqueous 10% sodium hydroxide solution, followed by stirring at 23° C. for 18 hours. To the mixture thus obtained, 100 parts of chloroform and 30 parts of ion-exchanged water were added and, after stirring at 23° C. for 30 minutes, an organic layer was isolated through separation. To the organic layer thus obtained, 50 parts of ion-exchanged water was added and, after stirring at 23° C. for 30 minutes, an organic layer was isolated through separation. This water washing operation was repeated five times. The organic layer thus obtained was concentrated, and the concentrated mass was isolated from a column (silica gel 60 N (spherical, neutral) 100-210 μm; manufactured by Kanto Chemical Co., Inc., developing solvent:ethyl acetate) to obtain 1.98 parts of a compound represented by formula (I-28).

MASS (ESI (+) Spectrum): 353.2 [M+H]$^+$

Example 8

Synthesis of Compound Represented by Formula (I-35)

1.76 Parts of a compound represented by formula (I-28) and 30 parts of acetonitrile were mixed, followed by stirring at 23° C. for 30 minutes, mixing of 0.85 part of a compound represented by formula (I-1-b) and further stirring at 50° C. for 2 hours. To the reaction product thus obtained, 0.58 part of a compound represented by formula (I-20-c) was added, followed by stirring at 50° C. for 4 hours and further cooling to 23° C. To the reaction mixture thus obtained, 50 parts of chloroform and 20 parts of an aqueous 5% oxalic acid solution were added and, after stirring at 23° C. for 30 minutes, an organic layer was isolated through separation. To the organic layer thus obtained, 20 parts of ion-exchanged water was added and, after stirring at 23° C. for 30 minutes, an organic layer was isolated through separation. This water washing operation was repeated five times. The organic layer thus obtained was concentrated, and the concentrated mass was isolated from a column (silica gel 60 N (spherical, neutral) 100-210 μm; manufactured by Kanto Chemical Co., Inc., developing solvent:ethyl acetate) to obtain 1.69 parts of a compound represented by formula (I-35).

MASS (ESI (+) Spectrum): 453.2 [M+H]$^+$

Example 9

Synthesis of Compound Represented by Formula (I-34)

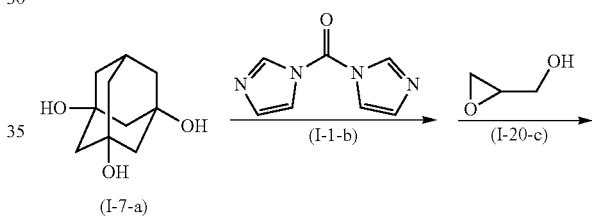

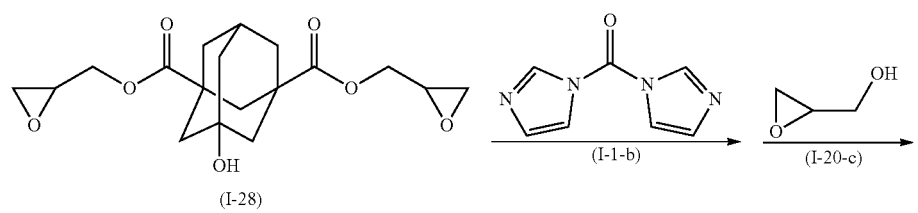

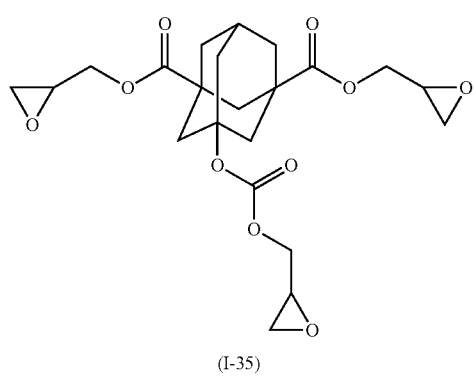

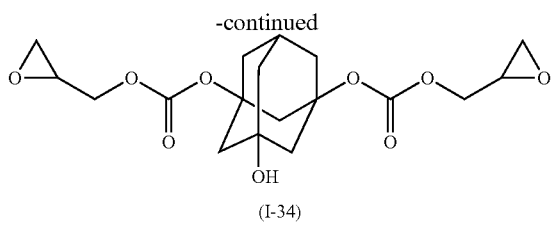

(I-34)

1.84 Parts of a compound represented by formula (I-7-a) and 30 parts of acetonitrile were mixed, followed by stirring at 23° C. for 30 minutes, mixing of 3.57 parts of a compound represented by formula (I-1-b) and further stirring at 50° C. for 2 hours. To the reaction product thus obtained, 1.48 parts of a compound represented by formula (I-20-c) was added, followed by stirring at 50° C. for 4 hours and further cooling to 23° C. To the reaction mixture thus obtained, 50 parts of chloroform and 20 parts of an aqueous 5% oxalic acid solution and, after stirring at 23° C. for 30 minutes, an organic layer was isolated through separation. To the organic layer thus obtained, 20 parts of ion-exchanged water was added and, after stirring at 23° C. for 30 minutes, an organic layer was isolated through separation. This water washing operation was repeated five times. The organic layer thus obtained was concentrated, and the concentrated mass was isolated from a column (silica gel 60 N (spherical, neutral) 100-210 μm; manufactured by Kanto Chemical Co., Inc., developing solvent:ethyl acetate) to obtain 0.59 part of a compound represented by formula (I-34).

MASS (ESI (+) Spectrum): 385.1 [M+H]⁺

Example 10

Synthesis of Compound Represented by Formula (I-36)

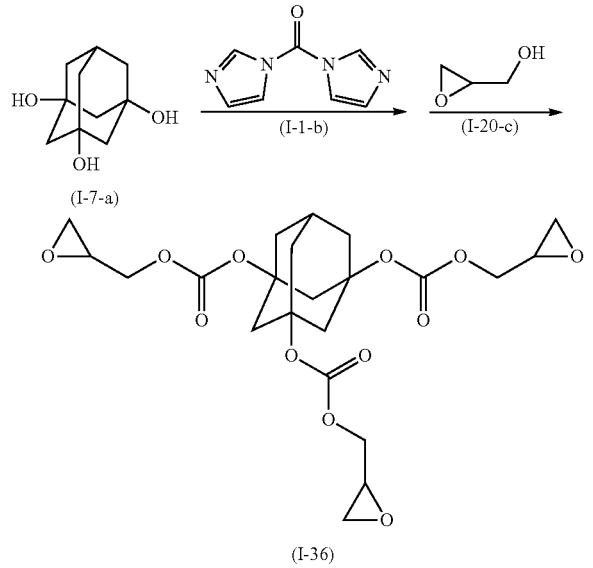

1.84 Parts of a compound represented by formula (I-7-a) and 30 parts of acetonitrile were mixed, followed by stirring at 23° C. for 30 minutes, mixing of 5.35 parts of a compound represented by formula (I-1-b) and further stirring at 50° C. for 2 hours. To the reaction product thus obtained, 2.22 parts of a compound represented by formula (I-20-c) was added, followed by stirring at 50° C. for 4 hours and further cooling to 23° C. To the reaction mixture thus obtained, 50 parts of chloroform and 20 parts of an aqueous 5% oxalic acid solution were added and, after stirring at 23° C. for 30 minutes, an organic layer was isolated through separation. To the organic layer thus obtained, 20 parts of ion-exchanged water was added and, after stirring at 23° C. for 30 minutes, an organic layer was isolated through separation. This water washing operation was repeated five times. The organic layer thus obtained was concentrated, and the concentrated mass was isolated from a column (silica gel 60 N (spherical, neutral) 100-210 μm; manufactured by Kanto Chemical Co., Inc., developing solvent:ethyl acetate) to obtain 1.26 parts of a compound represented by formula (I-36).

MASS (ESI (+) Spectrum): 485.2 [M+H]⁺

Example 11

Synthesis of Compound Represented by Formula (I-16)

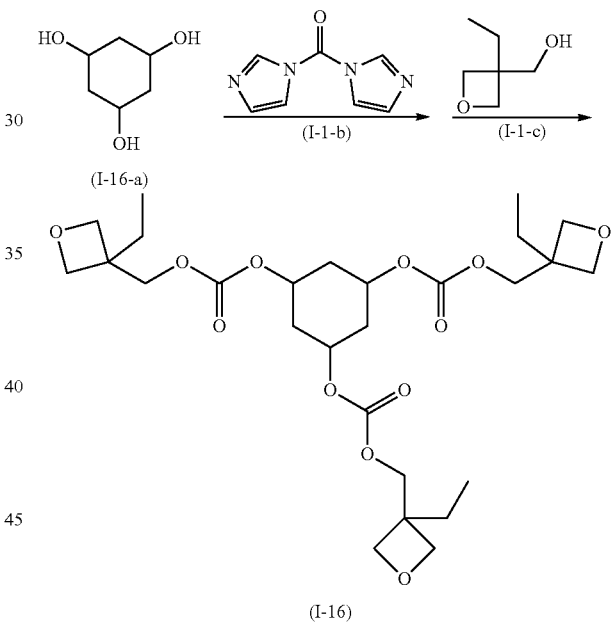

1.32 Parts of a compound represented by formula (I-16-a) and 30 parts of acetonitrile were mixed, followed by stirring at 23° C. for 30 minutes, mixing of 5.35 parts of a compound represented by formula (I-1-b) and further stirring at 50° C. for 2 hours. To the reaction product thus obtained, 3.48 parts of a compound represented by formula (I-1-c) was added, followed by stirring at 50° C. for 4 hours and further cooling to 23° C. To the reaction mixture thus obtained, 50 parts of chloroform and 20 parts of an aqueous 5% oxalic acid solution were added and, after stirring at 23° C. for 30 minutes, an organic layer was isolated through separation. To the organic layer thus obtained, 20 parts of ion-exchanged water was added and, after stirring at 23° C. for 30 minutes, an organic layer was isolated through separation. This water washing operation was repeated five times. The organic layer thus obtained was concentrated, and the concentrated mass was isolated from a column (silica gel 60 N (spherical, neutral) 100-210 µm; manufactured by Kanto Chemical Co., Inc., developing solvent:ethyl acetate) to obtain 1.01 parts of a compound represented by formula (I-16).

MASS (ESI (+) Spectrum): 559.3 [M+H]+

Synthesis of Resin

Compounds (monomers) used in the synthesis of resins (A) are shown below. Hereinafter, these compounds are referred to as "monomer (a1-1-3)" according to the number of formula.

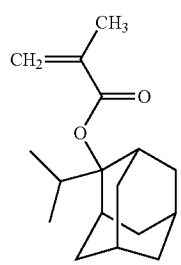
(a1-1-3)

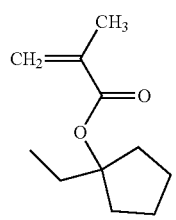
(a1-2-5)

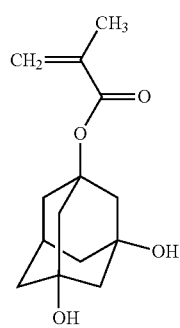
(a2-1-3)

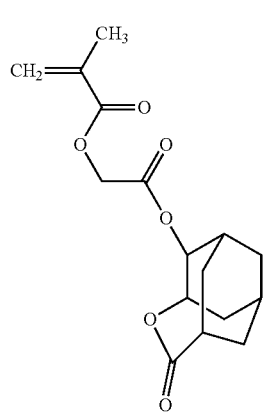
(a3-4-2)

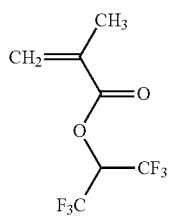
(a4-0-12)

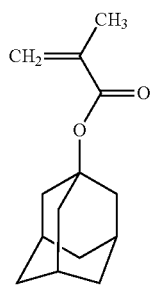
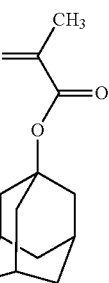
(a5-1-1)

Synthesis Example 1

Synthesis of Resin A1

Using a monomer (a1-1-3), a monomer (a1-2-5), a monomer (a2-1-3) and a monomer (a3-4-2) as monomers, these monomers were mixed in a molar ratio of 45:14:2.5:38.5 [monomer (a1-1-3):monomer (a1-2-9):monomer (a2-1-3):monomer (a3-4-2)], and propylene glycol monomethyl ether acetate was added in the amount of 1.5 mass times the total mass of all monomers to obtain a solution. To the solution thus obtained, azobisisobutyronitrile and azobis(2,4-dimethylvaleronitrile) as initiators were added in the amounts of 1 mol % and 3 mol % based on the total molar number of all monomers, and then the mixture was heated at 73° C. for about 5 hours. The reaction mixture thus obtained was poured into a large amount of a methanol/water mixed solvent to precipitate a resin, and this resin was filtered. After performing a reprecipitation operation in which the resin thus obtained is dissolved again in propylene glycol monomethyl ether acetate and the solution thus obtained is poured into a methanol/water mixed solvent to precipitate a resin, and this resin is filtered, twice, a resin A1 having a weight average molecular weight of $7.6 \times 10^3$ was obtained in a yield of 68%. This resin A1 includes the following structural units.

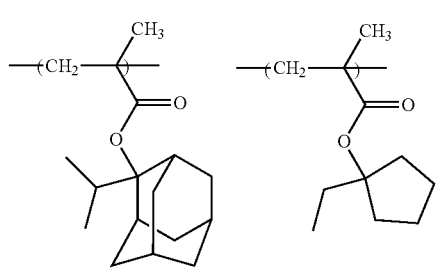
A1

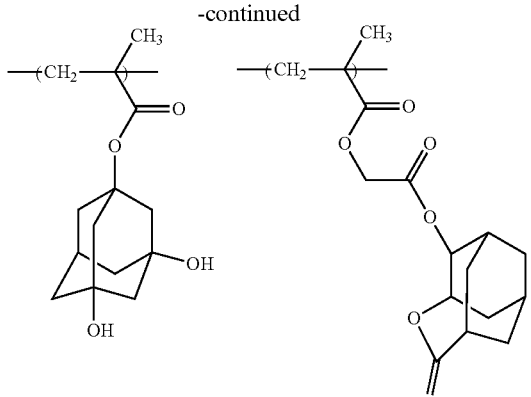

Synthesis Example 2

Synthesis of Resin X1

Using a monomer (a5-1-1) and a monomer (a4-0-12) as monomers, these monomers were mixed in a molar ratio of 50:50 [monomer (a5-1-1):monomer (a4-0-12)], and methyl isobutyl ketone was added in the amount of 1.2 mass times the total mass of all monomers to obtain a solution. To the solution thus obtained, azobis(2,4-dimethylvaleronitrile) as an initiator was added in the amount of 3 mol % based on the total molar number of all monomers, and then the mixture was heated at 70° C. for about 5 hours. The reaction mixture thus obtained was poured into a large amount of a methanol/water mixed solvent to precipitate a resin, and the resin was filtered to obtain a resin X1 having a weight average molecular weight of $1.0 \times 10^4$ in a yield of 91%. This resin X1 includes the following structural units.

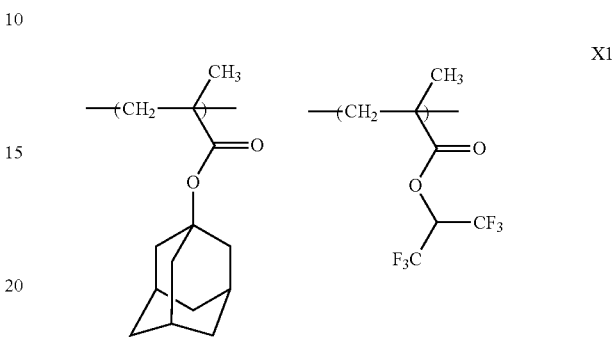

<Preparation of Resist Composition>

As shown in Table 1, the respective components shown below were mixed, and the mixtures thus obtained were filtered through a fluorine resin filter having a pore diameter of 0.2 μm to prepare resist compositions.

TABLE 1

| Resist composition | Resin | Acid generator | Compound (I) | Quencher (C) | PB/PEB |
|---|---|---|---|---|---|
| Composition 1 | X1/A1 = 0.2/10 parts | B1-21/B1-22 = 0.90/0.45 part | I-1 = 0.8 part | — | 90° C./85° C. |
| Composition 2 | X1/A1 = 0.2/10 parts | B1-21/B1-22 = 0.90/0.45 part | I-2 = 0.8 part | — | 90° C./85° C. |
| Composition 3 | X1/A1 = 0.2/10 parts | B1-21/B1-22 = 0.90/0.45 part | I-5 = 0.8 part | — | 90° C./85° C. |
| Composition 4 | X1/A1 = 0.2/10 parts | B1-21/B1-22 = 0.90/0.45 part | I-6 = 0.8 part | — | 90° C./85° C. |
| Composition 5 | X1/A1 = 0.2/10 parts | B1-21/B1-22 = 0.90/0.45 part | I-7 = 0.8 part | — | 90° C./85° C. |
| Composition 6 | X1/A1 = 0.2/10 parts | B1-21/B1-22 = 0.90/0.45 part | I-20 = 0.8 part | — | 90° C./85° C. |
| Composition 7 | X1/A1 = 0.2/10 parts | B1-21/B1-22 = 0.90/0.45 part | I-1 = 0.8 part | D1 = 0.1 part | 90° C./85° C. |
| Composition 8 | X1/A1 = 0.2/10 parts | B1-21/B1-22 = 0.90/0.45 part | I-1 = 0.8 part | D1 = 0.05 part | 90° C./85° C. |
| Composition 9 | X1/A1 = 0.2/10 parts | B1-21/B1-22 = 0.90/0.45 part | I-28 = 0.8 part | — | 90° C./85° C. |
| Composition 10 | X1/A1 = 0.2/10 parts | B1-21/B1-22 = 0.90/0.45 part | I-34 = 0.8 part | — | 90° C./85° C. |
| Composition 11 | X1/A1 = 0.2/10 parts | B1-21/B1-22 = 0.90/0.45 part | I-35 = 0.8 part | — | 90° C./85° C. |
| Composition 12 | X1/A1 = 0.2/10 parts | B1-21/B1-22 = 0.90/0.45 part | I-36 = 0.8 part | — | 90° C./85° C. |
| Composition 13 | X1/A1 = 0.2/10 parts | B1-21/B1-22 = 0.90/0.45 part | I-16 = 0.8 part | — | 90° C./85° C. |
| Comparative composition 1 | X1/A1 = 0.2/10 parts | B1-21/B1-22 = 0.90/0.45 part | — | C1 = 0.8 part | 90° C./85° C. |
| Comparative composition 2 | X1/A1 = 0.2/10 parts | B1-21/B1-22 = 0.90/0.45 part | — | C2 = 0.8 part | 90° C./85° C. |

<Resin>

A1, X1: Resin A1, Resin X1

<Acid Generator>

B1-21: Salt represented by formula (B1-21) (synthesized in accordance with Examples in JP 2012-224611 A)

B1-22: Salt represented by formula (B1-22) (synthesized in accordance with Examples in JP 2012-224611 A)

(B1-21)

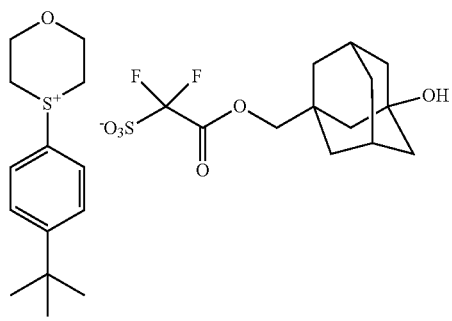

(B1-22)

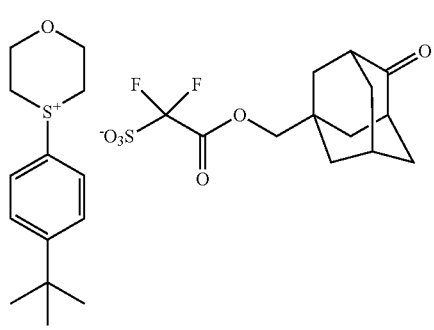

<Quencher (C)>

Quencher C1: (synthesized in accordance with Examples in JP 2012-252316 A)

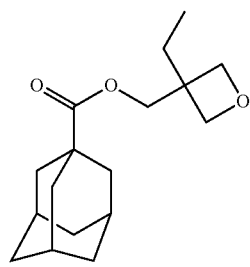 [SMILES: CCC1(COC(=O)C23CC4CC(CC(C4)C2)C3)COC1]

Quencher C2: (synthesized in accordance with Examples in JP 2012-252316 A)

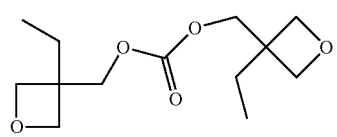 [SMILES: CCC1(COC(=O)OCC2(CC)COC2)COC1]

D1: (manufactured by Tokyo Chemical Industry Co., Ltd.)

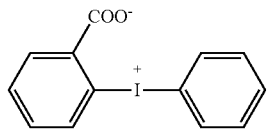

<Solvent>

| | |
|---|---|
| Propylene glycol monomethyl ether acetate | 265 parts |
| Propylene glycol monomethyl ether | 20 parts |
| 2-Heptanone | 20 parts |
| γ-Butyrolactone | 3.5 parts |

<Production of Resist Pattern>

Silicon wafers with 12 inches were each coated with an organic anti-reflective coating composition [ARC-29, manufactured by Nissan Chemical Industries, Ltd.] and then baked under the conditions at 205° C. for 60 seconds to form a 78 nm-thick organic anti-reflective coating. Then, each of the photoresist compositions was spin-coated on the anti-reflective coating so that the thickness of the resulting film became 170 nm after drying (prebaking). The silicon wafers thus coated with the respective photoresist compositions were prebaked on a direct hotplate at a temperature shown in the column "PB" in Table 1 for 60 seconds to form a composition layer on each silicon wafer.

Using a mask for forming a contact hole pattern (hole pitch of 200 nm/hole diameter of 90 nm), each silicon wafer formed with the composition layer was subjected to exposure with an exposure dose being varied stepwise by an ArF excimer stepper for immersion exposure (XT: 1900Gi, manufactured by ASML, NA=1.35, ¾ Annular, X-Y polarization). Ultrapure water was used as an immersion medium.

After the exposure, each silicon wafer was subjected to post-exposure baking on a hotplate at a temperature shown in the column "PEB" in Table 1 for 60 seconds. Then, each silicon wafer formed with the composition layer was developed at 23° C. for 20 seconds with butyl acetate (manufactured by Tokyo Chemical Industries, Co., Ltd) as a developing solution by a dynamic dispense method to form a negative photoresist pattern.

In the pattern formed after the development, the effective sensitivity [ES] was expressed as the exposure dose that the hole diameter formed using the mask became 80 nm.

<Evaluation of CD Uniformity (CDU)>

In the effective sensitivity, the hole diameter of the pattern formed using a mask having a hole diameter of 90 nm was determined by measuring 24 times per one hole and the average of the measured values was regarded as the average hole diameter. The standard deviation determined under the conditions that the average diameter of 400 holes about the patterns formed using the mask having a hole diameter of 90 nm in the same wafer was regarded to as population.

The results are shown in Table 2. The numerical value in the parenthesis represents the standard deviation (nm).

TABLE 2

| | Resist composition | CDU |
|---|---|---|
| Example 12 | Composition 1 | 1.75 |
| Example 13 | Composition 2 | 1.71 |

TABLE 2-continued

| | Resist composition | CDU |
|---|---|---|
| Example 14 | Composition 3 | 1.68 |
| Example 15 | Composition 4 | 1.74 |
| Example 16 | Composition 5 | 1.67 |
| Example 17 | Composition 6 | 1.82 |
| Example 18 | Composition 7 | 1.78 |
| Example 19 | Composition 8 | 1.76 |
| Example 20 | Composition 9 | 1.75 |
| Example 21 | Composition 10 | 1.78 |
| Example 22 | Composition 11 | 1.71 |
| Example 23 | Composition 12 | 1.69 |
| Example 24 | Composition 13 | 1.70 |
| Comparative Example 1 | Comparative composition 1 | 1.92 |
| Comparative Example 2 | Comparative composition 2 | 1.94 |

In the above resist composition, it is possible to reduce defects of the resist pattern thus obtained by using a resin (A1) and a resin (X1) in combination.

INDUSTRIAL APPLICABILITY

A resist composition including the salt of the present invention is capable of producing a resist pattern with satisfactory CD uniformity (CDU) and is suited for fine processing of semiconductors.

The invention claimed is:

1. A resist composition comprising a resin including a structural unit having an acid-labile group, an acid generator and a compound represented by formula (I):

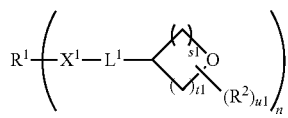

wherein, in formula (I),
$R^1$ represents a hydrocarbon group having 3 to 36 carbon atoms which has a substituent, and the hydrocarbon group includes an alicyclic hydrocarbon group, and the substituent is selected from the group consisting of a halogen atom, a cyano group, a hydroxy group, a carboxy group, an alkoxy group having 1 to 12 carbon atoms, an alkoxycarbonyl group having 2 to 13 carbon atoms, an alkylcarbonyl group having 2 to 13 carbon atoms or an alkylcarbonyloxy group having 2 to 13 carbon atoms,
$X^1$ represents *—CO—O—, *—O—CO— or *—O—CO—O, and * represents a bonding site to $R^1$,
$L^1$ represents a single bond or a hydrocarbon group having 1 to 36 carbon atoms which may have a substituent, and —$CH_2$— included in the hydrocarbon group may be replaced by —O—, —S—, —CO— or —$SO_2$—,
$R^2$ represents a saturated hydrocarbon group having 1 to 12 carbon atoms,
u1 represents an integer of 0 to 2,
s1 represents 1 or 2,
t1 represents 0 or 1, in which s1+t1 is 2,
n represents an integer of 2 or more, and
a plurality of $X^1$, $L^1$, s1, t1, $R^2$ and u1 each may be the same or different.

2. The resist composition according to claim 1, wherein $R^1$ is an alicyclic hydrocarbon group having 3 to 36 carbon atoms which has a substituent.

3. The resist composition according to claim 1, wherein $X^1$ is *—CO—O— or *—O—CO—O, wherein * represents a bonding site to $R^1$.

4. The resist composition according to claim 1, wherein $L^1$ is a methylene group.

5. The resist composition according to claim 1, wherein the acid generator is a salt represented by formula (B1):

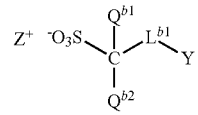

wherein, in formula (B1),
$Q^{b1}$ and $Q^{b2}$ each independently represent a fluorine atom or a perfluoroalkyl group having 1 to 6 carbon atoms,
$L^{b1}$ represents a divalent saturated hydrocarbon group having 1 to 24 carbon atoms, and —$CH_2$— included in the saturated hydrocarbon group may be replaced by —O— or —CO— and a hydrogen atom included in the saturated hydrocarbon group may be substituted with a fluorine atom or a hydroxy group,
Y represents a methyl group which may have a substituent or an alicyclic hydrocarbon group having 3 to 18 carbon atoms which may have a substituent, and —$CH_2$— included in the alicyclic hydrocarbon group may be replaced by —O—, —$SO_2$— or —CO—, and
$Z^+$ represents an organic cation.

6. A method for producing a resist pattern, which comprises:
(1) a step of applying the resist composition according to claim 1 on a substrate,
(2) a step of drying the applied composition to form a composition layer,
(3) a step of exposing the composition layer,
(4) a step of heating the exposed composition layer, and
(5) a step of developing the heated composition layer.

7. A compound represented by formula (I1):

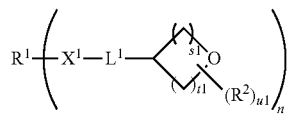

wherein, in formula (I1),
$R^1$ represents a hydrocarbon group having 3 to 36 carbon atoms which has a substituent, and the hydrocarbon group includes an alicyclic hydrocarbon group, and the substituent is selected from the group consisting of a halogen atom, a cyano group, a hydroxy group, a carboxy group, an alkoxy group having 1 to 12 carbon atoms, an alkoxycarbonyl group having 2 to 13 carbon atoms, an alkylcarbonyl group having 2 to 13 carbon atoms or an alkylcarbonyloxy group having 2 to 13 carbon atoms,
$X^1$ represents *—CO—O—, *—O—CO— or *—O—CO—O, and * represents a bonding site to $R^1$,
$L^1$ represents a single bond or a hydrocarbon group having 1 to 36 carbon atoms which may have a substituent, and —$CH_2$— included in the hydrocarbon group may be replaced by —O—, —S—, —CO— or —$SO_2$—, $R^2$ represents a saturated hydrocarbon group having 1 to 12 carbon atoms, u1 represents an integer of 0 to 2, s1 represents 1 or 2, t1 represents 0 or 1, in which s1+t1 is 2, n represents an integer of 2 or more, and a plurality of $X^1$, $L^1$, s1, t1, $R^2$ and u1 each may be the same or different from each other.

8. A resist composition comprising a resin including a structural unit having an acid-labile group, an acid generator and a compound represented by formula (I):

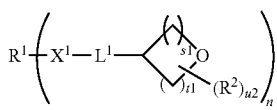

wherein, in formula (I), $R^1$ represents a hydrocarbon group having 4 to 36 carbon atoms which has a substituent, and the hydrocarbon group includes a polycyclic alicyclic hydrocarbon group, and the substituent is selected from the group consisting of a halogen atom, a cyano group, a hydroxy group, a carboxy group, an alkoxy group having 1 to 12 carbon atoms, an alkoxycarbonyl group having 2 to 13 carbon atoms, an alkylcarbonyl group having 2 to 13 carbon atoms or an alkylcarbonyloxy group having 2 to 13 carbon atoms, $X^1$ represents *—CO—O—, *—O—CO— or *—O—CO—O, and * represents a bonding site to $R^1$, $L^1$ represents a single bond or a hydrocarbon group having 1 to 36 carbon atoms which may have a substituent, and —$CH_2$— included in the hydrocarbon group may be replaced by —O—, —S—, —CO— or —$SO_2$—, $R^2$ represents a saturated hydrocarbon group having 1 to 12 carbon atoms, u1 represents an integer of 0 to 2, s1 represents 1 or 2, t1 represents 0 or 1, in which s1+t1 is 1 or 2, n represents an integer of 2 or more, and a plurality of $X^1$, $L^1$, s1, t1, $R^2$ and u1 each may be the same or different.

9. The resist composition according to claim 8, wherein $R^1$ is a polycyclic alicyclic hydrocarbon group having 4 to 36 carbon atoms which has a substituent.

10. The resist composition according to claim 8, wherein $X^1$ is *—CO—O— or *—O—CO—O, wherein * represents a bonding site to $R^1$.

11. The resist composition according to claim 8, wherein $L^1$ is a methylene group.

12. The resist composition according to claim 8, wherein the acid generator is a salt represented by formula (B1):

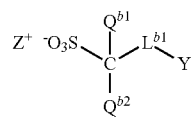

wherein, in formula (B1), $Q^{b1}$ and $Q^{b2}$ each independently represent a fluorine atom or a perfluoroalkyl group having 1 to 6 carbon atoms, $L^{b1}$ represents a divalent saturated hydrocarbon group having 1 to 24 carbon atoms, and —$CH_2$— included in the saturated hydrocarbon group may be replaced by —O— or —CO— and a hydrogen atom included in the saturated hydrocarbon group may be substituted with a fluorine atom or a hydroxy group, Y represents a methyl group which may have a substituent or an alicyclic hydrocarbon group having 3 to 18 carbon atoms which may have a substituent, and —$CH_2$— included in the alicyclic hydrocarbon group may be replaced by —O—, —$SO_2$— or —CO—, and $Z^+$ represents an organic cation.

13. A method for producing a resist pattern, which comprises:

(1) a step of applying the resist composition according to claim 8 on a substrate, (2) a step of drying the applied composition to form a composition layer, (3) a step of exposing the composition layer, (4) a step of heating the exposed composition layer, and (5) a step of developing the heated composition layer.

* * * * *